US011434504B2

(12) United States Patent
Chatterjee et al.

(10) Patent No.: US 11,434,504 B2
(45) Date of Patent: Sep. 6, 2022

(54) ADENO-ASSOCIATED VIRUS VECTOR VARIANTS FOR HIGH EFFICIENCY GENOME EDITING AND METHODS THEREOF

(71) Applicant: CITY OF HOPE, Duarte, CA (US)

(72) Inventors: Saswati Chatterjee, Altadena, CA (US); Laura Jane Smith, Westford, MA (US); Kamehameha Wong, Altadena, CA (US)

(73) Assignee: CITY OF HOPE, Duarte, CA (US)

( * ) Notice: Subject to any disclaimer, the term of this patent is extended or adjusted under 35 U.S.C. 154(b) by 73 days.

(21) Appl. No.: 16/858,199

(22) Filed: Apr. 24, 2020

(65) Prior Publication Data

US 2021/0079426 A1 Mar. 18, 2021

Related U.S. Application Data

(60) Continuation of application No. 16/543,072, filed on Aug. 16, 2019, now abandoned, which is a continuation of application No. 15/894,538, filed on Feb. 12, 2018, now Pat. No. 10,443,075, which is a division of application No. 15/273,892, filed on Sep. 23, 2016, now Pat. No. 9,890,396, which is a continuation of application No. PCT/US2015/051785, filed on Sep. 23, 2015.

(60) Provisional application No. 62/209,862, filed on Aug. 25, 2015, provisional application No. 62/063,587, filed on Oct. 14, 2014, provisional application No. 62/054,899, filed on Sep. 24, 2014.

(51) Int. Cl.
| | |
|---|---|
| *C12N 15/86* | (2006.01) |
| *A61K 48/00* | (2006.01) |
| *C12N 15/113* | (2010.01) |
| *C12N 9/22* | (2006.01) |
| *C07K 14/005* | (2006.01) |
| *C12N 15/90* | (2006.01) |
| *C12N 15/10* | (2006.01) |
| *C12N 7/00* | (2006.01) |

(52) U.S. Cl.
CPC .......... *C12N 15/907* (2013.01); *A61K 48/005* (2013.01); *A61K 48/0008* (2013.01); *C07K 14/005* (2013.01); *C12N 7/00* (2013.01); *C12N 15/102* (2013.01); *C12N 15/86* (2013.01); *A61K 48/00* (2013.01); *C12N 2710/16622* (2013.01); *C12N 2750/14121* (2013.01); *C12N 2750/14122* (2013.01); *C12N 2750/14143* (2013.01); *C12N 2750/14145* (2013.01); *C12N 2750/14152* (2013.01); *C12N 2750/14171* (2013.01); *C12N 2800/70* (2013.01); *C12N 2840/44* (2013.01)

(58) Field of Classification Search
CPC .......... C12N 15/86; C12N 2750/14143; C12N 2310/10; C12N 2310/20; C12N 2750/14145

See application file for complete search history.

(56) References Cited

U.S. PATENT DOCUMENTS

| | | | |
|---|---|---|---|
| 4,866,042 | A | 9/1989 | Neuwelt |
| 7,220,719 | B2 | 5/2007 | Case et al. |
| 7,906,111 | B2 | 3/2011 | Wilson et al. |
| 8,628,966 | B2 | 1/2014 | Chatterjee et al. |
| 8,735,153 | B2 | 5/2014 | Wolffe et al. |
| 8,846,387 | B2 | 9/2014 | Russell et al. |
| 8,927,514 | B2 | 1/2015 | Chatterjee et al. |
| 9,623,120 | B2 | 4/2017 | Chatterjee et al. |
| 2010/0310583 | A1 | 12/2010 | Lieberman et al. |
| 2011/0294218 | A1 | 12/2011 | Chatterjee et al. |
| 2013/0096182 | A1 | 4/2013 | Chatterjee et al. |
| 2015/0056705 | A1 | 2/2015 | Conway et al. |
| 2015/0056707 | A1 | 2/2015 | Mendez et al. |
| 2015/0174169 | A1 | 6/2015 | Genovese et al. |
| 2015/0344911 | A1 | 12/2015 | Chatterjee et al. |

(Continued)

FOREIGN PATENT DOCUMENTS

| | | |
|---|---|---|
| WO | WO-1993009239 A1 | 5/1993 |
| WO | WO-1997009442 A1 | 3/1997 |

(Continued)

OTHER PUBLICATIONS

Aalbers et al., "Advancements in adeno-associated viral gene therapy approaches: exploring a new horizon," F1000 Medicine Reports. 2011;3(17):1-8.

(Continued)

*Primary Examiner* — Barry A Chestnut
(74) *Attorney, Agent, or Firm* — Dechert LLP; Andrew T. Wilkins

(57) ABSTRACT

Adeno-associated virus (AAV) Clade F vectors or AAV vector variants (relative to AAV9) for precise editing of the genome of a cell and methods and kits thereof are provided. Targeted genome editing using the AAV Clade F vectors or AAV vector variants provided herein occurred at frequencies that were shown to be 1,000 to 100,000 fold more efficient than has previously been reported. Also provided are methods of treating a disease or disorder in a subject by editing the genome of a cell of the subject via transducing the cell with an AAV Clade F vector or AAV vector variant as described herein and further transplanting the transduced cell into the subject to treat the disease or disorder of the subject. Also provided herein are methods of treating a disease or disorder in a subject by in vivo genome editing by directly administering the AAV Clade F vector or AAV vector variant as described herein to the subject.

24 Claims, 95 Drawing Sheets

Specification includes a Sequence Listing.

(56) References Cited

U.S. PATENT DOCUMENTS

2017/0073703 A1 3/2017 Chatterjee et al.

FOREIGN PATENT DOCUMENTS

WO   WO-2012051343 A1   4/2012
WO   WO-2015143177 A1   9/2015

OTHER PUBLICATIONS

Anguela et al. "Robust Factor IX Expression Following ZFN-Mediated Genome Editing in an Adult Mouse Model of Hemophilia B," Blood. 2011; 118: Abstract No. 668.
Anguela et al., "ZFN Mediated Targeting of Albumin 'Safe Harbor' Results in Therapeutic Levels of Human-Factor VIII in a Mouse Model of Hemophilia A," Blood. 2013;122: Abstract No. 720.
Bainbridge et al., "Effect of Gene Therapy on Visual Function in Leber's Congenital Amaurosis," N. Eng. J. Med. 2008; 358(21):2231-239.
Batchu et al., "Adeno-Associated Virus Protects the Retinoblastoma Family of Proteins from Adenoviral-Induced Functional Inactivation," Cancer Res. 2002;62:2982-985.
Bell et al., "No. Evidence forTumorigenesis of AAV Vectors in a Large-Scale Study in Mice," Mol. Ther. 2005;12(2):299-306.
Berns et al., "Biology of Adeno-Associated Virus," Curr. Top. Microbiol. Immunol. 1996;218:1-23.
Biffi et al., "Human Hematopoietic Stem Cells in Gene Therapy: Pre-Clinical and Clinical Issues," Current Gene Ther. 2008;8:135-46.
Brantly et al., "Sustained Transgene Expression Despite T Lymphocyte Responses in a Clinical Trial of rAAV1-AAT Gene Therapy," Proc. Natl. Acad. Sci. USA. 2009;106(38):16363-68.
Chandra et al., "Genomic Integration Profile of AAVHSC Vectors in Human CD34+ Long-Term Engrafted -Hematopoietic Stem Cell Xenografts in Immune-Deficient Mice," Mol. Ther. 2015;23(Suppl 1):540-41. Abstract No. 96.
Chatterjee et al., "Dual-Target Inhibition of HIV-1 in Vitro by Means of an Adeno-Associated Virus Antisense Vector," Science. 1992;258:1485-488.
Chatterjee et al., "Transduction of Primitive Human Marrow and Cord Blood-Derived Hematopoietic Progenitor Cells with Adeno-Associated Virus Vectors," Blood. 1999;93:1882-894.
Chatterjee et al., Geneseq Accession No. AZQ17093. 2011.
Chatterjee et al., "Adeno-Associated Viral Vectors for the Delivery of Antisense RNA," Methods: A Companion to Methods in Enzymology. 1993;5:51-59.
Cideciyan et al., "Human RPE65 Gene Therapy for Leber Congenital Amaurosis: Persistence of Early Visual Improvements and Safety at 1 Year," Hum. Gene Ther. 2009;20:999-1004.
Einerhand et al., "Regulated High-Level Human beta-Globin Gene Expression in Erythroid Cells Following recombinant Adeno-Associated Virus-Mediated Gene Transfer," Gene Therapy. 1995;2:336-43.
Fisher-Adams et al., "Integration of Adeno-Associated Virus Vectors in CD34+ Human Hematopoietic Progenitor Cells After Transduction," Blood. 1996;88:492-504.
Flotte et al., "Phase I Trial of Intramuscular Injection of a Recombinant Adeno-Associated Virus Alpha 1-Antitrypsin (rAAV1-CB-hAAT) Gene Vectorto AAT-Deficient Adults," Human Gene Therapy. 2004;14:93-128.
Fu et al., "A Novel Peptide Delivers Plasminds Across Blood-Brain Barrier into Neuronal Cells as a Single-Component Transfer Vector," PLOS One. 2013;8(3):e59642.
Gao et al., "Glades of Adeno-Associated Viruses Are Widely Disseminated in Human Tissues," J. Viral. 2004;78(12):6381-388.
Hacein-Bey-Abina et al., "A Serious Adverse Event After Successful Gene Therapy for X-Linked Severe 3ombined Immunodeficiency," N. Eng. J. Med. 2003;348(3):255-56.
Hackel et al., "Modulation of Tight Junction Proteins in the Perineurium for Regional Pain Control," Ann. N.Y. Acad. Sci. 2012;1257:199-206.
Han et al., "Stable Integration of Recombinant Adeno-Associated Virus Vector Genomes After Transduction of Murine Hematopoietic Stem Cells," Human Gene Therapy. 2008;19:267-78.
Homology Medicines, Inc., "In Vivo Gene Correction Normalized Phe in PKU ENU2 Model", "HMI-103 PKU Gene Editing Human Development Candidate Showed Therapeutic Levels of Expression in an In Vivo Humanized Murine Model," corporate slide presentation published on company website on Jul. 19, 2019; 2 pages.
Jayandharan et al., "Strategies for Improving the Transduction Efficiency of Single-Stranded Adeno-Associated Virus Vectors In Vitro and In Vivo," Gene Therapy. 2008;15:1287-293.
Jordan et al., "Advanced in the Understanding of Retinal Drug Disposition and the Role of Blood-Ocular Barrier Transporters," Expert Opin. Drug Metab. Toxicol. 2013;9(9):1181-192.
Kaplitt et al., "Safety and Tolerability of Gene Therapy with an Adeno-Associated Virus (AAV) Borne GAD Gene for Parkinson's Disease: An Open Label, Phase I Trial," Lancet. 2007;369:2097-105.
Kells et al., "Efficient Gene Therapy-Based Method for the Delivery of Therapeutics to Primate Cortex," PNAS. 2009;106(7):2407-411.
Kessler et al., "Gene Delivery to Skeletal Muscle Results in Sustained Expression and Systemic Delivery of a Therapeutic Protein," Ptoc. Natl. Acad. Sci. USA. 1996;93:14082-087.
Khan et al., "AAV-mediated gene targeting methods for human cells," Nat. Protocols. 2011;6(4):482-501.
Manno et al., "AAV-Mediated Factor IX Gene Transfer to Skeletal Muscle in Patients with Severe Hemophilia 3," Blood. 2003;101:2963-972.
Martz, "Homology responds to reproducibility concerns," published online on biocentury.com website on Jul. 25, 2019; 1 page.
McCormack et al., "Activation oftheT-Cell Oncogene LM02 After Gene Therapy for X-Linked Severe 3ombined Immunodeficiency," N. Eng. J. Med. 2004;350(9):913-22.
Miller et al., "Gene Transfer by Retrovirus Vectors Occurs Only in Cells that are Actively Replicating at the Time of Infection," Mol. Cell. Biol. 1990;10(8):4239-242.
Miller et al., "Gene targeting in vivo by adeno-associated virus vectors," Nature Biotechnology. 2006;24(8):1022-026.
Natsoulis et al., Geneseq Accession No. AAT63408; 1997.
Paz et al., "Quiescent Subpopulations of Human CD34-Positive Hematopoietic Stem Cells are Preferred Targets for Stable Recombinant Adeno-Associated Virus Type 2 Transduction," Human Gene Therapy. 2007;18:614-626.
PCT International Search Report from PCT/ US2015/051785, dated Jan. 12, 2016.
Petrs-Silva et al., "High-Efficiency Transduction of the Mouse Retina by Tyrosine-Mutant AAV Serotype Vectors," Mol. Ther. 2009;17(3):463-71.
Podsakoff et al., "Efficient Gene Transfer into Nondividing Cells by Adeno-Associated Virus-based Vectors," J. Virol. 1994;68(9):5656-666.
Ponnazhagan et al., "Adeno-Associated Virus Type 2-Mediated Transduction of Murine Hematopoietic Cells with Long-Term Repopulating Ability and Sustained Expression of a Human Globin Gene In Vivo," J. Virol. 1997;71 (A):3098-104.
Raj et al., "Virus-Mediated Killing of Cells that Lack p53 Activity," Nature. 2001;412:914-917.
Rogers et al., "Homologous recombination-based genome editing by clade F AAVs is inefficient in the absence of a targeted DNA break," non-peer reviewed manuscript posted to bioRxiv.org website on Jul. 21, 2019; 33 pages.
Santat et al., "Recombinant AAV2 Transduction of Primitive Human Hematopoietic Stem Cells Capable of Serial Engraftment in Immune-Deficient Mice," PNAS. 2005;102(31):11053-058.
Smith et al., "Gene Transfer Properties and Structural Modeling of Human Stem Cell-Derived AAV," Mol. Ther. 2014;22(9):1625-34.
Smith et al., "AAVHSC Vectors Encoding Zinc-Finger Nucleases Mediate Efficient Targeted Integration at the Human AAVS1 Locus in CD34+ Humans Hematopoietic Stem Cells," Abstract Presented

(56) References Cited

OTHER PUBLICATIONS

In; The American Society of Gene and Cell Therapy 18th Annual Meeting. New Orleans, LA. May 13-16, 2015. Mol. Ther. 23(Suppl 1):524. Abstract No. 55.
Smith et al., "AAVHSC Vectors Encoding Zinc-Finger Nucleases Mediate Efficient Targeted Integration at the Human AAVS1 Locus in CD34+ Humans Hematopoietic Stem Cells," Presentation Slides Presented In; The American Society of Gene and Cell Therapy 18th Annual Meeting. New Orleans, LA. May 13-16, 2015, 16 pages.
Smith et al., "Receptor Binding and Post-Entry Processing of Stem Cell-Derived AAV Isolates in CD34+ Cells," Mol. Ther. 2014;22(Suppl 1):527-528. Abstract No. 72.
Smith et al., "Efficient Targeted Integration into AAVS1 by AAVHSC Vectors Encoding Zinc-Finger Nucleases," Poster Presented In; National Heart, Lung and Blood Institutes 13th Annual Gene Therapy Symposium for Heart, Lung, and Blood Diseases, Nov. 19-21, 2014. Sonoma, California, 1 page.
Smith et al., "Efficient Targeted Integration into AAVS1 by AAVHSC Vectors Encoding Zinc-Finger Nucleases," Presentation Slides Presented In; National Heart, Lung and Blood Institutes 13th Annual Gene Therapy Symposium for Heart, Lung, and Blood Diseases, Nov. 19-21, 2014. Sonoma, California, 11 pages.
Smith et al., "Efficient Targeted Integration into AAVS1 by AAVHSC Vectors Encoding Zinc-Finger Nucleases," Abstract Presented In; National Heart, Lung and Blood Institutes 13th Annual Gene Therapy Symposium for Heart, Lung, and Blood Diseases, Nov. 19-21, 2014. Sonoma, California, 1 page.
Smith et al., "AAVHSC Vectors Mediate Highly Precise and Efficient Homologous Recombination-Based Gene Editing," Abstract presented at ASGCT 20th Annual Meeting, May 13, 2017, 1 page.
Smith et al., "Stem cell-derived clade F AAVs mediate high-efficiency homologous recombinationbased genome editing," Proceedings of the National Academy of Sciences of the United States of America, published online on Dec. 24, 2018, 10 pages.
Srivastava, "Hematopoietic Stem and Progenitor Cells by AAV2 Vectors," Methods Mol. Biol. 2004;246:245-254.
Srivastava, Geneseq Accession No. AAQ41448; 1993.
Towne et al., "Efficient Transduction of Non-Human Primate Motor Neurons After Intramuscular Delivery of Recombinant AAV Serotype 6," Gene Ther. 2010;17:141-46.
Ul-Hasan et al., "Novel AAV Vecotrs Mediate Efficient Intramuscular Gene Delivery," Mol. Ther. 2014;22(Suppl 1):S115-S116. Abstract No. 300.
Wright, "Nuclease-free and Promoter-less AAVHSC-mediated Genome Editing in vivo Corrects the Disease Phenotype of Phenylketonuria in a Mouse Model," slide presentation at ASGCT 22nd Annual Meeting, May 2, 2019; 18 pages.
Zhong et al., "Self-Complementary Adeno-Associated Virus 2 (AAV)-T Cell Protein Tyrosine Phosphatase Vectors as Helper Viruses to Improve Transduction Efficiency of Conventional Single-Stranded AAV Vectors In Vitro and In Vivo," Mol. Ther. 2004;10(5):950-957.
Zhong et al., "Impaired Nuclear Transport and Uncoating Limit Recombinant Adeno-Associated Virus 2 Vector-Mediated Transduction of Primary Murine Hematopoietic Cells," Human Gene Therapy. 2004;15:1207-218.
Zhong et al., "A Dual Role of EGFR Protein Tyrosine Kinase Signaling in Ubiquitination of AAV2 Capsids and Viral Second-Strand DNA Synthesis," Mol. Ther. 2007;15(7):1323-330.
Zhong et al., "Next Generation of Adeno-Associated Virus 2 Vectors: Point Mutations in Tyrosines Lead to High-Efficiency Transduction at Lower Doses," PNAS. 2008; 105(22)7827-832.
Zhong et al., "Tyrosine Phosphorylation of AAV2 Vectors and Its Consequences on Viral Intracellular Trafficking and Transgene Expression," Virology. 2008;381(2):194-202.
Zhou et al., "Adeno-Associated Virus 2-Mediated Gene Transfer in Murine Hematopoietic Progenitor Cells," Experimental Hematology. 1993;21:928-933.

```
                                    721              736
HSC1  Amino Acid Sequence  (721)   YSEPRPIGTRYLTRNL
HSC2  Amino Acid Sequence  (721)   YSEPRPIGTRYLTRNL
HSC11 Amino Acid Sequence  (721)   YSEPRPIGTRYLTRNL
HSC3  Amino Acid Sequence  (721)   YSEPRPIGTRYLTRNL
HSC4  Amino Acid Sequence  (721)   YSEPRPIGTRYLTRNL
HSC6  Amino Acid Sequence  (721)   YSEPRPIGTRYLTRNL
HSC7  Amino Acid Sequence  (721)   YSEPRPIGTRYLTRNL
HSC8  Amino Acid Sequence  (721)   YSEPRPIGTRYLTRNL
HSC9  Amino Acid Sequence  (721)   YSEPRPIGTRYLTRNL
HSC5  Amino Acid Sequence  (721)   YSEPRPIGTRYLTRNL
HSC12 Amino Acid Sequence  (721)   YSEPRPIGTRYLTRNL
HSC17 Amino Acid Sequence  (721)   YSEPRPIGTRYLTRNL
HSC13 Amino Acid Sequence  (721)   YSEPRPIGTRYLTRNL
HSC14 Amino Acid Sequence  (721)   YSEPRPIGTRYLTRNL
HSC15 Amino Acid Sequence  (721)   YSEPRPIGTRYLTRNL
HSC16 Amino Acid Sequence  (721)   YSEPRPIGTRYLTRNL
AAV9  Amino Acid Sequence  (721)   YSEPRPIGTRYLTRNL
```

Figure 2

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC1 SEQ ID NO: 2 | G to A | GCT - Alanine | ACT - Threonine | Alanine is nonpolar & neutral; Threonine is polar & neutral | 4 bases into capsid; 2nd amino acid; Not in HVR, VP1 |
| HSC1 SEQ ID NO: 2 | G to A | CGA - Arginine | CAA - Glutamine | Arginine is polar & strongly basic; Glutamine is polar & neutral | 935 bases into the capsid; 312th amino acid; Not in HVR, VP3 |
| HSC2 SEQ ID NO: 3 | A to G | GGA - Glycine | GGG - Glycine | No Amino Acid Difference | 1515 bases into the capsid; 505th amino acid; 1st amino acid after HVR 7, VP3 |
| HSC2 SEQ ID NO: 3 | A to G | GAC - Aspartic Acid | GGC - Glycine | Aspartic Acid is polar & acidic; Glycine is nonpolar & neutral | 1877 bases into the capsid; 626th amino acid; Not in HVR, VP3 |
| HSC2 SEQ ID NO: 3 | A to G | GAA - Glutamic Acid | GGA - Glycine | Glutamic Acid is polar & acidic; Glycine is nonpolar & neutral | 2153 bases into the capsid; 718th amino acid; In HVR 12 last amino acid, VP3 |
| HSC3 SEQ ID NO: 5 | G to A | GGC - Glycine | GAC - Aspartic Acid | Glycine is nonpolar & neutral; Aspartic Acid is polar and acidic | 479 bases into the capsid; 160th amino acid; Not in HVR, VP1 |
| HSC3 SEQ ID NO: 5 | A to G | TCA - Serine | TCG - Serine | No Amino Acid Difference | 1044 bases into the capsid, 348th amino acid; Not in HVR VP3 |
| HSC4 SEQ ID NO: 6 | T to C | TTC - Phenylalanine | CTC - Leucine | Phenylalanine is nonpolar & neutral; Leucine is nonpolar & neutral | 355 bases into the capsid, 119th amino acid; Not in HVR; VP1 |
| HSC4 SEQ ID NO: 6 | C to T | CCC - Proline | TCC - Serine | Proline is nonpolar & neutral; Serine is polar & neutral | 1402 bases into the capsid; 468th amino acid; In HVR 5, VP3 |
| HSC4 SEQ ID NO: 6 | G to A | CCG - Proline | CCA - Proline | No Amino Acid Difference | 1809 bases into the capsid; 603rd amino acid; Not in HVR, VP3 |

Figure 2 (cont.)

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC6 SEQ ID NO: 8 | A to G | CAG - Glutamine | CGG - Arginine | Glutamine is polar & neutral; Arginine is polar & strongly basic | 1769 bases into the capsid; 590th amino acid; In HVR 10; VP3 |
| HSC5 SEQ ID NO: 11 | A to G | AAG - Lysine | AGG - Arginine | Lysine is polar & basic; Arginine is polar & strongly basic | 230 bases into the capsid; 77th amino acid; Not in HVR, VP1 |
| HSC5 SEQ ID NO: 11 | C to T | CCC - Proline | CCT - Proline | No Amino Acid Difference | 1404 bases into the capsid; 468th amino acid; In HVR 5, VP3 |
| HSC5 SEQ ID NO: 11 | G to A | GAA - Glutamic Acid | AAA - Lysine | Glutamic Acid is polar & acidic; Lysine is polar & basic | 2068 bases into the capsid; 690th amino acid; Not in HVR, VP3 |
| HSC5 SEQ ID NO: 11 | T to C | AAT - Asparagine | AAC - Asparagine | No Amino Acid Difference | 2148 bases into the capsid; 716th amino acid; In HVR 13, VP3 |
| HSC11 SEQ ID NO: 5 | G to A | GTC - Valine | ATC - Isoleucine | Isoleucine is nonpolar & neutral; valine is nonpolar & neutral | 193 bases into the capsid; 65th amino acid; Not in HVR; VP1 |
| HSC11 SEQ ID NO: 4 | G to T | GAC - Aspartic Acid | TAC - Tyrosine | Aspartic Acid is polar & acidic; Tyrosine is polar & neutral | 1876 bases into the capsid; 626th amino acid; Not in HVR; VP3 |
| HSC7 SEQ ID NO: 8 | C to T | GCA - Alanine | GTA - Valine | Alanine is nonpolar & neutral; Valine is nonpolar & neutral | 203 bases into the capsid; 68th amino acid; Not in HVR; VP1 |
| HSC7 SEQ ID NO: 8 | C to T | TTC - Phenylalanine | TTT - Phenylalanine | No Amino Acid Difference | 924 bases into the capsid; 308th amino acid; In HVR; VP3 |
| HSC8 SEQ ID NO: 9 | A to G | CAG - Glutamine | CGG - Arginine | Glutamine is polar & neutral; Arginine is polar & strongly basic | 452 bases into the capsid; 151st amino acid; In HVR 1; VP1 |

Figure 2 (cont.)

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC8 SEQ ID NO: 9 | G to A | GAG - Glutamine Acid | GAA - Glutamine Acid | No Amino Acid Difference | 2058 bases into the capsid; 686th amino acid; Not in HVR; VP3 |
| HSC9 SEQ ID NO: 10 | T to C | TTT - Phenylalanine | TTC - Phenylalanine | No Amino Acid Difference | 357 bases into the capsid; 119th amino acid; Not in HVR; VP1 |
| HSC9 SEQ ID NO: 10 | T to G | TGT - Cysteine | GGT - Glycine | Cysteine is polar & neutral; Glycine is nonpolar & neutral | 616 bases into the capsid; 206th amino acid; Not in HVR; Very beginning of VP3 |
| HSC12 SEQ ID NO: 12 | A to T | GCA - Alanine | GCT - Alanine | No Amino Acid Difference | 579 bases into capsid; 193rd amino acid into capsid, in the end of VP2 near HVR 2 |
| HSC12 SEQ ID NO: 12 | G to A | CGT - Arginine | CAT - Histidine | Arginine is polar and strongly basic; Histidine is polar and weakly basic | 887 bases into capsid; 296th amino acid into capsid; in VP3, not in HVR |
| HSC12 SEQ ID NO: 12 | G to A | AGT - Serine | AAT - Asparagine | Serine is polar and neutral; Asparagine is polar and neutral | 1391 bases into capsid; 464th amino acid into capsid; in VP3 in HVR 5 |
| HSC12 SEQ ID NO: 12 | T to C | GCT - Alanine | GCC - Alanine | No Amino Acid Difference | 1506 bases into capsid; 502nd amino acid into capsid; in VP3 in HVR 7 |
| HSC12 SEQ ID NO: 12 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC12 SEQ ID NO: 12 | G to A | GTG - Valine | ATG - Methionine | Valine is nonpolar and neutral; Methionine is nonpolar and neutral | 2041 bases into capsid; 681st amino acid into capsid; in VP3; not in HVR |
| HSC13 SEQ ID NO: 14 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |

Figure 2 (cont.)

| Capsid | Base Change | AAV 9 hu. Isolate Amino Acid | Clone New Amino Acid | Difference in Amino Acids | Placement of Amino Acid (HVR = Hypervariable Region) |
|---|---|---|---|---|---|
| HSC14 SEQ ID NO: 15 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC14 SEQ ID NO: 15 | T to G | CTG - Leucine | CGG - Arginine | Leucine is nonpolar and neutral; Arginine is polar and strongly basic | 2060 bases into capsid; 687th amino acid into capsid; in VP3; Not in HVR. |
| HSC15 SEQ ID NO: 16 | A to G | ACG - Threonine | GCG - Alanine | Threonine is polar and neutral; Arginine is polar and strongly basic | 1036 bases into capsid; 346th amino acid into the capsid; In VP3; Not in HVR |
| HSC15 SEQ ID NO: 16 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC16 SEQ ID NO: 17 | T to A | TTT - Phenylalanine | ATT - Isoleucine | Phenylalanine is nonpolar and neutral; Isoleucine is nonpolar and neutral | 1501 bases into capsid; 501st amino acid into capsid; In VP3, In HVR7 |
| HSC16 SEQ ID NO: 17 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |
| HSC16 SEQ ID NO: 17 | G to A | CCG - Proline | CCA - Proline | No Amino Acid Difference | 1713 bases into capsid; 571st amino acid into capsid; In VP3 Not in HVR |
| HSC16 SEQ ID NO: 17 | A to G | TAC - Tyrosine | TGC - Cysteine | Tyrosine is polar and neutral; Cysteine is polar and neutral | 2117 bases into capsid; 706th amino acid into capsid; In VP3; In HVR 12 and is next to a YF mutation |
| HSC17 SEQ ID NO: 13 | C to T | GAC - Aspartic Acid | GAT - Aspartic Acid | No Amino Acid Difference | 180 bases into the capsid; 60th amino acid into capsid; In VP1; Not in HVR |
| HSC17 SEQ ID NO: 13 | G to A | GGA - Glycine | AGA - Arginine | Glycine is nonpolar and neutral; Arginine is polar and strongly basic | 1513 bases into capsid; 505th amino acid into capsid; in VP3, right after HVR 7 |

% FP Positive Cells

|  | 4 day | 18 day | 20 day | 39 day |
|---|---|---|---|---|
| Untransduced | 0 | 0 | 0 | 0 |
| AAVHSC7 FP Donor | 3 | 7.23 | 4.07 | 4.61 |
| AAVHSC17 FP Donor | 20.2 | 5.43 | 2.85 | 9.18 |

➢ AAVF mediates efficient gene targeting in primary CD34+ cells

➢ High efficiency targeting is observed in human leukemic & liver cell lines

➢ AAVF editing does not require DNA synthesis

HA-L: 5'-Homology Arm
HA-R: 3'-Homology Arm
NTC: No Template Control
Untd: Untransduced Cells

AAVF VECTORS FOR NUCLEOTIDE SUBSTITUTION

- Mutates TA to AT
- Changes an Nhe1 site to a Sph1 site

Nhe 1 ⟶ Sph 1
GCTAGC ⟶ GCATGC

Wild type (Nhe 1)

K562/AAVF7  K562/AAVF17
NS Mut

RFLP: Nhe 1 cuts, Sph 1 does not cut
NS Mut: Sph 1 cuts, Nhe 1 does not cut

HepG2/AAVF7  HepG2/AAVF17
NS Mut

|          | GFP+ BrdU-<br>(Non-dividing Cells) | GFP+BrdU+<br>(Dividing Cells) |
|----------|---|---|
| AAVHSC7  | 12   | 14.6  |
| AAVHSC17 | 6.15 | 6.9   |
| AAV9     | 4.31 | 3.73  |
| AAV8     | 1.37 | 0.839 |

Figure 30

1e6 Human Cord blood CD34+ Stem Cells

Analysis of Human Blood Lineages in Marrow & Spleen
- Flow analysis
- Flow sort
- Venus, CD34+, Glyco A+ (erythroid)

| EXPT | | 1A | 1B | 2A | 2A | 2B | 2B | 3 | 3 |
|---|---|---|---|---|---|---|---|---|---|
| | | AAVF7 | AAVF17 | AAVF7 | AAVF7 | AAVF17 | AAVF17 | AAVF17 | AAVF17 |
| | | CD45+ VEN+* | CD45+ VEN+* | CD45+ VEN+* | CD34+ VEN+* | CD45+ VEN+* | CD34+ VEN+* | GLYCO A+ VEN+* | CD34+ VEN+* |
| WKS POST TX TO VENUS | | 1 | 1 | 1 | 1 | 1 | 1 | 7 | 7 |
| WKS POST VENUS TO HARVEST | | 5 | 5 | 6 | 6 | 6 | 6 | 12.5 | 12.5 |
| WKS POST TX TO HARVEST | | 6 | 6 | 7 | 7 | 7 | 7 | 19 | 19 |
| | VBM | 32.4 | 14.7 | 32.4 | 54.9 | 14.7 | 49.9 | ND | ND |
| | FBM | 11.2 | 9.49 | 9.49 | 20.3 | 11.2 | 26.8 | 99.4 | 75.5 |
| | SPLN | 15.9 | 24.8 | 15.9 | 71.1 | 24.8 | 82 | 99.2 | 58.1 |

VBM: Vertebral marrow, FBM: Femoral marrow, Spln: Spleen
TX: Transplant

\* Percentage of lineage that is Venus+ve

➢ Editing is stable long term
➢ Editing is stably inherited & insert is efficiently expressed in differentiated progeny cells
➢ In vivo editing may be much more efficient than ex vivo transduction followed transplant
➢ Progeny of edited CD34+ cells retain Venus expression long term

*Fig. 32A*

| % Venus Positive | Mid-Term AAVF7 | Mid-Term AAVF7 | Mid-Term AAVF17 | Mid-Term AAVF17 | Long-Term AAVF17 | Long-Term AAVF17 |
|---|---|---|---|---|---|---|
| *Compartment* | CD34+ | CD45+ | CD34+ | CD45+ | CD34+ | GlycoA+ |
| Vertebral Marrow | 54.9 | 33.4 | 49.9 | 14.7 | ND* | ND* |
| Femoral Marrow | 20.3 | 3.49 | 26.8 | 11.2 | 75.5 | 99.4 |
| Spleen | 71.1 | 15.9 | 82 | 24.8 | 58.1 | 99.2 |

* ND: Not Done

Figure 32B

Sequence Analysis Showing Chromosomal Insertion of Venus into Intron 1 of PPP1R12C by AAVF Vectors

ALIGNMENT OF AAV-TARGETED SEQUENCES IN AAVS1

```
» K562    AAVHSC7  #1 (2) GGCCCTGGCCATTGTCACTTTGGCTCTCTTGCTGCCTTTCTGTGCCTGTGCCCG
» K562    AAVHSC7  #2 (2) GGCCCTGGCCATTGTCACTTTGGCTCTCTTGCTGCCTTTCTGTGCCTGTGCCCG
» K562    AAVHSC7  #3 (2) GGCCCTGGCCATTGTCACTTTGGCTCTCTTGCTGCCTTTCTGTGCCTGTGCCCG
» K562    AAVHSC7  #4 (2) GGCCCTGGCCATTGTCACTTTGGCTCTCTTGCTGCCTTTCTGTGCCTGTGCCCG
» K562    AAVHSC7  #5 (2) GGCCCTGGCCATTGTCACTTTGGCTCTCTTGCTGCCTTTCTGTGCCTGTGCCCG
» PBSC    AAVHSC7  #1 (2) GGCCCTGGCCATTGTCACTTTGGCTCTCTTGCTGCCTTTCTGTGCCTGTGCCCG
» PBSC    AAVHSC7  #2 (2) GGCCCTGGCCATTGTCACTTTGGCTCTCTTGCTGCCTTTCTGTGCCTGTGCCCG
» PBSC    AAVHSC7  #3 (2) GGCCCTGGCCATTGTCACTTTGGCTCTCTTGCTGCCTTTCTGTGCCTGTGCCCG
» PBSC    AAVHSC7  #4 (2) GGCCCTGGCCATTGTCACTTTGGCTCTCTTGCTGCCTTTCTGTGCCTGTGCCCG
» PBSC    AAVHSC15 #1 (2) GGCCCTGGCCATTGTCACTTTGGCTCTCTTGCTGCCTTTCTGTGCCTGTGCCCG
» PBSC    AAVHSC15 #2 (2) GGCCCTGGCCATTGTCACTTTGGCTCTCTTGCTGCCTTTCTGTGCCTGTGCCCG
» PBSC    AAVHSC17 #1 (2) GGCCCTGGCCATTGTCACTTTGGCTCTCTTGCTGCCTTTCTGTGCCTGTGCCCG
» PBSC    AAVHSC17 #2 (2) GGCCCTGGCCATTGTCACTTTGGCTCTCTTGCTGCCTTTCTGTGCCTGTGCCCG
» PBSC    AAVHSC17 #3 (2) GGCCCTGGCCATTGTCACTTTGGCTCTCTTGCTGCCTTTCTGTGCCTGTGCCCG
» PBSC    AAVHSC17 #4 (2) GGCCCTGGCCATTGTCACTTTGGCTCTCTTGCTGCCTTTCTGTGCCTGTGCCCG
» HepG2   AAVHSC7  #1 (2) GGCCCTGGCCATTGTCACTTTGGCTCTCTTGCTGCCTTTCTGTGCCTGTGCCCG
» AC010327 AAVS1      (2) GGCCCTGGCCATTGTCACTTTGGCTCTCTTGCTGCCTTTCTGTGCCTGTGCCCG
» Venus Donor          (1)
» Homology Arm 5'      (1)
```

| | | |
|---|---|---|
| » K562 AAVHSC7 #1 | (1367) | CGAAGGCTACGTCCAGGAGCGGCACCATCTTTCTTCAAGGACGACGGCAACTACAAGACCCGGCCG |
| » K562 AAVHSC7 #2 | (1367) | CGAAGGCTACGTCCAGGAGCGGCACCATCTTTCTTCAAGGACGACGGCAACTACAAGACCCGGCCG |
| » K562 AAVHSC7 #3 | (1367) | CGAAGGCTACGTCCAGGAGCGGCACCATCTTTCTTCAAGGACGACGGCAACTACAAGACCCGGCCG |
| » K562 AAVHSC7 #4 | (1367) | CGAAGGCTACGTCCAGGAGCGGCACCATCTTTCTTCAAGGACGACGGCAACTACAAGACCCGGCCG |
| » K562 AAVHSC7 #5 | (1367) | CGAAGGCTACGTCCAGGAGCGGCACCATCTTTCTTCAAGGACGACGGCAACTACAAGACCCGGCCG |
| » PBSC AAVHSC7 #1 | (1367) | CGAAGGCTACGTCCAGGAGCGGCACCATCTTTCTTCAAGGACGACGGCAACTACAAGACCCGGCCG |
| » PBSC AAVHSC7 #2 | (1367) | CGAAGGCTACGTCCAGGAGCGGCACCATCTTTCTTCAAGGACGACGGCAACTACAAGACCCGGCCG |
| » PBSC AAVHSC7 #3 | (1367) | CGAAGGCTACGTCCAGGAGCGGCACCATCTTTCTTCAAGGACGACGGCAACTACAAGACCCGGCCG |
| » PBSC AAVHSC7 #4 | (1367) | CGAAGGCTACGTCCAGGAGCGGCACCATCTTTCTTCAAGGACGACGGCAACTACAAGACCCGGCCG |
| » PBSC AAVHSC15 #1 | (1367) | CGAAGGCTACGTCCAGGAGCGGCACCATCTTTCTTCAAGGACGACGGCAACTACAAGACCCGGCCG |
| » PBSC AAVHSC15 #2 | (1367) | CGAAGGCTACGTCCAGGAGCGGCACCATCTTTCTTCAAGGACGACGGCAACTACAAGACCCGGCCG |
| » PBSC AAVHSC17 #1 | (1367) | CGAAGGCTACGTCCAGGAGCGGCACCATCTTTCTTCAAGGACGACGGCAACTACAAGACCCGGCCG |
| » PBSC AAVHSC17 #2 | (1367) | CGAAGGCTACGTCCAGGAGCGGCACCATCTTTCTTCAAGGACGACGGCAACTACAAGACCCGGCCG |
| » PBSC AAVHSC17 #3 | (1367) | CGAAGGCTACGTCCAGGAGCGGCACCATCTTTCTTCAAGGACGACGGCAACTACAAGACCCGGCCG |
| » PBSC AAVHSC17 #4 | (1367) | CGAAGGCTACGTCCAGGAGCGGCACCATCTTTCTTCAAGGACGACGGCAACTACAAGACCCGGCCG |
| » HepG2 AAVHSC7 #1 | (1367) | CGGAGGCTACGTCCAGGAGCGGCACCATCTTTCTTCAAGGACGACGGCAACTACAAGACCCGGCCG |
| » AC010327 AAVS1 | (-174) | |
| » Venus Donor | (1193) | CGAAGGCTACGTCCAGGAGCGGCACCATCTTTCTTCAAGGACGACGGCAACTACAAGACCCGGCCG |
| » Homology Arm 5' | (-801) | |
| » Venus-pA | (271) | CGAAGGCTACGTCCAGGAGCGGCACCATCTTTCTTCAAGGACGACGGCAACTACAAGACCCGCGCCG |

AAVF TARGETS INTEGRATION OF SMALL INSERTS INTO AAVS1 - CD34+ CELLS

- 10bp insert
- Located between the two homology arms
- Does not encode a protein Chromosome-specific primer — Insert-specific primer Amplicon: 1kb GFP Expression (% Cells)

| | 24H | 48H |
|---|---|---|
| AAVF7 | 18.5 | 15.2 |
| AAVF17 | 31.6 | 26.4 |
| AAV6 | 0 | ND |
| AAV8 | 0 | ND |
| AAV9 | 2.81 | ND |

Genome integration

AAVF-Venus    AAVF-RFLP

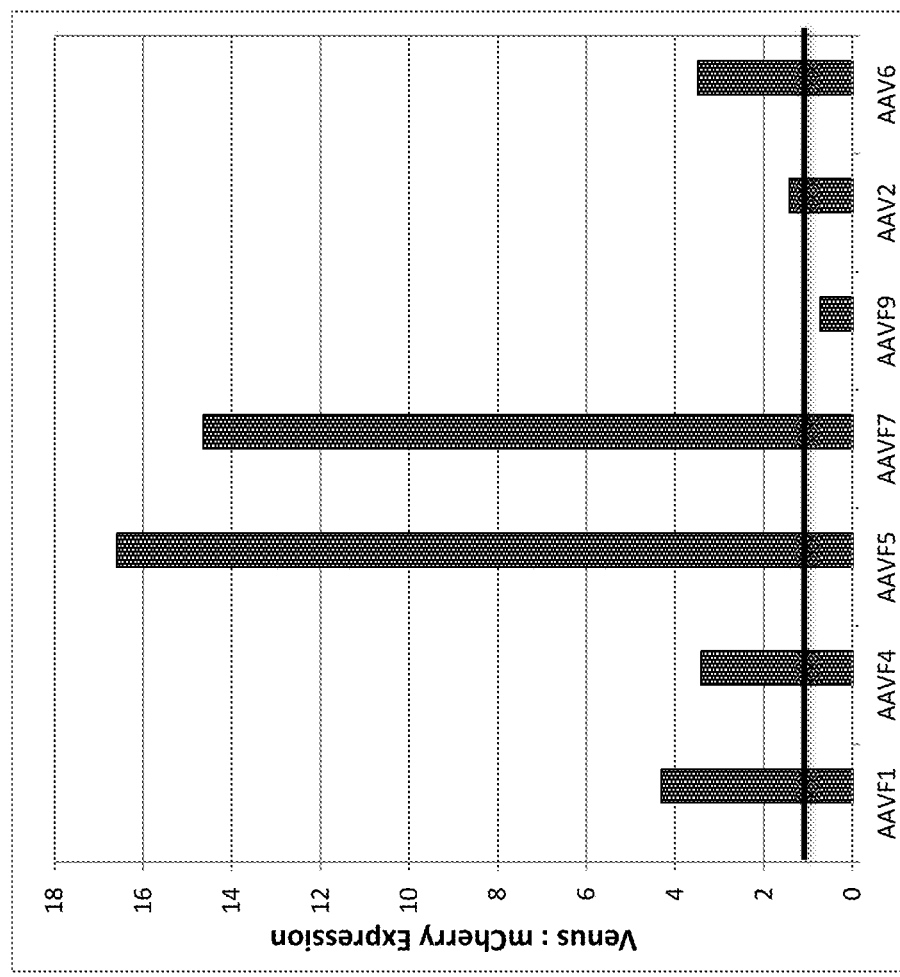

ADENO-ASSOCIATED VIRUS VECTOR VARIANTS FOR HIGH EFFICIENCY GENOME EDITING AND METHODS THEREOF

CROSS-REFERENCE TO RELATED APPLICATIONS

This application is a continuation of U.S. patent application Ser. No. 16/543,072, filed Aug. 16, 2019, which is a continuation of U.S. patent application Ser. No. 15/894,538, filed Feb. 12, 2018, now U.S. Pat. No. 10,443,075, which is a divisional of U.S. patent application Ser. No. 15/273,892, filed Sep. 23, 2016, now U.S. Pat. No. 9,890,396, which is a continuation of International Patent Application No. PCT/US2015/051785, filed Sep. 23, 2015, which claims the benefit of the priority date of U.S. Provisional Patent Application Ser. No. 62/209,862, filed Aug. 25, 2015, of U.S. Provisional Patent Application Ser. No. 62/063,587, filed Oct. 14, 2014, and of U.S. Provisional Patent Application Ser. No. 62/054,899, filed Sep. 24, 2014. The contents of each of these referenced applications are incorporated herein by reference in their entirety.

STATEMENT OF GOVERNMENT INTEREST

The present invention was made with government support under Grant No. HL087285 awarded by the National Institutes of Health. The Government has certain rights in the invention.

BACKGROUND

The adeno-associated virus (AAV) genome is built of single-stranded deoxyribonucleic acid (ssDNA), either positive- or negative-sensed, which is about 4.9 kilobase long. The genome comprises inverted terminal repeats (ITRs) at both ends of the DNA strand, and two open reading frames (ORFs): rep and cap. Rep is composed of four overlapping genes encoding rep proteins required for the AAV life cycle, and cap contains overlapping nucleotide sequences of capsid proteins: VP1, VP2 and VP3, which interact together to form a capsid of an icosahedral symmetry.

Recombinant adeno-associated virus (rAAV) vectors derived from the replication defective human parvovirus AAV2 are proving to be safe and effective gene transfer vehicles that have yet to be definitively identified as either pathogenic or oncogenic [3-4, 6, 18-19, 26, 31]. rAAV transduce non-dividing primary cells, are low in immunogenicity, and direct sustained transgene expression in vivo [6, 10, 20]. Infection with wild type AAV is associated with inhibition of oncogenic transformation and AAV inverted terminal repeats may actually confer oncoprotection [2, 28, 52-55]. A recent survey of panels of human tissues found that the marrow and liver were the two most common sites of naturally occurring AAV isolates in humans, suggesting that infection of marrow cells by AAV is not rare.

Use of viral vectors for gene therapy has been long considered. Due to its potential for long-lived correction and the ease of ex vivo manipulation, the hematopoietic system was one of the earliest targets of gene therapy. Despite significant effort, however, actual therapeutic success remains elusive [5]. This is due to the recognized inability of most viral vectors to efficiently transduce quiescent, non-dividing hematopoietic stem cells (HSC) [23] as well as safety concerns arising from insertional oncogenesis [15, 22]. However, stable gene transfer has been successfully demonstrated to both murine and human HSC by rAAV [8, 11-12, 24, 27, 29-30, 37].

It has been additionally difficult to effectively use viral vectors in gene therapy for treating neurological conditions, particularly central nervous system diseases or disorders due to the difficulty of crossing the blood-brain barrier, a cellular and metabolic separation of the circulating blood from the brain extracellular fluid created by tight junctions between endothelial cells that restrict the passage of solutes.

CD34 is cell surface glycoprotein and a cell-cell adhesion factor. CD34 protein is expressed in early hematopoietic and vascular tissue and a cell expressing CD34 is designated $CD34^+$. Chromosomal integration of rAAV in human $CD34^+$ HSC [8, 12, 16, 29] and efficient transduction of primitive, pluripotent, self-renewing human HSC capable of supporting primary and secondary multi-lineage engraftment has been demonstrated in immune-deficient NOD-SCID mice [29]. Transduction of primitive HSC capable of supporting serial engraftment was shown to be attributable to the propensity of rAAV to efficiently transduce primitive, quiescent CD34+ CD38− cells residing in G0 [24]. Despite several reports of successful rAAV-mediated gene transfer into human HSC in vitro and in murine and non-human primate HSC in vivo, controversy regarding the utility of rAAV for HSC transduction still persists. These discrepancies arose primarily from short-term in vitro studies that assessed transduction by expression profiling and are attributable to the identified restrictions to transgene expression from rAAV2, including viral uncoating [35], intracellular trafficking [33], nuclear transport and second strand synthesis [36].

While AAV2 remains the best-studied prototypic virus for AAV-based vectors [1, 13, 18, 21], the identification of a large number of new AAV serotypes significantly enhances the repertoire of potential gene transfer vectors [14]. AAV1, 3 and 4 were isolated as contaminants of adenovirus stocks, and AAV5 was isolated from a human condylomatous wart. AAV6 arose as a laboratory recombinant between AAV1 and AAV2. Recently, more than 100 distinct isolates of naturally occurring AAV in human and non-human primate tissues were identified. This led to the use of capsids derived from some of these isolates for pseudotyping, replacing the envelope proteins of AAV2 with the novel envelopes, whereby rAAV2 genomes are then packaged using AAV2 rep and novel capsid genes. The use of novel capsids, the proteins as part of the viral shell, resulted in the circumvention of many limitations in transgene expression associated with AAV2 [32, 35-36].

In an effort to circumvent these restrictions, recent research has shown that novel capsid sequences result in reduced proteasome-mediated capsid degradation, increased nuclear trafficking and retention. Novel capsids, many of which utilize novel receptors, broadens the tropism of rAAV allowing for efficient transduction of previously refractory tissues and provides a means of circumventing highly prevalent pre-existing serologic immunity to AAV2, which posed major clinical limitations in a recent trial. Notably, some novel capsids appear to alter the intracellular processing of rAAV. For example, uncoating and transgene expression is accelerated in the context of AAV8 as compared to native AAV2 capsids. Recently, transgene expression was shown to be based upon capsid proteins, regardless of the serotype origin of the inverted terminal repeats (ITRs).

Naturally occurring AAV is identifiable in cytokine-primed peripheral blood stem cells. Capsid sequences of these AAV are unique. These capsids are capable of pseudotyping recombinant AAV2 genomes. US Patent Publication Number 20130096182A1 describes capsids AAVF1-17, and use thereof for cell transduction and gene transfer. Any improvement in the area of gene therapy regarding both permanent and reversible gene transfer and expression for therapeutic purposes would be a significant improvement in the art. Moreover, safe and efficient gene delivery to stem cells remains a significant challenge in the field despite decades of research. Therefore the ability to genetically modify stem cells safely would represent a significant advance.

Further, genome editing by gene targeting or correction at a specific site in the genome without leaving a footprint in the genome is attractive for the precise correction of inherited and acquired diseases. Current technology accomplishes this through the use of exogenous endonucleases such as zinc finger nucleases, TAL endonucleases or caspase 9/CRISPR systems. However, these "traditional" approaches are associated with toxicity and off target effects of endonuclease cleavage. Therefore, the ability to genetically modify stem cells safely and efficiently at high frequencies without the need for exogenous endonuclease cleavage would represent a significant advance.

Additionally, current methods of genetic transduction of human HSCs involve ex vivo transduction of purified donor stem cells followed by transplantation into usually "conditioned" recipients. The cell harvest procedures are invasive and involve either bone marrow harvest or multiple days of granulocyte-colony stimulating factor (G-CSF) priming of the donor followed by apheresis. The ex vivo transduction procedures can affect the hematopoietic potential of the stem cells. Additionally, in vitro transduced cells must be tested for sterility, toxicity, etc. before transplantation. Prior to transplanting into recipients, the stem cells often have to undergo conditioning with chemotherapy or radiation to ensure engraftment. The process usually requires hospitalization of patients for at least several days and sometimes longer. Overall, this is an arduous, expensive and high risk procedure that greatly limits the utility of stem cell gene therapy. A procedure is needed that offers a better alternative to current stem cell transduction methods without the need for purification and ex vivo transduction.

SUMMARY

Provided herein are adeno-associated virus (AAV) vectors (e.g., Clade F vectors such as a replication-defective adeno-associated virus (AAV) comprising a correction genome enclosed in a capsid, the capsid being an AAV Clade F capsid) for editing the genome of a cell via homologous recombination and methods of use and kits thereof.

In some aspects, the disclosure provides a replication-defective adeno-associated virus (AAV) comprising a correction genome enclosed in a capsid, the capsid being an AAV Clade F capsid; and the correction genome comprising (a) an editing element selected from an internucleotide bond or a nucleotide sequence for integration into a target locus of a mammalian chromosome, (b) a 5' homologous arm nucleotide sequence 5' of the editing element, having homology to a 5' region of the mammalian chromosome relative to the target locus, and (c) a 3' homologous arm nucleotide sequence 3' of the editing element, having homology to a 3' region of the mammalian chromosome relative to the target locus. In some aspects, the also disclosure provides replication-defective adeno-associated virus (AAV) comprising a correction genome enclosed in a capsid, the capsid being an AAV Clade F capsid; and the correction genome comprising an editing element nucleotide sequence for integration into a target locus of a mammalian chromosome, the correction genome having an essential absence of a promoter operatively linked to the editing element nucleotide sequence. In further aspects, the disclosure provides a replication-defective adeno-associated virus (AAV) comprising a correction genome enclosed in a capsid, wherein the capsid being an AAV Clade F capsid; the correction genome comprising an editing element selected from an internucleotide bond or a nucleotide sequence for integration into a target locus of a mammalian chromosome in a cell; and the AAV having a chromosomal integration efficiency of at least about 1% for integrating the editing element into the target locus of the mammalian chromosome in the cell. Other aspects of the disclosure relate to a gene editing vector comprising a replication-defective adeno-associated virus (AAV) comprising a correction genome enclosed in an AAV capsid, the correction genome comprising an editing element selected from an internucleotide bond or a nucleotide sequence for integration into a target locus of a mammalian cell chromosome; a 5' homologous arm nucleotide sequence 5' of the editing element having homology to a 5' region of the chromosome relative to the target locus; a 3' homologous arm nucleotide sequence 3' of the editing element having homology to a 3' region of the chromosome relative to the target locus; and wherein the AAV has a chromosomal integration efficiency of at least 10% for integrating the editing element into the target locus of the mammalian cell chromosome in the absence of an exogenous nuclease.

In some embodiments of any one of the AAVs provided herein, the AAV has a chromosomal integration efficiency of at least about 1% in the absence of an exogenous nuclease for integrating the editing element into the target locus of the mammalian chromosome in the cell.

In some embodiments of any one of the AAVs provided herein, the correction genome comprises a 5' inverted terminal repeat (5' ITR) nucleotide sequence 5' of the 5' homologous arm nucleotide sequence, and a 3' inverted terminal repeat (3' ITR) nucleotide sequence 3' of the 3' homologous arm nucleotide sequence. In some embodiments, the 5' ITR nucleotide sequence and the 3' ITR nucleotide sequence are substantially identical to an AAV2 virus 5'ITR and an AAV2 virus 3' ITR, respectively. In some embodiments, the 5' ITR nucleotide sequence and the 3' ITR nucleotide sequence are substantially mirror images of each other. In some embodiments, the 5' ITR nucleotide sequence has at least 95% sequence identity to SEQ ID NO:36, and the 3' ITR nucleotide sequence has at least 95% sequence identity to SEQ ID NO:37. In some embodiments, the 5' ITR nucleotide sequence and the 3' ITR nucleotide sequence are substantially identical to an AAV5 virus 5'ITR and an AAV5 virus 3' ITR, respectively. In some embodiments, the 5' ITR nucleotide sequence and the 3' ITR nucleotide sequence are substantially mirror images of each other. In some embodiments, the 5' ITR nucleotide sequence has at least 95% sequence identity to SEQ ID NO:38, and the 3' ITR nucleotide sequence has at least 95% sequence identity to SEQ ID NO:39.

In some embodiments of any one of the AAVs provided herein, the correction genome has an essential absence of a promoter operatively linked to the editing element nucleotide sequence. In some embodiments of any one of the AAVs provided herein, the correction genome further comprises an exogenous promoter operatively linked to the editing element.

In some embodiments of any one of the AAVs provided herein, the replication-defective AAV genome comprises an essential absence of an AAV rep gene and an AAV cap gene.

In some embodiments of any one of the AAVs provided herein, each of the 5' and 3' homologous arm nucleotide sequences independently has a nucleotide length of between about 500 to 1000 nucleotides or between about 600 to 1000 nucleotides. In some embodiments, the 5' and 3' homologous arm nucleotide sequences have substantially equal nucleotide lengths. In some embodiments, the 5' and 3' homologous arm nucleotide sequences have asymmetrical nucleotide lengths. In some embodiments, the 5' homologous arm nucleotide sequence has at least about 95% nucleotide sequence identity to the 5' region of the mammalian chromosome relative to the target locus. In some embodiments, the 3' homologous arm nucleotide sequence has at least about 95% nucleotide sequence identity to the 3' region of the mammalian chromosome relative to the target locus. In some embodiments, the 5' homologous arm nucleotide sequence has 100% sequence identity to the 5' region of the mammalian chromosome relative to the target locus and the 3' homologous arm nucleotide sequence has 100% sequence identity to the 3' region of the mammalian chromosome relative to the target locus.

In some embodiments of any one of the AAVs provided herein, the editing element consists of one nucleotide. In some embodiments, the target locus is a nucleotide sequence consisting of one nucleotide, and the target locus represents a point mutation of the mammalian chromosome.

In some embodiments, the target locus can comprise an intron of a mammalian chromosome. In some embodiments, the target locus can comprise an exon of a mammalian chromosome. In some embodiments, the target locus can comprise a non-coding region of a mammalian chromosome. In some embodiments, the target locus can comprise a regulatory region of a mammalian chromosome. In some embodiments, the target locus may be a locus associated with a disease state as described herein.

In some embodiments of any one of the AAVs provided herein, the editing element comprises at least 1, 2, 10, 100, 200, 500, 1000, 1500, 2000, 3000, 4000, or 5000 nucleotides. In some embodiments, the editing element comprises 1 to 5500, 1 to 5000, 1 to 4500, 1 to 4000, 1 to 3000, 1 to 2000, 1 to 1000, 1 to 500, 1 to 200, or 1 to 100 nucleotides, or 2 to 5500, 2 to 5000, 2 to 4500, 2 to 4000, 2 to 3000, 2 to 2000, 2 to 1000, 2 to 500, 2 to 200, or 2 to 100 nucleotides, or 10 to 5500, 10 to 5000, 10 to 4500, 10 to 4000, 10 to 3000, 10 to 2000, 10 to 1000, 10 to 500, 10 to 200, or 10 to 100 nucleotides.

In some embodiments of any one of the AAVs provided herein, the editing element comprises an exon, an intron, a 5' untranslated region (UTR), a 3' UTR, a promoter, a splice donor, a splice acceptor, a sequence encoding or non-coding RNA, an insulator, a gene, or a combination thereof. In some embodiments of any one of the AAVs provided herein, the editing element is a fragment of a coding sequence of a gene within or spanning the target locus.

In some embodiments of any one of the AAVs provided herein, the target locus is a nucleotide sequence comprising n nucleotides where n is an integer greater than or equal to one; the editing element comprises m nucleotides where m is an integer equal to n; and the editing element represents a substitution for the target locus of the mammalian chromosome. In some embodiments of any one of the AAVs provided herein, the target locus is a nucleotide sequence comprising n nucleotides where n is an integer greater than or equal to one; the editing element comprises m nucleotides where m is an integer greater than n; and the editing element represents a substitutive addition for the target locus of the mammalian chromosome. In some embodiments of any one of the AAVs provided herein, the target locus is a nucleotide sequence comprising n nucleotides where n is an integer greater than or equal to two; the editing element comprises m nucleotides where m is an integer less than n; and the editing element represents a substitutive deletion for the target locus of the mammalian chromosome. In some embodiments of any one of the AAVs provided herein, the target locus is an internucleotide bond; the editing element comprises m nucleotides where m is an integer greater than or equal to one; and the editing element represents an addition for the target locus of the mammalian chromosome.

In some embodiments of any one of the AAVs provided herein, the editing element is an internucleotide bond. In some embodiments, the target locus is a nucleotide sequence comprising one or more nucleotides, and the editing element comprises a deletion for the target locus of the mammalian chromosome.

In some embodiments of any one of the AAVs provided herein, the target locus of the mammalian chromosome is a mutant target locus comprising one or more mutant nucleotides, relative to a corresponding wild type mammalian chromosome. In some embodiments, the mutant target locus comprises a point mutation, a missense mutation, a nonsense mutation, an insertion of one or more nucleotides, a deletion of one or more nucleotides, or combinations thereof. In some embodiments, the mutant target locus comprises an amorphic mutation, a neomorphic mutation, or an antimorphic mutation. In some embodiments, the mutant target locus comprises an autosomal dominant mutation, an autosomal recessive mutation, a heterozygous mutation, a homozygous mutation, or combinations thereof. In some embodiments, the mutant target locus is selected from a promoter, an enhancer, a signal sequence, an intron, an exon, a splice donor site, a splice acceptor site, an internal ribosome entry site, an inverted exon, an insulator, a gene, a chromosomal inversion, and a chromosomal translocation within the mammalian chromosome.

In some embodiments of any one of the AAVs provided herein, the AAV Clade F capsid comprises at least one protein selected from Clade F VP1, Clade F VP2 and Clade F VP3. In some embodiments, the AAV Clade F capsid comprises at least two proteins selected from Clade F VP1, Clade F VP2 and Clade F VP3. In some embodiments, the AAV Clade F capsid comprises Clade F VP1, Clade F VP2 and Clade F VP3 proteins. In some embodiments, the AAV Clade F capsid comprises a VP1, VP2, or VP3 protein that has at least 90% amino acid sequence identity to amino acids 1 to 736, amino acids 138 to 736 or amino acids 203 to 736 of SEQ ID NO:1, respectively, which correspond to the amino acid sequences of AAV9 capsid proteins VP1, VP2 and VP3, respectively. In some embodiments, the AAV Clade F capsid comprises VP1 and VP2 proteins that have at least 90% amino acid sequence identity to amino acids 1 to 736 and amino acids 138 to 736 of SEQ ID NO:1, respectively, which correspond to the amino acid sequences of AAV9 capsid proteins VP1 and VP2, respectively; VP1 and VP3 proteins that have at least 90% amino acid sequence identity to amino acids 1 to 736 and amino acids 203 to 736 of SEQ ID NO:1, respectively, which correspond to the amino acid sequences of AAV9 capsid proteins VP1 and VP3, respectively; or VP2 and VP3 proteins that have at least 90% amino acid sequence identity to amino acids 138 to 736 and amino acids 203 to 736 of SEQ ID NO:1, respectively, which correspond to the amino acid sequences of AAV9 capsid proteins VP2 and VP3, respectively. In some embodiments, the AAV Clade F capsid comprises VP1, VP2, and VP3 proteins that have at least 90% amino acid sequence identity to amino acids 1 to 736, amino acids 138 to 736 and amino acids 203 to 736 of SEQ ID NO:1, respectively, which correspond to the amino acid sequences of AAV9 capsid proteins VP1, VP2 and VP3, respectively. In some embodiments, the AAV Clade F capsid comprises a VP1, VP2, or VP3 protein that has at least 90% amino acid sequence identity to amino acids 1 to 736, amino acids 138 to 736 or amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1, VP2 and VP3, respectively. In some embodiments, the AAV Clade F capsid comprises VP1 and VP2 proteins that have at least 90% amino acid sequence identity to amino acids 1 to 736 and amino acids 138 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1 and VP2, respectively; VP1 and VP3 proteins that have at least 90% amino acid sequence identity to amino acids 1 to 736 and amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1 and VP3, respectively; or VP2 and VP3 proteins that have at least 90% amino acid sequence identity to amino acids 138 to 736 and amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP2 and VP3, respectively. In some embodiments, the AAV Clade F capsid comprises VP1, VP2, and VP3 proteins that have at least 90% amino acid sequence identity to amino acids 1 to 736, amino acids 138 to 736 and amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1, VP2 and VP3, respectively. In some embodiments, the AAV Clade F capsid comprises a VP1, VP2, or VP3 protein that is encoded by a nucleotide sequence comprising at least 90% nucleotide sequence identity to SEQ ID NO:18, respectively, which corresponds to a nucleotide sequence encoding AAV9 capsid proteins VP1, VP2 and VP3, respectively. In some embodiments, the AAV Clade F capsid comprises VP1 and VP2 proteins that are encoded by nucleotide sequences comprising at least 90% nucleotide sequence identity to SEQ ID NOs:18; VP1 and VP3 proteins that are encoded by a nucleotide sequence comprising at least 90% nucleotide sequence identity to SEQ ID NOs:18; or VP2 and VP3 proteins that are encoded by a nucleotide sequence comprising at least 90% nucleotide sequence identity to SEQ ID NOs:18. In some embodiments, the AAV Clade F capsid comprises VP1, VP2, and VP3 proteins that are encoded by a nucleotide sequence comprising at least 90% nucleotide sequence identity to SEQ ID NO:18, which corresponds to a nucleotide sequence encoding AAV9 capsid proteins VP1, VP2 and VP3. In some embodiments, the AAV Clade F capsid comprises a VP1, VP2, or VP3 protein that is encoded by a nucleotide sequence comprising at least 90% nucleotide sequence identity to any one of SEQ ID NOs: 20, 21, 22, 23, 25, 24, 27, 28, 29, 26, 30, 31, 32, 33, 34 or 35, respectively, which correspond to nucleotide sequences encoding AAVF1 through AAVF9 and AAVF11 through AAVF17 capsid proteins VP1, VP2 and VP3, respectively. In some embodiments, the AAV Clade F capsid comprises VP1 and VP2 proteins that are encoded by nucleotide sequences comprising at least 90% nucleotide sequence identity to any one of SEQ ID NOs:20-35; VP1 and VP3 proteins that are encoded by a nucleotide sequence comprising at least 90% nucleotide sequence identity to any one of SEQ ID NOs:20-35; or VP2 and VP3 proteins that are encoded by a nucleotide sequence comprising at least 90% nucleotide sequence identity to any one of SEQ ID NOs:20-35. In some embodiments, the AAV Clade F capsid comprises VP1, VP2, and VP3 proteins that are encoded by a nucleotide sequence comprising at least 90% nucleotide sequence identity to any one of SEQ ID NOs: 20, 21, 22, 23, 25, 24, 27, 28, 29, 26, 30, 31, 32, 33, 34 or 35, which correspond to nucleotide sequences encoding AAVF1 through AAVF9 and AAVF11 through AAVF17 capsid proteins VP1, VP2 and VP3, respectively. In some embodiments, the AAV Clade F capsid comprises AAV9 VP1, VP2, or VP3 capsid proteins, which correspond to amino acids 1 to 736, amino acids 138 to 736 and amino acids 203 to 736 as set forth in SEQ ID NO:1, respectively. In some embodiments, the AAV Clade F capsid comprises AAV9 VP1 and VP2 capsid proteins, which correspond to amino acids 1 to 736 and amino acids 138 to 736 as set forth in SEQ ID NO:1, respectively; AAV9 VP1 and VP3 capsid proteins, which correspond to amino acids 1 to 736 and amino acids 203 to 736 as set forth in SEQ ID NO:1, respectively; or AAV9 VP2 and VP3 capsid proteins, which correspond to amino acids 138 to 736 and amino acids 203 to 736 as set forth in SEQ ID NO:1, respectively. In some embodiments, the AAV Clade F capsid comprises AAV9 capsid proteins VP1, VP2 and VP3, which correspond to amino acids 1 to 736, amino acids 138 to 736 and amino acids 203 to 736 as set forth in SEQ ID NO:1, respectively. In some embodiments, the AAV Clade F capsid comprises a VP1 capsid protein selected from a VP1 capsid protein of any one of AAVF1 through AAVF9 and AAVF11 through AAVF17, which corresponds to amino acids 1 to 736 as set forth in SEQ ID NOs: 2, 3, 5, 6, 11, 7, 8, 9, 10, 4, 12, 14, 15, 16, 17 or 13, respectively. In some embodiments, the AAV Clade F capsid comprises a VP1 and a VP2 capsid protein independently selected from a VP1 and VP2 capsid protein of any one of AAVF1 through AAVF9 and AAVF11 through AAVF17, which correspond to amino acids 1 to 736 and amino acids 138 to 736 as set forth in SEQ ID NOs: 2, 3, 5, 6, 11, 7, 8, 9, 10, 4, 12, 14, 15, 16, 17 or 13, respectively. In some embodiments, the AAV Clade F capsid comprises a VP1, a VP2 and a VP3 capsid protein independently selected from a VP1, VP2 and VP3 capsid protein of any one of AAVF1 through AAVF9 and AAVF11 through AAVF17, which correspond to amino acids 1 to 736, amino acids 138 to 736 and amino acids 203 to 736 as set forth in SEQ ID NOs: 2, 3, 5, 6, 11, 7, 8, 9, 10, 4, 12, 14, 15, 16, 17 or 13, respectively. In some embodiments, the AAV Clade F capsid comprises each of the VP1, VP2 and VP3 capsid proteins of any one of AAVF1 through AAVF9 and AAVF11 through AAVF17, which correspond to amino acids 1 to 736, amino acids 138 to 736 and amino acids 203 to 736 as set forth in SEQ ID NOs: 2, 3, 5, 6, 11, 7, 8, 9, 10, 4, 12, 14, 15, 16, 17 or 13, respectively.

In some embodiments of any one of the AAVs provided, the Clade F capsids comprises a polypeptide sequence having a percent sequence identity of at least 95% to a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), AAVF9 (SEQ ID NO: 10), AAVF16 (SEQ ID NO: 17), variants, fragments, mutants and any combination thereof. As used herein, AAVF1, AAVF2, AAVF3, AAVF4, AAVF5, AAVF6, AAVF7, AAVF8, AAVF9, AAVF10, AAVF11, AAVF12, AAVF13, AAVF14, AAVF15, AAVF16, and AAVF17 are also referred to as AAVHSC1, AAVHSC2, AAVHSC3, AAVHSC4, AAVHSC5, AAVHSC6, AAVHSC7, AAVHSC8, AAVHSC9, AAVHSC10, AAVHSC11, AAVHSC12 AAVHSC13, AAVHSC14 AAVHSC15, AAVHSC16, and AAVHSC17, respectively. In other words, any recitation of AAVF1, AAVF2, AAVF3, AAVF4, AAVF5, AAVF6, AAVF7, AAVF8, AAVF9, AAVF10, AAVF11, AAVF12, AAVF13, AAVF14, AAVF15, AAVF16, or AAVF17 is equivalent to and may be replaced with AAVHSC1, AAVHSC2, AAVHSC3, AAVHSC4, AAVHSC5, AAVHSC6, AAVHSC7, AAVHSC8, AAVHSC9, AAVHSC10, AAVHSC11, AAVHSC12, AAVHSC13, AAVHSC14, AAVHSC15, AAVHSC16, or AAVHSC17, respectively.

In some embodiments of any one of the AAVs provided herein, the mammalian chromosome is selected from human chromosome 1, 2, 3, 4, 5, 6, 7, 8, 9, 10, 11, 12, 13, 14, 15, 16, 17, 18, 19, 20, 21, 22, X and Y. In some embodiments of any one of the AAVs provided herein, the mammalian chromosome is selected from mouse chromosome 1, 2, 3, 4, 5, 6, 7, 8, 9, 10, 11, 12, 13, 14, 15, 16, 17, 18, 19, X and Y. In some embodiments, the mammalian chromosome is not human chromosome 19.

In some embodiments of any one of the AAVs provided herein, the mammalian chromosome is a somatic cell chromosome. In some embodiments, the somatic cell is from a tissue selected from the group consisting of connective tissue (including blood), muscle tissue, nervous tissue, and epithelial tissue. In some embodiments, the somatic cell is from an organ selected from the group consisting of lung, heart, liver, kidney, muscle, brain, eye, breast, bone, and cartilage. In some embodiments, the somatic cell is a CD34+ cell.

In some embodiments of any one of the AAVs provided herein, the cell is a stem cell. In some embodiments, the stem cell is a hematopoietic stem cell, a cord blood stem cell, a bone marrow stem cell, a fetal liver stem cell, or a peripheral blood stem cell. In some embodiments, the cell is selected from the group consisting of a CD34+ Hematopoietic stem cell line (HSC), a K562 CD34+ leukemia cell line, a HepG2 human liver cell line, a peripheral blood stem cell, a cord blood stem cell, a CD34+ peripheral blood stem cell, a WI-38 human diploid fibroblast cell line, a MCF7 human breast cancer cell line, a Y79 human retinoblastoma cell line, a SCID-X1 LBL human EBV-immortalized B cell line, a primary human hepatocyte, a primary hepatic sinusoidal endothelial cell, and a primary skeletal muscle myoblast.

In some embodiments of any one of the AAVs provided herein, the AAV has a chromosomal integration efficiency of at least about 5% for integrating the editing element into the target locus of the mammalian chromosome in the cell. In some embodiments, the AAV has a chromosomal integration efficiency of at least about 10% for integrating the editing element into the target locus of the mammalian chromosome in the cell.

Other aspects of the disclosure relate to a composition comprising an AAV as described herein, wherein the composition is in a pharmaceutically acceptable formulation. In some embodiments, the formulation is constituted for administration to a mammal. In some embodiments, the formulation is constituted for administration to a mammal via intravenous injection, subcutaneous injection, intramuscular injection, autologous cell transfer, or allogeneic cell transfer. In some embodiments, the pharmaceutically acceptable formulation comprises an excipient. In some embodiments, the excipient is selected from a carrier, an adjuvant and a vehicle, or combinations thereof.

Yet other aspects of the disclosure relate to a packaging system for recombinant preparation of an adeno-associated virus (AAV), wherein the packaging system comprises a Rep nucleotide sequence encoding one or more AAV Rep proteins; a Cap nucleotide sequence encoding one or more AAV Cap proteins of an AAV Clade F capsid; and a correction genome as described herein; wherein the packaging system is operative in a cell for enclosing the correction genome in the capsid to form the adeno-associated virus. In some embodiments, the packaging system comprises a first vector comprising the Rep nucleotide sequence and the Cap nucleotide sequence, and a second vector comprising the correction genome. In some embodiments, the AAV Clade F capsid comprises at least one protein selected from Clade F VP1, Clade F VP2 and Clade F VP3. In some embodiments, the AAV Clade F capsid comprises at least two proteins selected from Clade F VP1, Clade F VP2 and Clade F VP3. In some embodiments, the AAV Clade F capsid comprises Clade F VP1, Clade F VP2 and Clade F VP3 proteins. In some embodiments, the AAV Clade F capsid is any AAV Clade F capsid as described herein. In some embodiments, the Rep nucleotide sequence encodes an AAV2 Rep protein. In some embodiments, the AAV2 Rep protein encoded is at least one of Rep 78/68 or Rep 68/52. In some embodiments, the nucleotide sequence encoding the AAV2 Rep protein comprises a nucleotide sequence having a minimum percent sequence identity to the AAV2 Rep nucleotide sequence of SEQ ID NO:40, wherein the minimum percent sequence identity is at least 70% across the length of the nucleotide sequence encoding the AAV2 Rep protein. In some embodiments of any one of the packaging systems provided, the packaging system further comprises a third vector, wherein the third vector is a helper virus vector. In some embodiments, the helper virus vector is an independent third vector. In some embodiments, the helper virus vector is integral with the first vector. In some embodiments, the helper virus vector is integral with the second vector. In some embodiments, the third vector comprises genes encoding helper virus proteins. In some embodiments, the helper virus is selected from the group consisting of adenovirus, herpes virus (including herpes simplex virus (HSV)), vaccinia virus, and cytomegalovirus (CMV). In some embodiments, the helper virus is adenovirus. In some embodiments, the adenovirus genome comprises one or more adenovirus RNA genes selected from the group consisting of E1, E2, E4 and VA. In some embodiments, the helper virus is HSV. In some embodiments, the HSV genome comprises one or more of HSV genes selected from the group consisting of UL5/8/52, ICPO, ICP4, ICP22 and UL30/UL42. In some embodiments, the first vector and the third vector are contained within a first transfecting plasmid. In some embodiments, the nucleotides of the second vector and the third vector are contained within a second transfecting plasmid. In some embodiments, the nucleotides of the first vector and the third vector are cloned into a recombinant helper virus. In some embodiments, the nucleotides of the second vector and the third vector are cloned into a recombinant helper virus. In some embodiments, the AAV capsid is the capsid of a Clade F AAV selected from the group consisting of AAV9, AAVF1, AAVF2, AAVF3, AAVF4, AAVF5, AAVF6, AAVF7, AAVF8, AAVF9, AAVF11, AAVF12, AAVF13, AAVF14, AAVF15, AAVF16, AAVF17, AAVHU31, and AAVHU32. In some embodiments, any of the packaging systems described herein are comprised within a kit.

Other aspects of the disclosure relate to a method for recombinant preparation of an adeno-associated virus (AAV), wherein the method comprises transfecting or transducing a cell with a packaging system as described herein under conditions operative for enclosing the correction genome in the capsid to form the AAV.

In other aspects, the disclosure provides a method for editing a target locus of a mammalian genome, wherein the method comprises transducing a cell comprising the mammalian genome with an adeno-associated virus (AAV) as described herein. In some embodiments, the cell is a mammalian stem cell. In some embodiments, the mammalian cell is from a tissue selected from the group consisting of connective tissue (including blood), muscle tissue, nervous tissue, and epithelial tissue. In some embodiments, the mammalian cell is from an organ selected from the group consisting of lung, heart, liver, kidney, muscle, brain, eye, breast, bone, and cartilage. In some embodiments, the mammalian cell is a stem cell. In some embodiments, the stem cell is a hematopoietic stem cell, a cord blood stem cell, or peripheral blood stem cell. In some embodiments, the mammalian cell is a myoblast, an endothelial cell, a liver cell, a fibroblast, a breast cell, a lymphocyte, or a retinal cell. Other aspects of the disclosure relate to a cell obtainable by any method described herein.

Another aspect of the disclosure relates to a method for editing a target locus of a mammalian genome, wherein the method comprises: (a) obtaining mammalian cells from a mammal; (b) culturing the mammalian cells ex-vivo to form an ex-vivo culture; (c) transducing the mammalian cells with an adeno-associated virus (AAV) as described herein in the ex-vivo culture to form transduced mammalian cells; and (d) administering the transduced mammalian cells to the mammal.

In other aspects, the disclosure provides a method for editing a target locus of a mammalian genome, wherein the method comprises: (a) obtaining mammalian cells from a first mammal; (b) culturing the mammalian cells ex-vivo to form an ex-vivo culture; (c) transducing the mammalian cells with an adeno-associated virus (AAV) as described herein in the ex-vivo culture to form transduced mammalian cells; and (d) administering the transduced mammalian cells to a second mammal. In some embodiments, the first mammal and the second mammal are the same species. In some embodiments, the mammalian cells are from a tissue selected from the group consisting of connective tissue (including blood), muscle tissue, nervous tissue, and epithelial tissue. In some embodiments, the mammalian cells are from an organ selected from the group consisting of lung, heart, liver, kidney, muscle, brain, eye, breast, bone, and cartilage. In some embodiments, the mammalian cells are stem cells. In some embodiments, the stem cells are hematopoietic stem cells, cord blood stem cells, or peripheral blood stem cells. In some embodiments, the mammalian cells are a CD34+ cells. In some embodiments, the mammalian cells are myoblasts, endothelial cells, liver cells, fibroblasts, breast cells, lymphocytes, or retinal cells.

Another aspect of the disclosure provides a method for editing a target locus of a mammalian genome, wherein the method comprises administering an AAV as described herein or a composition as described herein to a mammal in an amount effective to transduce cells of the mammal with the AAV in-vivo.

In some embodiments of any one of the methods provided, the AAV is transduced or administered without co-transducing or co-administering an exogenous nuclease or a nucleotide sequence that encodes an exogenous nuclease.

In some embodiments of any one of the methods provided, the AAV has a chromosomal integration efficiency of at least about 1% for integrating the editing element into the target locus of the mammalian chromosome. In some embodiments, the chromosomal integration efficiency of the AAV is at least about 2%, 3%, 4% or 5% for integrating the editing element into the target locus of the mammalian chromosome. In some embodiments, the editing element of the correction genome is integrated into the target locus of the mammalian chromosome with a chromosomal integration efficiency of at least 10%, 20%, 40%, or 50% of the mammalian cells. In some embodiments, the editing element of the correction genome is integrated into the target locus of the mammalian chromosome with a chromosomal integration efficiency ranging from 10% to 70%, 20% to 70%, 40% to 70%, or 50% to 70% of the mammalian cells.

In some embodiments of any one of the methods provided, the AAV has a chromosomal integration efficiency further characterized by an allele frequency in a population of cells of at least about 10% for the allele comprising the editing element integrated into the target locus of the mammalian chromosome. In some embodiments, the AAV has a chromosomal integration efficiency further characterized by an allele frequency in a population of cells of at least about 50% for the allele comprising the editing element integrated into the target locus of the mammalian chromosome. In some embodiments, the AAV has a chromosomal integration efficiency further characterized by an allele frequency in a population of cells of at least about 75% for the allele comprising the editing element integrated into the target locus of the mammalian chromosome. In some embodiments, the allele frequency in a population of cells is an allele frequency in a population of cells in vitro.

Other aspects of the disclosure relate to a method for generating a transgenic non-human animal, the method comprising administering an AAV as described herein or a composition as described herein to a non-human animal; or transducing a non-human animal cell with the AAV as described herein or the composition as described herein and implanting the cell into a host non-human animal under conditions sufficient to generate a transgenic non-human animal from the host non-human animal (e.g., by allowing the implanted cell to form or become part of an embryo, which then develops in the host into a transgenic non-human animal). In some embodiments, the transgenic non-human animal is crossed with another non-human animal to generate further transgenic non-human animals. In some embodiments, the non-human animal cell is derived from a zygote or an embryo of a non-human animal. In some embodiments, the non-human animal is a mouse, rat, rabbit, pig, bovine, sheep, goat, chicken, cat, dog, ferret, or primate.

Other aspects of the disclosure relate to a transgenic non-human animal obtainable by a method described herein, such as a method described above. In some embodiments, the transgenic non-human animal is a mouse, rat, rabbit, pig, bovine, sheep, goat, chicken, cat, dog, ferret, or primate.

Yet other aspects of the disclosure relate to tissue derived from a transgenic non-human animal as described herein. In some embodiments, the tissue is selected from the group consisting of connective tissue (including blood), muscle tissue, nervous tissue, endothelial tissue and epithelial tissue. In some embodiments, the tissue is from an organ selected from the group consisting of lung, heart, liver, kidney, muscle, brain, eye, breast, bone, and cartilage.

Other aspects of the disclosure relate to a cell derived from a transgenic non-human animal as described herein. In some embodiments, the cell is a primary cell. In some embodiments, the cell is a CD34+ cell, a myoblast, an endothelial cell, a liver cell, a fibroblast, a breast cell, a lymphocyte, or a retinal cell. In some embodiments, the cell is an inducible pluripotent stem (iPS) cell. In some embodiments, the cell is from a tissue selected from the group consisting of connective tissue (including blood), muscle tissue, nervous tissue, endothelial tissue, and epithelial tissue. In some embodiments, the cell is from an organ selected from the group consisting of lung, heart, liver, kidney, muscle, brain, eye, breast, bone, and cartilage. In some embodiments, the cell is a stem cell. In some embodiments, the stem cell is a hematopoietic stem cell, a cord blood stem cell, or peripheral blood stem cell.

According to certain embodiments, adeno-associated virus (AAV) Clade F vectors (e.g., replication-defective AAVs comprising correction genomes enclosed in a Clade F capsid) or AAV vector variants (e.g., replication-defective AAVs comprising capsid variants relative to AAV9 capsids) for editing the genome of a cell are provided. In certain embodiments, an AAV Clade F vector or AAV vector variant may comprise one or more Clade F capsids or one or more capsid variants (relative to an AAV9 capsid), an editing element (also referred to herein as a targeting cassette) comprising one or more therapeutic nucleotide sequences to be integrated into a target locus (also referred to herein as a target site) of the genome, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site). The editing element (target cassette) may be contained within a correction genome as described herein comprising inverted terminal repeats (ITRs) as described herein. In certain embodiments, the one or more Clade F capsids or capsid variants may be any of the Clade F capsids or capsid variants described herein. In certain embodiments, the one or more Clade F capsids or capsid variants may comprise a polypeptide sequence selected from the group of AAVF7 (SEQ ID NO: 8), AAVF12 (SEQ ID NO: 12), AAVF15 (SEQ ID NO: 16), AAVF17 (SEQ ID NO: 13), variants, fragments, mutants and any combination thereof. In certain embodiments, the one or more Clade F capsids or the one or more capsid variants may comprise a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), AAVF5 (SEQ ID NO: 10), AAVF16 (SEQ ID NO: 17), variants, fragments, mutants and any combination thereof. In certain embodiments, the one or more Clade F capsids or capsid variants may comprise a polypeptide sequence having a percent sequence identity of at least 95% to a polypeptide sequence selected from the group of AAVF7 (SEQ ID NO: 8), AAVF12 (SEQ ID NO: 12), AAVF15 (SEQ ID NO: 16), AAVF17 (SEQ ID NO: 13), variants, fragments, mutants and any combination thereof. In certain embodiments, the one or more Clade F capsids or capsid variants may comprise a polypeptide sequence having a percent sequence identity of at least 95% to a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), AAVF9 (SEQ ID NO: 10), AAVF16 (SEQ ID NO: 17), variants, fragments, mutants and any combination thereof. In certain embodiments, the target locus (target site) may be a safe harbor site. In certain embodiments, the safe harbor site may be the AAVS1 locus on chromosome 19. In certain embodiments, the target locus (target site) may be a locus associated with a disease state as described herein. In certain embodiments, the cell may be a stem cell. In certain embodiments, the stem cell may be a hematopoietic stem cell, a pluripotent stem cell, an embryonic stem cell, or a mesenchymal stem cell.

According to certain embodiments, methods of editing the genome of a cell are provided. In certain embodiments, the methods of editing the genome of a cell may comprise transducing the cell with one or more AAV Clade F vectors (e.g., replication-defective AAVs comprising correction genomes enclosed in a Clade F capsid) or AAV vector variants (e.g., replication-defective AAVs comprising capsid variants relative to AAV9 capsids) as described herein. In certain embodiments, the transduction may be performed without additional exogenous nucleases. In certain embodiments, AAV Clade F vectors or AAV vector variants may comprise one or more Clade F capsids or capsid variants (relative to an AAV9 capsid), an editing element (targeting cassette) comprising one or more therapeutic nucleotide sequences to be integrated into a target locus (target site) of the genome, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site). The editing element (target cassette) may be contained within a correction genome as described herein comprising ITRs as described herein. In certain embodiments, the one or more Clade F capsids or capsid variants may comprise a polypeptide sequence selected from the group of AAVF7 (SEQ ID NO: 8), AAVF12 (SEQ ID NO: 12), AAVF15 (SEQ ID NO: 16), AAVF17 (SEQ ID NO: 13), variants, fragments, mutants and any combination thereof. In certain embodiments, the one or more Clade F capsids or capsid variants may comprise a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), AAVF9 (SEQ ID NO: 10), AAVF16 (SEQ ID NO: 17), variants, fragments, mutants and any combination thereof. In certain embodiments, the one or more Clade F capsids or capsid variants may comprise a polypeptide sequence having a percent sequence identity of at least 95% to a polypeptide sequence selected from the group of AAVF7 (SEQ ID NO: 8), AAVF12 (SEQ ID NO: 12), AAVF15 (SEQ ID NO: 16), AAVF17 (SEQ ID NO: 13), variants, fragments, mutants and any combination thereof. In certain embodiments, the one or more Clade F capsids or capsid variants may comprise a polypeptide sequence having a percent sequence identity of at least 95% to a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), AAVF9 (SEQ ID NO: 10), AAVF16 (SEQ ID NO: 17), variants, fragments, mutants and any combination thereof. In certain embodiments, the AAV Clade F vector or AAV vector variant does not contain a promoter for the one or more therapeutic nucleotide sequences. In certain embodiments, the target locus (target site) may be a safe harbor site. In certain embodiments, the safe harbor site may be the AAVS1 locus on chromosome 19. In certain embodiments, the target locus (target site) may be a locus associated with a disease state as described herein. In certain embodiments, the cell may be a stem cell. In certain embodiments, the stem cell may be a hematopoietic stem cell, a pluripotent stem cell, an embryonic stem cell, or a mesenchymal stem cell.

According to certain embodiments, methods of treating a disease or disorder in a subject by editing a genome of a cell of the subject are provided. In certain embodiments, methods of treating a disease or disorder in a subject by editing a genome of a cell of the subject include the steps of transducing the cell of the subject with an AAV Clade F vector or AAV vector variant as described herein and transplanting the transduced cell into the subject, wherein the transduced cell treats the disease or disorder. In certain embodiments, transduction of the cell may be performed without additional exogenous nucleases. In certain embodiments, AAV Clade F vectors or AAV vector variants may comprise one or more Clade F capsids or capsid variants (relative to an AAV9 capsid), an editing element (targeting cassette) comprising one or more therapeutic nucleotide sequences to be integrated into a target locus (target site) of the genome, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site). The editing element (target cassette) may be contained within a correction genome as described herein comprising ITRs as described herein. In certain embodiments, the Clade F capsids or capsid variants may comprise a polypeptide sequence selected from the group of AAVF7 (SEQ ID NO: 8), AAVF12 (SEQ ID NO: 12), AAVF15 (SEQ ID NO: 16), AAVF17 (SEQ ID NO: 13), variants, fragments, mutants and any combination thereof. In certain embodiments, the one or more Clade F capsids or capsid variants may comprise a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), AAVF9 (SEQ ID NO: 10), AAVF16 (SEQ ID NO: 17), variants, fragments, mutants and any combination thereof. In certain embodiments, the one or more Clade F capsids or capsid variants may comprise a polypeptide sequence having a percent sequence identity of at least 95% to a polypeptide sequence selected from the group of AAVF7 (SEQ ID NO: 8), AAVF12 (SEQ ID NO: 12), AAVF15 (SEQ ID NO: 16), AAVF17 (SEQ ID NO: 13), variants, fragments, mutants and any combination thereof. In certain embodiments, the one or more Clade F capsids or capsid variants may comprise a polypeptide sequence having a percent sequence identity of at least 95% to a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), AAVF9 (SEQ ID NO: 10), AAVF16 (SEQ ID NO: 17), variants, fragments, mutants and any combination thereof. In certain embodiments, the AAV Clade F vector or AAV vector variant does not contain a promoter for the one or more therapeutic nucleotide sequences. In certain embodiments, the target locus (target site) may be a safe harbor site. In certain embodiments, the safe harbor site may be the AAVS1 locus on chromosome 19. In certain embodiments, the target locus (target site) may be a locus associated with a disease state as described herein. In certain embodiments, the cell may be a stem cell. In certain embodiments, the stem cell may be a hematopoietic stem cell, a pluripotent stem cell, an embryonic stem cell, or a mesenchymal stem cell. In certain embodiments, the disease or disorder may be caused by one or more mutations in the cell genome. In certain embodiments, the disease or disorder may be selected from an inherited metabolic disease, lysosomal storage disease, mucopolysaccharidodosis, immunodeficiency disease, and hemoglobinopathy disease and infection.

Also disclosed herein are methods of treating a disease or disorder in a subject by in vivo genome editing by directly administering the AAV Clade F vector or AAV vector variant as described herein to the subject. In certain embodiments, methods of treating a disease or disorder in a subject by in vivo genome editing of a cell of the subject by directly administering an AAV Clade F vector or AAV vector variant to the subject are disclosed. In certain embodiments, the AAV Clade F vector or AAV vector variant may comprise one or more Clade F capsids or capsid variants (relative to an AAV9 capsid), an editing element (targeting cassette) comprising one or more therapeutic nucleotide sequences to be integrated into a target locus (target site) of the genome, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site), wherein the vector transduces a cell of the subject and integrates the one or more therapeutic nucleotide sequences into the genome of the cell. The editing element (target cassette) may be contained within a correction genome as described herein comprising ITRs as described herein. In certain embodiments, the one or more Clade F capsids or capsid variants may comprise a polypeptide sequence selected from the group of AAVF1 (SEQ ID NO: 2), AAVF2 (SEQ ID NO: 3), AAVF11 (SEQ ID NO: 4), AAVF3 (SEQ ID NO: 5), AAVF4 (SEQ ID NO: 6), AAVF6 (SEQ ID NO: 7), AAVF7 (SEQ ID NO: 8), AAVF8 (SEQ ID NO: 9), AAVF9 (SEQ ID NO: 10), AAVF5 (SEQ ID NO: 11), AAVF12 (SEQ ID NO: 12), AAVF17 (SEQ ID NO: 13), AAVF13 (SEQ ID NO: 14), AAVF14 (SEQ ID NO: 15), AAVF15 (SEQ ID NO: 16), AAVF16 (SEQ ID NO: 17), variants, fragments, mutants, and any combination thereof. In certain embodiments, the AAV Clade F vector or AAV vector variant does not contain a promoter for the one or more therapeutic nucleotide sequences. In certain embodiments, the target locus (target site) may be a safe harbor site. In certain embodiments, the safe harbor site may be the AAVS1 locus on chromosome 19. In certain embodiments, the target locus (target site) may be a locus associated with a disease state as described herein. In certain embodiments, the cell may be a stem cell. In certain embodiments, the stem cell may be a hematopoietic stem cell, a pluripotent stem cell, an embryonic stem cell, or a mesenchymal stem cell. In certain embodiments, the disease or disorder may be caused by one or more mutations in the cell genome. In certain embodiments, the disease or disorder may be selected from an inherited metabolic disease, lysosomal storage disease, mucopolysaccharidodosis, immunodeficiency disease, and hemoglobinopathy disease and infection. Also disclosed herein are kits comprising one or more AAV Clade F vectors or AAV vector variants for editing the genome of a cell.

BRIEF DESCRIPTION OF THE DRAWINGS

Figure 1:
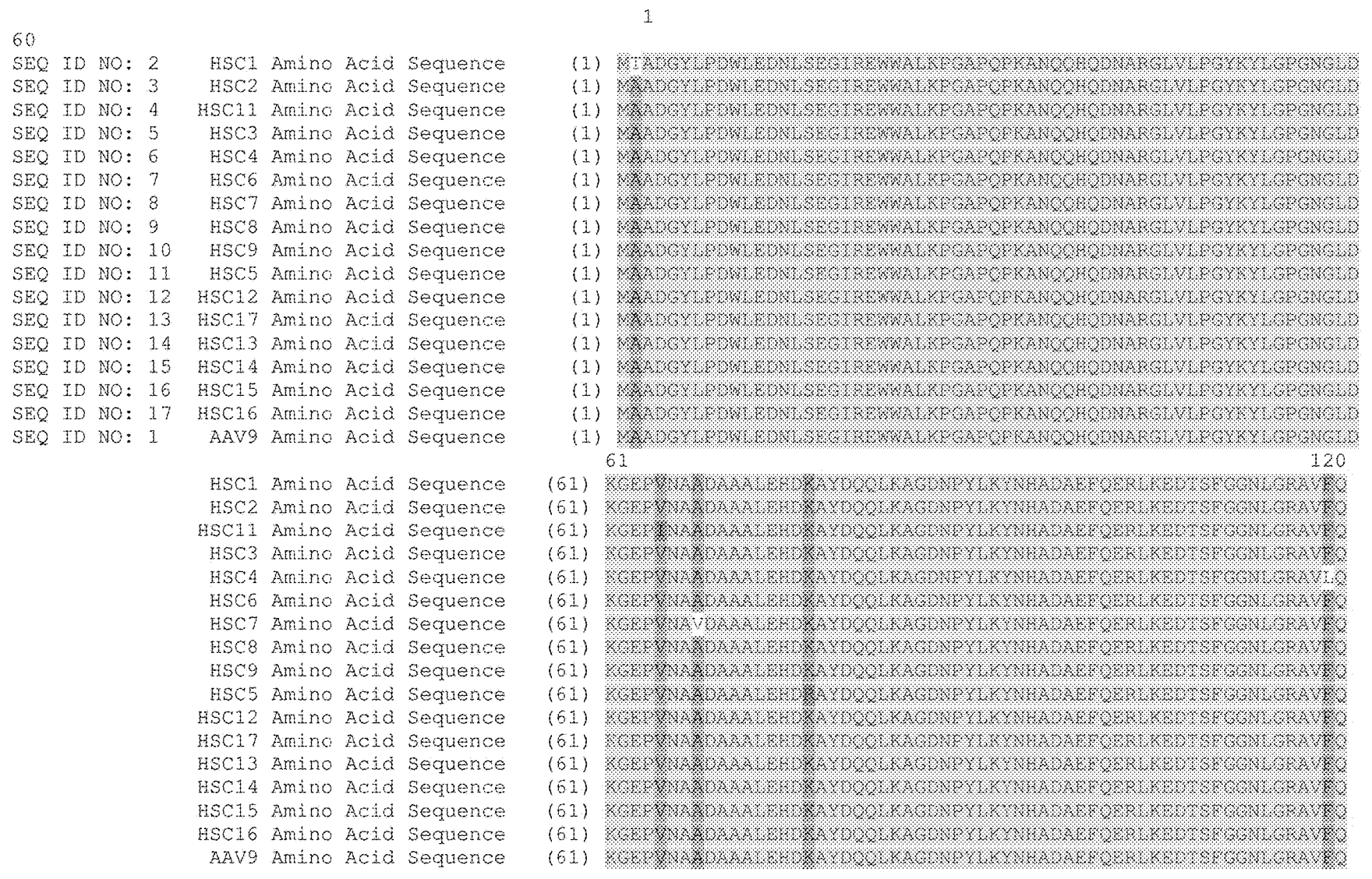
Figure 1:
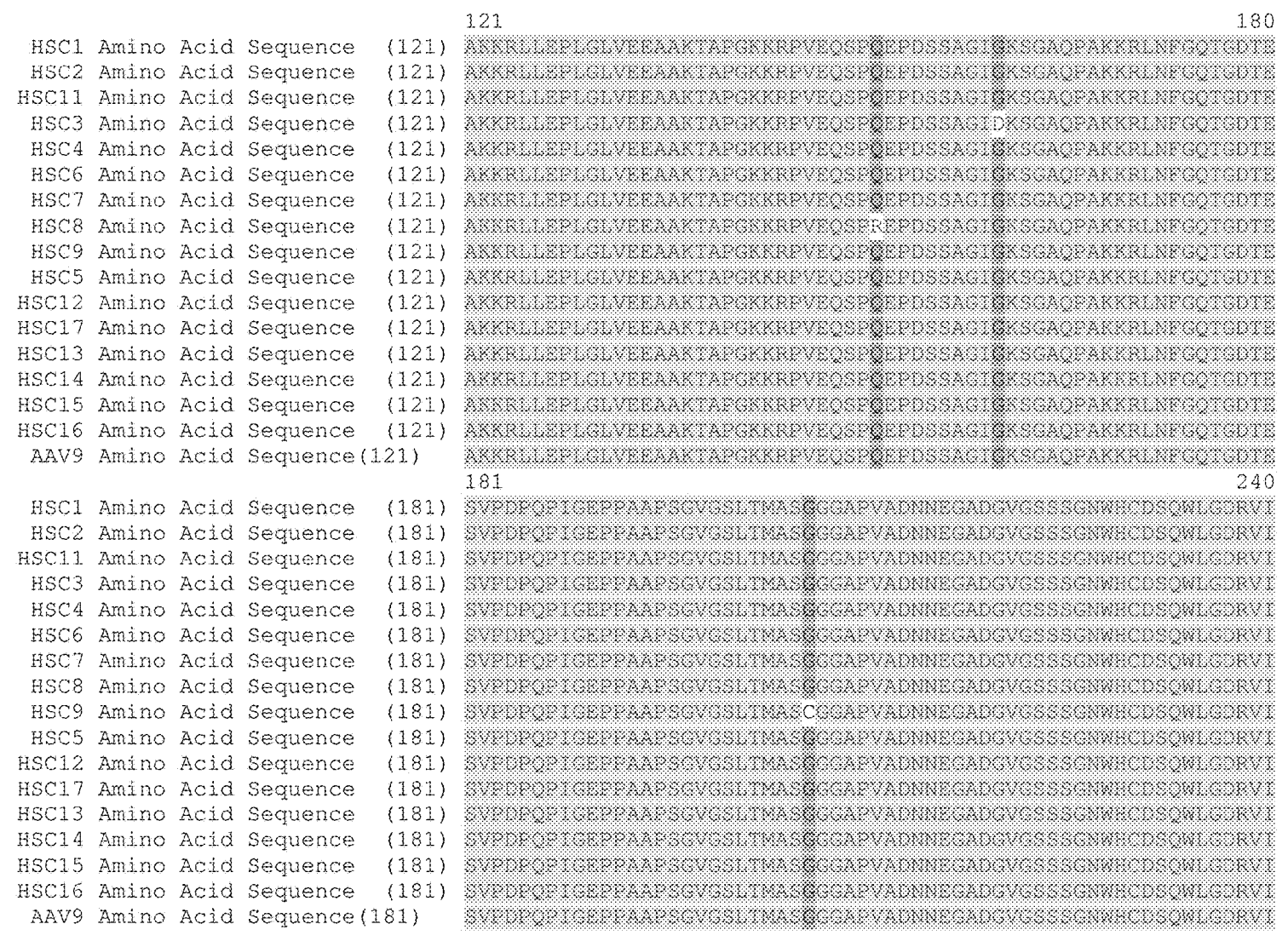
Figure 1:
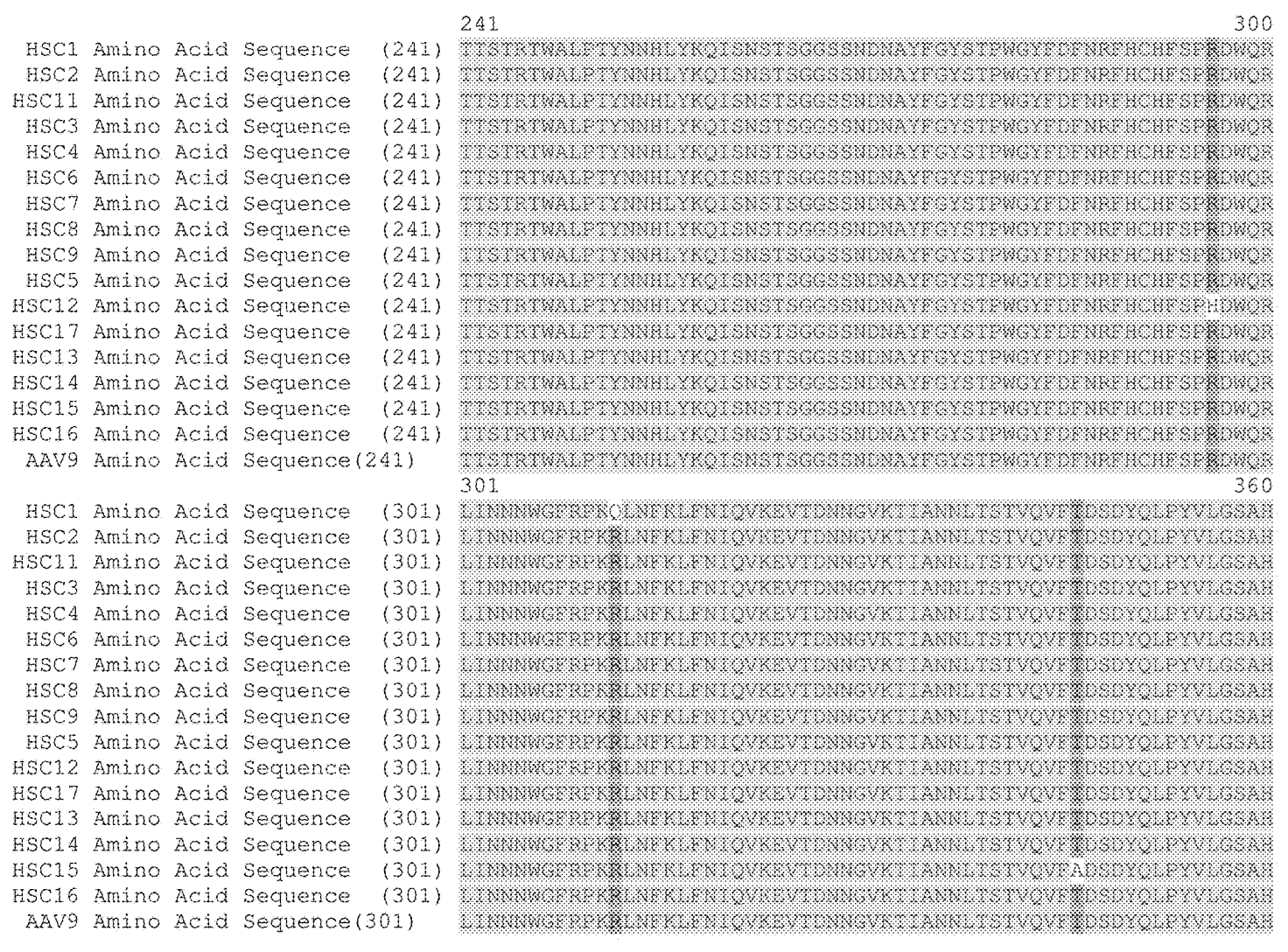
Figure 1:
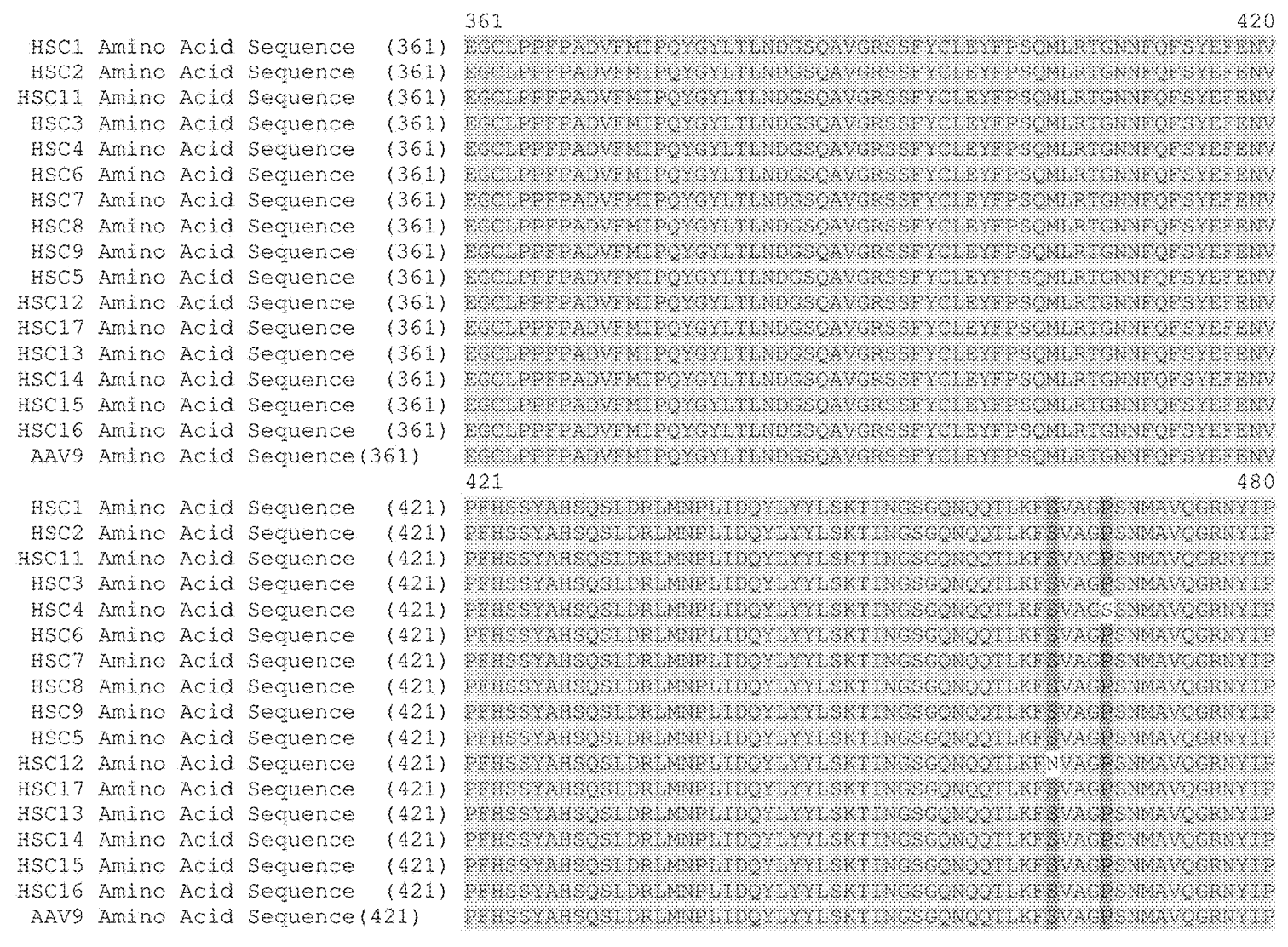
Figure 1:
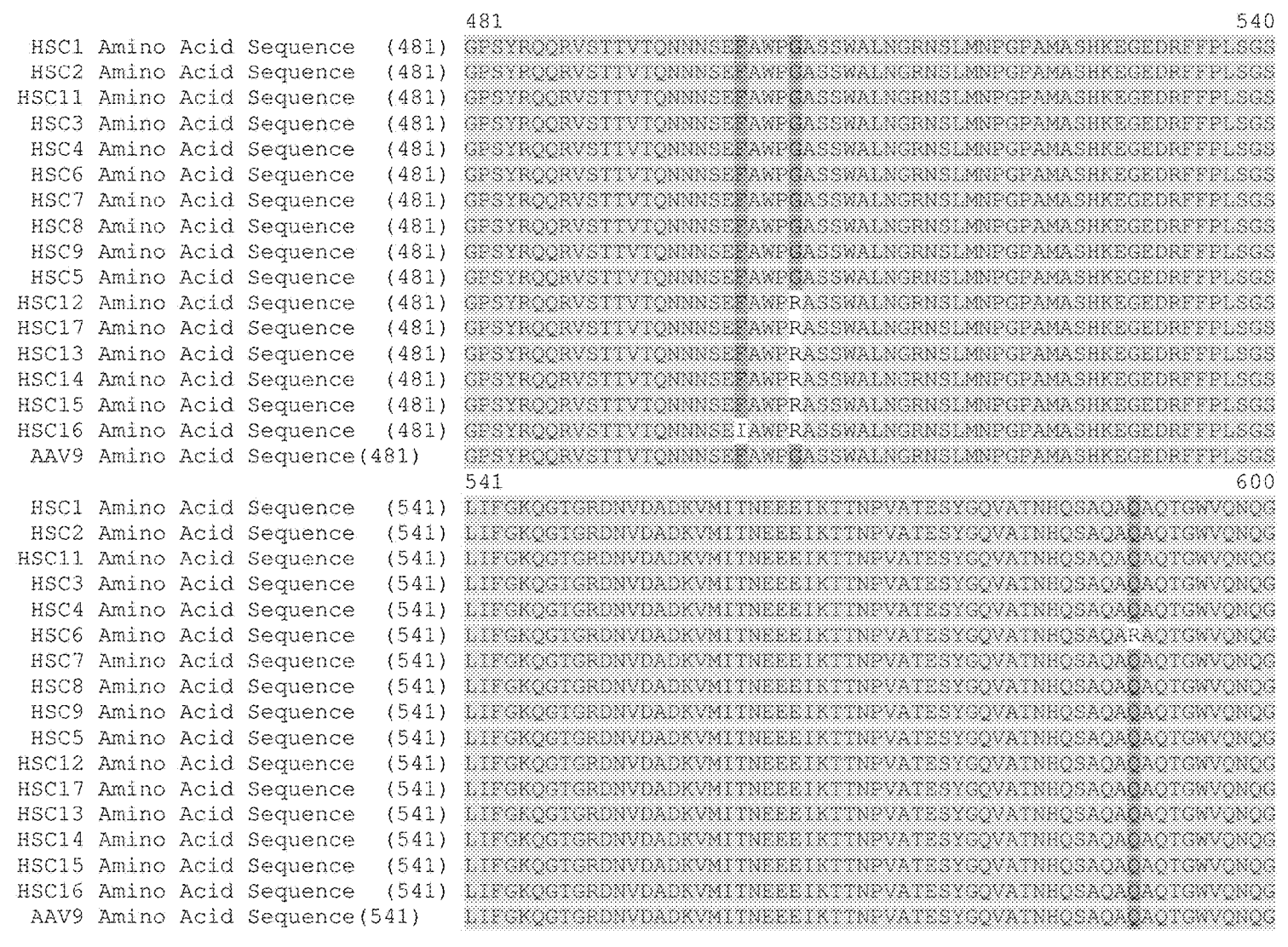
Figure 1:
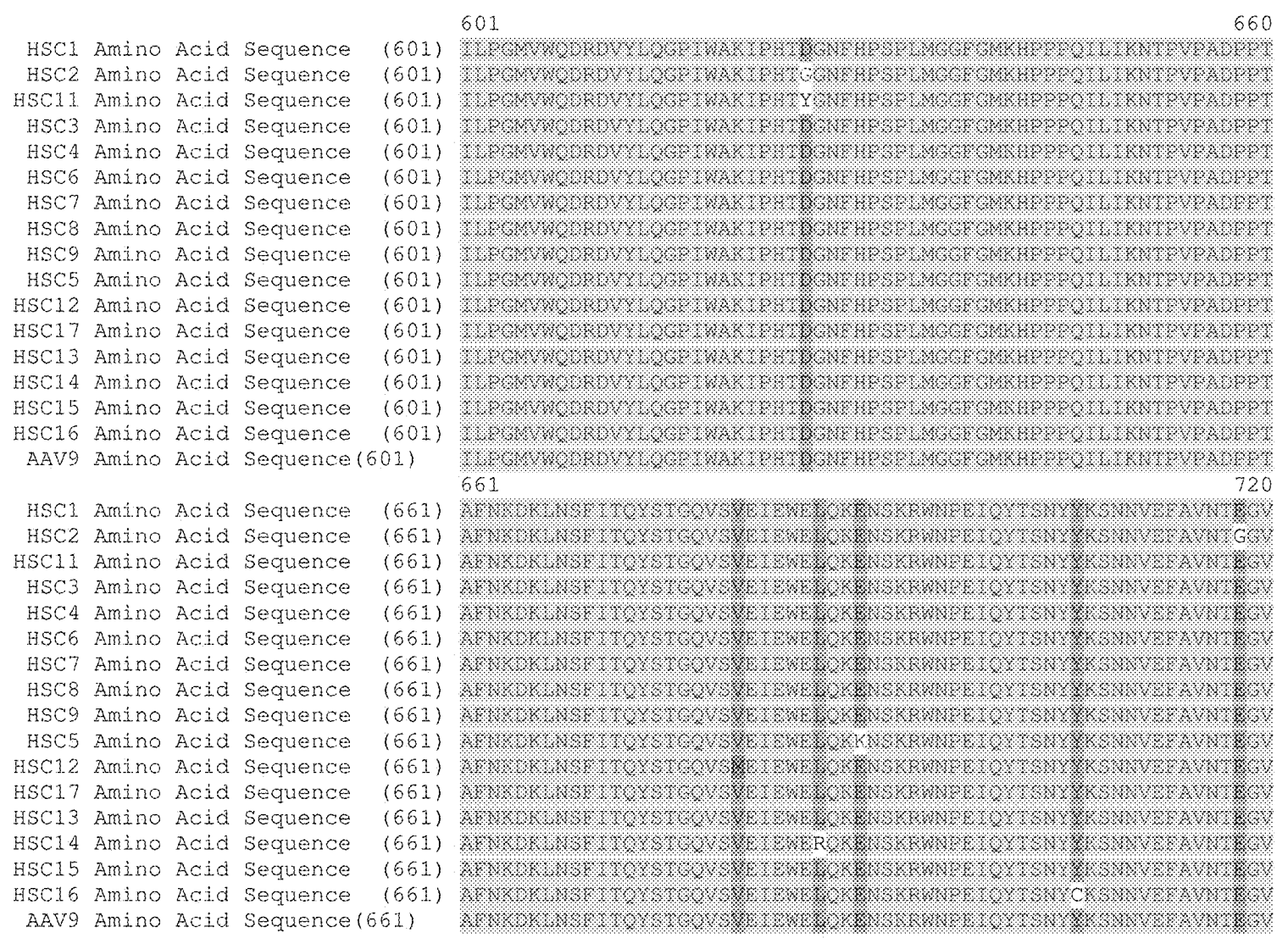

FIG. 1 shows the alignment of Clade F AAV capsid variant polypeptide sequences in comparison to AAV9. A corresponding alignment of Clade F AAV capsid variant polynucleotide sequences is provided in FIG. 1 of US Patent Publication Number US20130096182A1.

FIG. 2 is a chart listing some of the nucleotide mutations in the capsid of each sequence, including the base change, the amino acid change, and whether it is in VP1 or VP3.

FIG. 21A shows that adult immune-deficient mice previously xenografted with human cord blood CD34+ HSCs that received intravenous injections of AAVF-Luciferase vector displayed specific luciferase expression in vertebrae, spleen, hips, and long bones, all sites of hematopoiesis after transplantation. Arrows indicate luciferase expression in vertebrae, spleen, liver, hips, and long bones. Flux for the liver and spleen was 4.08e9 and flux for the tail was 1.74e9. FIG. 21B shows that adult immune-deficient mice that were not previously xenografted with human cord blood CD34+ HSCs that received intravenous injections of AAVF-Luciferase vector did not display high levels of specific luciferase expression. Flux for the liver and spleen was 1.47e8 and flux for the tail was 2.22e8.

FIG. 22A shows flow cytometry data from femoral CD34+ cells of xenografted mice injected with AAVF7-Venus vector. 9.23% of engrafted human hematopoietic cells expressed Venus. FIG. 22B shows flow cytometry data from femoral CD45+ cells of xenografted mice injected with AAVF7-Venus vector. 8.35% of engrafted human hematopoietic cells expressed Venus. FIG. 22C shows flow cytometry data from femoral CD34+ cells of xenografted mice injected with AAVF17-Venus vector. 8.92% of engrafted human hematopoietic cells expressed Venus. FIG. 22D shows flow cytometry data from femoral CD45+ cells of xenografted mice injected with AAVF17-Venus vector. 8.59% of engrafted human hematopoietic cells expressed Venus.

FIG. 22E shows flow cytometry data from vertebral CD45+ cells of xenografted mice injected with AAVF7-Venus vector. 15.3% of engrafted human hematopoietic cells expressed Venus. FIG. 22F shows flow cytometry data from vertebral CD45+ cells of xenografted mice injected with AAVF17-Venus vector. 70.2% of engrafted human hematopoietic cells expressed Venus. FIG. 22G shows flow cytometry data from spleen CD45+ cells of xenografted mice injected with AAVF7-Venus vector. 10.3% of engrafted human hematopoietic cells expressed Venus. FIG. 22H shows flow cytometry data from spleen CD45+ cells of xenografted mice injected with AAVF17-Venus vector. 9.90% of engrafted human hematopoietic cells expressed Venus. Results from FIG. 22 are also provided in Table 5.

FIG. 26A: CD34+ represents primary human CD34+ cytokine-primed peripheral blood stem cells. FIG. 26B: K562 is a human CD34+ erythroleukemia cell line. FIG. 26C: HepG2 is a human liver cell line. The percent of cells displaying Venus expression, indicative of precise insertion, is shown for FIGS. 26A-C. FIG. 26D shows representative flow profiles showing a distinct Venus expressing population of CD34+ cells after transduction with recombinant AAVF viruses, as compared with untransduced cells. FIG. 26E shows editing activity of AAVF7, AAVF12, AAVF15, AAVF17 and AAV9 as compared with AAV6 and AAV8 in a K562 erythroleukemia line. FIG. 26F shows editing activity of the same virus in HepG2, a liver cell line. Data shows the percent of cells displaying editing and Venus expression.

FIG. 28A shows maps of single stranded AAV vector genomes for the insertion of a 10 bp insert in intron 1 of the human PPP1R12C gene. This vector encodes a wild type left homology arm (HA-L) which contains an Nhe1 restriction enzyme recognition site (GCTAGC). The NS mut vector, was designed to change the TA sequence in the left homology arm on chromosome 19 to AT. This change results in the conversion of an Nhe1 site to an Sph1 site, changing the sequence from GCTAGC to GCATGC. FIG. 28B shows that the left homology arm was amplified using a forward primer located in upstream chromosomal sequences and a reverse primer located in the 10 bp insert in Intron 1 of the PPP1R12C gene on chromosome 19. The upper schematic designates the relative sizes of the expected fragments created when genomic DNA from K562 cells is edited using either the wild type or the NS Mut AAVF vectors. FIG. 28C is a gel that shows the actual amplicons derived from genomic DNA of K562 cells edited with a wild type AAVF vector. Lanes show the uncut amplicon (Un), the amplicon cut with Nhe 1 (Nhe1) and with Sph 1 (Sph 1). FIG. 28D shows gel electrophoresis of K562 DNA after editing with AAVF7 or an AAVF17 vectors encoding either wild type or NS Mut genomes. FIG. 28E shows gel electrophoresis of a hepatocellular carcinoma cell line, HepG2 after editing with AAVF7 or an AAVF17 vectors encoding either wild type or NS Mut genomes.

FIG. 30 is a table that showing AAVF vectors mediate editing in both dividing and non-dividing cells and that AAVF-mediated gene editing does not require DNA synthesis. The figure shows frequency of edited cells expressing Venus in the dividing and non-dividing subsets of primary human CD34+ cells. The percentage of all CD34+ cells that were Venus positive and either BrdU positive or negative was determined by flow cytometry. BrdU positive cells represent dividing cells and BrdU negative cells represent non-dividing cells.

FIG. 31A shows a diagram of the experimental design. Immune deficient NOD/SCID mice were engrafted with human cord blood CD34+ hematopoietic stem cells. Cells were allowed to engraft for 7 weeks prior to intravenous injection of AAVF17-Venus. Hematopoietic cells were harvested from the vertebral and femoral marrow and spleen of xenografted mice 12.5 weeks after AAVF injection. Cells were analyzed by multi-color flow cytometry for Venus expression as well as the presence of human-specific surface markers. Specifically, Venus expression was analyzed in the primitive CD34+ human hematopoietic stem/progenitor cells, CD45+ human differentiated mononuclear hematopoietic cells and glycophorin A+ cells of the erythroid lineage. FIG. 31B shows a schematic of the differentiation pathway of the human erythroid lineage, from CD34+ progenitor cells to the glycophorin A+ red blood cells. FIG. 31C shows flow cytometric profiles of long term engrafted human cells in the marrow and spleen cells of xenografted mice, 20 weeks after transplantation. Cells were analyzed for both expression of Venus, a marker of editing as well as specific human cell surface markers.

FIGS. 32A and B are a summary of in vivo data following intravenous injection of AAVF vectors into immune deficient mice xenografted with human cord blood CD34+ hematopoietic stem/progenitor cells. Venus expression reflects targeted insertion of the promoterless Venus cassette into Intron 1 of the human PPP1R12C gene in in vivo engrafted human hematopoietic stem cells and their progeny. FIG. 32B is a summary of the data in FIG. 32A. FIGS. 32A and B show that editing is long term, that editing is stably inherited (the insert is efficiently expressed in differentiated progeny cells), that in vivo editing may be much more efficient than ex vivo transduction followed by transplant, and that progeny of edited CD34+ cells retain Venus expression long term.

FIG. 33 shows a sequence analysis of targeted chromosomal insertion of a promoterless SA/2A venus ORF in K562 erythroleukemia cell line, primary human cytokine-primed peripheral blood CD34+ cells (PBSC) and HepG2 human liver cell line. Site-specifically integrated sequences were amplified using a chromosome-specific primer and an insert-specific primer. The amplified product was cloned into a TOPO-TA vector and sequenced using Sanger sequencing.

FIG. 34 shows a sequence analysis of targeted chromosomal insertion of a 10 bp insert in primary human cytokine-primed peripheral blood CD34+ cells and the HepG2 human liver cell line. Site-specifically integrated sequences were amplified using a chromosome-specific primer and an insert-specific primer. The amplified product was cloned into a TOPO-TA vector and sequenced using Sanger sequencing.

FIG. 40D shows a comparison of the relative expression of Venus to mCherry (Editing Ratio). Bars denote the ratio of the proportion of cells expressing Venus as a ratio of those expressing mCherry with the corresponding capsid. The black horizontal bar denotes a ratio of 1, which would indicate equal efficiencies of Venus:mCherry expression.

DETAILED DESCRIPTION

Figure 3:
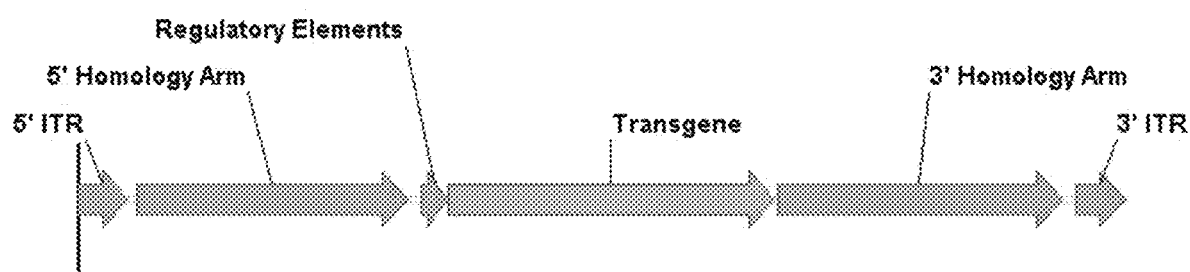
FIG. 3 shows a schematic of a portion of one set of donor ITR-AAVS1-FP vector constructs that were used for genome editing. The AAV vector contained 5' homology and 3' homology arms, and regulatory elements, which included a 2A sequence, splice acceptor sequence, and polyadenylation sequence. Yellow fluorescent protein ("YFP" or "FP") was used as the transgene. AAV2 ITRs flanked the homologous arms and the vector genome was packaged in AAVF capsids to form the AAVF-AAVS1-FP donor vectors. Importantly, the vector containing the FP gene does not contain a promoter to drive expression. The FP gene will only be expressed if it integrates correctly into AAVS1, downstream from an endogenous chromosomal promoter.

Certain embodiments of the invention are described in detail, using specific examples, sequences, and drawings. The enumerated embodiments are not intended to limit the invention to those embodiments, as the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. Unless defined otherwise, all technical and scientific terms used herein have the same meaning as commonly understood by one of ordinary skill in the art to which this invention belongs. All publications and/or patents are incorporated by reference as though fully set forth herein.

Provided herein are adeno-associated virus (AAV) Clade F vectors (e.g., replication-defective AAVs comprising correction genomes enclosed in a Clade F capsid) or AAV vector variants (e.g., replication-defective AAVs comprising capsid variants relative to AAV9 capsids) and related methods thereof that were developed for precise editing of the genome of a cell using homologous recombination without the need for addition of exogenous nucleases. In certain embodiments, genome editing may include, without limitation, introducing insertions, deletions, alterations, point mutations or any combination thereof into the genome sequence of a cell (e.g., a target locus of a mammalian chromosome). In certain embodiments, the AAV Clade F vectors or AAV vector variants and related methods thereof provided herein may be used to insert one or more nucleotide sequences into a specific location of a cell genome without the need for addition of exogenous nucleases prior to integration of the one or more nucleotide sequences. In certain embodiments, the Clade F vectors or AAV vector variants and related methods thereof provided herein may be used to insert an internucleotide bond into a specific location of a cell genome without the need for addition of exogenous nucleases prior to integration of the internucleotide bond. Also provided in certain embodiments are methods of treating a disease or disorder in a subject by ex-vivo editing the genome of a cell of the subject via transducing the cell with a Clade F vector or AAV vector variant as described herein and further transplanting the transduced cell into the subject to treat the disease or disorder of the subject. Also provided herein are methods of treating a disease or disorder in a subject by in vivo genome editing by directly administering the Clade F vector or AAV vector variant as described herein to the subject. Also provided herein are kits for genome editing of a cell comprising one or more of the Clade F vectors or AAV vector variants described herein.

Homologous recombination using various AAV vectors (e.g., AAV2, AAV6, and AAV8) has been previously reported; however, the reported efficiencies were very low—approximately 1 in a million cells. As shown in Examples 1 and 2 below, AAV Clade F vectors (or AAV vector variants) were used to reproducibly target gene insertion to specified chromosomal locations at significantly greater frequencies than previously seen. For example, targeted genome editing was achieved by transducing primary cells with AAV Clade F vectors (or AAV vector variants) resulting in the insertion of the transgene into the genome of the primary cells at surprisingly high frequencies, with approximately 10% of the primary cells displaying insertion of the transgene six weeks post-transduction. This frequency is 1,000 to 100,000 fold more efficient than previously reported (see, e.g., Khan, 2011). As shown in Examples 1 and 2 below, high level genome editing was achieved using primary human CD34+ hematopoietic stem cells (K562) and CD34+ primary peripheral blood-derived human hematopoietic stem cells (PBSCs). Targeted gene insertion was observed in both short term (one day) and long term (up to almost six weeks) CD34+ cultures and was verified by transgene expression and sequence analysis. Furthermore, the Clade F vector or AAV vector variant targeted recombination as described herein allows for specific genome engineering with no associated toxicity. As shown in Example 3 below, intravenous injection of AAV vectors pseudotyped with AAVF7 or AAVF17 resulted in transduction of human CD34+ hematopoietic stem and progenitor cells in vivo. As shown in Example 4 below, genome editing was achieved both in cell culture and in vivo for both small (~10 bps) and large inserts (~800 bps) and was shown by sequencing to be precisely integrated into the target locus. As shown in Example 5 below, genome editing of various human cell lines (e.g., fibroblasts, hepatocellular carcinoma cells, breast cancer cells, retinoblastoma cells, leukemia cells and B cells) was achieved, demonstrating that Clade F vectors could be used to edit genomes in several distinct cell types, such as fibroblasts, liver cells, breast cells, retinal cells, and B cells. As such, this technique has tremendous potential for targeted genome editing in cells ex vivo as well as in vivo in specific organs.

Provided herein are Clade F vectors (e.g., replication-defective AAVs comprising correction genomes enclosed in a Clade F capsid) or AAV vector variants (e.g., replication-defective AAVs comprising capsid variants relative to AAV9 capsids) for editing a genome of a cell and methods thereof (via recombination, and preferably without the use of exogenous nucleases). In certain embodiments, genome editing may include, without limitation, correction or insertion of one or more mutations in the genome, deletion of one or more nucleotides in the genome, alteration of genomic sequences including regulatory sequences, insertion of one or more nucleotides including transgenes at safe harbor sites or other specific locations in the genome, or any combination thereof. In certain embodiments, genome editing using the Clade F vectors or AAV vector variants and methods thereof as described herein may result in the induction of precise alterations of one or more genomic sequences without inserting exogenous viral sequences or other footprints.

In some aspects, the disclosure provides a replication-defective adeno-associated virus (AAV) comprising a correction genome enclosed in a capsid as described herein, e.g., an AAV Clade F capsid. In some embodiments, a "correction genome" is a nucleic acid molecule that contains an editing element as described herein along with additional element(s) (e.g., a 5' inverted terminal repeat (5' ITR) nucleotide sequence, or a fragment thereof, and a 3' inverted terminal repeat (3' ITR) nucleotide sequence, or a fragment thereof) sufficient for encapsidation within a capsid as described herein. It is to be understood that the term "correction genome" does not necessarily require that an editing element contained within the correction genome will "correct" a target locus in a genome, once integrated into the target locus (e.g., correction of target locus containing a mutation by replacement with a wild-type sequence). Accordingly, in some embodiments, a correction genome may contain an editing element which may comprise a nucleotide sequence that is additive to the target locus (e.g., the target locus is the 3' end of a first open reading frame and the editing element is a second open reading frame that, when integrated into the target locus, will create a gene that encodes a fusion protein).

In some embodiments, the replication-defective adeno-associated virus (AAV) comprises a correction genome, the correction genome comprising (a) an editing element selected from an internucleotide bond or a nucleotide sequence for integration into a target locus of a mammalian chromosome, (b) a 5' homologous arm nucleotide sequence 5' of the editing element, having homology to a 5' region of the mammalian chromosome relative to the target locus, and (c) a 3' homologous arm nucleotide sequence 3' of the editing element, having homology to a 3' region of the mammalian chromosome relative to the target locus. In some embodiments, the replication-defective AAV comprises a correction genome, the correction genome comprising an editing element nucleotide sequence for integration into a target locus of a mammalian chromosome, the correction genome having an essential absence of a promoter operatively linked to the editing element nucleotide sequence. In some embodiments, the replication-defective AAV comprises a correction genome, the correction genome comprising an editing element selected from an internucleotide bond or a nucleotide sequence for integration into a target locus of a mammalian chromosome in a cell; the AAV having a chromosomal integration efficiency of at least about 1% (e.g., at least about 2%, at least about 5%, at least about 10%, at least about 20%, at least about 30%, at least about 40%, at least about 50%, at least about 60%, at least about 70%, at least about 80%, or at least about 90%) for integrating the editing element into the target locus of the mammalian chromosome in the cell. In some embodiments, the replication-defective AAV comprises a correction genome, the correction genome comprising an editing element selected from an internucleotide bond or a nucleotide sequence for integration into a target locus of a mammalian chromosome in a cell; the AAV having a chromosomal integration efficiency of at least about 1% (e.g., at least about 2%, at least about 5%, at least about 10%, at least about 20%, at least about 30%, at least about 40%, at least about 50%, at least about 60%, at least about 70%, at least about 80%, or at least about 90%) in the absence of an exogenous nuclease for integrating the editing element into the target locus of the mammalian chromosome in the cell. In some embodiments of any one of the correction genomes, the correction genome has an essential absence of a promoter operatively linked to the editing element nucleotide sequence. In some embodiments of any one of the correction genomes, the correction genome further comprises an exogenous promoter operatively linked to the editing element. In some embodiments of any one of the replication-defective AAVs, the AAV has a chromosomal integration efficiency of at least about 1%, at least about 2%, at least about 3%, at least about 4%, at least about 5%, at least about 10%, at least about 20%, at least about 30%, at least about 40%, at least about 50%, at least about 60%, at least about 70%, at least about 80%, or at least about 90% for integrating an editing element into a target locus of a mammalian chromosome in a cell.

Other aspects of the disclosure relate to a gene editing vector comprising a replication-defective adeno-associated virus (AAV) comprising a correction genome enclosed in an AAV capsid, the correction genome as described herein (e.g., comprising an editing element selected from an internucleotide bond or a nucleotide sequence for integration into a target locus of a mammalian cell chromosome; a 5' homologous arm nucleotide sequence 5' of the editing element having homology to a 5' region of the chromosome relative to the target locus; a 3' homologous arm nucleotide sequence 3' of the editing element having homology to a 3' region of the chromosome relative to the target locus); wherein the AAV has a chromosomal integration efficiency of at least 10% (e.g., at least 15%, at least 20%, at least 30%, at least 40%, at least 50%, at least 60%, at least 70%, at least 80%, or at least 90%) for integrating an editing element as described herein into a target locus as described herein. In some embodiments, the chromosomal integration efficiency is at least 10% (e.g., at least 15%, at least 20%, at least 30%, at least 40%, at least 50%, at least 60%, at least 70%, at least 80%, or at least 90%) for integrating an editing element as described herein into a target locus as described herein in the absence of an exogenous nuclease.

A correction genome as described herein can comprise a 5' inverted terminal repeat (5' ITR) nucleotide sequence 5' of the 5' homologous arm nucleotide sequence, and a 3' inverted terminal repeat (3' ITR) nucleotide sequence 3' of the 3' homologous arm nucleotide sequence. In some embodiments, the 5' ITR nucleotide sequence and the 3' ITR nucleotide sequence are substantially identical (e.g., at least 90%, at least 95%, at least 98%, at least 99% identical or 100% identical) to an AAV2 virus 5'ITR and an AAV2 virus 3' ITR, respectively. In some embodiments, the 5' ITR nucleotide sequence has at least 95% (e.g., at least 96%, at least 97%, at least 98%, at least 99%, or 100%) sequence identity to SEQ ID NO:36, and the 3' ITR nucleotide sequence has at least 95% (e.g., at least 96%, at least 97%, at least 98%, at least 99%, or 100%) sequence identity to SEQ ID NO:37. In some embodiments, the 5' ITR nucleotide sequence and the 3' ITR nucleotide sequence are substantially identical (e.g., at least 90%, at least 95%, at least 98%, at least 99% identical or 100% identical) to an AAV5 virus 5'ITR and an AAV5 virus 3' ITR, respectively. In some embodiments, the 5' ITR nucleotide sequence has at least 95% (e.g., at least 96%, at least 97%, at least 98%, at least 99%, or 100%) sequence identity to SEQ ID NO:38, and the 3' ITR nucleotide sequence has at least 95% (e.g., at least 96%, at least 97%, at least 98%, at least 99%, or 100%) sequence identity to SEQ ID NO:39. In some embodiments, the 5' ITR nucleotide sequence and the 3' ITR nucleotide sequence are substantially mirror images of each other (e.g., are mirror images of each other except for at 1, 2, 3, 4 or 5 nucleotide positions in the 5' or 3' ITR).

Exemplary AAV2 5' ITR (SEQ ID NO: 36)

ttggccactccctctctgcgcgctcgctcgctcactgaggccgggcgacc aaaggtcgcccgacgcccgggctttgcccgggcggcctcagtgagcgagc gagcgcgcagagagggagtggccaactccatcactaggggttcct Exemplary AAV2 3' ITR (SEQ ID NO: 37)

aggaaccccctagtgatggagttggccactccctctctgcgcgctcgctcg ctcactgaggccgggcgaccaaaggtcgcccgacgcccgggctagcccgg gcggcctcagtgagcgagcgagcgcgcagagagggagtggccaa Exemplary AAV5 5' ITR (SEQ ID NO: 38)

ctctccccctgtcgcgttcgctcgctcgctggctcgtttggggggtgg cagctcaaagagctgccagacgacggccctctggccgtcgccccccaaa cgagccagcgagcgagcgaacgcgacaggggggagagtgccacactctca agcaaggggttttgta Exemplary AAV5 3' ITR (SEQ ID NO: 39)

tacaaaacctccttgcttgagagtgtggcactctccccctgtcgcgttc gctcgctcgctggctcgtttggggggtggcagctcaaagagctgccaga cgacggccctctggccgtcgccccccaaacgagccagcgagcgagcgaa cgcgacaggggggagag In some embodiments, a correction genome as described herein is no more than 7 kb (kilobases), no more than 6 kb, no more than 5 kb, or no more than 4 kb in size. In some embodiments, a correction genome as described herein is between 4 kb and 7 kb, 4 kb and 6 kb, 4 kb and 5 kb, or 4.1 kb and 4.9 kb.

In certain embodiments, AAV Clade F vectors or AAV vector variants for editing a genome of a cell comprise one or more Clade F capsids or capsid variants (variant relative to an AAV9 capsid). In certain embodiments, AAV Clade F vectors or AAV vector variants for editing a genome of a cell comprise one or more AAV Clade F capsids. In certain embodiments, a donor vector may be packaged into the Clade F capsids or capsid variants described herein according to a standard AAV packaging method resulting in formation of the AAV Clade F vector or AAV vector variant (see e.g., Chatterjee, 1992). In certain embodiments, the one or more Clade F capsids or capsid variants influence the tropism of the AAV Clade F vector or AAV vector variant for a particular cell.

According to certain embodiments, the one or more Clade F capsids or capsid variants may be derived from human stem cell-derived AAV. It has been previously shown that that cytokine-primed peripheral blood CD34+ stem cells from healthy donors harbor endogenous natural AAV sequences in their genome (see, e.g., US Patent Publication Number US20130096182A1 and US20110294218A1). The efficacy of the AAV isolate variants (variant relative to AAV9) has been previously demonstrated, including the efficacy of individual capsid nucleotides and proteins for use in cell transduction (see, e.g., US Patent Publication Number US20130096182A1 and US20110294218A1).

Full length AAV capsid variant genes (variant relative to AAV9) from the donors harboring endogenous natural AAV sequences in their genome were isolated and sequenced. The polynucleotide and polypeptide sequences of the capsid variants are provided in FIG. 1 and in U.S. patent application Ser. No. 13/668,120, filed Nov. 2, 2012, published as US Patent Publication Number US20130096182A1, and U.S. patent application Ser. No. 13/097,046, filed Apr. 28, 2011, US20110294218A1, published as US Patent Publication Number US20130096182A1, which issued on Jan. 14, 2014 as U.S. Pat. No. 8,628,966, all of which are hereby incorporated by reference in their entirety, as if fully set forth herein. In certain embodiments, the AAV Clade F vectors or AAV vector variants described herein may comprise one or more Clade F capsids or capsid variants comprising a polynucleotide sequence selected from the group of AAVF1 (SEQ ID NO: 20), AAVF2 (SEQ ID NO: 21), AAVF3 (SEQ ID NO: 22), AAVF4 (SEQ ID NO: 23), AAVF5 (SEQ ID NO: 25), AAVF11 (SEQ ID NO: 26), AAVF7 (SEQ ID NO: 27), AAVF8 (SEQ ID NO: 28), AAVF9 (SEQ ID NO: 29), AAVF12 (SEQ ID NO: 30), AAVF13 (SEQ ID NO: 31), AAVF14 (SEQ ID NO: 32), AAVF15 (SEQ ID NO: 33), AAVF16 (SEQ ID NO: 34), AAVF17 (SEQ ID NO: 35), variants, fragments, mutants, and any combination thereof. In certain embodiments, the AAV Clade F vectors or AAV vector variants described herein may comprise one or more Clade F capsids or capsid variants comprising a polypeptide sequence selected from the group of AAVF1 (SEQ ID NO: 2), AAVF2 (SEQ ID NO: 3), AAVF11 (SEQ ID NO: 4), AAVF3 (SEQ ID NO: 5), AAVF4 (SEQ ID NO: 6), AAVF6 (SEQ ID NO: 7), AAVF7 (SEQ ID NO: 8), AAVF8 (SEQ ID NO: 9), AAVF9 (SEQ ID NO: 10), AAVF5 (SEQ ID NO: 11), AAVF12 (SEQ ID NO: 12), AAVF17 (SEQ ID NO: 13), AAVF13 (SEQ ID NO: 14), AAVF14 (SEQ ID NO: 15), AAVF15 (SEQ ID NO: 16), AAVF16 (SEQ ID NO: 17), variants, fragments, mutants, and any combination thereof (see, e.g., FIG. 1).

According to certain embodiments, the polynucleotide or polypeptide sequences of the Clade F capsids or capsid variants may have at least about 95%, 96%, 97%, more preferably about 98%, and most preferably about 99% sequence identity to the sequences taught in the present specification. Percentage identity may be calculated using any of a number of sequence comparison programs or methods such as the Pearson & Lipman, Proc. Natl. Acad. Sci. USA, 85:2444 (1988), and programs implementing comparison algorithms such as GAP, BESTFIT, FASTA, or TFASTA (from the Wisconsin Genetics Software Package, Genetics Computer Group, 575 Science Drive, Madison, Wis.), or BLAST, available through the National Center for Biotechnology Information web site.

The Clade F capsids or capsid variant sequences may be modified at one or more positions in the V1 and/or V3 cap genes, these genes or functional portions of the genes can be used separately or together in any of the AAV Clade F vectors or AAV vector variants and methods described herein. Cap genes, V1, V2, and V3, may be substituted out from multiple mutated sequences, and are typically used in a colinear fashion V1-V2-V3. However the sequences may be truncated such as partial V1-V2-V3 or V1-V3 or V1-V1-V2-V3. For example, one sequence could be V1 of (AAVF8)-V2 of (AAVF4)-V3 of AAVF14. Preferably, the Clade F capsids or capsid variants transduce the target cells on a level at or higher than AAV2.

In certain embodiments, the one or more capsid variants may comprise a combination of one or more V1, V2, and V3 polynucleotide sequences of capsid variants (e.g., SEQ ID NOs: 20-35, variant relative to AAV9 capsid), the AAV9 capsid (SEQ ID NO: 18), the AAV2 capsid (SEQ ID NO: 19), variants, fragments, or mutants thereof. In certain embodiments, the one or more or capsid variants may comprise a combination of one or more V1, V2, and V3 polynucleotide sequences of capsid variants (SEQ ID NOs: 20-35, variant relative to AAV9 capsid), any other known AAV capsids, variants, fragments, or mutants thereof.

In certain embodiments, the one or more Clade F capsids or capsid variants may comprise a combination of V1, V2, and V3 polypeptide sequences of the capsid variants (SEQ ID NOs: 2-17, variant relative to AAV9 capsid), the AAV9 capsid (SEQ ID NO: 1), variants, fragments, or mutants thereof. In certain embodiments, the one or more capsid variants may comprise a combination of V1, V2, and V3 polypeptide sequences of the Clade F capsid variants (SEQ ID NOs: 2-17, variant relative to AAV9), any other known AAV capsid, variants, fragments, or mutants thereof.

In some embodiments, an AAV Clade F vector or AAV vector variant for editing a genome of a cell comprises a AAV Clade F capsid. In some embodiments, an "AAV Clade F capsid" refers to a capsid that has an AAV VP1, VP2, and/or VP3 sequence that has at least 86% (e.g., at least 86%, at least 87%, at least 88%, at least 89%, at least 90%, at least 91%, at least 92%, at least 93%, at least 94%, at least 95%, at least 96%, at least 97%, at least 98%, or at least 99%) sequence identity with the AAV VP1, VP2, and/or VP3 sequence of AAV9, respectively. Exemplary Clade F capsids include AAVF1-17 (also referred to herein as AAVHSC1-17), AAV9, AAVHU31, AAVHU32, and AAVAnc110 (see, e.g., Zinn et al. In Silicic Reconstruction of the Viral Evolutionary Lineage Yields a Potent Gene Therapy Vector (2015) Cell Reports, Vol 12, pp. 1056-1.068).

In some embodiments, an AAV Clade F capsid comprises at least one or at least two proteins selected from Clade F VP1, Clade F VP2 and Clade F VP3. In some embodiments, an AAV Clade F capsid comprises Clade F VP1, Clade F VP2 and Clade F VP3 proteins.

Exemplary AAV VP1, VP2, and VP3 protein sequences of AAV Clade F capsids are provided in the below table.

| AAV capsid | VP1 | VP2 | VP3 |
|---|---|---|---|
| AAV9 | Amino acids 1 to 736 of SEQ ID NO: 1 | Amino acids 138 to 736 of SEQ ID NO: 1 | Amino acids 203 to 736 of SEQ ID NO: 1 |
| AAVF1 | Amino acids 1 to 736 of SEQ ID NO: 2 | Amino acids 138 to 736 of SEQ ID NO: 2 | Amino acids 203 to 736 of SEQ ID NO: 2 |
| AAVF2 | Amino acids 1 to 736 of SEQ ID NO: 3 | Amino acids 138 to 736 of SEQ ID NO: 3 | Amino acids 203 to 736 of SEQ ID NO: 3 |
| AAVF3 | Amino acids 1 to 736 of SEQ ID NO: 5 | Amino acids 138 to 736 of SEQ ID NO: 5 | Amino acids 203 to 736 of SEQ ID NO: 5 |
| AAVF4 | Amino acids 1 to 736 of SEQ ID NO: 6 | Amino acids 138 to 736 of SEQ ID NO: 6 | Amino acids 203 to 736 of SEQ ID NO: 6 |
| AAVF5 | Amino acids 1 to 736 of SEQ ID NO: 11 | Amino acids 138 to 736 of SEQ ID NO: 11 | Amino acids 203 to 736 of SEQ ID NO: 11 |
| AAVF6 | Amino acids 1 to 736 of SEQ ID NO: 7 | Amino acids 138 to 736 of SEQ ID NO: 7 | Amino acids 203 to 736 of SEQ ID NO: 7 |
| AAVF7 | Amino acids 1 to 736 of SEQ ID NO: 8 | Amino acids 138 to 736 of SEQ ID NO: 8 | Amino acids 203 to 736 of SEQ ID NO: 8 |
| AAVF8 | Amino acids 1 to 736 of SEQ ID NO: 9 | Amino acids 138 to 736 of SEQ ID NO: 9 | Amino acids 203 to 736 of SEQ ID NO: 9 |
| AAVF9 | Amino acids 1 to 736 of SEQ ID NO: 10 | Amino acids 138 to 736 of SEQ ID NO: 10 | Amino acids 203 to 736 of SEQ ID NO: 10 |
| AAVF10 | Amino acids 1 to 736 of SEQ ID NO: 3 | Amino acids 138 to 736 of SEQ ID NO: 3 | Amino acids 203 to 736 of SEQ ID NO: 3 |
| AAVF11 | Amino acids 1 to 736 of SEQ ID NO: 4 | Amino acids 138 to 736 of SEQ ID NO: 4 | Amino acids 203 to 736 of SEQ ID NO: 4 |
| AAVF12 | Amino acids 1 to 736 of SEQ ID NO: 12 | Amino acids 138 to 736 of SEQ ID NO: 12 | Amino acids 203 to 736 of SEQ ID NO: 12 |
| AAVF13 | Amino acids 1 to736 of SEQ ID NO: 14 | Amino acids 138 to 736 of SEQ ID NO: 14 | Amino acids 203 to 736 of SEQ ID NO: 14 |
| AAVF14 | Amino acids 1 to 736 of SEQ ID NO: 15 | Amino acids 138 to 736 of SEQ ID NO: 15 | Amino acids 203 to 736 of SEQ ID NO: 15 |
| AAVF15 | Amino acids 1 to 736 of SEQ ID NO: 16 | Amino acids 138 to 736 of SEQ ID NO: 16 | Amino acids 203 to 736 of SEQ ID NO: 16 |
| AAVF16 | Amino acids 1 to 736 of SEQ ID NO: 17 | Amino acids 138 to 736 of SEQ ID NO: 17 | Amino acids 203 to 736 of SEQ ID NO: 17 |
| AAVF17 | Amino acids 1 to 736 of SEQ ID NO: 13 | Amino acids 138 to 736 of SEQ ID NO: 13 | Amino acids 203 to 736 of SEQ ID NO: 13 |

In some embodiments, an AAV Clade F capsid comprises a VP1, VP2, or VP3 protein that has at least 85% (e.g., at least 86%, at least 88%, at least 90%, at least 92%, at least 94%, at least 96%, at least 97%, at least 98%, at least 99%, or 100%) amino acid sequence identity to amino acids 1 to 736, amino acids 138 to 736 or amino acids 203 to 736 of SEQ ID NO:1, respectively, which correspond to the amino acid sequences of AAV9 capsid proteins VP1, VP2 and VP3, respectively. In some embodiments, an AAV Clade F capsid comprises VP1 and VP2 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 1 to 736 and amino acids 138 to 736 of SEQ ID NO:1, respectively, which correspond to the amino acid sequences of AAV9 capsid proteins VP1 and VP2, respectively; VP1 and VP3 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 1 to 736 and amino acids 203 to 736 of SEQ ID NO:1, respectively, which correspond to the amino acid sequences of AAV9 capsid proteins VP1 and VP3, respectively; or VP2 and VP3 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 138 to 736 and amino acids 203 to 736 of SEQ ID NO:1, respectively, which correspond to the amino acid sequences of AAV9 capsid proteins VP2 and VP3, respectively. In some embodiments, an AAV Clade F capsid comprises VP1, VP2, and VP3 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 1 to 736, amino acids 138 to 736 and amino acids 203 to 736 of SEQ ID NO:1, respectively, which correspond to the amino acid sequences of AAV9 capsid proteins VP1, VP2 and VP3, respectively.

In some embodiments, an AAV Clade F capsid comprises a VP1, VP2, or VP3 protein that has at least 85% (e.g., at least 86%, at least 88%, at least 90%, at least 92%, at least 94%, at least 96%, at least 97%, at least 98%, at least 99%, or 100%) amino acid sequence identity to amino acids 1 to 736, amino acids 138 to 736 or amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1, VP2 and VP3, respectively. In some embodiments, an AAV Clade F capsid comprises VP1 and VP2 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 1 to 736 and amino acids 138 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1 and VP2, respectively; VP1 and VP3 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 1 to 736 and amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1 and VP3, respectively; or VP2 and VP3 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 138 to 736 and amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP2 and VP3, respectively. In some embodiments, an AAV Clade F capsid comprises VP1, VP2, and VP3 proteins that have at least 85% (e.g., at least 86%, at least 88%, at least 90%, at least 92%, at least 94%, at least 96%, at least 97%, at least 98%, at least 99%, or 100%) amino acid sequence identity to amino acids 1 to 736, amino acids 138 to 736 and amino acids 203 to 736 of any one of SEQ ID NOs: 2, 3, 5, 6, 11, 7, 8, 9, 10, 4, 12, 14, 15, 16, 17 or 13, respectively, which correspond to the amino acid sequences of AAVF1 through AAVF9 and AAVF11 through AAVF17 capsid proteins VP1, VP2 and VP3, respectively.

In some embodiments, an AAV Clade F capsid comprises a VP1, VP2, or VP3 protein that is encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to SEQ ID NO:18, which corresponds to the nucleotide sequence encoding AAV9 capsid proteins VP1, VP2 and VP3, respectively. In some embodiments, an AAV Clade F capsid comprises VP1 and VP2 proteins that are encoded by nucleotide sequences comprising at least 85% (e.g., at least 86%, at least 88%, at least 90%, at least 92%, at least 94%, at least 96%, at least 97%, at least 98%, at least 99%, or 100%) nucleotide sequence identity to SEQ ID NO: 18, which corresponds to the nucleotide sequence encoding AAV9 capsid proteins VP1, VP2, and VP3; VP1 and VP3 proteins that are encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to SEQ ID NO: 18; or VP2 and VP3 proteins that are encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to SEQ ID NO: 18. In some embodiments, an AAV Clade F capsid comprises VP1, VP2, and VP3 proteins that are encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to SEQ ID NO: 18, which corresponds to a nucleotide sequence encoding AAV9 capsid proteins VP1, VP2 and VP3.

In some embodiments, an AAV Clade F capsid comprises a VP1, VP2, or VP3 protein that is encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to any one of SEQ ID NOs: 20, 21, 22, 23, 25, 24, 27, 28, 29, 26, 30, 31, 32, 33, 34 or 35, which correspond to nucleotide sequences encoding AAVF1 through AAVF17 capsid proteins VP1, VP2 and VP3, respectively. In some embodiments, an AAV Clade F capsid comprises VP1 and VP2 proteins that are encoded by nucleotide sequences comprising at least 85% (e.g., at least 86%, at least 88%, at least 90%, at least 92%, at least 94%, at least 96%, at least 97%, at least 98%, at least 99%, or 100%) nucleotide sequence identity to any one of SEQ ID NOs:20-35; VP1 and VP3 proteins that are encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to any one of SEQ ID NOs:20-35; or VP2 and VP3 proteins that are encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to any one of SEQ ID NOs:20-35. In some embodiments, an AAV Clade F capsid comprises VP1, VP2, and VP3 proteins that are encoded by a nucleotide sequence comprising at least 85% (e.g., at least 86%, at least 88%, at least 90%, at least 92%, at least 94%, at least 96%, at least 97%, at least 98%, at least 99%, or 100%) nucleotide sequence identity to any one of SEQ ID NOs: 20, 21, 22, 23, 25, 24, 27, 28, 29, 26, 30, 31, 32, 33, 34 or 35, which correspond to nucleotide sequences encoding AAVF1 through AAVF17 capsid proteins VP1, VP2 and VP3, respectively.

In some embodiments, an AAV Clade F capsid comprises an AAV9 VP1, VP2, or VP3 capsid protein, which corresponds to amino acids 1 to 736, amino acids 138 to 736 and amino acids 203 to 736 as set forth in SEQ ID NO:1, respectively. In some embodiments, an AAV Clade F capsid comprises AAV9 VP1 and VP2 capsid proteins, which correspond to amino acids 1 to 736 and amino acids 138 to 736 as set forth in SEQ ID NO:1, respectively; AAV9 VP1 and VP3 capsid proteins, which correspond to amino acids 1 to 736 and amino acids 203 to 736 as set forth in SEQ ID NO:1, respectively; or AAV9 VP2 and VP3 capsid proteins, which correspond to amino acids 138 to 736 and amino acids 203 to 736 as set forth in SEQ ID NO:1, respectively. In some embodiments, an AAV Clade F capsid comprises AAV9 VP1, VP2 and VP3 capsid proteins, which correspond to amino acids 1 to 736, amino acids 138 to 736 and amino acids 203 to 736 as set forth in SEQ ID NO:1, respectively.

In some embodiments, an AAV Clade F capsid comprises a VP1 capsid protein selected from a VP1 capsid protein of any one of AAVF1 through AAVF9 and AAVF11 through AAVF17, which corresponds to amino acids 1 to 736 as set forth in SEQ ID NOs: 2, 3, 5, 6, 11, 7, 8, 9, 10, 4, 12, 14, 15, 16, 17 or 13, respectively. In some embodiments, an AAV Clade F capsid comprises a VP1 and a VP2 capsid protein independently selected from a VP1 and VP2 capsid protein of any one of AAVF1 through AAVF9 and AAVF11 through AAVF17, which correspond to amino acids 1 to 736 and amino acids 138 to 736 as set forth in SEQ ID NOs: 2, 3, 5, 6, 11, 7, 8, 9, 10, 4, 12, 14, 15, 16, 17 or 13, respectively. In some embodiments, an AAV Clade F capsid comprises a VP2 and a VP3 capsid protein independently selected from a VP2 and VP3 capsid protein of any one of AAVF1 through AAVF9 and AAVF11 through AAVF17, which correspond to amino acids 138 to 736 and amino acids 203 to 736 as set forth in SEQ ID NOs: 2, 3, 5, 6, 11, 7, 8, 9, 10, 4, 12, 14, 15, 16, 17 or 13, respectively. In some embodiments, an AAV Clade F capsid comprises each of the VP1, VP2 and VP3 capsid proteins of any one of AAVF1 through AAVF9 and AAVF11 through AAVF17, which correspond to amino acids 1 to 736, amino acids 138 to 736 and amino acids 203 to 736 as set forth in SEQ ID NOs: 2, 3, 5, 6, 11, 7, 8, 9, 10, 4, 12, 14, 15, 16, 17 or 13, respectively.

As used herein, a fragment of a polynucleotide sequence may be a portion of the polynucleotide that encodes a polypeptide which provides substantially the same function as the polypeptide encoded by the full length polynucleotide sequence. As used herein, mutants of a polynucleotide sequence may be obtained by deletion, substitution, addition, and/or insertion of one or more nucleotides to the specific polynucleotide sequence. It should be understood that such fragments, and/or mutants of a polynucleotide sequence encode a polypeptide having substantially the same function as the polypeptide encoded by the full length polynucleotide sequence.

As used herein, a polypeptide sequence may include fragments, and/or mutants of the polypeptide sequence, while still providing substantially the same function as the full length polypeptide sequence. A fragment of a polypeptide sequence means a part of the polypeptide sequence that provides substantially the same function as the full length polypeptide sequence. Examples of mutants of a polypeptide sequence include deletions, substitutions, additions, and/or insertions of one or more amino acids to the polypeptide sequence.

In certain embodiments, a polynucleotide sequence may be a recombinant or non-naturally occurring polynucleotide. In certain embodiments, a polynucleotide sequence may be cDNA.

In certain embodiments, the AAV Clade F vectors or AAV vector variants provided herein may comprise any of the AAVF (or AAVHSC) or any other AAV Clade F vectors described herein. In certain embodiments, a AAV Clade F vector or AAV vector variant may comprise any of the AAVF (or AAVHSC) vectors described in herein, such as AAVF1, AAVF2, AAVF3, AAVF4, AAVF5, AAVF6, AAVF7, AAVF8, AAVF9, AAVF10, AAVF11, AAVF12, AAVF13, AAVF14, AAVF15, AAVF16, AAVF17, variants, fragments, mutants, or any combination thereof. In certain embodiments, a Clade F vector or AAV vector variant may comprise any of AAV9, AAVF1, AAVF2, AAVF3, AAVF4, AAVF5, AAVF6, AAVF7, AAVF8, AAVF9, AAVF10, AAVF11, AAVF12, AAVF13, AAVF14, AAVF15, AAVF16, AAVF17, AAVHU31, AAVHU32, variants, fragments, mutants, or any combination thereof.

In certain embodiments, the AAV Clade F vectors or AAV vector variants provided herein may comprise an editing element (also referred to herein as a targeting cassette, meaning the terms "editing element" and "targeting cassette" are used interchangeably herein) comprising one or more nucleotide sequences or an internucleotide bond to be integrated into a target locus (also referred to herein as a target site, meaning the terms are used interchangeably herein) of the genome, a 5' homologous arm nucleotide sequence 5' of the editing element, having homology to a 5' region of the mammalian chromosome relative to the target locus (e.g., a 5' homologous arm polynucleotide sequence flanking the editing element (targeting cassette) and having homology to a region that is upstream of the target locus (target site)), and a 3' homologous arm nucleotide sequence 3' of the editing element, having homology to a 3' region of the mammalian chromosome relative to the target locus (e.g., a 3' homologous arm polynucleotide sequence flanking the editing element (targeting cassette) and having homology to a region that is downstream of the target locus (target site)).

In certain embodiments, the one or more nucleotide sequences to be integrated into a target site of the genome may be one or more therapeutic nucleotide sequences. The term "therapeutic" as used herein refers to a substance or process that results in the treatment of a disease or disorder. "Therapeutic nucleotide sequence" is a nucleotide sequence that provides a therapeutic effect. The therapeutic effect can be direct (e.g., substitution of a nucleic acid of a gene expressed as a protein, or insertion of a cDNA into an intron for expression) or indirect (e.g., correction of a regulatory element such as a promoter). In certain embodiments, the therapeutic nucleotide sequence may include one or more nucleotides. In certain embodiments, the therapeutic nucleotide sequence may be a gene, variant, fragment, or mutant thereof. In certain embodiments, when gene therapy is desired, the therapeutic nucleotide sequence may be any nucleotide sequence that encodes a protein that is therapeutically effective, including therapeutic antibodies. The Clade F vectors or AAV vector variants comprising the therapeutic nucleotide sequences are preferably administered in a therapeutically effective amount via a suitable route of administration, such as injection, inhalation, absorption, ingestion or other methods.

In some embodiments, an editing element as described herein consists of one nucleotide. In some embodiments, an editing element as described herein consists of one nucleotide and a target locus as described herein is a nucleotide sequence consisting of one nucleotide, the target locus representing a point mutation. In some embodiments, an editing element as described herein comprises at least 1, 2, 10, 100, 200, 500, 1000, 1500, 2000, 3000, 4000, or 5000 nucleotides. In some embodiments, an editing element as described herein comprises or consists of 1 to 5500, 1 to 5000, 1 to 4500, 1 to 4000, 1 to 3000, 1 to 2000, 1 to 1000, 1 to 500, 1 to 200, or 1 to 100 nucleotides, or 2 to 5500, 2 to 5000, 2 to 4500, 2 to 4000, 2 to 3000, 2 to 2000, 2 to 1000, 2 to 500, 2 to 200, or 2 to 100 nucleotides, or 10 to 5500, 10 to 5000, 10 to 4500, 10 to 4000, 10 to 3000, 10 to 2000, 10 to 1000, 10 to 500, 10 to 200, or 10 to 100 nucleotides. In some embodiments, an editing element as described herein comprises or consists of an exon, an intron, a 5' untranslated region (UTR), a 3' UTR, a promoter, a splice donor, a splice acceptor, a sequence encoding or non-coding RNA, an insulator, a gene, or a combination thereof. In some embodiments, an editing element as described herein is a fragment (e.g., no more than 2 kb, no more than 1 kb, no more than 500 bp, no more than 250 bp, no more than 100 bp, no more than 50 bp, or no more than 25 bp) of a coding sequence of a gene within or spanning a target locus as described herein. In some embodiments, an editing element as described herein is an internucleotide bond (e.g., a phosphodiester bond connecting two adjacent nucleotides). In some embodiments, an editing element as described herein is an internucleotide bond, a target locus in a chromosome as described herein is a nucleotide sequence comprising one or more nucleotides, and the editing element comprises a deletion for the target locus in the chromosome.

In certain embodiments, the editing element (or targeting cassette) of the AAV Clade F vector or AAV vector variant may comprise one or more regulatory element polynucleotide sequences. For example, in certain embodiments, the one or more regulatory element polynucleotide sequences may be selected from a 2A sequence, splice acceptor sequence, polyadenylation sequence, and any combination thereof. In certain embodiments, the targeting cassette may comprise one or more AAV inverted terminal repeat (ITR) polynucleotide sequences flanking the 5' and 3' homologous arm polynucleotide sequences. In certain embodiments, the editing element (or targeting cassette) does not contain a promoter to drive expression of the one or more nucleotide sequences. In certain embodiments, if the editing element (or targeting cassette) does not contain a promoter, the expression of the one or more nucleotide sequences after integration into the cell genome may be controlled by one or more regulatory elements of the cell. In certain embodiments, expression of the promoterless one or more nucleotide sequences demonstrates that the one or more nucleotide sequences was correctly integrated into the cell.

In certain embodiments, the AAV Clade F vector or AAV vector variant may comprise one or more homologous arm polynucleotide sequences. In certain embodiments, the one or more homologous arm polynucleotide sequences may be homologous to a region of the target locus (target site) of the genome. In certain embodiments, the one or more homologous arm polynucleotide sequences may be a 5' homologous arm polynucleotide sequence. In certain embodiments, the 5' homologous arm polynucleotide sequence may flank the 5' end of the editing element (or targeting cassette). In certain embodiments, the 5' homologous arm polynucleotide sequence flanking the editing element (or targeting cassette) may be homologous to a region that is upstream of a target locus (target site) of the genome. In certain embodiments, the one or more homologous arm polynucleotide sequences may be a 3' homologous arm polynucleotide sequence. In certain embodiments, the 3' homologous arm polynucleotide sequence may flank the 3' end of the editing element (or targeting cassette). In certain embodiments, the 3' homologous arm polynucleotide sequence flanking the editing element (or targeting cassette) may be homologous to a region that is downstream of the target locus (target site) of the genome. In certain embodiments, the homologous arm polynucleotide sequences may be approximately 500 to 1,000 nucleotides long. For example, in certain embodiments, the homologous arm polynucleotide sequences may be approximately 800 nucleotides long. In certain embodiments, the homologous arm polynucleotide sequence may be up to approximately 3,000 nucleotides long. In some embodiments, each of the 5' and 3' homologous arm nucleotide sequences independently has a nucleotide length of between about 50 to 2000 nucleotides, such as between about 500-1000, about 600-1000, or about 700-900 nucleotides. In some embodiments, each of the 5' and 3' homologous arm nucleotide sequences independently has a nucleotide length of between about 600, about 800, or about 1000 nucleotides.

In some embodiments, the 5' and 3' homologous arm nucleotide sequences have substantially equal nucleotide lengths. In some embodiments, the 5' and 3' homologous arm nucleotide sequences have asymmetrical nucleotide lengths. In some embodiments, the asymmetry in nucleotide length is defined by a difference between the 5' and 3' homologous arm nucleotide sequence lengths of up to 50% in the length, such as up to 40%, 30%, 20%, or 10% difference in the length. In some embodiments, the asymmetry in nucleotide length is defined by on arm of the 5' and 3' homologous arm having a length of about 600 nucleotides and the other arm of the 5' and 3' homologous arm having a length of about 800 or about 900 nucleotides.

In some embodiments, the 5' homologous arm nucleotide sequence has at least about 90% (e.g., at least about 90%, at least about 95%, at least about 96%, at least about 97%, at least about 98%, at least about 99%, or at least about 99.5%) nucleotide sequence identity to the 5' region of the mammalian chromosome relative to the target locus. In some embodiments, the 3' homologous arm nucleotide sequence has at least about 90% (e.g., at least about 90%, at least about 95%, at least about 96%, at least about 97%, at least about 98%, at least about 99%, or at least about 99.5%) nucleotide sequence identity to the 3' region of the mammalian chromosome relative to the target locus. In some embodiments, differences in nucleotide sequences of the 5' homologous arm or the 3' homologous arm and the corresponding 5' region or 3' region of the mammalian chromosome, respectively, can comprise, consist essentially of or consist of non-coding differences in nucleotide sequences. In some embodiments, differences in nucleotide sequences of the 5' homologous arm or the 3' homologous arm and the corresponding 5' region or 3' region of the mammalian chromosome, respectively, can comprise, consist essentially of or consist of differences in nucleotide sequences that result in conservative amino acid changes (e.g., a basic amino acid changed to a different basic amino acid). In some embodiments, the 5' homologous arm nucleotide sequence has 100% sequence identity to the 5' region of the mammalian chromosome relative to the target locus and the 3' homologous arm nucleotide sequence has 100% sequence identity to the 3' region of the mammalian chromosome relative to the target locus. In some embodiments, the 5' homologous arm nucleotide sequence and the 3' homologous arm nucleotide sequence are considered homologous with the 5' region and 3' of the mammalian chromosome relative to the target locus, respectively, even if the target locus contains one or more mutations, such as one or more naturally occurring SNPs, compared to the 5' or 3' homologous arm.

In certain embodiments, the target locus (target site) of the cell genome may be any region of the genome where it is desired that the editing of the cell genome occur. For example, the target locus (target site) of the cell genome may comprise a locus of a chromosome in the cell (e.g., a region of a mammalian chromosome). In certain embodiments, the locus of the chromosome may be a safe harbor site. A safe harbor site is a location in the genome where a nucleotide sequence may integrate and function in a predictable manner without perturbing endogenous gene activity. In certain embodiments, the safe harbor site may be the AAVS1 locus in human chromosome 19 (also known as PPP1R12C locus). In certain embodiments, the safe harbor site may be the first intron of PPP1R12C in the AAVS1 locus in human chromosome 19. The AAVS1 locus on chromosome 19 qter13.3-13.4 was previously shown to be a "safe harbor" site for the insertion of transgenes since genes inserted here are expressed with no pathogenic consequences, which is similar to wild-type AAV that integrates at this locus with no pathogenic consequences (Giraud 1994; Linden, 1996A; Linden 1996B). In some embodiments, the target locus (target site) is a locus associated with a disease state as described herein.

In certain embodiments, the target locus is a mutant target locus in a mammalian chromosome comprising one or more mutant nucleotides, relative to a corresponding wild type mammalian chromosome. In some embodiments, the mutant target locus comprises a point mutation, a missense mutation, a nonsense mutation, an insertion of one or more nucleotides, a deletion of one or more nucleotides, or combinations thereof. In some embodiments, the mutant target locus comprises an amorphic mutation, a neomorphic mutation, or an antimorphic mutation. In some embodiments, the mutant target locus comprises an autosomal dominant mutation, an autosomal recessive mutation, a heterozygous mutation, a homozygous mutation, or combinations thereof. In some embodiments of any one of the mutant target loci described herein, the mutant target locus is selected from a promoter, an enhancer, a signal sequence, an intron, an exon, a splice donor site, a splice acceptor site, an internal ribosome entry site, an inverted exon, an insulator, a gene, a chromosomal inversion, and a chromosomal translocation within the mammalian chromosome.

In some embodiments, a target locus in a chromosome as described herein is a nucleotide sequence comprising n nucleotides where n is an integer greater than or equal to one (e.g., 1, 2, 3, 4, 5, 10, 20, 30, 40, 50, 100, 500, 1000, 2000, 3000, 4000. 5000, or any integer therebetween), an editing element as described herein comprises m nucleotides where m is an integer equal to n, and the editing element represents a substitution for the target locus of the chromosome. In some embodiments, a target locus in a chromosome as described herein is a nucleotide sequence comprising n nucleotides where n is an integer greater than or equal to one (e.g., 1, 2, 3, 4, 5, 10, 20, 30, 40, 50, 100, 500, 1000, 2000, 3000, 4000. 5000, or any integer therebetween), an editing element as described herein comprises m nucleotides where m is an integer greater than n, and the editing element represents a substitutive addition for the target locus of the chromosome. In some embodiments, a target locus in a chromosome as described herein is a nucleotide sequence comprising n nucleotides where n is an integer greater than or equal to two (e.g., 2, 3, 4, 5, 10, 20, 30, 40, 50, 100, 500, 1000, 2000, 3000, 4000. 5000, or any integer therebetween), an editing element as described herein comprises m nucleotides where m is an integer less than n; and the editing element represents a substitutive deletion for the target locus of the chromosome. In some embodiments, a target locus in a chromosome as described herein is an internucleotide bond, an editing element as described herein comprises m nucleotides where m is an integer greater than or equal to one (e.g., 1, 2, 3, 4, 5, 10, 20, 30, 40, 50, 100, 500, 1000, 2000, 3000, 4000. 5000, or any integer therebetween); and the editing element represents an addition for the target locus of the chromosome.

In some embodiments, a target locus in a chromosome is a target locus in a mammalian chromosome (e.g. a human, mouse, bovine, equine, canine, feline, rat, or rabbit chromosome). In some embodiments, the target locus can comprise an intron of a mammalian chromosome. In some embodiments, the target locus can comprise an exon of a mammalian chromosome. In some embodiments, the target locus can comprise a non-coding region of a mammalian chromosome. In some embodiments, the target locus can comprise a regulatory region of a mammalian chromosome. In some embodiments, the mammalian chromosome is selected from human chromosome 1, 2, 3, 4, 5, 6, 7, 8, 9, 10, 11, 12, 13, 14, 15, 16, 17, 18, 19, 20, 21, 22, X and Y. In some embodiments, the mammalian chromosome is selected from mouse chromosome 1, 2, 3, 4, 5, 6, 7, 8, 9, 10, 11, 12, 13, 14, 15, 16, 17, 18, 19, X and Y. In some embodiments, the mammalian chromosome is not human chromosome 19. In some embodiments, the mammalian chromosome is a somatic cell chromosome. Exemplary somatic cells are further described herein.

In certain embodiments, the one or more nucleotide sequences or editing element may be integrated into the genome through homologous recombination without the need for DNA cleavage prior to integration. In certain embodiments, the one or more nucleotide sequences or editing element may be integrated into the genome through homologous recombination without the need for the addition of exogenous nucleases such as a zinc finger nuclease (ZFN), a transcription activator-like effector nuclease (TALEN), or an RNA guided nuclease (CRISPR/Cas).

In certain embodiments, the cell that is edited by the AAV Clade F vectors or AAV vector variants described herein may be any type of cell. In certain embodiments, the cell may be a wide variety of mammalian cells, for example, cells of the liver, lung, cartilage and other connective tissue, eye, central and peripheral nervous system, lymphatic system, bone, muscle, blood, brain, skin, heart, and digestive tract. When the cell to be edited by the AAV Clade F vectors or AAV vector variants is, for example, a liver cell, the inserted nucleotide sequence is directed to treating (improving or curing a disorder or stopping further progression of a disease or disorder) or preventing a condition. When the cell to be edited by the AAV Clade F vectors or AAV vector variants is a liver cell, the liver conditions treated or prevented comprise hemophilia, enzyme delivery, cirrhosis, cancer, or atherosclerosis, among other liver conditions. In certain embodiments, the cell may be a somatic cell (e.g., a mammalian somatic cell). In certain embodiments, the cell (e.g., somatic cell such as mammalian somatic cell) may be from a tissue selected from the group consisting of connective tissue (including blood), muscle tissue, nervous tissue, and epithelial tissue. In certain embodiments, the cell (e.g., somatic cell such as mammalian somatic cell) may be from an organ selected from the group consisting of lung, heart, liver, kidney, muscle, brain, eye, breast, bone, and cartilage. In some embodiments, the cell is a CD34+ cell (e.g., a CD34+ somatic cell). In some embodiments, the cell (e.g., somatic cell such as mammalian somatic cell) is a liver cell, a fibroblast, a breast cell, a lymphocyte, or a retinal cell.

As shown herein, AAV packaged with the Clade F capsids or capsid variants described herein demonstrate specific tropism for certain target tissues, such as blood stem cells, liver, heart, eye, breast, and joint tissue, and may be used to transduce stem cells for introduction of genes of interest into the target tissues. Certain of the vectors are able to cross tightly controlled biological junctions, such as the blood-brain barrier, which open up additional novel uses and target organs for the vectors, providing for methods of gene therapy through genome editing. Thus, Clade F vectors or AAV vector variants may demonstrate a tropism for a particular cell based on their Clade F capsids or capsid variants. For example a) for muscle tissue or cells, the AAV Clade F vector or AAV vector variant may be selected from the group of AAVF5, AAVF7, AAVF13, AAVF15, and AAVF17; b) for heart or lung tissue or cells, the vector may be selected from the group of AAVF13, AAVF15, and AAVF17; c) for liver or CNS tissue or cells, the vector may be selected from AAVF5, AAVF13, AAVF17, AAVF7 or AAVF15; d) for stem cells, the vector may be AAVF17; e) for B cell progenitors, the vector may be AAVF5; 0 for myeloid and erythroid progenitors, the vector may be AAVF12; and g) for lymph node, kidney, spleen, cartilage and bone tissues or cells, the vector may be selected from the group of the vector selected from the group of AAVF7, AAVF13, AAVF15, and AAVF17.

In addition, Clade F vectors or AAV vector variants may have a tropism for cells containing various tags, such as a six-His tag or an affinity tag, or for interferon responses, such as naturally occurring antibodies elicited or introduced monoclonal antibodies administered in response to a pathogen or tumor cell.

In certain embodiments, the cell may be a stem cell (e.g., a mammalian stem cell). In certain embodiments, the stem cell may be any type of stem cell including a hematopoietic stem cell, a pluripotent stem cell, an embryonic stem cell or a mesenchymal stem cell. In certain embodiments, the stem cell (e.g., mammalian stem cell) may be a hematopoietic stem cell, a cord blood stem cell, a bone marrow stem cell, a fetal liver stem cell, or a peripheral blood stem cell. In some embodiments, the stem cell may be a CD34+ stem cell. In certain embodiments, the stem cell (e.g., mammalian stem cell) may be a hematopoietic stem cell or peripheral blood stem cell. Transduction of the stem cell may be either transient or permanent (also called persistent). If transient, one embodiment allows for the length of time the therapeutic nucleotide is used or expressed to be controlled either by the vector, by substance attached to the vector, or by external factors or forces.

In certain embodiments, the cell may be selected from the group consisting of a CD34+ Hematopoietic stem cell line (HSC), a K562 CD34+ leukemia cell line, a HepG2 human liver cell line, a peripheral blood stem cell, a cord blood stem cell, a CD34+ peripheral blood stem cell, a WI-38 human diploid fibroblast cell line, a MCF7 human breast cancer cell line, a Y79 human retinoblastoma cell line, a SCID-X1 LBL human EBV-immortalized B cell line, a primary human hepatocyte, a primary hepatic sinusoidal endothelial cell, and a primary skeletal muscle myoblast.

Also provided herein are methods of ex-vivo editing a genome of a cell of a subject comprising transducing the cell with a Clade F or an AAV vector variant as described herein. In certain embodiments, transducing the cell with a Clade F vector or an AAV vector variant may occur without additional exogenous nucleases, such as a zinc finger nuclease (ZFN), a transcription activator-like effector nuclease (TALEN), or an RNA guided nuclease (CRISPR/Cas). In certain embodiments, the cell may be any type of cell. In certain embodiments, the cell may be a stem cell as described herein. For example, in certain embodiments, methods of editing the genome of a stem cell may comprise transducing the stem cell with one or more Clade F vectors or AAV vector variants. In certain embodiments, transduction of the stem cell may be performed without the need for additional exogenous nucleases. In certain embodiments, the cell may be a somatic cell as described herein. For example, in certain embodiments, methods of editing the genome of a somatic cell may comprise transducing the somatic cell with one or more Clade F vectors or AAV vector variants. In certain embodiments, transduction of the somatic cell may be performed without the need for additional exogenous nucleases. In certain embodiments, the Clade F vector or AAV vector variant comprises one or more Clade F capsids or capsid variants (variant relative to AAV9), an editing element (targeting cassette) selected from an internucleotide bond or a nucleotide sequence for integration into a target locus of a mammalian chromosome or comprising one or more therapeutic nucleotide sequences to be integrated into a target locus (target site) of the genome, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site). In certain embodiments, the internucleotide bond or nucleotide sequence or the one or more therapeutic nucleotide sequences may be integrated into the genome without the need for additional exogenous nucleases for DNA cleavage prior to integration.

Also provided herein are methods of treating a disease or disorder in a subject by ex-vivo editing a genome of a cell of the subject including transducing the cell with a Clade F vector or an AAV vector variant and further transplanting the transduced cell into the subject to treat the disease or disorder. In certain embodiments, the method may comprise transducing the cell of the subject with a Clade F vector or an AAV vector variant vector described herein. In certain embodiments, the cell may be transduced without additional exogenous nucleases. In certain embodiments, transduction of the cell with the Clade F vector or the AAV vector variant may be performed as provided herein or by any method of transduction known to one of ordinary skill in the art. In certain embodiments, the cell may be transduced with the Clade F vector or the AAV vector variant at a multiplicity of infection (MOI) of 50,000; 100,000; 150,000; 200,000; 250,000; 300,000; 350,000; 400,000; 450,000; or 500,000, or at any MOI that provides for optimal transduction of the cell. In certain embodiments, the transduced cell is further transplanted into the subject, wherein the transduced cell treats the disease or disorder. In certain embodiments, the cell may be any type of cell described herein.

Also provided herein are methods of editing a target locus of a mammalian genome as described herein. In some embodiments, the method comprises transducing a cell (such as a human, mouse, bovine, equine, canine, feline, rat, or rabbit cell) comprising the mammalian genome with an AAV as described herein (e.g., a replication-defective AAV comprising a correction genome enclosed in a capsid). In some embodiments, the method comprises (a) obtaining mammalian cells from a mammal (such as a human, mouse, bovine, equine, canine, feline, rat, or rabbit); (b) culturing the mammalian cells ex-vivo to form an ex-vivo culture; (c) transducing the mammalian cells with an AAV as described herein (e.g., a replication-defective AAV comprising a correction genome enclosed in a capsid) in the ex-vivo culture to form transduced mammalian cells; and (d) administering the transduced mammalian cells to the mammal. In some embodiments, the method comprises (a) obtaining mammalian cells from a first mammal; (b) culturing the mammalian cells ex-vivo to form an ex-vivo culture; (c) transducing the mammalian cells with an AAV as described herein (e.g., a replication-defective AAV comprising a correction genome enclosed in a capsid in the ex-vivo culture to form transduced mammalian cells; and (d) administering the transduced mammalian cells to a second mammal. In some embodiments, the first mammal and the second mammal are different species (e.g., the first mammal is human, mouse, bovine, equine, canine, feline, rat, or rabbit and the second mammal is a different species). In some embodiments, the first mammal and the second mammal are the same species (e.g., are both human, mouse, bovine, equine, canine, feline, rat, or rabbit). In some embodiments, the method comprises administering an AAV as described herein (e.g., a replication-defective AAV comprising a correction genome enclosed in a capsid) to a mammal (such as a human, mouse, bovine, equine, canine, feline, rat, or rabbit) in an amount effective to transduce cells of the mammal with the AAV in-vivo.

In some embodiments of any one of the methods, the mammalian cells are from a tissue selected from the group consisting of connective tissue (including blood), muscle tissue, nervous tissue, and epithelial tissue. In some embodiments of any one of the methods, the mammalian cells are from an organ selected from the group consisting of lung, heart, liver, kidney, muscle, brain, eye, breast, bone, and cartilage. In some embodiments of any one of the methods, the mammalian cells are stem cells. In some embodiments, the stem cells are hematopoietic stem cells or peripheral blood stem cells. In some embodiments of any one of the methods, the mammalian cells are a CD34+ cells.

In some embodiments of any one of the methods, the AAV (e.g., Clade F AAV) is transduced or administered without co-transducing or co-administering an exogenous nuclease or a nucleotide sequence that encodes an exogenous nuclease. Exemplary exogenous nucleases include a zinc finger nuclease (ZFN), a transcription activator-like effector nuclease (TALEN), or an RNA guided nuclease (CRISPR/Cas). In some embodiments of any one of the methods, the AAV is transduced or administered without co-transducing or co-administering an exogenous zinc finger nuclease or a nucleotide sequence that encodes an exogenous zinc finger nuclease. In some embodiments, the zinc finger nuclease is a zinc finger nuclease comprising a DNA-binding domain that targets the AAVS1 locus (e.g., a DNA-binding domain that targets the first intron of PPP 1R12C in the AAVS1 locus).

In some embodiments of any one of the methods, the AAV (e.g., Clade F AAV) has a chromosomal integration efficiency of at least about 1% (e.g., at least about 2%, at least about 3%, at least about 4%, at least about 5%, at least about 10%, at least about 20%, at least about 30%, at least about 40%, at least about 50%, at least about 60%, at least about 70%, at least about 80%, at least about 90%, at least about 95%, at least about 98%, or about 100%) for integrating the editing element into the target locus of the mammalian chromosome. In some embodiments of any one of the methods, the AAV (e.g. Clade F AAV) has a chromosomal integration efficiency of at least about 1% (e.g., at least about 2%, at least about 3%, at least about 4%, at least about 5%, at least about 10%, at least about 20%, at least about 30%, at least about 40%, at least about 50%, at least about 60%, at least about 70%, at least about 80%, at least about 90%, at least about 95%, at least about 98%, or about 100%) for integrating the editing element into the target locus of the mammalian chromosome in the absence of an exogenous nuclease. In some embodiments of any one of the methods, the editing element of the correction genome is integrated into the target locus of the mammalian chromosome with a chromosomal integration efficiency ranging from 10% to 70%, 20% to 70%, 40% to 70%, 50% to 70%, 10% to 80%, 20% to 80%, 40% to 80%, 50% to 80%, 10% to 90%, 20% to 90%, 40% to 90%, 50% to 90%, 10% to 100%, 20% to 100%, 40% to 100%, or 50% to 100% of the mammalian cells. In some embodiments of any one of the methods, the editing element of the correction genome is integrated into the target locus of the mammalian chromosome with a chromosomal integration efficiency ranging from 10% to 70%, 20% to 70%, 40% to 70%, 50% to 70%, 10% to 80%, 20% to 80%, 40% to 80%, 50% to 80%, 10% to 90%, 20% to 90%, 40% to 90%, 50% to 90%, 10% to 100%, 20% to 100%, 40% to 100%, or 50% to 100% of the mammalian cells in the absence of an exogenous nuclease.

In some embodiments of any one of the methods, the AAV (e.g., Clade F AAV) has a chromosomal integration efficiency further characterized by an allele frequency in a population of cells of at least about 10% (e.g., at least about 20%, at least about 30%, at least about 40%, at least about 50%, at least about 60%, at least about 75%, at least about 85%, at least about 90%, or at least about 95%) for the allele comprising the editing element integrated into the target locus of the mammalian chromosome. In some embodiments, the allele frequency in a population of cells is an allele frequency in a population of cells in vitro, such as population of a cell type provided herein in vitro (e.g., a CD34+ Hematopoietic stem cell line (HSC), a K562 CD34+ leukemia cell line, a HepG2 human liver cell line, a peripheral blood stem cell, a cord blood stem cell, a CD34+ peripheral blood stem cell, a WI-38 human diploid fibroblast cell line, a MCF7 human breast cancer cell line, a Y79 human retinoblastoma cell line, a SCID-X1 LBL human EBV-immortalized B cell line, a primary human hepatocyte, a primary hepatic sinusoidal endothelial cell, or a primary skeletal muscle myoblast).

According to certain embodiments, methods of treating a disease or disorder in a subject by ex-vivo editing a genome of stem cell of the subject and further transplanting the edited cell into the subject to treat the disease or disorder are provided. In certain embodiments, the methods of treating a disease or disorder in a subject by editing a genome of a stem cell of the subject may comprise the steps of transducing the stem cell of the subject with a AAV Clade F vector or an AAV vector variant as described herein and transplanting the transduced stem cell into the subject, wherein the transduced stem cell treats the disease or disorder. In certain embodiments, the AAV Clade F vector or the AAV vector variant may comprise one or more Clade F capsids or capsid variants, an editing element (targeting cassette) comprising one or more therapeutic nucleotide sequences to be integrated into a target locus (target site) in the genome of the stem cell, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site). In certain embodiments, transducing the stem cell may be performed without additional exogenous nucleases. In certain embodiments, the one or more therapeutic nucleotide sequences may be integrated into the genome without the need for additional exogenous nucleases for DNA cleavage prior to integration.

In certain embodiments, when the cell is a stem cell, the disease or disorder that is treated may be any disease or disorder that is caused by one or more mutations of the genome. In certain embodiments, the disease or disorder that is treated is selected from inherited metabolic diseases, lysosomal storage diseases, mucopolysaccharidodosis, immunodeficiency diseases, and hemoglobinopathy diseases and infections. In certain embodiments, when the cell to be edited is a stem cell, the AAV Clade F vector or AAV vector variant may be selected from the group of AAVF7, AAVF12, AAVF15, AAVF17, variants, mutants, and a combination thereof. In certain embodiments, when the cell to be edited is a stem cell, the Clade F vector or AAV vector variant may be selected from the group of AAVF5, AAVF7, AAVF12, AAVF15, AAVF17, variants, mutants, and a combination thereof. In certain embodiments, the Clade F vector or AAV vector variant may comprise one or more Clade F capsids or capsid variants comprising a polynucleotide sequence selected from the group of AAVF7 (SEQ ID NO: 27), AAVF12 (SEQ ID NO: 30), AAVF15 (SEQ ID NO: 33), AAVF17 (SEQ ID NO: 35), variants, fragments, mutants and combinations thereof. In certain embodiments, the Clade F vector or the AAV vector variant may comprise one or more Clade F capsids or capsid variants comprising a polynucleotide sequence selected from the group of AAVF5 (SEQ ID NO: 25), AAVF7 (SEQ ID NO: 27), AAVF12 (SEQ ID NO: 30), AAVF15 (SEQ ID NO: 33), AAVF17 (SEQ ID NO: 35), variants, fragments, mutants and combinations thereof. In certain embodiments, the AAV Clade F vector or the AAV vector variant may comprise one or more Clade F capsids or capsid variants comprising a polypeptide sequence selected from the group of AAVF7 (SEQ ID NO: 8), AAVF12 (SEQ ID NO: 12), AAVF15 (SEQ ID NO: 16), AAVF17 (SEQ ID NO: 13), variants, fragments, mutants and combinations thereof. In certain embodiments, the AAV Clade F vector or AAV vector variant may comprise one or more Clade F capsids or capsid variants comprising a polypeptide sequence selected from the group of AAVF5 (SEQ ID NO: 11), AAVF7 (SEQ ID NO: 8), AAVF12 (SEQ ID NO: 12), AAVF15 (SEQ ID NO: 16), AAVF17 (SEQ ID NO: 13), variants, fragments, mutants and combinations thereof.

In another embodiment, the AAV Clade F vectors or AAV vector variants capable of genome editing, from CD34+ HSC or from another source, may be used for high efficiency transduction of stem cells, including HSC and iPSC, and other cells, such as those of the heart, joint, central nervous system, including the brain, muscle, and liver. If the AAV Clade F vectors or AAV vector variants are used in vitro, they may be used for research and investigation purposes or to prepare cells or tissues that will later be implanted into a subject. Preferably, the subject is a mammal, such as a human, but may be any other animal that has tissues that can be transduced by the present vectors and methods of using those vectors. The present AAV Clade F vectors or the AAV vector variants are well suited for both human and veterinary use. The AAV Clade F vectors or AAV vector variants may also be used in vitro for the transient transduction of stem cells, such as HSC. The length of transduction may be controlled by culture conditions. If the AAV Clade F vectors or AAV vector variants are used in vivo, they may be directly administered to the subject receiving the therapy for uptake or use in the target cells, such as liver or cartilage cells. If the AAV Clade F vectors or AAV vector variants are used for transducing cells of the central nervous system, they are preferably able to traverse the blood-brain barrier and maintain their efficacy.

Also provided herein are methods of treating a disease or disorder in a subject by in vivo genome editing of a cell of the subject by directly administering an AAV Clade F vector or AAV vector variant to the subject. In certain embodiments, the AAV Clade F vector or AAV vector variant may be any AAV Clade F vector or AAV vector variant described herein. In certain embodiments, the AAV Clade F vector or the AAV vector variant may comprise one or more Clade F capsids or capsid variants, an editing element (targeting cassette) comprising one or more therapeutic nucleotide sequences to be integrated into a target locus (target site) in the genome of the stem cell, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site). In certain embodiments, the AAV Clade F vector or AAV vector variant that is administered treats the disease or disorder by genome editing of the cell of the subject. In certain embodiments, the in vivo genome editing may occur without additional exogenous nucleases. In certain embodiments, the one or more Clade F capsids or capsid variants comprise a polynucleotide or polypeptide sequence as provided herein. In certain embodiments, the polynucleotide or polypeptide sequence may be selected from the sequences provided in FIG. 1 of US Patent Publication Number 20130096182A1 or in FIG. 1 herein, variants, fragments, mutants, and combinations thereof. In certain embodiments, the AAV Clade F vectors or AAV vector variants are preferably administered in a therapeutically effective amount via a suitable route of administration, such as injection, inhalation, absorption, ingestion or other methods.

Previous studies, including Xu et al., Wang et al., and Carbonaro et al., have shown transduction of HSCs following in vivo delivery of a viral vector (see Xu 2004; Wang 2014; and Carbonaro 2006). However, all three of these studies involved either retroviruses (Xu 2004) or lentiviruses (Wang 2014 and Carbonaro 2006). Additionally, the injections in Xu et al. and Carbonaro et al. were performed in neonatal mice, and rapamycin and intrafemoral injection was required for efficient transduction in Wang et al. None of these papers, however, report transduction of HSCs by in vivo transduction of Clade F vectors or AAV vector variants into adult mice. The novel results provided in Example 3 are the first to show AAV vector transduction on HSCs by intravenous injection.

As shown in Example 3 below, intravenous injection of Clade F vectors (or AAV vector variants) pseudotyped with AAVF7 or AAVF17 resulted in transduction of human CD34+ hematopoietic stem and progenitor cells in vivo. The intravenous injected Clade F vectors or AAV vectors trafficked to sites of human hematopoiesis and transduced human cells. Intravenous injection of Clade F vectors or AAV vector variants resulted in Venus expression in human CD34+ stem progenitor cells as well as their CD45+ progeny. These data show that intravenous injection of Clade F vectors or AAV vector variants can be used for in vivo genome engineering without the need for stem cell harvest, ex vivo transduction, conditioning of the recipient, and subsequent transplantation of transduced cells. This approach makes stem cell gene therapy significantly safer, more accessible to patients worldwide, less expensive, and obviates the need for hospitalization.

In certain embodiments, methods of treating a disease or disorder in a subject by in vivo genome editing of a cell of the subject by directly administering an AAV Clade F vector or an AAV vector variant to the subject are disclosed. In certain embodiments, the AAV Clade F vector or AAV vector variant may comprise one or more Clade F capsids or capsid variants, an editing element (targeting cassette) comprising one or more therapeutic nucleotide sequences to be integrated into a target locus (target site) of the genome, a 5' homologous arm polynucleotide sequence flanking the editing element (targeting cassette) and having homology to a region that is upstream of the target locus (target site), and a 3' homologous arm polynucleotide sequence flanking the editing element (targeting cassette) and having homology to a region that is downstream of the target locus (target site), wherein the vector transduces a cell of the subject and integrates the one or more therapeutic nucleotide sequences into the genome of the cell. In certain embodiments, the one or more Clade F capsids or capsid variants may comprise a polypeptide sequence selected from the group of AAVF1

(SEQ ID NO: 2), AAVF2 (SEQ ID NO: 3), AAVF11 (SEQ ID NO: 4), AAVF3 (SEQ ID NO: 5), AAVF4 (SEQ ID NO: 6), AAVF6 (SEQ ID NO: 7), AAVF7 (SEQ ID NO: 8), AAVF8 (SEQ ID NO: 9), AAVF5 (SEQ ID NO: 10), AAVF5 (SEQ ID NO: 11), AAVF12 (SEQ ID NO: 12), AAVF17 (SEQ ID NO: 13), AAVF13 (SEQ ID NO: 14), AAVF14 (SEQ ID NO: 15), AAVF15 (SEQ ID NO: 16), AAVF16 (SEQ ID NO: 17), variants, fragments, mutants, and any combination thereof. In certain embodiments, the one or more Clade F capsids or capsid variants may comprise a polypeptide sequence of AAVF7 (SEQ ID NO: 8) or AAVF17 (SEQ ID NO: 13). In certain embodiments, the one or more Clade F capsids or capsid variants may comprise a polypeptide sequence of AAVF5 (SEQ ID NO: 11), AAVF (SEQ ID NO: 8) or AAVF17 (SEQ ID NO: 13). In certain embodiments, the AAV Clade F vector or AAV vector variant does not contain a promoter for the one or more therapeutic nucleotide sequences. In certain embodiments, the target locus (target site) may be a safe harbor site. In certain embodiments, the safe harbor site may be the AAVS1 locus on chromosome 19. In certain embodiments, the cell may be a stem cell. In certain embodiments, the stem cell may be a hematopoietic stem cell, a pluripotent stem cell, an embryonic stem cell, or a mesenchymal stem cell. In certain embodiments, the disease or disorder may be caused by one or more mutations in the cell genome. In certain embodiments, the disease or disorder may be selected from an inherited metabolic disease, lysosomal storage disease, mucopolysaccharidodosis, immunodeficiency disease, and hemoglobinopathy disease and infection.

Further demonstrating the efficacy of vivo applications, transplantation of transduced cells to immune-deficient mice with the isolate variants (relative to AAV9) resulted in prolonged and sustained transgene expression and may be used for gene therapy. In certain embodiments, when delivered systemically, these vectors display a tropism for the liver and cartilage, with implications for therapy of inherited, acquired, infectious and oncologic diseases. With respect to the liver transduction, the present AAV isolates have up to approximately 10-fold higher liver transduction levels than the current gold standard for systemic gene delivery to the liver, AAV8. This property can be exploited for gene-based enzyme replacement therapy from the liver for diseases such as hemophilia, enzyme deficiency diseases, and atherosclerosis. The additional tropism of the present AAV isolates for cartilaginous tissue in joints may be exploited for the treatment of bone disorders such as arthritis, osteoporosis or other cartilage/bone based diseases. The variant sequences and methods may accordingly be used for transient transduction where long term integration is not desirable.

Members of the AAV Clade F capsid family or AAV capsid variant family transduce HSC, e.g. AAVF 15 and AAVF 17, giving rise to long-term engraftment with sustained gene expression and are thus strong candidates for stem cell gene therapy vectors. AAVF17 and AAVF15 (also referred in abbreviated form as "HSC17" and "HSC15") supported the highest levels of long-term in vivo transduction, up to 22 weeks post-transplantation. Serial bioluminescent imaging following intravenous injection of the AAV variants revealed that AAVF15 generally supported the highest levels of long-term transgene expression in vivo. Other AAV variants including AAVF13 and 17 also supported strong in vivo transduction.

AAVF15 was found to be highly liver tropic, about 5-10 fold higher than AAV9. AAVF13 and AAVF15 also transduced the heart and skeletal muscle at least 10-fold better than AAV9. In vitro neutralization titers revealed that the prevalence of antibodies to AAVF 1-9 capsids in pooled human IVIG were similar to AAV9, while antibodies to AAVF13, AAVF15, AAVF16 and AAVF17 were somewhat less prevalent. In vivo neutralization assays confirmed that over 100-fold higher vector genome copies/cell were found in liver and muscle following IVIG administration with AAVF15 compared to AAV9, suggesting that pre-existing antibodies did not completely neutralize AAVF15. Muscle diseases or disorders may comprise any cell, tissue, organ, or system containing muscle cells which have a disease or disorder, including the heart, such as coronary heart disease or cardiomyopathy.

In addition, site-specific mutagenesis experiments indicate that the R505G mutation in AAVF15 is responsible for the enhanced liver tropism. The AAV Clade F vectors or AAV vector variants may be used to treat a whole host of genetic diseases such as hemophilia, atherosclerosis and a variety of inborn errors of metabolism. In one instance, AAVF15 effectively treats hemophilia B. Some members of this family also target the joints after systemic injection, which may be used to treat joint and cartilage diseases such as arthritis. Other members of the family target the heart upon intravenous injection. Yet other members of the family target the brain. In some embodiments, a vector comprising AAVF5 capsid proteins is provided as part of a method, kit or composition provided herein, as AAVF5 was shown to transduce multiple cell types (see FIG. 4).

In certain embodiments, methods of treating a neurological disease or disorder in a subject by genome editing may comprise administering an AAV Clade F vector or AAV vector variant capable of crossing the blood-brain barrier, blood-ocular barrier, or blood-nerve barrier. Certain of the AAV Clade F vectors or AAV vector variants disclosed herein have the unique ability to traverse the biological junctions that were previously unknown to be accessible to any vector for gene therapy or other diagnostic or therapeutic purposes using a modified viral vector. These junctions have common characteristics. The blood-brain barrier is a separation between blood circulating in the body and the brain extracellular fluid in the central nervous system and is created by tight junctions around capillaries. The blood-brain barrier generally allows only the passage of by diffusion of small hydrophobic molecules. The blood-ocular barrier is a separation made by between the local blood vessels and most parts of the eye and is made by endothelium of capillaries of the retina and iris. The blood-nerve barrier is the physiological space within which the axons, Schwann cells, and other associated cells of a peripheral nerve function and is made of endoneurial microvessels within the nerve fascicle and the investing perineurium. As with three of these barriers, there is restricted permeability to protect in the internal environment, here, the nerve, from drastic concentration changes in the vascular and other extracellular spaces. The vector that traverses any of these barriers has a unique ability to deliver one or more therapeutic nucleotide sequences for treating the neurological disease or disorder or to act as a labeled and or diagnostic agent. Certain of the AAV Clade F vectors or AAV vector variants that have been experimentally validated as being particularly well suited for crossing these biological barriers include AAVF15, AAVF15 A346T, and AAVF15 R505G.

There are many neurological diseases or disorders that are well known to one of skill in the art, which may be generally classified by cell or organ-type such as a disease or disorder of the brain, spinal cord, ganglia, motor nerve, sensory nerve, autonomic nerve, optic nerve, retinal nerve, and auditory nerve. By way of example, brain diseases or disorders may include cancer or other brain tumor, inflammation, bacterial infections, viral infections, including rabies, amoeba or parasite infections, stroke, paralysis, neurodegenerative disorders such as Alzheimer's Disease, Parkinson's Disease, or other dementia or reduction in cognitive functioning, plaques, encephalopathy, Huntington's Disease, aneurysm, genetic or acquired malformations, acquired brain injury, Tourette Syndrome, narcolepsy, muscular dystrophy, tremors, cerebral palsy, autism, Down Syndrome, attention deficit and attention deficit hyperactivity disorder, chronic inflammation, epilepsy, coma, meningitis, multiple sclerosis, myasthenia gravis, various neuropathies, restless leg syndrome, and Tay-Sachs disease.

Muscle diseases or disorders include, by way of example only, myopathies, chronic fatigue syndrome, fibromyalgia, muscular dystrophy, multiple sclerosis, atrophy, spasms, cramping, rigidity, various inflammations, such as dermatomyositis, rhabdomyolysis, myofacial pain syndrome, swelling, compartment syndrome, eosinophilia-myalgia syndrome, mitochondrial myopathies, myotonic disorder, paralysis, tendinitis, polymyalgia rheumatic, cancer, and tendon disorders such as tendinitis and tenosynovitis.

Heart diseases or disorders include, by way of example only, coronary artery disease, coronary heart disease, congestive heart failure, cardiomyopathy, myocarditis, pericardial disease, congenital heart disease, cancer, endocarditis, and valve disease.

Lung diseases or disorders include, by way of example only, asthma, allergies, chronic obstructive pulmonary disease, bronchitis, emphysema, cystic fibrosis, pneumonia, tuberculosis, pulmonary edema, cancer, acute respiratory distress syndrome, pneumonconiosis, and interstitial lung disease.

Liver diseases or disorders include, by way of example only, cancer, hepatitis A, B, and C, cirrhosis, jaundice, and liver disease. Kidney diseases or disorders include, by way of example only, cancer, diabetes, nephrotic syndrome, kidney stones, acquired kidney disease, congenital disease, polycystic kidney disease, nephritis, primary hyperoxaluria, and cystinuria. Spleen diseases or disorders include, by way of example only, cancer, splenic infarction, sarcoidosis, and Gaucher's disease. Bone diseases or disorders include, by way of example only, osteoporosis, cancer, low bone density, Paget's disease, and infection.

With any of these diseases or disorders treated using therapeutic nucleotide sequences or even small molecules transported by or with the AAV Clade F vectors or AAV vector variants, the therapeutic nucleotide sequence may be, by way of example, a nucleic acid encoding a protein therapeutic, such as for cancer—an apoptotic protein, miRNA, shRNA, siRNA, other RNA-subtypes or a combination thereof. In some embodiments, the vectors are isolated and purified as described herein. Isolation and purification are preferred in vivo administration to increase efficacy and reduce contamination. The vector may permanently or transiently transduce a transgene, which is a gene or other genetic material that has been isolated from one organism and introduced into another. Here, the other organism may be the subject receiving the vector.

In certain embodiments, the AAV Clade F vectors or AAV vector variants for genome editing may be selected based on experimental results of the highest efficacy in the given target cell or tissue for the given disease or disorder as shown herein. For example a) for muscle disease or disorders and for antibody genes or other vaccine treatments administered to the subject via the muscle, the AAV Clade F vector or AAV vector variant selected from the group of AAVF5, AAVF7, AAVF13, AAVF15, and AAVF17; b) for heart and lung disease or disorders, the vector selected from the group of AAVF13, AAVF15, and AAVF17; c) for liver or neurological diseases or disorders, the vector selected from AAVF5 and AAVF15; d) for conditions treated by engrafting stem cells, vector AAVF17; e) for conditions treated by transducing B cell progenitors, vector AAVF5; f) for conditions treated by transducing myeloid and erythroid progenitors, vector AAVF12; and g) for lymph node, kidney, spleen, cartilage and bone disease or disorders, the vector selected from the group of the vector selected from the group of AAVF7, AAVF13, AAVF15, and AAVF17; wherein the AAV Clade F vector or AAV vector variant transduces the cell or tissue and the one or more therapeutic nucleotide sequences are integrated into the genome of the cell and treat the disease or disorder. In certain embodiments, the AAV Clade F vector or AAV vector variant may comprise one or more Clade F capsids or capsid variants (relative to AAV9) that demonstrates tropism for a cell as described herein.

The subject is any animal for which the method works, but is preferably a mammal, which may be a human. If the vector contains an antibody gene or other vaccine treatment it may be administered via injection in the muscle and may provide immunological protection against diseases including from HIV, influenza, malaria, tetanus, measles, mumps, rubella, HPV, pertussis, or any other vaccine. The vector may be packaged, isolated, and purified and may transduce a stem cell of any type with the at least one therapeutic nucleotide sequence. The vector may also transduce a transgene or carry corrective genes endogenous to the subject and/or to the other subjects of the same species.

"AAV" is an adeno-associated virus. The term may be used to refer to the virus or derivatives thereof, virus subtypes, and naturally occurring and recombinant forms, unless otherwise indicated. AAV has over 100 different subtypes, which are referred to as AAV-1, AAV-2, etc., and includes both human and non-human derived AAV. There are about a dozen AAV serotypes. The various subtypes of AAVs can be used as recombinant gene transfer viruses to transduce many different cell types.

"Recombinant," as applied to a polynucleotide means that the polynucleotide is the product of various combinations of cloning, restriction or ligation steps, and other procedures that result in a construct that is distinct from a naturally-occurring polynucleotide. A recombinant virus is a viral particle comprising a recombinant polynucleotide, including replicates of the original polynucleotide construct and progeny of the original virus construct. A "rAAV vector" refers to a recombinant AAV vector comprising a polynucleotide sequence not of AAV origin (i.e., a polynucleotide heterologous to AAV), which is usually a sequence of interest for the genetic transformation of a cell.

A "helper virus" for AAV as used herein is virus that allows AAV to be replicated and packaged by a mammalian cell. Helper viruses for AAV are known in the art, and include, for example, adenoviruses (such as Adenovirus type 5 of subgroup C), herpes viruses (such as herpes simplex viruses, Epstein-Bar viruses, and cytomegaloviruses) and poxviruses.

"Joint tissue" is comprised of a number of tissues including cartilage, synovial fluid, and mature, progenitor and stem cells that give rise to, or are: (i) cartilage producing cells; (ii) Type I synoviocytes; (iii) Type II synoviocytes; (iv) resident or circulating leukocytes; (v) fibroblasts; (vi) vascular endothelial cells; and (vii) pericytes.

A "replication-competent" virus refers to a virus that is infectious and capable of being replicated in an infected cell. In the case of AAV, replication competence generally requires the presence of functional AAV packaging genes, as well as helper virus genes, such as adenovirus and herpes simplex virus. In general, rAAV vectors are replication-incompetent (also referred to herein as replication-defective) because they lack of one or more AAV packaging genes. In some embodiments, an AAV may be considered replication defective (or replication-incompetent) if the AAV has an essential absence of an AAV rep gene and/or an AAV cap gene. In some embodiments, an AAV may be considered replication defective (or replication-incompetent) if the AAV lacks an AAV rep gene and/or an AAV cap gene. In some embodiments, a composition comprising AAV Clade F vectors or AAV variant isolates is a cell-free composition. The composition is generally free of cellular proteins and/or other contaminants and may comprise additional elements such as a buffer (e.g., a phosphate buffer, a Tris buffer), a salt (e.g., NaCl, MgCl2), ions (e.g., magnesium ions, manganese ions, zinc ions), a preservative, a solubilizing agent, or a detergent, (e.g., a non-ionic detergent; dimethylsulfoxide).

In another embodiment, an expression cassette comprises a polynucleotide sequence encoding a polypeptide comprising one or more of the Clade F capsids or AAV variant isolates, wherein the polynucleotide sequence encoding the polypeptide comprises a sequence having at least about 95%, 96%, 97%, more preferably about 98%, and most preferably about 99% sequence identity to the sequences taught in the present specification. Percentage identity may be calculated using any of a number of sequence comparison programs or methods such as the Pearson & Lipman, Proc. Natl. Acad. Sci. USA, 85:2444 (1988), and programs implementing comparison algorithms such as GAP, BESTFIT, FASTA, or TFASTA (from the Wisconsin Genetics Software Package, Genetics Computer Group, 575 Science Drive, Madison, Wis.), or BLAST, available through the National Center for Biotechnology Information web site.

In another aspect, an expression cassette comprises a polynucleotide sequence encoding a polypeptide comprising one or more of the Clade F capsids or AAV variant isolates, wherein the sequence is comprised of portions of the three genes comprising the capsid protein, V1-V3 (also referred to as VP1-VP3). For example, the cassette may comprise V1 from capsid AAVF1, a standard V2 as compared to AAV9 hu.14, and V3 from AAVF17 capsids. In yet another embodiment, a capsid may comprise more than one of each of the capsid gene components. For example, Clade F capsids or capsid variants may be selected from any of the VP1-VP3 (V1-V3) for the capsid sequences set forth herein and may be combined in any order and in any combination so long as the desired property of increased transduction is achieved. For example, the capsid sequence could be VP1A-VP1B-VP2-VP3 (V1A-V1B-V2-V3), VP3-VP1-VP2 (V3-V1-V2), or VP1-VP2-VP3A-VP3B (V1-V2-V3A-V3B).

Another embodiment includes methods of immunization of a subject. Compositions comprising the Clade F capsids or capsid variants may be introduced into a subject in a manner that causes an immunological reaction resulting in immunity in the subject. The Clade F capsids or capsid variants may be in the composition alone or as part of an expression cassette. In one embodiment, the expression cassettes (or polynucleotides) can be introduced using a gene delivery vector. The gene delivery vector can, for example, be a non-viral vector or a viral vector. Exemplary viral vectors include, but are not limited to Sindbis-virus derived vectors, retroviral vectors, and lentiviral vectors.

Compositions useful for generating an immunological response can also be delivered using a particulate carrier. Further, such compositions can be coated on, for example, gold or tungsten particles and the coated particles delivered to the subject using, for example, a gene gun. The compositions can also be formulated as liposomes. In one embodiment of this method, the subject is a mammal and can, for example, be a human.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., EMBO J. 4:1075, 1985; Nilsson et al., Methods Enzymol. 198:3, 1991), glutathione S transferase (Smith and Johnson, Gene 67:31, 1988), Glu-Glu affinity tag (Grussenmeyer et al., Proc. Natl. Acad. Sci. USA 82:7952-4, 1985), substance P, Flag™ peptide (Hopp et al., Biotechnology 6:1204-10, 1988), streptavidin binding peptide, or other antigenic epitope or binding domain. See, in general, Ford et al., Protein Expression and Purification 2: 95-107, 1991, DNAs encoding affinity tags are available from commercial suppliers (e.g., Pharmacia Biotech, Piscataway, N.J.).

Of the number of affinity tag purification systems available, the most frequently employed utilize polyhistidine (His) or glutathione S-transferase (GST) tags. His binds with good selectivity to matrices incorporating $Ni^{+2}$ ions, typically immobilized with either iminodiacetic acid or nitrilotriacetic acid chelating groups. The technique is known as immobilized metal affinity chromatography. Absorption of the His-tagged protein is performed at neutral to slightly alkaline pH to prevent protonation and loss of binding capacity of the weakly basic histidine imidazole groups. Elution of the bound protein is caused by displacement with imidazole or low pH conditions.

Methods of generating induced pluripotent stem cells from somatic cells without permanent introduction of foreign DNA are also described. The method involved transiently transducing stem cells with vectors comprising a Clade F capsid or capsid variant nucleotide sequence as described herein encoding a polypeptide sequence, or VP1 (V1) or VP3 (V3) portion thereof.

For these and other experiments, a person skilled in the art knows how to modify and propagate AAV. For example, AAV-2 can be propagated both as lytic virus and as a provirus. For lytic growth, AAV requires co-infection with a helper virus. Either adenovirus or herpes simplex can supply helper function. When no helper is available, AAV can persist as an integrated provirus, which involves recombination between AAV termini and host sequences and most of the AAV sequences remain intact in the provirus. The ability of AAV to integrate into host DNA allows propagation absent a helper virus. When cells carrying an AAV provirus are subsequently infected with a helper, the integrated AAV genome is rescued and a productive lytic cycle occurs. The construction of rAAV vectors carrying particular modifications and the production of rAAV particles, e.g., with modified capsids, is described, e.g., in Shi et al. (2001), Human Gene Therapy 12:1697-1711; Rabinowitz et al. (1999), Virology 265:274-285; Nicklin et al. (2001), Molecular Therapy 4:174-181; Wu et al. (2000), J. Virology 74:8635-8647; and Grifman et al. (2001), Molecular Therapy 3:964-974.

Yet another aspect relates to a pharmaceutical composition containing an AAV Clade F vector or AAV vector variant or AAV particle as described herein. The pharmaceutical composition containing an AAV Clade F vector or AAV vector variant or particle, preferably, contains a pharmaceutically acceptable excipient, adjuvant, diluent, vehicle or carrier, or a combination thereof. A "pharmaceutically acceptable carrier" includes any material which, when combined with an active ingredient of a composition, allows the ingredient to retain biological activity and without causing disruptive physiological reactions, such as an unintended immune reaction. Pharmaceutically acceptable carriers include water, phosphate buffered saline, emulsions such as oil/water emulsion, and wetting agents. Compositions comprising such carriers are formulated by well-known conventional methods such as those set forth in Remington's Pharmaceutical Sciences, current Ed., Mack Publishing Co., Easton Pa. 18042, USA; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., 7th ed., Lippincott, Williams, & Wilkins; and Handbook of Pharmaceutical Excipients (2000) A. H. Kibbe et al., 3rd ed. Amer. Pharmaceutical Assoc. Such carriers can be formulated by conventional methods and can be administered to the subject at a suitable dose. Administration of the suitable compositions may be effected by different ways, e.g. by intravenous, intraperitoneal, subcutaneous, intramuscular, topical or intradermal administration. In some embodiments, the composition is formulated for administration to a mammal. In some embodiments, the composition is formulated for administration to a mammal via intravenous injection, subcutaneous injection, intramuscular injection, autologous cell transfer, or allogeneic cell transfer. The route of administration, of course, depends, inter alia, on the kind of vector contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and stage of infection or disease, general health and other drugs being administered concurrently.

Some of the AAV Clade F vectors or capsid variants are capable of supporting long-term stable transgene expression in vivo after transplantation of transduced hematopoietic stem cells or after direct systemic delivery of rAAV.

In certain embodiments, a nucleic acid comprising the Clade F capsids or AAV capsid isolate variants may be inserted into the genome of a new virus, where in the addition of the Clade F capsid or capsid isolate variant genes transmits the same or similar tissue or organ tropisms of the Clade F capsids or AAV capsid isolates to the new virus. Such gene therapy may be effected using in vivo and ex vivo gene therapy procedures; see, e.g., U.S. Pat. No. 5,474,935; Okada, Gene Ther. 3:957-964, 1996. Gene therapy using the AAV Clade F capsid or AAV capsid variant gene will typically involve introducing the target gene in vitro into the new virus, either alone or with another gene intended for therapeutic purposes. If the tropic gene is introduced with one or more additional genes, preferably the resulting polypeptides are administered for therapeutic purposes in the tissue for which the Clade F capsid or AAV isolate has a tropism. The virus may then be administered to patient in need of such therapy or may be administered ex vivo, such as to an organ awaiting transplant. The virus may be a retrovirus, an RNA virus, a DNA virus such as an adenovirus vector, an adeno-associated virus vector, a vaccinia virus vector, a herpes virus vector, and the like. A transfection method using a virus vector that uses a liposome for administration in which the new virus vector is encapsulated is also contemplated.

According to certain embodiments provided herein, kits are provided that comprise one or more AAV Clade F vectors or AAV vector variants described herein or compositions or formulations thereof. In certain embodiments, the one or more AAV Clade F vectors or AAV vector variants in the kits may be used for genome editing of a cell. In certain embodiments, the kit may be used as a research tool to investigate the effect of genome editing by the one or more AAV Clade F vectors or AAV vector variants.

Other aspects of the disclosure relate to a packaging system for recombinant preparation of an AAV as described herein (e.g., an AAV Clade F vector or an AAV variant vector) and methods of use thereof. In some embodiments, the packaging system comprises a Rep nucleotide sequence encoding one or more AAV Rep proteins; a Cap nucleotide sequence encoding one or more AAV Cap proteins of an AAV Clade F capsid as described herein; and a correction genome as described herein, wherein the packaging system is operative in a cell for enclosing the correction genome in the capsid to form an adeno-associated virus.

In some embodiments, the packaging system comprises a first vector comprising the Rep nucleotide sequence and the Cap nucleotide sequence, and a second vector comprising the correction genome. As used in the context of a packaging system as described herein, a "vector" refers to a nucleic acid molecule that is a vehicle for introducing nucleic acids into a cell (e.g., a plasmid, a virus, a cosmid, an artificial chromosome, etc.).

In some embodiments of the packaging system, the AAV Clade F capsid comprises at least one or at least two proteins selected from Clade F VP1, Clade F VP2 and Clade F VP3. In some embodiments of the packaging system, the AAV Clade F capsid comprises Clade F VP1, Clade F VP2 and Clade F VP3 proteins. In some embodiments of the packaging system, the AAV Clade F capsid is selected from the group consisting of AAV9, AAVHSC1, AAVHSC2, AAVHSC3, AAVHSC4, AAVHSC5, AAVHSC6, AAVHSC7, AAVHSC8, AAVHSC9, AAVHSC10, AAVHSC11, AAVHSC12, AAVHSC13, AAVHSC14, AAVHSC15, AAVHSC16, AAVHSC17, AAVHU31, and AAVHU32.

In some embodiments of the packaging system, the Rep nucleotide sequence encodes an AAV2 Rep protein. In some embodiments of the packaging system, the AAV2 Rep protein encoded is at least one of Rep 78/68 or Rep 68/52. In some embodiments of the packaging system, the nucleotide sequence encoding the AAV2 Rep protein comprises a nucleotide sequence that encodes a protein having a minimum percent sequence identity to the AAV2 Rep amino acid sequence of SEQ ID NO:40, wherein the minimum percent sequence identity is at least 70% (e.g., at least 75%, at least 80%, at least 85%, at least 90%, at least 95%, at least 98%, at least 99%, or 100%) across the length of the amino acid sequence of the AAV2 Rep protein.

Exemplary AAV2 Rep amino acid sequence (SEQ ID NO: 40)—mpgfyeivikvpsdldehlpgisdsfvnwvaekewelppdsdmdln-lieqapltvaeklqrdfltewayskapealffv qfekgesyfhmhvl-vettgvksmvlgrflsqirekliqriyrgieptlpnwfavtktrngagggnkvv-decyipnyllpktqpelq
wawtnmeqylsaclniterkrlvaqhlthvsqtqeqnkenqnpnsdapvir-sktsarymelvgwlvdkgitsekqwiqedqas yisfnaasnsrsqikaaldnagkimsltktapdylvgqqpvedissnriykilelngydpqyaasvflg-
watkkfgkrntiwlfgpa
ttgktniaeaiahtvpfygcvnwt-
nenfpfndcvdkmviwweegkmtakvvesakailggskvrvdqkcks-
saqidptpvivt sntnmcavidgnsttfehqqplqdrmfkfel-
trrldhdfgkvtkqevkdffrwakdhvvevehefyvkkggakkrpapsdadis
epkrvresvaqpstsdaeasinyadryqnkcsrhvgmnlmlfperqcer-
mnqnsnicfthgqkdclecfpvsesqpvsvvkka yqklcyihhimgkvp-
dactacdlvnvdlddcifeq In some embodiments of the packaging system, the packaging system further comprises a third vector, e.g., a helper virus vector. The third vector may be an independent third vector, integral with the first vector, or integral with the second vector. In some embodiments, the third vector comprises genes encoding helper virus proteins.

In some embodiments of the packaging system, the helper virus is selected from the group consisting of adenovirus, herpes virus (including herpes simplex virus (HSV)), poxvirus (such as vaccinia virus), cytomegalovirus (CMV), and baculovirus. In some embodiments of the packaging system, where the helper virus is adenovirus, the adenovirus genome comprises one or more adenovirus RNA genes selected from the group consisting of E1, E2, E4 and VA. In some embodiments of the packaging system, where the helper virus is HSV, the HSV genome comprises one or more of HSV genes selected from the group consisting of UL5/8/52, ICP0, ICP4, ICP22 and UL30/UL42.

In some embodiments of the packaging system, the first, second, and/or third vector are contained within one or more transfecting plasmids. In some embodiments, the first vector and the third vector are contained within a first transfecting plasmid. In some embodiments the second vector and the third vector are contained within a second transfecting plasmid.

In some embodiments of the packaging system, the first, second, and/or third vector are contained within one or more recombinant helper viruses. In some embodiments, the first vector and the third vector are contained within a recombinant helper virus. In some embodiments, the second vector and the third vector are contained within a recombinant helper virus.

In some aspects, the disclosure provides a method for recombinant preparation of an AAV as described herein (e.g., an AAV Clade F vector or AAV variant vector), wherein the method comprises transfecting or transducing a cell with a packaging system as described under conditions operative for enclosing the correction genome in the capsid to form the AAV as described herein (e.g., an AAV Clade F vector or AAV variant vector). Exemplary methods for recombinant preparation of an AAV include transient transfection (e.g., with one or more transfection plasmids containing a first, and a second, and optionally a third vector as described herein), viral infection (e.g. with one or more recombinant helper viruses, such as a adenovirus, poxvirus (such as vaccinia virus), herpes virus (including herpes simplex virus (HSV), cytomegalovirus, or baculovirus, containing a first, and a second, and optionally a third vector as described herein), and stable producer cell line transfection or infection (e.g., with a stable producer cell, such as a mammalian or insect cell, containing a Rep nucleotide sequence encoding one or more AAV Rep proteins and/or a Cap nucleotide sequence encoding one or more AAV Cap proteins of an AAV Clade F capsid as described herein, and with a correction genome as described herein being delivered in the form of a transfecting plasmid or a recombinant helper virus).

Other exemplary, non-limiting embodiments of the disclosure are provided below.

Embodiment 1. An adeno-associated virus (AAV) vector variant for editing the genome of a stem cell comprising one or more capsid variants; a targeting cassette comprising one or more therapeutic nucleotide sequences to be integrated into a target site of the genome; a 5' homologous arm polynucleotide sequence flanking the targeting cassette and having homology to a region that is upstream of the target site; and a 3' homologous arm polynucleotide sequence flanking the targeting cassette and having homology to a region that is downstream of the target site.

Embodiment 2. The AAV vector variant of embodiment 1, wherein the one or more capsid variants comprise a polypeptide sequence selected from the group of HSC7 (SEQ ID NO: 8), HSC12 (SEQ ID NO: 12), HSC15 (SEQ ID NO: 16), HSC17 (SEQ ID NO: 13), variants, fragments, mutants and any combination thereof.

Embodiment 3. The AAV vector variant of embodiment 2, wherein the one or more capsid variants comprise a polypeptide sequence having a percent sequence identity of at least 95% to a polypeptide sequence selected from the group of HSC7 (SEQ ID NO: 8), HSC12 (SEQ ID NO: 12), HSC15 (SEQ ID NO: 16), HSC17 (SEQ ID NO: 13), variants, fragments, mutants and any combination thereof.

Embodiment 4. The AAV vector variant of embodiment 1, wherein the target site is a safe harbor site.

Embodiment 5. The AAV vector variant of embodiment 4, wherein the safe harbor site is the AAVS1 locus on chromosome 19.

Embodiment 6. The AAV vector variant of embodiment 1, wherein the stem cell is a hematopoietic stem cell, a pluripotent stem cell, an embryonic stem cell, or a mesenchymal stem cell.

Embodiment 7. A method of editing the genome of a stem cell, comprising transducing, without additional exogenous nucleases, the stem cell with one or more adeno-associated virus (AAV) vector variants comprising one or more capsid variants; a targeting cassette comprising one or more therapeutic nucleotide sequences to be integrated into a target site of the genome; a 5' homologous arm polynucleotide sequence flanking the targeting cassette and having homology to a region that is upstream of the target site; and a 3' homologous arm polynucleotide sequence flanking the targeting cassette and having homology to a region that is downstream of the target site.

Embodiment 8. The method of embodiment 7, wherein the one or more capsid variants comprise a polypeptide sequence selected from the group of HSC7 (SEQ ID NO: 8), HSC12 (SEQ ID NO: 12), HSC15 (SEQ ID NO: 16), HSC17 (SEQ ID NO: 13), variants, fragments, mutants and any combination thereof.

Embodiment 9. The method of embodiment 7, wherein the AAV vector variant does not contain a promoter for the one or more therapeutic nucleotide sequences.

Embodiment 10. The method of embodiment 7, wherein the target site is a safe harbor site.

Embodiment 11. The method of embodiment 10, wherein the safe harbor site is the AAVS1 locus on chromosome 19.

Embodiment 12. The method of embodiment 7, wherein the stem cell is a hematopoietic stem cell, a pluripotent stem cell, an embryonic stem cell, or a mesenchymal stem cell.

Embodiment 13. A method of treating a disease or disorder in a subject by editing a genome of a stem cell of the subject, comprising transducing, without additional exogenous nucleases, the stem cell of the subject with an adeno-associated virus (AAV) vector variant comprising one or more capsid variants; a targeting cassette comprising one or more therapeutic nucleotide sequences to be integrated into a target site in the genome of the stem cell; a 5' homologous arm polynucleotide sequence flanking the targeting cassette and having homology to a region that is upstream of the target site; a 3' homologous arm polynucleotide sequence flanking the targeting cassette and having homology to a region that is downstream of the target site; and transplanting the transduced stem cell into the subject, wherein the transduced stem cell treats the disease or disorder.

Embodiment 14. The method of embodiment 13, wherein the one or more capsid variants comprise a polypeptide sequence from the group of HSC7 (SEQ ID NO: 8), HSC12 (SEQ ID NO: 12), HSC15 (SEQ ID NO: 16), HSC17 (SEQ ID NO: 13), variants, fragments, mutants and any combination thereof.

Embodiment 15. The method of embodiment 13, wherein the AAV vector variant does not contain a promoter for the one or more therapeutic nucleotide sequences.

Embodiment 16. The method of embodiment 13, wherein the target site is a safe harbor site.

Embodiment 17. The method of embodiment 16, wherein the safe harbor site is the AAVS1 locus on chromosome 19.

Embodiment 18. The method of embodiment 13, wherein the stem cell is a hematopoietic stem cell, a pluripotent stem cell, an embryonic stem cell, or a mesenchymal stem cell.

Embodiment 19. The method of embodiment 13, wherein the disease or disorder is caused by one or more mutations in the cell genome.

Embodiment 20. The method of embodiment 19, wherein the disease or disorder is selected from an inherited metabolic disease, lysosomal storage disease, mucopolysaccharidosis, immunodeficiency disease, and hemoglobinopathy disease and infection.

Embodiment 21. A method of treating a disease or disorder in a subject by in vivo genome editing of a cell of the subject by directly administering an AAV vector variant to the subject, said vector comprising one or more capsid variants; a targeting cassette comprising one or more therapeutic nucleotide sequences to be integrated into a target site of the genome; a 5' homologous arm polynucleotide sequence flanking the targeting cassette and having homology to a region that is upstream of the target site; and a 3' homologous arm polynucleotide sequence flanking the targeting cassette and having homology to a region that is downstream of the target site, wherein the vector transduces the cell of the subject and integrates the one or more therapeutic nucleotide sequences into the genome of the cell.

Embodiment 22. The method of embodiment 21, wherein the one or more capsid variants comprise a polypeptide sequence selected from the group of HSC1 (SEQ ID NO: 2), HSC2 (SEQ ID NO: 3), HSC11 (SEQ ID NO: 4), HSC3 (SEQ ID NO: 5), HSC4 (SEQ ID NO: 6), HSC6 (SEQ ID NO: 7), HSC7 (SEQ ID NO: 8), HSC8 (SEQ ID NO: 9), HSC9 (SEQ ID NO: 10), HSCS (SEQ ID NO: 11), HSC12 (SEQ ID NO: 12), HSC17 (SEQ ID NO: 13), HSC13 (SEQ ID NO: 14), HSC14 (SEQ ID NO: 15), HSC15 (SEQ ID NO: 16), HSC16 (SEQ ID NO: 17), variants, fragments, mutants, and any combination thereof.

Embodiment 23. The method of embodiment 21, wherein the cell is a stem cell.

Embodiment 24. The method of embodiment 23, wherein the stem cell is a hematopoietic stem cell, a pluripotent stem cell, an embryonic stem cell, or a mesenchymal stem cell.

Embodiment 25. The method of embodiment 24, wherein the disease or disorder is caused by one or more mutations in the cell genome.

Embodiment 26. The method of embodiment 25, wherein the disease or disorder is selected from an inherited metabolic disease, lysosomal storage disease, mucopolysaccharidosis, immunodeficiency disease, and hemoglobinopathy disease and infection.

Embodiment 27. The method of embodiment 21, wherein the AAV vector variant does not contain a promoter for the one or more therapeutic nucleotide sequences.

Embodiment 28. The method of embodiment 22, wherein the target site is a safe harbor site.

Embodiment 29. The method of embodiment 23, wherein the safe harbor site is the AAVS1 locus on chromosome 19.

The following examples are intended to illustrate various embodiments of the disclosure. As such, the specific embodiments discussed are not to be construed as limitations on the scope of the invention. It will be apparent to one skilled in the art that various equivalents, changes, and modifications may be made without departing from the scope of the disclosure, and it is understood that such equivalent embodiments are to be included herein. Further, all references cited in the disclosure are hereby incorporated by reference in their entirety, as if fully set forth herein.

EXAMPLES

Example 1: AAV Clade F Vector Variant Mediated Genome Editing in a CD34+ Human Hematopoietic Stem Cell Line or a K562 Cell Line Genome editing through site-specific insertion or targeted integration of specific DNA sequences using AAVF (AAVHSC) vectors without the use of an exogenous nuclease was performed in human CD34+ hematopoietic cell lines from healthy donors or the K562 cell line, which is a CD34+ erythroleukemic cell line. One set of donor recombinant AAV vectors, ITR-AAVS1-FP vectors, was constructed and was used to integrate a transgene into the AAVS1 locus on chromosome 19, the natural wild-type AAV integration site (Kotin, 1992; Giraud, 1994). The AAVS1 locus on chromosome 19 qter13.3-13.4 was previously shown to be a "safe harbor" site for the insertion of transgenes since genes inserted here are expressed with no pathogenic consequences, which is similar to wild-type AAV that integrates at this locus with no pathogenic consequences (Giraud, 1994; Linden, 1996A; Linden 1996B). The transgene to be integrated was a Venus yellow fluorescent protein ("YFP" or "FP") gene, which was flanked on each side by approximately 800 nucleotides having homology with the AAVS1 locus on human chromosome 19 (see schematic in FIG. 3). The donor AAV vector was designed such that the transgene was promoterless and would only be expressed if it was integrated at the correct locus, which would be downstream from chromosomally encoded regulatory sequences (see FIG. 4). Thus, any Venus YFP transgene expression that occurred was under the control of a chromosomal promoter located in or near AAVS1.

The donor vector, ITR-AAVS1-FP, was packaged into AAVHSC capsids according to the standard AAV packaging method described in Chatterjee et al, 1992. Specifically, ITR-AAVS1-FP was packaged into AAVHSC7, AAVHSC15, or AAVHSC17 capsids forming the pseudotyped AAVHSC-AAVS1-FP vector (i.e., a AAV vector variant). Human CD34+ hematopoietic stem cell lines or K562 cells were transduced with the pseudotyped AAVHSC-AAVS1-FP at different multiplicities of infection (MOI) (i.e., 50,000 MOI; 100,000 MOI; 200,000 MOI; 300,000 MOI; and 400,000 MOI).

Figure 7A:
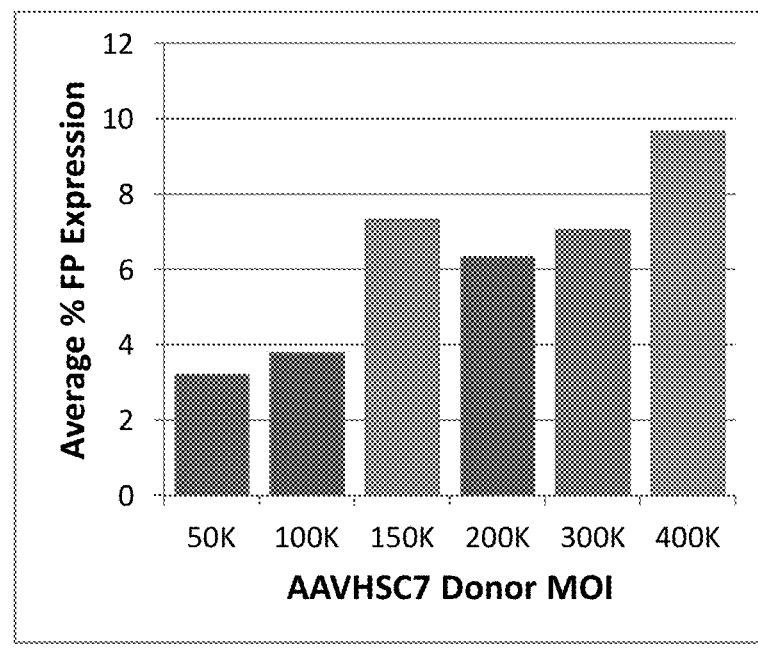
FIGS. 7A-7B show the average percentage of YFP expression following targeted integration of the promoterless YFP transgene in the AAVS1 locus in CD34+ K562 leukemic cells. (A) A bar graph showing YFP expression 24 hours post-transduction with AAVF7 vector in cells with MOIs of 50,000; 100,000; 150,000; 200,000; 300,000; and 400,000. (B) A bar graph showing YFP expression 72 hours post-transduction with AAVF7 vector in cells with MOIs of 50,000; 100,000; 150,000; 200,000; and 400,000. Each bar represents data compiled from up to 7 samples.
Figure 7B:
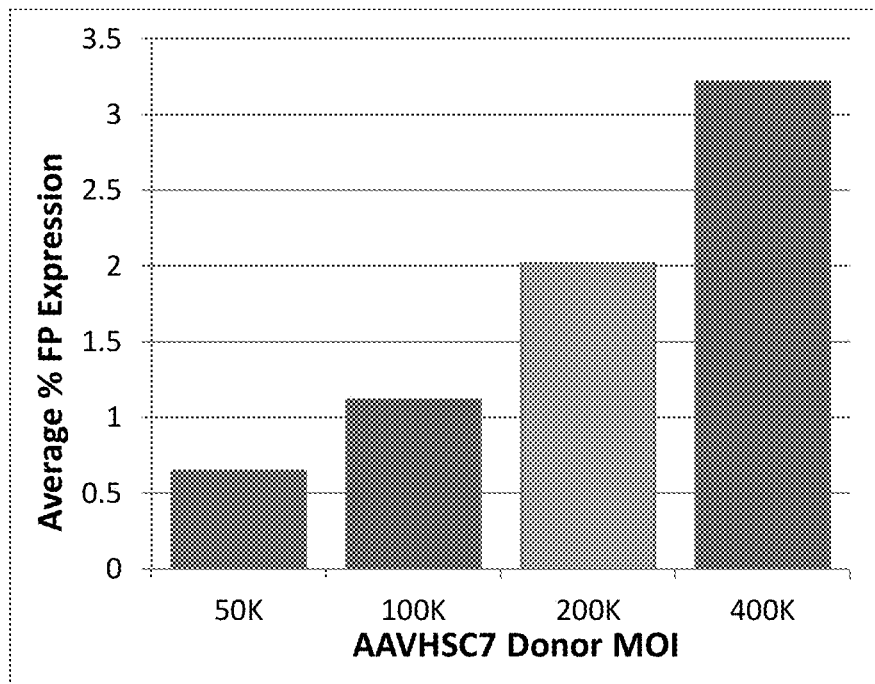

Integration of the YFP transgene into the AAVS1 locus by homologous recombination was initially assayed by cytofluorometric analysis of YFP expression in transduced K562 cells. Targeted integration using the AAVHSC7 FP vector resulted in expression of the YFP transgene 24 hours post-transduction (FIGS. 5 and 7A) and 72 hours post-transduction (FIGS. 6 and 7B). Additionally, as the MOI of the AAVHSC7 FP vector was increased, the average percentage of YFP expression also increased (FIGS. 7A and B).

Figure 4A:
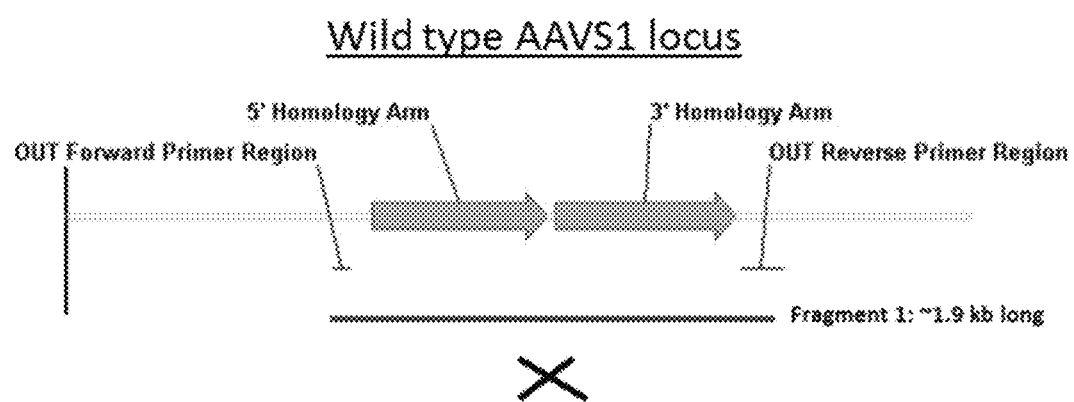
FIGS. 4A-4B show a schematic map of the targeted chromosomal AAVS1 locus and the edited AAVS1 locus that was the target site for transgene integration mediated by the AAVF vector. The top schematic (FIG. 4A), "Wild type AAVS1 locus", illustrates the wild-type AAVS1 locus that contains a 5' homology arm and a 3' homology arm, but does not contain a transgene. Amplification with primers located outside of the homology region using an "OUT Forward Primer Region" primer and an "OUT Reverse Primer Region" primer results in a fragment-1.9 kb long (see line labeled "Fragment 1"), which indicates that the fragment does not contain an integrated transgene. The bottom schematic (FIG. 4B), "Edited AAVS1 locus", illustrates the edited AAVS1 locus which contains a 5' homology arm, regulatory elements, an integrated transgene, and the 3' homology arm. Amplification with primers located outside of the homology region using an "OUT Forward Primer Region" primer and an "OUT Reverse Primer Region" primer results in a fragment ~3.0 kb long (see line labeled "Fragment 2"), which indicates that the fragment contains a transgene. Amplification of the 5' junction region (the junction between the 5' homology arm and the transgene) using an "OUT Forward Primer Region" primer and an "In Reverse Primer" results in a fragment-1.7 kb long (see line labeled "Fragment 3"). Amplification of the 3' junction region (the junction between the transgene and the 3' homology arm) using an "OUT Reverse Primer Region" primer and an "In Forward Primer" results in a fragment-1.2 kb long (see line labeled "Fragment 4"). If the transgene is not integrated, there is no resulting product upon amplification of the 5' junction region or the 3' junction region.
Figure 4B:
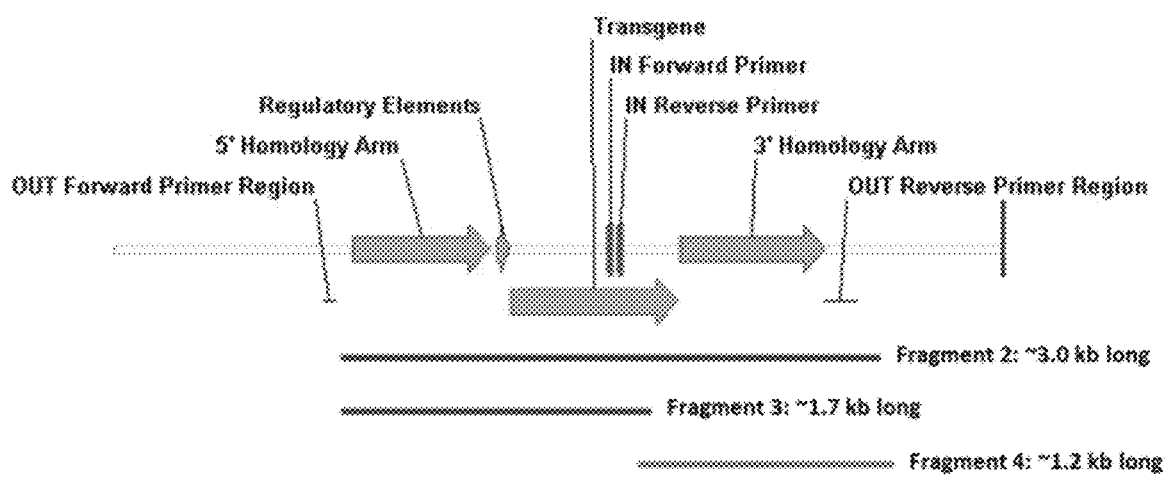
Figure 5A:
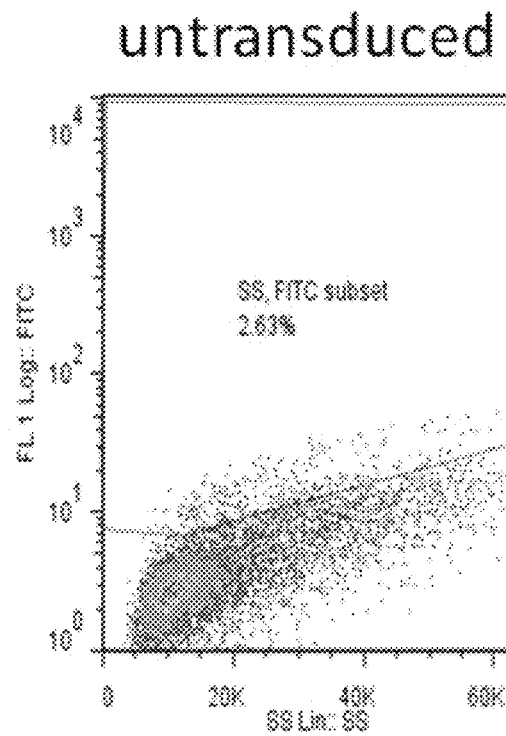
FIGS. 5A-5E show representative scatter plots from flow cytometric analyses of YFP expression in K562 cells 24 hours after transduction. Cells were transduced with the AAVF7 FP vector at a variety of multiplicity of infections (MOIs) (A) Cells not transduced with any vector (untransduced), (B) 50,000 MOI, (C) 100,000 MOI, (D) 200,000 MOI, and (E) 400,000 MOI. Data shown is from representative samples. Events above the line of demarcation within each scatter plot represent FP expressing cells, indicating that in these cells, the promoterless FP gene from the Donor ITR-AAVS1-FP vector integrated correctly into AAVS1 in the human chromosome 19, downstream from the endogenous chromosomal promoter.
Figure 5B:
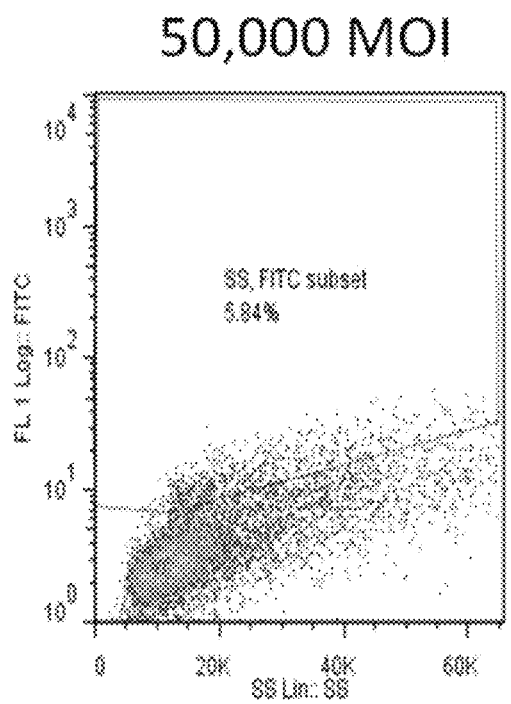
Figure 5C:
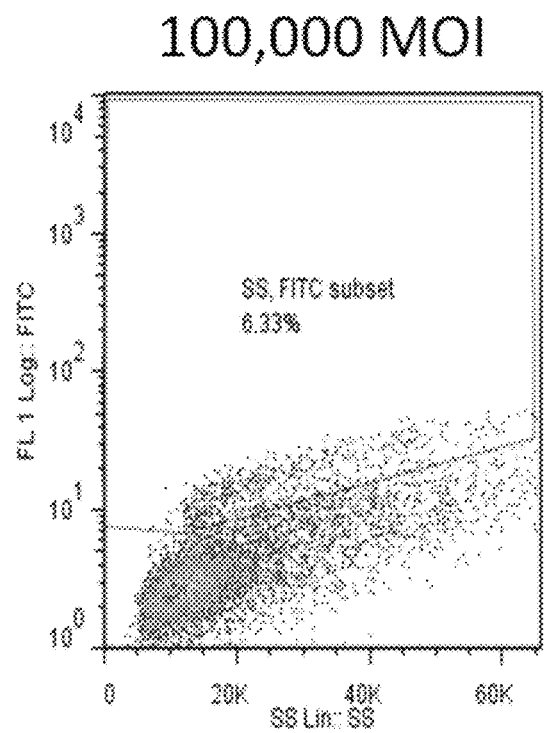
Figure 5D:
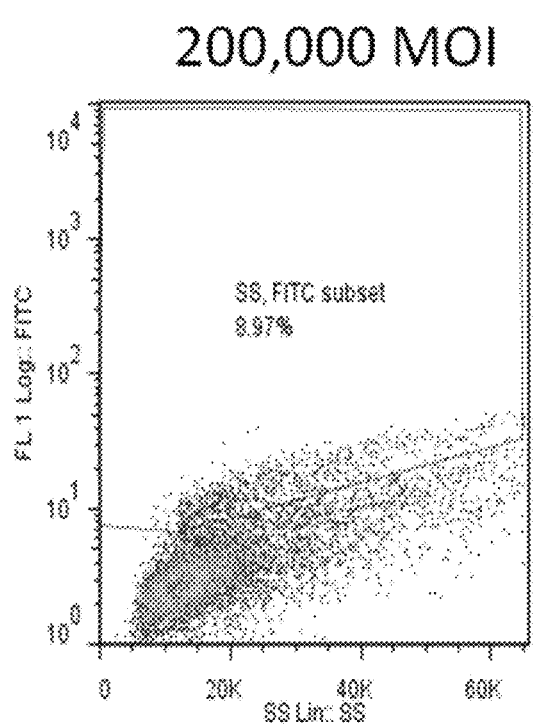
Figure 5E:
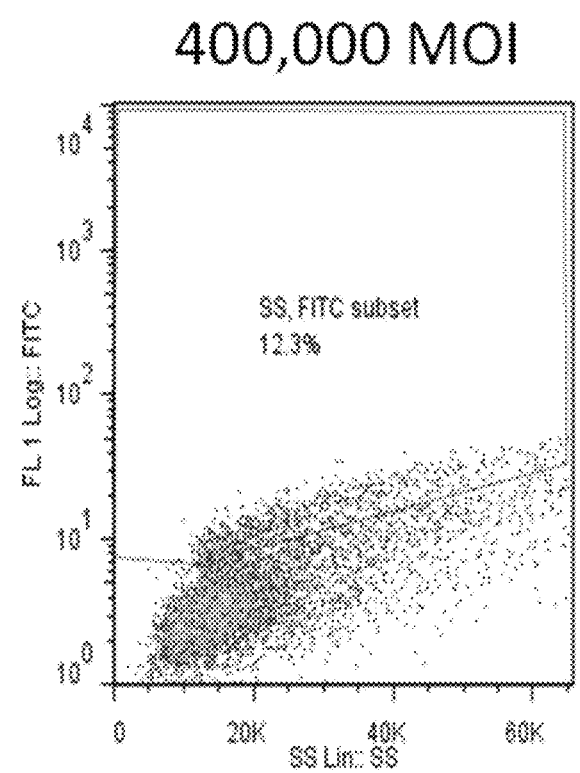
Figure 6A:
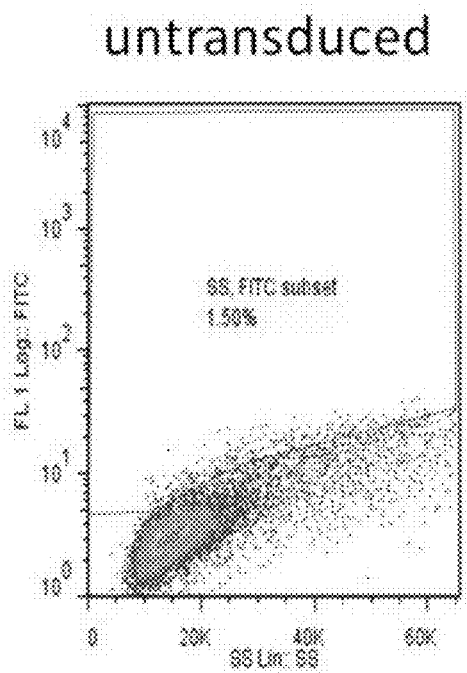
FIGS. 6A-6E show representative scatter plots from flow cytometric analyses of YFP expression in K562 cells 72 hours after transduction. Cells were transduced with the AAVF7 FP vector at variety of multiplicity of infections (MOIs) (A) Cells not transduced with any vector (untransduced), (B) 50,000 MOI, (C) 100,000 MOI, (D) 200,000 MOI, and (E) 400,000 MOI. Events above the line of demarcation represent cells with correctly targeted integration of the promoterless FP gene in the Donor ITR-AAVS1-FP vector.
Figure 6B:
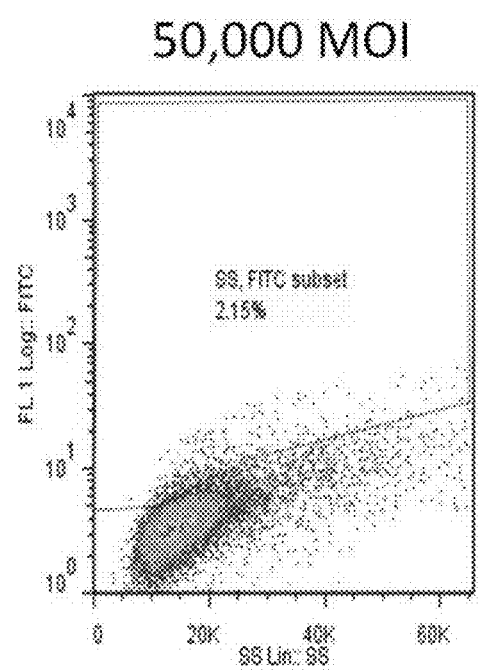
Figure 6C:
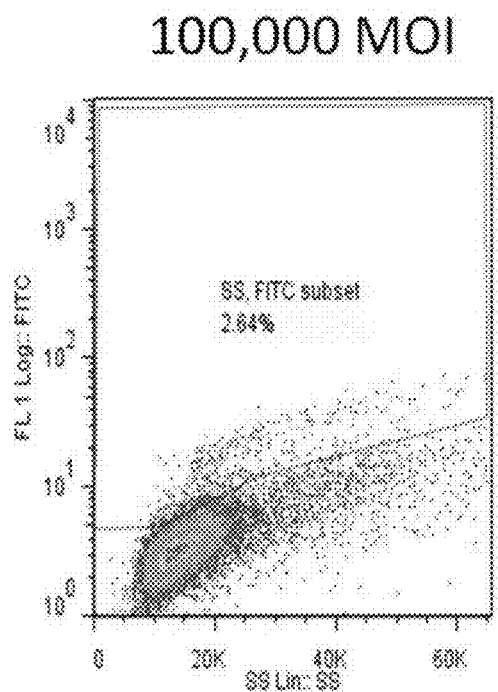
Figure 6D:
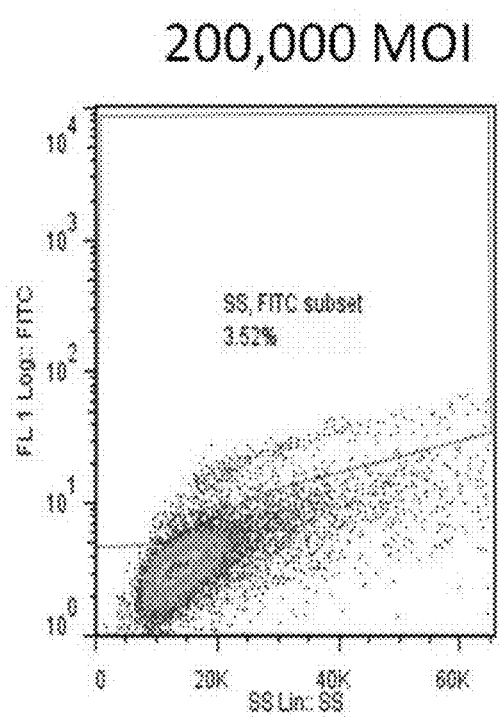
Figure 6E:
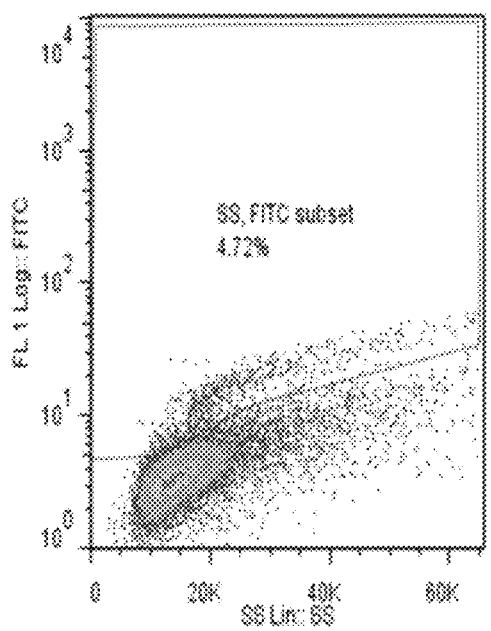
Figure 8A:
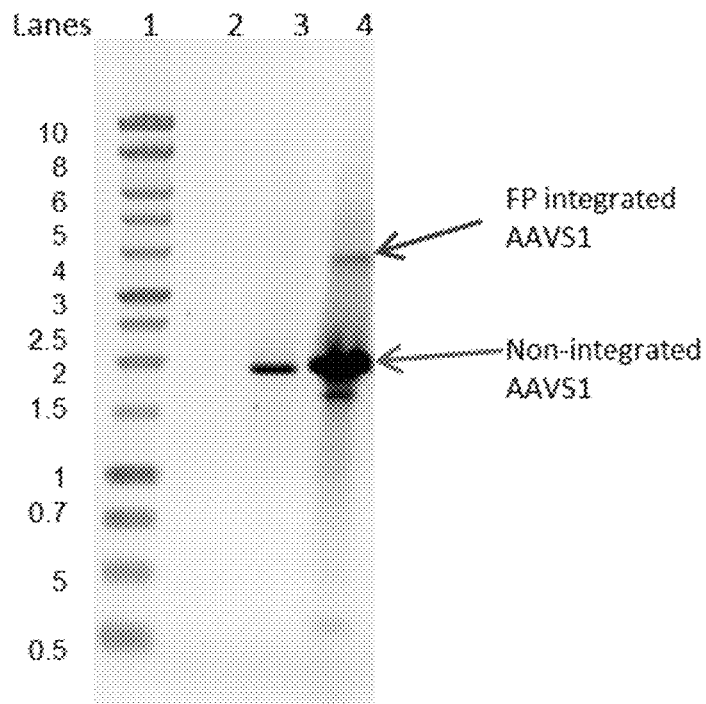
FIGS. 8A-8B show PCR confirmation of targeted integration of the YFP transgene into AAVS1 locus in K562 cells. A) Gel showing amplified DNA from representative samples from K562 cells with no template, untransduced, or transduced with AAVF7 FP vector at an MOI of 100,000. Lane 1: DNA ladder, lane 2: no template control, lane 3: untransduced control, and lane 4: AAVF7 FP transduced K562. Arrows point to either the FP integrated AAV ~3.1 kb fragment or the non-integrated AAV ~1.9 kb fragment. B) Gel showing amplified DNA from representative samples from K562 cells with no template, untransduced, or transduced with AAVF7 FP vector with an MOI of 100,000. Lane 1: DNA ladder, lane 2: no template control, lane 3: untransduced control, lane 4: AAVF7 FP vector transduced K562. The arrows point to either the amplified FP integrated AAVS1 ~3.1 kb fragment or the amplified non-integrated AAVS1 ~1.9 kb fragment.
Figure 8B:
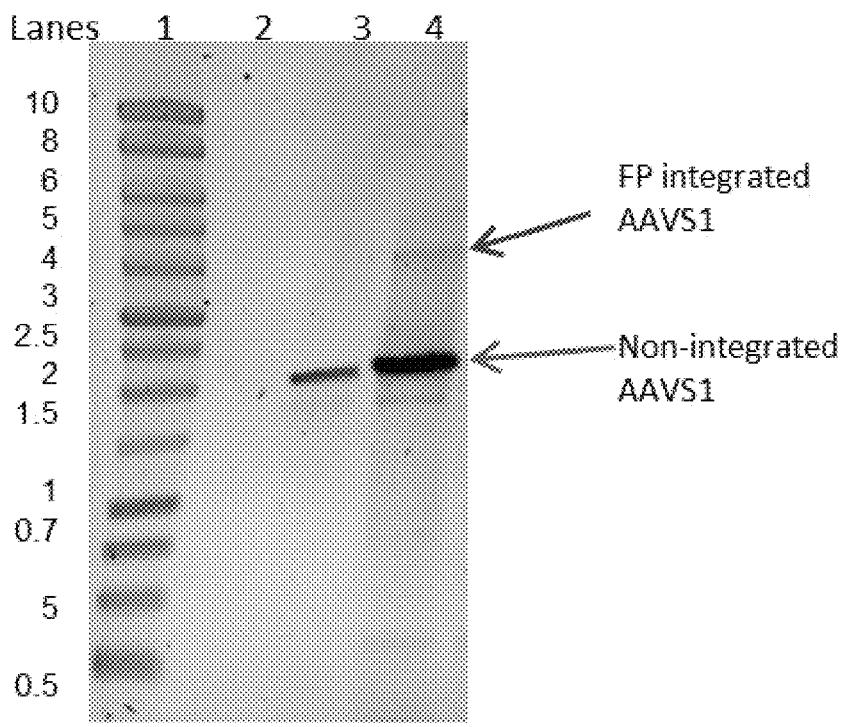

Targeted integration of the YFP transgene was further confirmed by PCR amplification of the edited genome using primers located outside of the homology regions. Briefly, DNA was extracted from K562 cells transduced at an MOI of 100,000 vector genomes/cell with AAVHSC7 FP vector. PCR amplification was performed using the "OUT Forward Primer Region" and "OUT Reverse Primer Region" primers (see FIG. 4). Integration of the YFP transgene resulted in an increase in size of the AAV locus from the wild type size of ~1.9 kb to the YFP transgene containing ~3.1 kb fragment (see FIG. 4, compare line labeled "Fragment 1" with line labeled "Fragment 2"). Amplification of the ~3.1 kb fragment containing the YFP transgene within the chromosome 19 AAVS1 locus indicated that the YFP transgene was effectively integrated into the AAVS1 locus in cells transduced with the AAVHSC7 FP vector (see FIGS. 8A and 8B, lane 4).

Example 2: AAV Vector Variant Mediated Genome Editing in Primary Human CD34+ Peripheral Blood Stem Cells Genome editing through site-specific insertion or targeted integration of specific DNA sequences using AAVHSC vectors without the use of an exogenous nuclease was also performed in human CD34+ primary peripheral blood-derived human hematopoietic stem cells (PBSCs). Briefly, the vector, ITR-AAVS1-FP, was packaged in AAVHSC capsids including AAVHSC7, AAVHSC12, AAVHSC15, and AAVHSC17 (see Chatterjee, 1992 for the standard AAV packaging method). Primary CD34+ cells were transduced with the pseudotyped AAVHSC-AAVS1-FP vector (i.e., a AAV vector variant) at MOIs of 100,000 and 150,000.

Figure 9A:
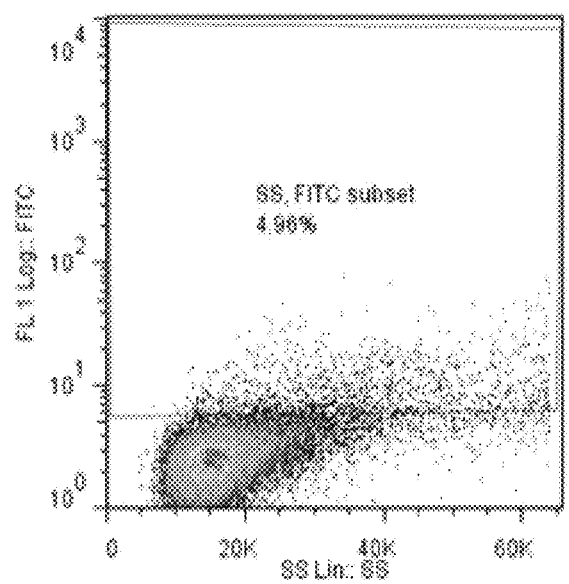
FIGS. 9A-9C show representative scatter plots of YFP expression in primary CD34+ cells after targeted integration 1 day post-transduction with AAVF FP vectors. (A) Cells not transduced with any vector (untransduced), (B) cells transduced with AAVF7 FP vector, and (C) cells transduced with AAVF17 FP vector. Cells transduced with either AAVF7 or AAVF17 vector showed a significant amount of YFP expression compared with the untransduced cells (compare B and C, respectively, with A). YFP expression in (B) and (C) indicates that the promoterless FP gene delivered by the AAVF vector accurately integrated into the chromosomal AAVS1 locus.
Figure 9B:
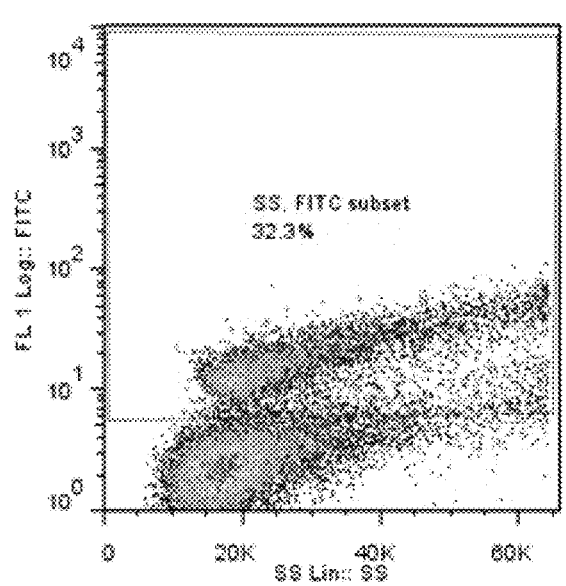
Figure 9C:
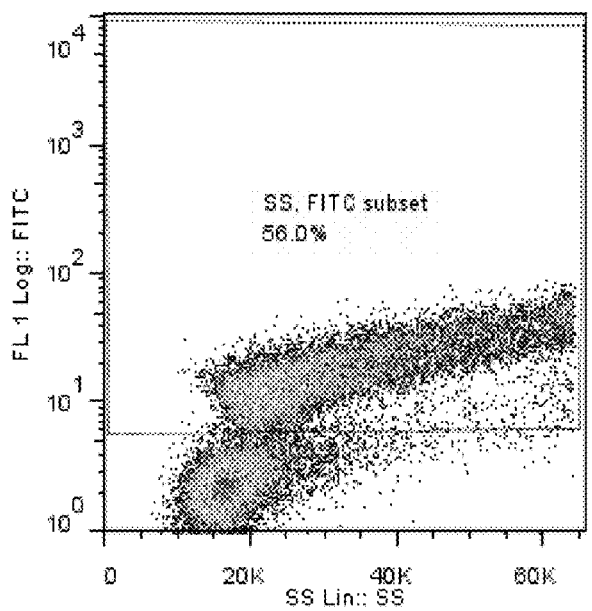
Figure 10A:
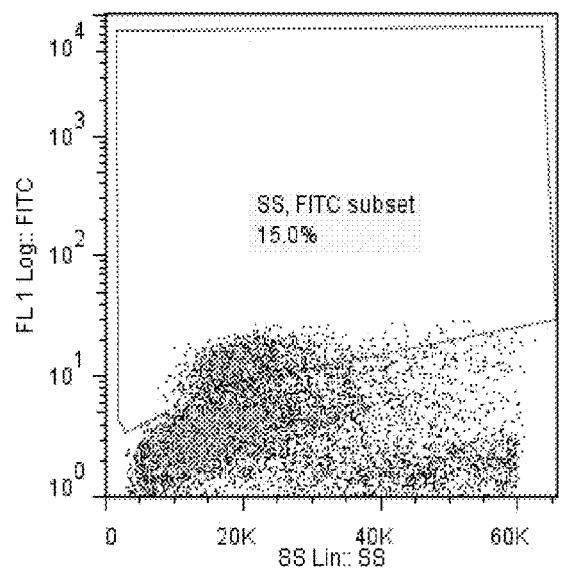
FIGS. 10A-10C show representative scatter plots of YFP expression in primary CD34+ cells after targeted integration 4 days post-transduction with AAVF FP vectors. (A) Cells not transduced with any vector (untransduced), (B) cells transduced with AAVF7 FP vector, and (C) cells transduced with AAVF17 FP vector. Cells transduced with either AAVF7 or AAVF17 FP vector showed a significant amount of YFP expression compared with the untransduced cells (compare B and C, respectively, with A), indicating accurate targeted integration of the gene delivered by the AAVF vector.
Figure 10B:
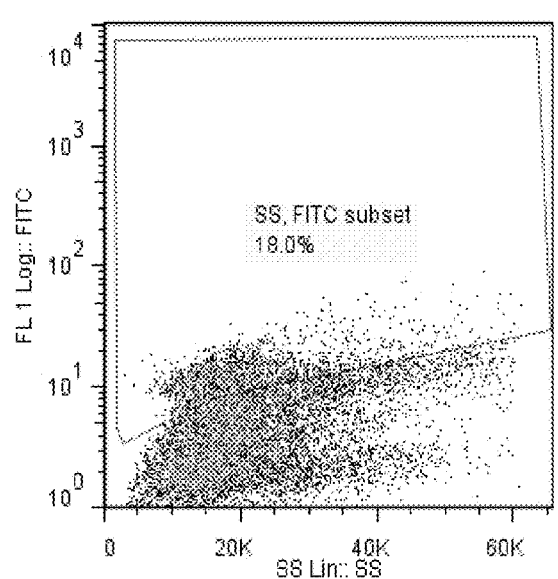
Figure 10C:
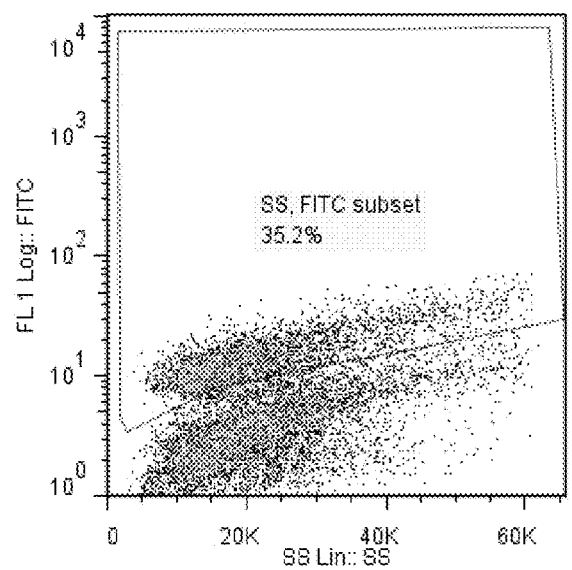
Figure 11A:
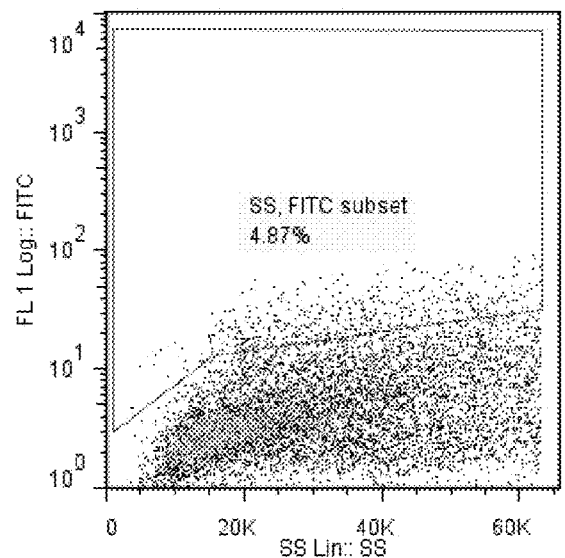
FIGS. 11A-11C show representative scatter plots of YFP expression in primary CD34+ cells after targeted integration 18 days post-transduction with AAVF FP vectors from representative samples. (A) Cells not transduced with any vector (untransduced), (B) cells transduced with AAVF7 FP vector, and (C) cells transduced with AAVF17 FP vector. Cells transduced with either AAVF7 or AAVF17 FP vector showed a significant amount of YFP expression compared with the untransduced cells (compare B and C, respectively, with A).
Figure 11B:
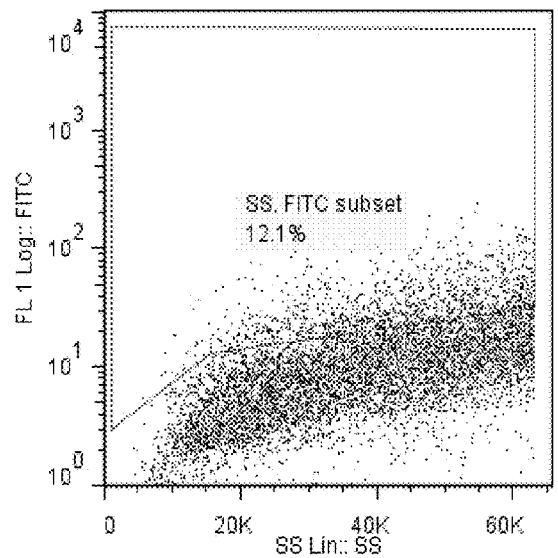
Figure 11C:
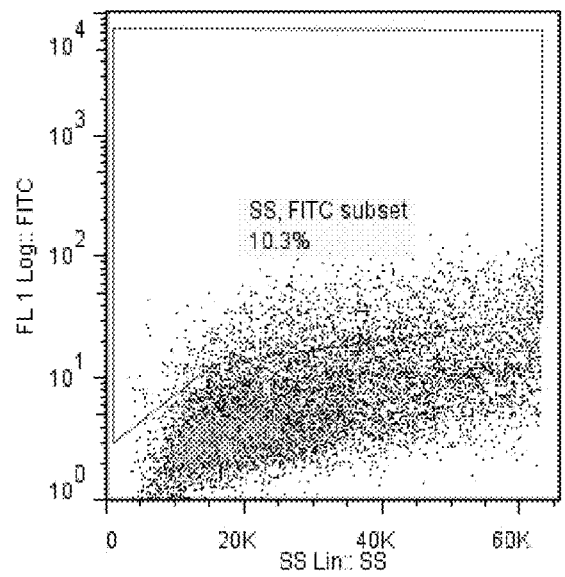
Figures 12A, 12B:
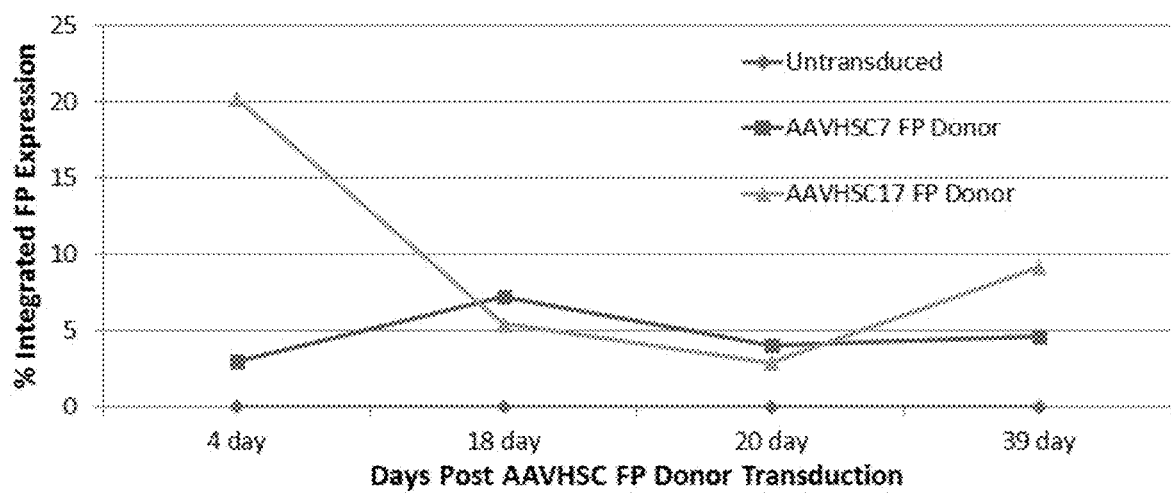
FIGS. 12A-12B show YFP expression in primary CD34+ cells after targeted integration. (A) A table showing the percentage of YFP positive cells for untransduced cells and cells transduced with either AAVF7 FP vector or AAVF17 FP vector at 4, 18, 20, and 39 days post-transduction. (B) A line graph showing the frequency of YFP expressing primary CD34+ cells at 4, 18, 20, and 39 days post AAVF FP transduction with an MOI of 100,000. The line with diamonds represents untransduced cells, the line with squares represents cells transduced with AAVF7 FP vector, and the line with triangles represents cells transduced with AAVF17 FP vector.

Integration of the YFP transgene into the AAVS1 locus by homologous recombination was assayed by cytofluorometric analysis of YFP expression. Targeted integration using the AAVHSC7 FP and AAVHSC17 FP vectors in primary CD34+ cells resulted in expression of the YFP transgene 1 day post-transduction at an MOI of 150,000 (FIG. 9), 4 days post-transduction at an MOI of 100,000 (FIG. 10), and 18 days post-transduction at an MOI of 100,000 (FIG. 11). The percentage of positive cells expressing YFP at 5.5 weeks post transduction at an MOI of 100,000 (39 days) did not decline (see FIGS. 12A and B, compare 20 day results with 39 day results). This long term expression of a promoterless YFP transgene in a dividing cell population indicates accurate integration of the transgene.

Figure 13:
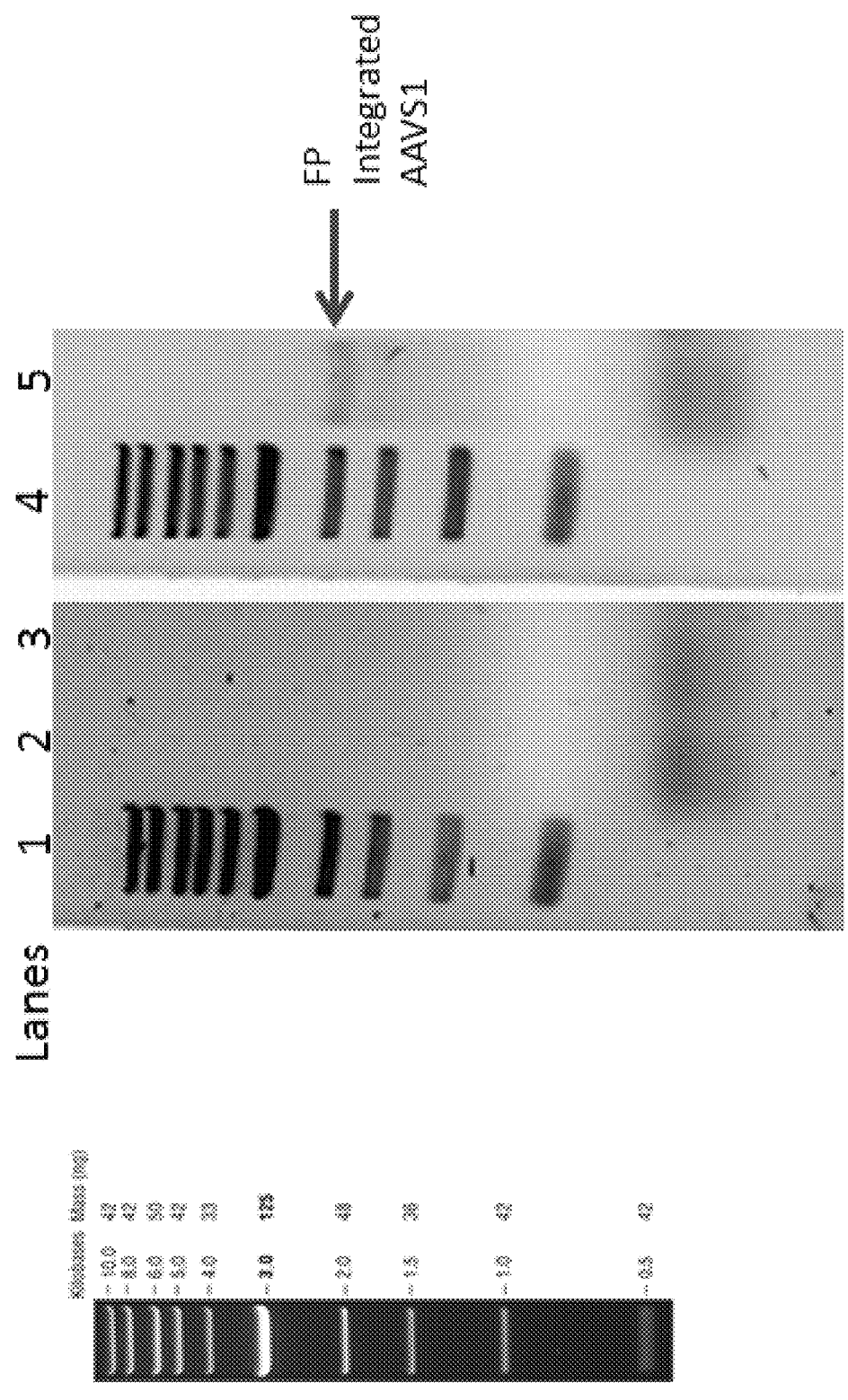
FIG. 13 shows PCR confirmation of targeted integration into the AAVS1 locus in primary CD34+ cells. A gel showing amplified DNA from representative samples of primary CD34+ cells with no template, untransduced, or transduced with AAVF7 FP vector with an MOI of 150,000. Lane 1: DNA ladder, lane 2: no template control, lane 3: untransduced control, lane 4: DNA marker, and lane 5: AAVF7 FP vector transduced. The arrow points to the FP integrated AAVS1 (~1.7 kb fragment) showing the amplification product of the 5' junction region. Inset to the left shows the DNA ladder that was loaded in lane 1.

Targeted integration of the YFP transgene was further confirmed by PCR analysis. The edited genome was amplified using primers that amplify the 5' junction region between the inserted transgene sequence and the native chromosomal 5' homology arm sequence (see FIG. 4, see line labeled "Fragment 3"). Briefly, DNA was extracted from primary CD34+ cells transduced at an MOI of 150,000 vector genomes/cell with the AAVHSC7 FP vector. PCR amplification was performed using the "OUT Forward Primer Region" and the "In Reverse Primer" primers (see FIG. 4). Amplification of a ~1.7 kb fragment of the 5' junction region for transduced primary CD34+ cells indicated that the YFP transgene was successfully integrated into the AAVS1 locus (see FIG. 13, lane 5). Whereas, there was no amplified product for those cells that were not transduced with the AAVHSC7 FP vector (see FIG. 13, lane 3).

Figure 14:
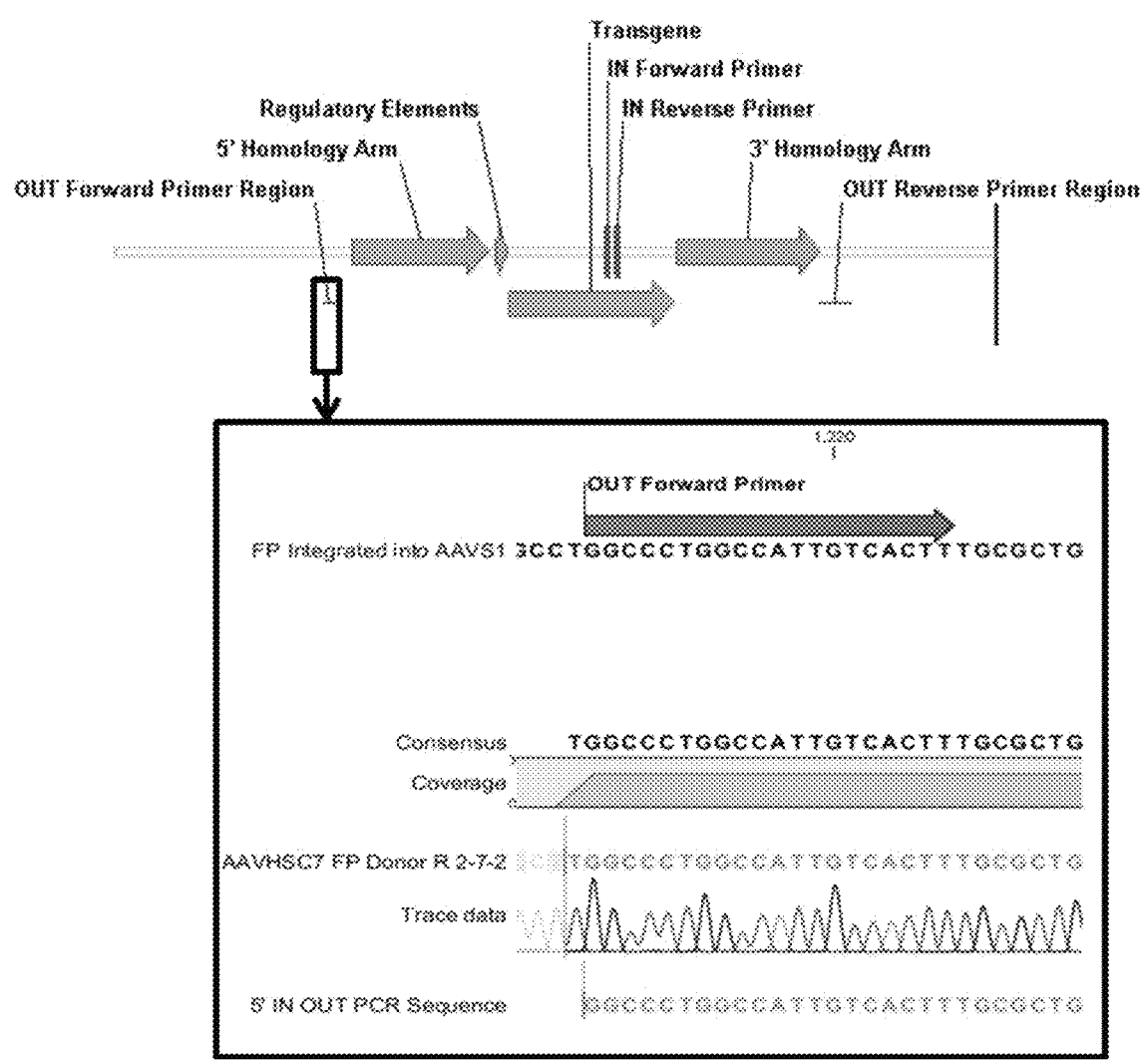
FIG. 14 shows sequence confirmation of targeted integration of YFP gene sequences in the AAVS1 locus beginning at the OUT Forward Primer Region. Sequencing results indicate that the YFP gene was present and was integrated correctly into the AAVS1 locus.
Figure 15:
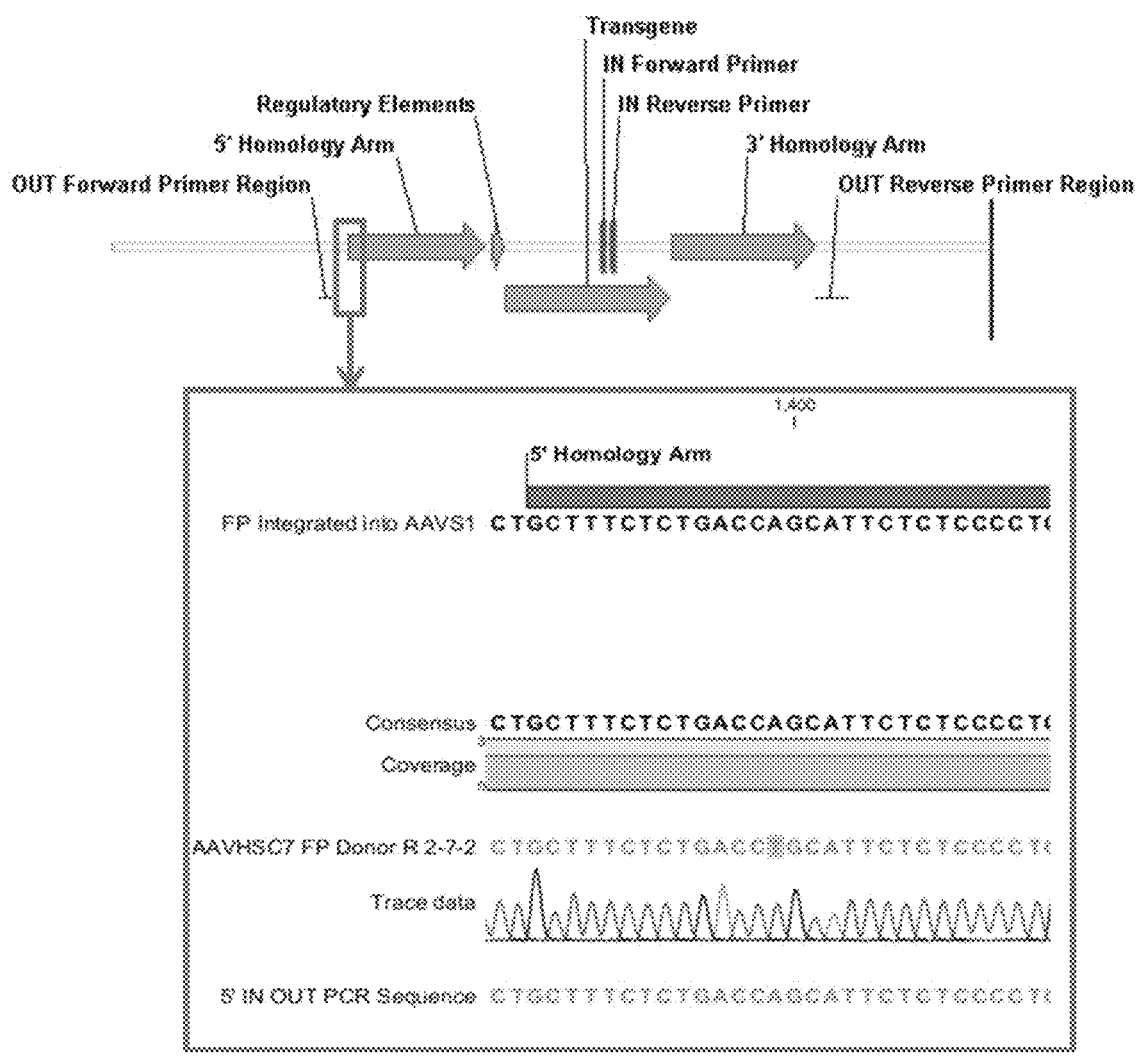
FIG. 15 shows sequence confirmation of targeted integration of YFP sequences in the AAVS1 locus beginning near the 5' homology arm. Sequencing results indicate that the YFP gene was present and was integrated into the AAVS1 locus.
Figure 16:
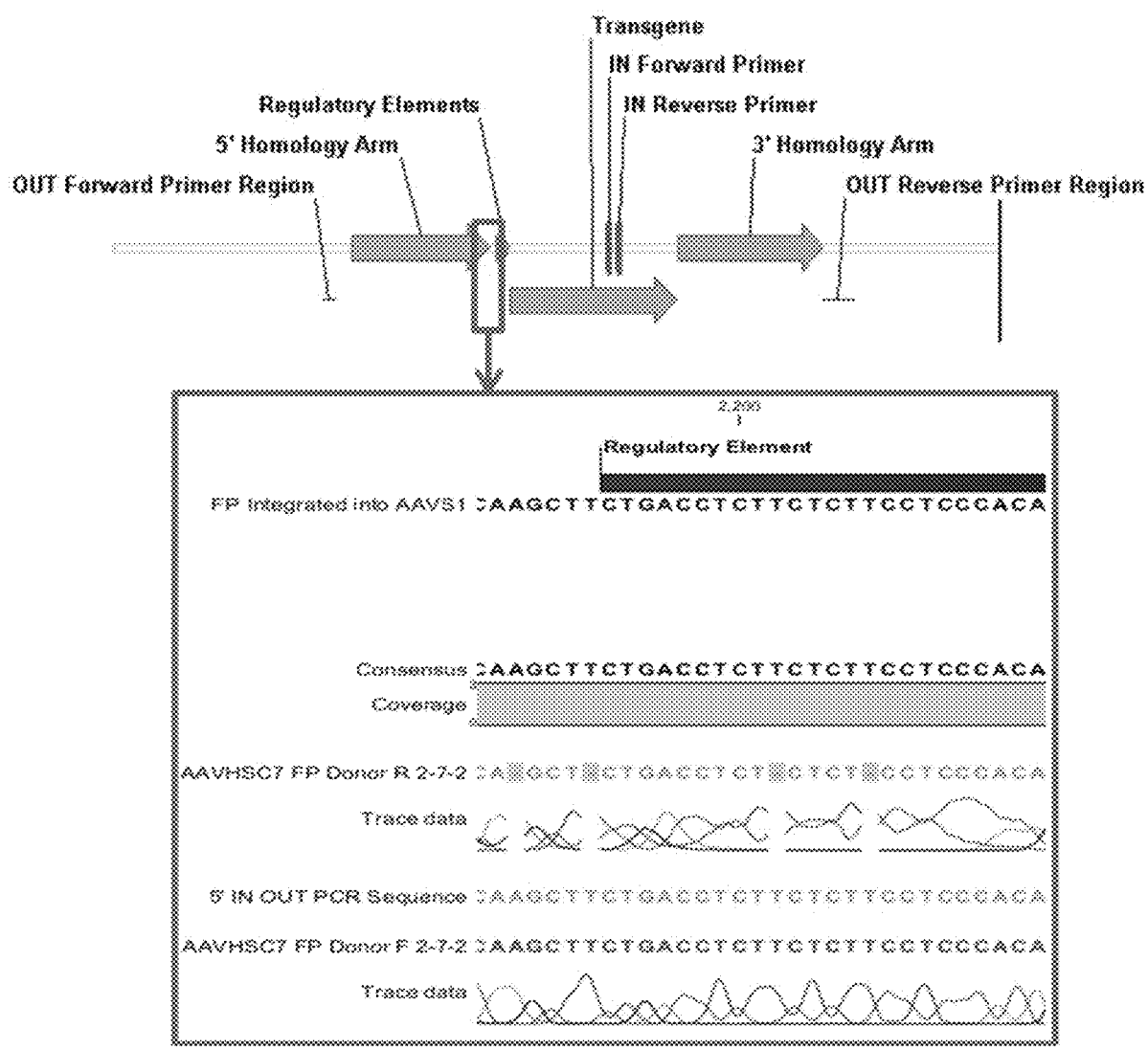
FIG. 16 shows sequence confirmation of targeted integration of YFP sequences in the AAVS1 locus beginning near the 5' region of the regulatory elements. Sequencing results indicate that the YFP gene was present and was integrated into the AAVS1 locus.
Figure 17:
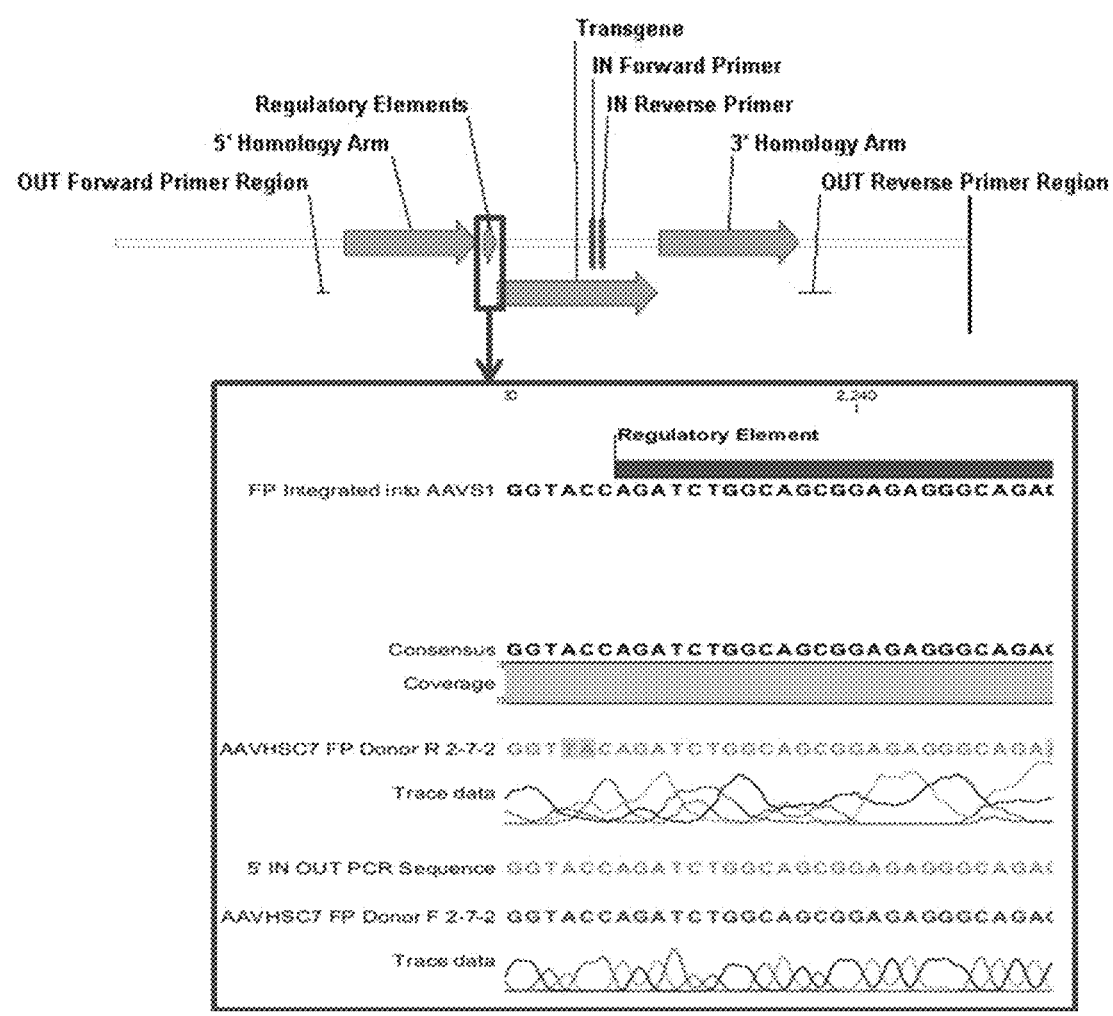
FIG. 17 shows sequence confirmation of targeted integration of YFP sequences in the AAVS1 locus beginning near the 3' region of the regulatory elements. Sequencing results indicate that the YFP gene was present and was integrated into the AAVS1 locus.
Figure 18:
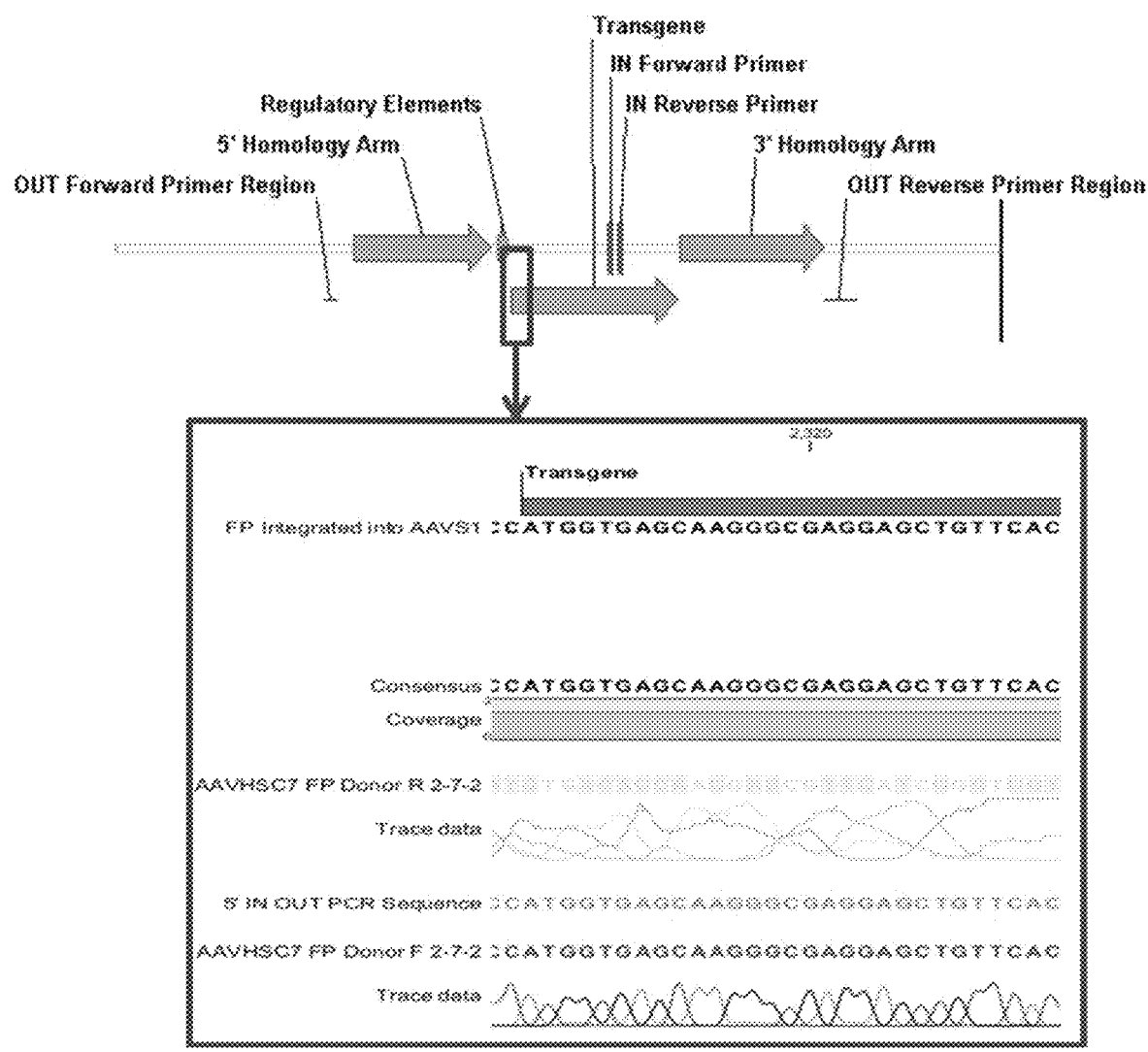
FIG. 18 shows sequence confirmation of targeted integration of YFP sequences in the AAVS1 locus beginning near the 5' region of the transgene. Sequencing results indicate that the YFP gene was present and was integrated into the AAVS1 locus.
Figure 19:
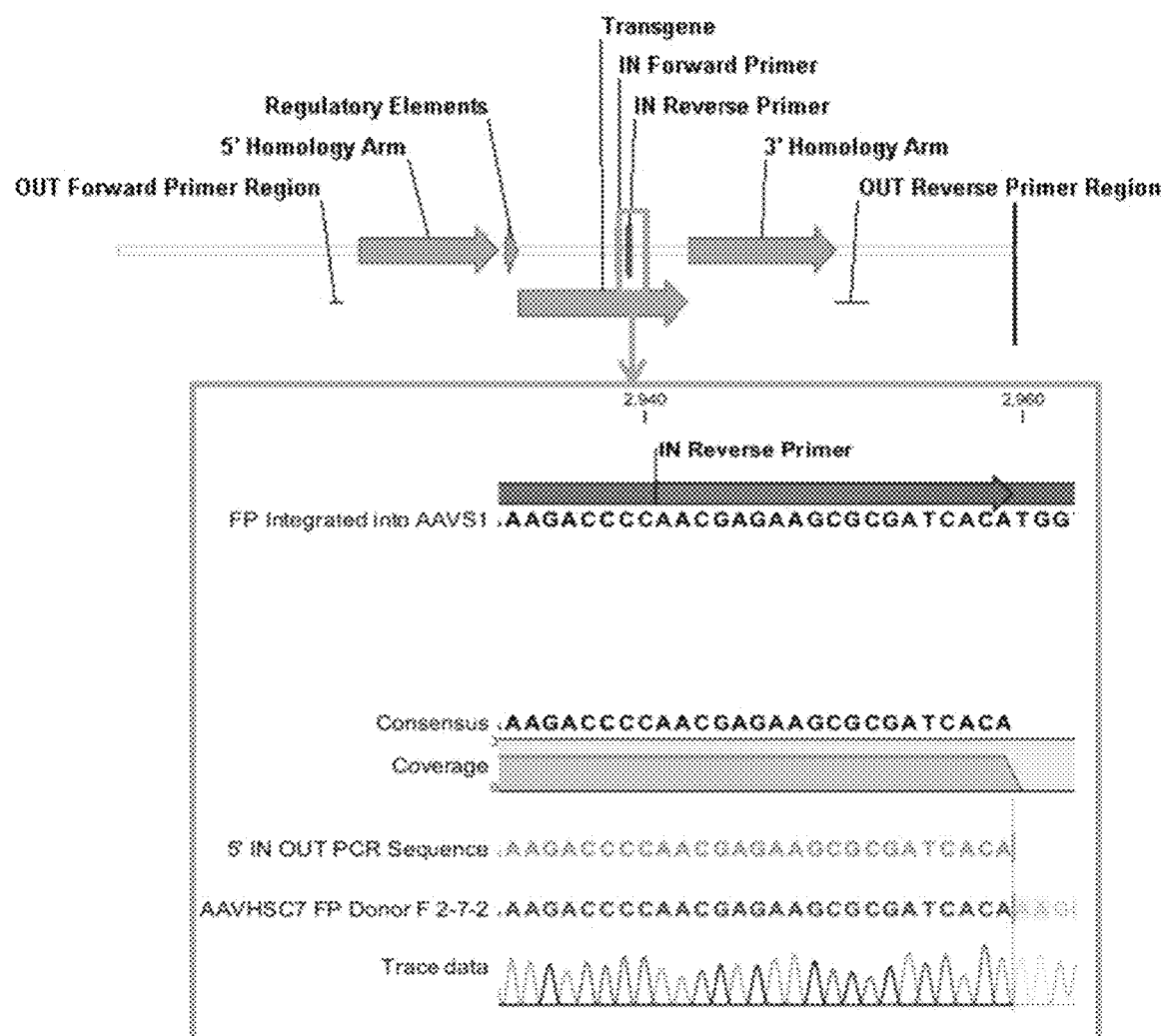
FIG. 19 shows sequence confirmation of targeted integration of YFP sequences in the AAVS1 locus beginning near the "IN Reverse Primer" region. Sequencing results indicate that the YFP gene was present and was integrated into the AAVS1 locus.

Targeted integration of the YFP transgene was further confirmed by sequence analysis of different portions of the edited AAVS1 locus. Sequencing was performed beginning near the "OUT Forward Primer Region" (see FIG. 14), near the 5' homology arm (see FIG. 15), near the 5' region of the regulatory elements (see FIG. 16), near the 3' region of the regulatory elements (see FIG. 17), near the 5' region of the transgene (see FIG. 18), and near the "IN Reverse Primer" region (see FIG. 19). Sequencing results indicated that the YFP gene was present and was successfully integrated into the AAVS1 locus.

As provided in Examples 1 and 2, the AAVHSC vectors successfully mediated efficient targeted genome editing in human CD34+ hematopoietic cell lines and CD34+ PBSCs without the need for addition of exogenous endonucleases. AAVHSC vectors were capable of directing integration of the YFP transgene to the AAVS1 locus on chromosome 19 based upon flanking homology arms corresponding to the AAVS1 locus. AAV-mediated transgenesis has previously been reported; however, reported frequencies have been low, usually on the order of 1 in 1e6 cells to 1 in 1e4 cells. As shown herein, targeted genome editing using AAVHSC vectors occurred at frequencies of approximately 10% of primary cells long term, which is 1,000 to 100,000 fold more efficient than previously reported (see, e.g., Khan, 2011). Expression of the YFP transgene in human CD34+ hematopoietic cell lines was observed as early as day one post-transduction and was confirmed on day three. Expression of the YFP transgene in PBSCs was observed starting from day one and continued long term (up to almost 6 weeks), which was the latest time point analyzed. No overt toxicity was observed as a result of AAVHSC vector transduction. Based upon the high frequency of insertion, ease of use, and lack of toxicity observed, therapies based upon targeted genome editing using AAVHSC vectors is practical and feasible.

Example 3: In Vivo Genome Engineering with AAV Vector Variants

AAVHSC vectors encoding luciferase and AAVHSC vectors encoding Venus were injected into adult immune-deficient mice previously xenografted with human cord blood CD34+ HSCs. As shown below, intravenous injection of AAVHSC vectors resulted in transduction of human CD34+ hematopoietic stem and progenitor cells in vivo, and the intravenous injected AAVHSC vectors trafficked to sites of human hematopoiesis and transduced human cells.

Methods. Briefly, immune-deficient NOD/SCID adult mice were first irradiated with a sublethal dose of 350cGy from a $^{137}$Cs source. Second, one million human cord blood CD34+ cells were injected into the sublethally-irradiated immune-deficient NOD/SCID mice. Next, two hours after CD34+ HSC transplantation, the mice were injected intravenously with approximately 1E11-5e11 particles of AAVHSC-Luciferase vector (either AAVHSC7-Luciferase vector or AAVHSC17-Luciferase vector). These vectors were used in the absence of an exogenous nuclease. The AAVHSC-Luciferase vectors encode the single-stranded firefly luciferase gene (ssLuc) under the control of the ubiquitous CBA promoter to permit serial in vivo bioluminescent monitory of transgene expression. These vectors are described specifically in U.S. application Ser. No. 13/668, 120 (published as US Patent Publication Number 20130096182A1) and in Smith et al., which is hereby incorporated by reference in its entirety, as if fully set forth herein (see Smith, 2014). The AAVHSC-Luciferase vector was pseudotyped in the HSC7 capsid variant (the polynucleotide sequence of HSC7 capsid is provided as SEQ ID NO: 27 and the polypeptide sequence of HSC7 capsid is provided as SEQ ID NO:8 (see FIG. 1)) or the HSC17 capsid variant (the polynucleotide sequence of HSC17 capsid is provided as SEQ ID NO: 35 and the polypeptide sequence of HSC17 capsid is provided as SEQ ID NO:13 (see FIG. 1)) as described in U.S. application Ser. No. 13/668,120 (published as US Patent Publication Number 20130096182A1) and Smith et al, to form the AAVHSC7-Luciferase vector and the AAVHSC17-Luciferase vector (see Smith, 2014) (see Chatterjee, 1992 for the standard AAV packaging method). Note that the AAVHSC-Luciferase vectors can transduce both mouse and human cells. However, in contrast to the Venus encoded in the AAVHSC-Venus vector described below, the luciferase will not integrate into AAVS1. Instead, the luciferase may integrate randomly or stay episomal.

Two to seven days after injection with the AAVHSC-Luciferase vector, the mice were injected with approximately 1E11-5e11 particles of AAVHSC-Venus vectors. Specifically, mice that were first injected with AAVHSC7-Luciferace vector were injected with AAVHSC7-Venus vector and mice that were first injected with AAVHSC17-Luciferase vector were injected with AAVHSC17-Venus vector. The Venus donor vector used is described specifically in Examples 1 and 2 above. The donor AAV vector was designed such that the Venus transgene was promoterless and would only be expressed if it was integrated at the correct AAVS1 locus, which would be downstream from chromosomally encoded regulatory sequences (see FIGS. 3 and 4). Thus, any Venus transgene expression that occurred was under the control of a chromosomal promoter located in or near AAVS1. Importantly, the vector containing the Venus gene does not contain a promoter to drive expression. The Venus gene will only be expressed if it integrates correctly into AAVS1 in human cells, downstream from an endogenous chromosomal promoter. The donor vector, ITR-AAVS1-Venus (see FIG. 3), was packaged into AAVHSC capsids according to the standard AAV packaging method described in Chatterjee et al, 1992. The vector was pseudotyped in the HSC7 capsid variant (the polynucleotide sequence of HSC7 capsid is provided as SEQ ID NO: 27 and the polypeptide sequence of HSC7 capsid is provided as SEQ ID NO:8 (see FIG. 1)) or the HSC17 capsid variant (the polynucleotide sequence of HSC17 capsid is provided as SEQ ID NO: 35 and the polypeptide sequence of HSC17 capsid is provided as SEQ ID NO:13 (see FIG. 1)) to form the AAVHSC7-Venus vector and the AAVHSC17-Venus vector.

Figure 20:
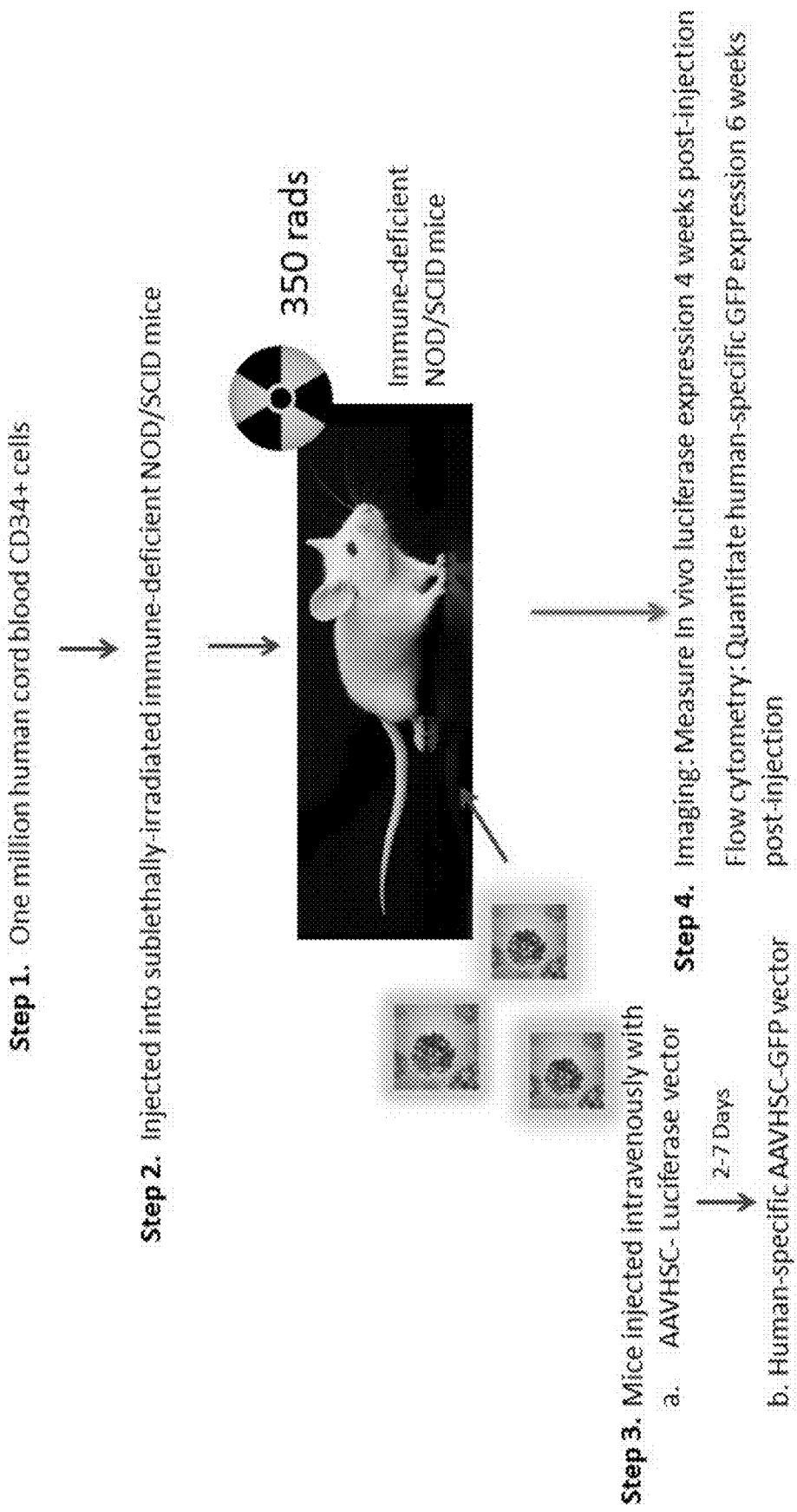
FIG. 20 shows a schematic of the steps performed in the experiments in Example 4. One million human cord blood CD34+ cells were obtained (see Step 1) and injected into sublethally-irradiated immune deficient NOD/SCID adult mice (see Step 2). Two hours after injection with CD34+ cells, the mice were injected with AAVF-Luciferase vector (i.e., AAVF7-Luciferase vector or AAVF17-Luciferase vector). Two to seven days later the mice were injected with AAVF-Venus vectors (i.e., AAVF7-Venus vector or AAVF17-Venus vector) (see Step 3). Finally, in vivo luciferase expression was measured 4 weeks post injection and Venus expression was quantitated 6 weeks post-injection (see Step 4).

Finally, in vivo luciferase expression was measured 4 weeks post-injection. Six weeks post-injection, engraftment of human CD34+ and CD45+ cells was measured and Venus expression was quantitated. See FIG. 20 for an overall schematic of the experiments performed in this Example.

Figure 21B:
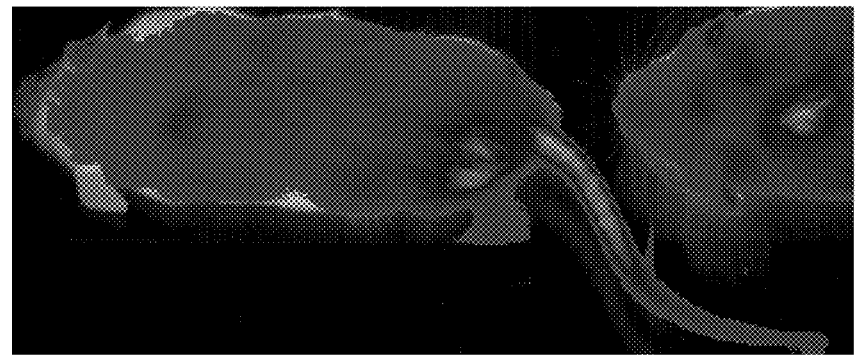
FIGS. 21A-21B show in vivo specific luciferase expression in representative recipients.
Figure 21A:
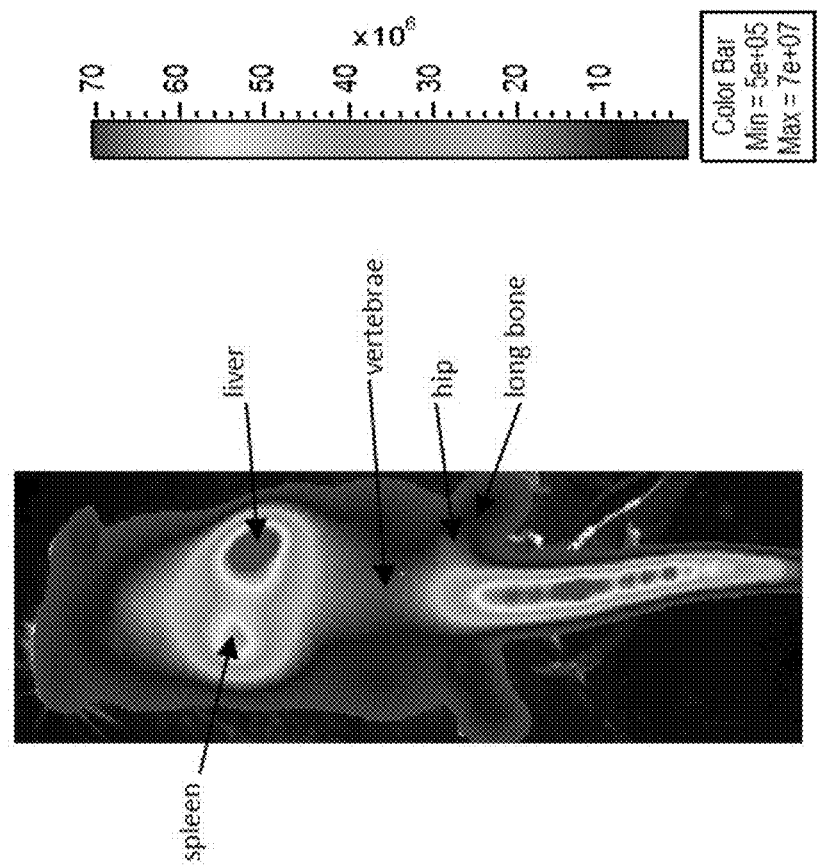

Results. Four weeks post-injection, in vivo imaging was performed on xenotransplanted and non-xenotransplanted mice that received intravenous injections of AAVHSC-Luciferase vectors. Results showed specific luciferase expression in vertebrae, spleen, hips, and long bones, which are all sites of hematopoiesis after transplantation (see FIG. 21A). However, no specific luciferase expression in hematopoietic organs was observed in mice that were not previously xenografted with human cord blood CD34+ HSCs (see FIG. 21B). These results indicate that intravenously injected AAVHSC vectors traffic to in vivo sites of human hematopoiesis and preferentially transduce stem and progenitor cells.

Six weeks after injection with the AAVHSC-Venus vectors, human CD34+ and CD45+ cells were analyzed using flow cytometry. Results indicated that the injected human cord blood CD34+ cells engrafted into the mice and gave rise to more mature blood cells. Specifically, primitive human blood progenitor cells (i.e., CD34+ cells) were observed in the bone marrow (see Table 1, CD34+ cells and femoral marrow). Additionally, human mononuclear blood cells (i.e., CD45+ cells) were evident in the femoral marrow, vertebral marrow, and spleen as shown in Table 1.

TABLE 1

Engraftment of Human Blood Cells in Immune Deficient Mice

| Cell type | Femoral Marrow | Vertebral Marrow | Spleen |
|---|---|---|---|
| AAVHSC7 | | | |
| CD45+ | 68.4 | 30.4 | 24.3 |
| CD34+ | 22 | NT* | NT |
| AAVHSC17 | | | |
| CD45+ | 46.6 | 24 | 18.3 |
| CD34+ | 13.1 | NT | NT |

*NT = Not Tested
CD45+ cells: human mononuclear blood cells
CD34+ cells: human hematopoietic progenitor cells Six weeks post injection, flow cytometry was used to analyze Venus expression from human HSCs of xenotransplanted mice that received intravenous injections of either AAVHSC7-Venus or AAVHSC17-Venus vectors. Results revealed that AAVHSC transduction was readily observed in the CD45+ human HSCs as well as CD34+ human HSCs from the femoral and vertebral marrow (see Table 2 and FIGS. 22A-F).

TABLE 2

Percentage of Engrafted Human Hematopoietic Cells Expressing Venus

| Cell Type | Femoral Marrow | Vertebral Marrow | Spleen |
|---|---|---|---|
| AAVHSC7 | | | |
| CD45+ | 8.35 | 15.3 | 10.3 |
| CD34+ | 9.23 | NT* | NT |
| AAVHSC17 | | | |
| CD45+ | 8.59 | 70.2 | 9.9 |
| CD34+ | 8.92 | NT | NT |

Figure 22A:
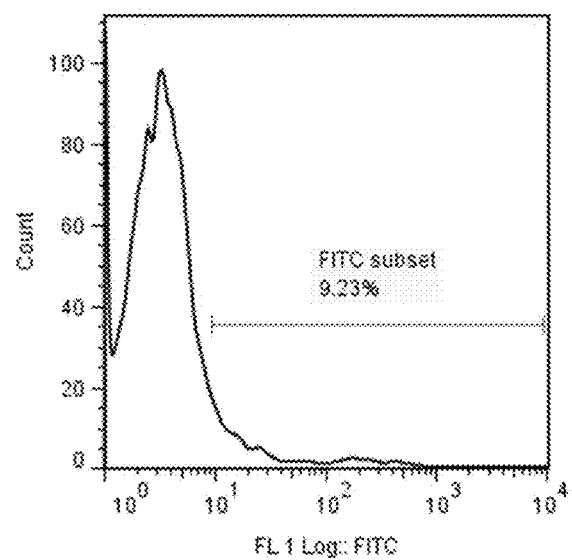
FIGS. 22A-H show histograms illustrating flow cytometry data of Venus-expressing human CD34+ or CD45+ cells in adult immune-deficient mice previously xenografted with human cord blood CD34+ HSCs that received intravenous injections of either AAVF7-Venus or AAVF17-Venus vectors.
Figure 22B:
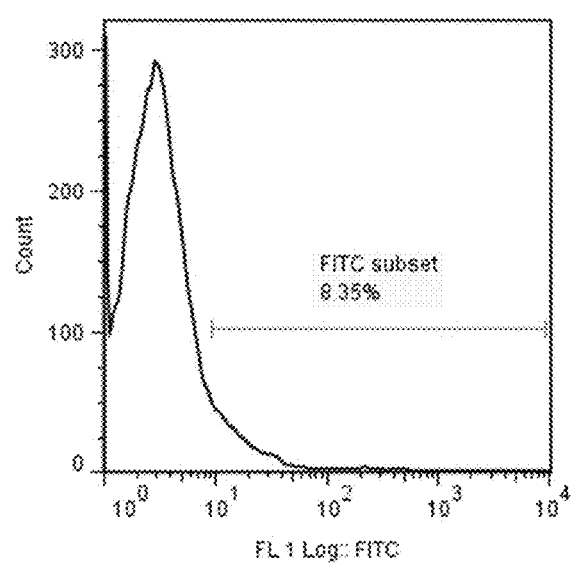
Figure 22C:
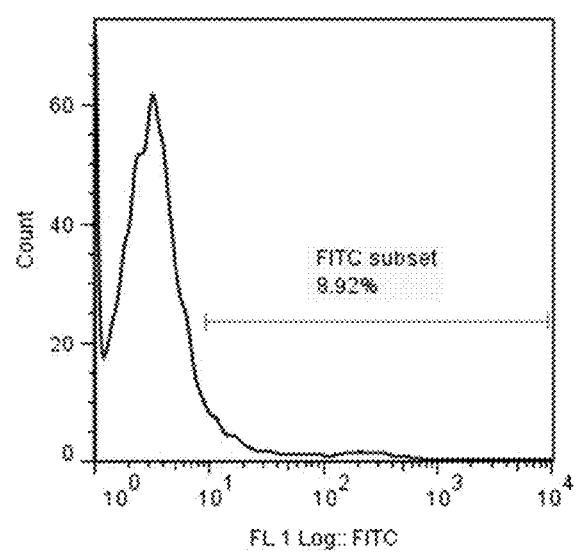
Figure 22D:
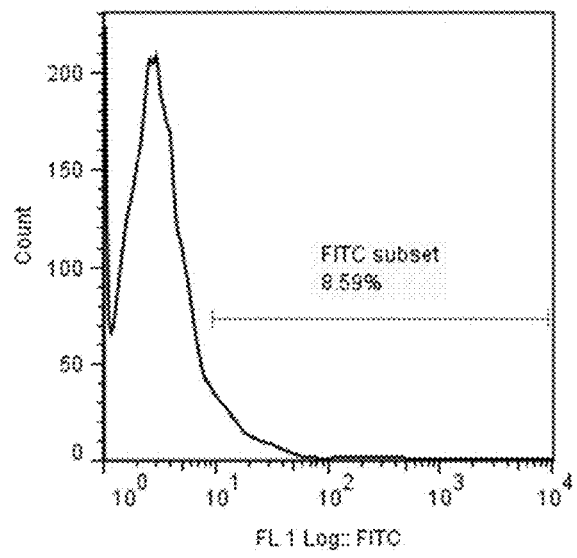
Figure 22E:
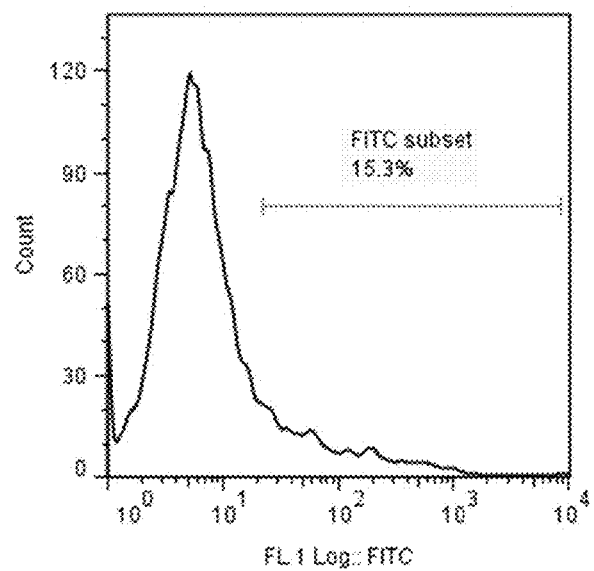
Figure 22F:
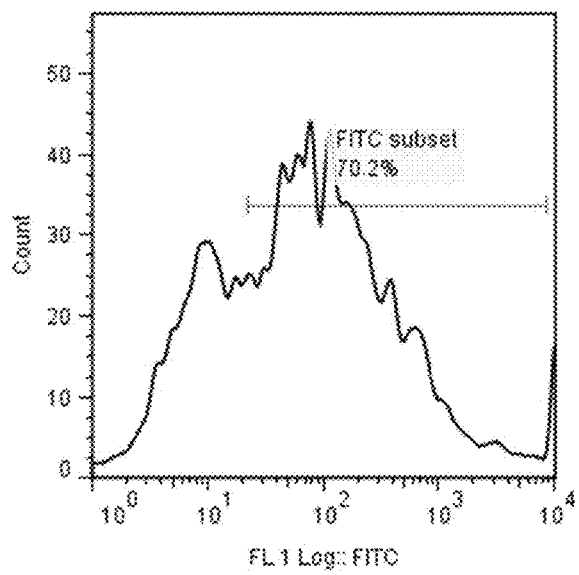
Figure 22G:
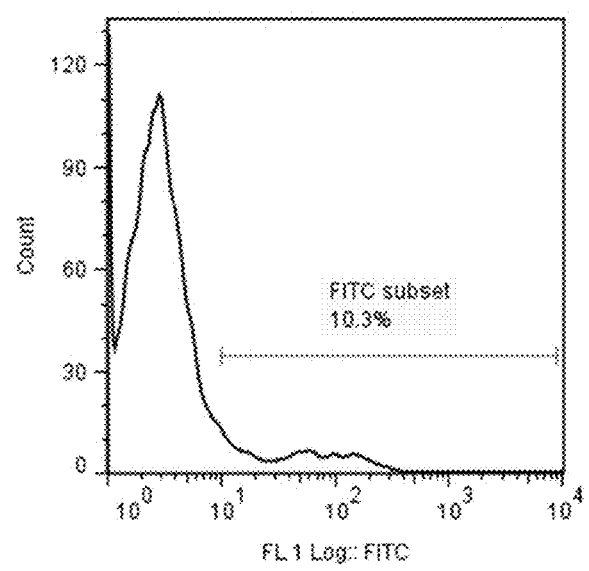
Figure 22H:
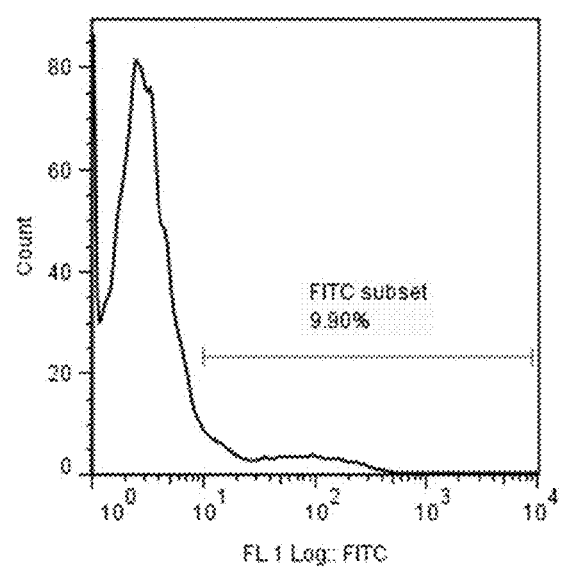

*NT = Not Tested
CD45+ cells: human mononuclear blood cells
CD34+ cells: human hematopoietic progenitor cells Additionally, human CD45+ cells in the spleen readily showed evidence of transduction as Venus was expressed in these cells (see Table 2 and FIGS. 22G and H). This demonstrates that CD45+ cells arising from the transplanted human cord blood CD34+ cells express Venus. These results indicate that intravenous injection of AAVHSC vectors in vivo results in transduction of human hematopoietic cells.

Example 4: Insertion of Large and Small Editing Elements into a Genome Using AAV Clade F Vectors Methods. rAAV Production, Purification, and Titration. All targeting genomes were cloned into an AAV2 backbone using New England Biolabs Gibson Assembly Cloning Kit with primers designed using NEBuilder v.1.6.2 (Ipswich, Mass.). All targeting genomes were sequenced and AAV2 ITR integrity was confirmed using restrictions digest and sequencing. Single-stranded targeting genomes were packaged into the AAVF capsids in herpes simplex virus (HSV)-infected 293 cells. The resulting recombinant AAV vectors were purified through two rounds of CsCl2 density centrifugation gradients and titers were determined using qPCR with transgene-specific primers and probe.

K562, HepG2 and PBSC Transductions. The chronic myelogenous leukemia (CML) cell line, K562 and the hepatocellular carcinoma cell line HepG2, were obtained from American Type Culture Collection (ATCC) (Manassas, Va.) and cultured according to ATCC guidelines. Peripheral blood stem cells (PBSCs) were purified from mononuclear cells from cytokine primed PB of healthy donors using CD34+ Indirect isolation kits (Miltenyi Biotech) and transductions performed immediately after isolation. PBSCs were cultured in Iscove's Modified Dulbecco's Medium (IMDM) (Irvine Scientific) containing 20% FCS, 100 ug/mL streptomycin, 100 U/mL penicillin, 2 mmol/L L-glutamine, IL-3 (10 ng/mL; R&D Systems), IL-6 (10 ng/mL; R&D Systems), and stem cell factor (1 ng/mL; R&D Systems. HepG2 cells were split and plated approximately 24 hours prior to transductions. K562 cells were plated immediately prior to transductions. K562s, HepG2s or PBSCs were transduced with AAVF targeting vectors at MOIs ranging from 5E4 to 4E5. The cells were transduced and homologous recombination was achieved in the absence of an exogenous nuclease. Cells were harvested for flow and molecular analysis at time points between 1 to 39 days post transduction. BrdU labeling of in vitro transductions were performed prior to harvesting using the APC BrdU Flow Kit (BD Biosciences) as instructed.

TI PCR and Sequencing. High molecular weight DNA was isolated from K562s, HepG2s or PBSCs transduced with AAVF targeting vectors. TI specific PCR was performed using a primer that anneal to the chromosomal region outside the homology arms, Sigma AAV5 I forward primer (5'-GGC CCT GGC CAT TGT CAC TT-3') and a primer that anneal to the inserted cassette, either Venus reverse primer (5'-AAC GAG AAG CGC GAT CAC A-3') or RFLP HindIII reverse primer (5'-CCAATCCTGTCCCTAGTAAAGCTT-3'). Roche Expand Hifidelity PCR system (Indianapolis, Ind.) was used and cycling conditions as follows: 1 cycle, 5 minutes—95° C.; 15 cycles, 30 seconds—95° C., 30 seconds—start at 62° C. and decrease by 0.5° C. per cycle, 2 minutes—68° C.; 20 cycles, 30 seconds—95° C., 30 seconds—53° C., 2 minutes—68° C.; 1 cycle, 5 minutes—68° C. PCR products were PCR purified for direct sequencing using Qiaquick PCR Purification Kit (Qiagen) or cloned using TOPO TA Cloning Kit for Sequencing and clones sequenced by Sanger Sequencing (Life Technologies).

Transplantation of CD34+ Cells. All animal care and experiments were performed under protocols approved by a Institutional Animal Care and Use Committee. 6-8-week old male NOD.CB17-Prkdcscid/NCrCrl (NOD/SCID) mice were maintained in a specific pathogen free facility. Mice were placed on sulfamethoxazole and trimethoprim oral pediatric antibiotic (Hi-Tech Pharmacal (Amityville, N.Y.), 10 ml/500 ml H2O) for at least 48 hours before transplant. Mice were irradiated with a sublethal dose of 350cGy from a 137Cs source and allowed to recover for a minimum of 4 hours prior to transplantation. Umbilical cord blood (CB) CD34+ cells were isolated using CD34+ Indirect isolation kits (Miltenyi Biotech). 1×10$^6$ CB CD34+ cells were resuspended in approximately 200 ul and transplanted by tail vein injection. 2.4E11 to 6.0E11 particles of AAVF targeting vectors were injected intravenously through the tail vein at 1 or 7 weeks post CB CD34+ transplantation. Femoral bone marrow (BM), vertebral BM and spleen were harvested 6, 7 or 19 week post transplantation.

Flow Cytometric Analysis. In vitro transductions were analyzed for AAVF targeting vector mediated integration, and BrdU and 7-AAD using a Cyan ADP Flow Cytometer (Dako). Specific fluorescence was quantified following the subtraction of autofluorescence. In vivo expression of integrated fluorescent cassette in CD34+ and erthyroid cells was analyzed in harvested vertebral BM, femoral BM and spleen of xenografted mice by staining with human specific antibodies, APC-conjugated anti-CD34 and PE-conjugated anti-Glycophorin A, and PE- and APC-conjugated IgG controls (BD Biosciences) on an FACS Aria SORP (BD Biosciences). Flow cytometry data was analyzed using FlowJo software (Treestar).

Figure 23:
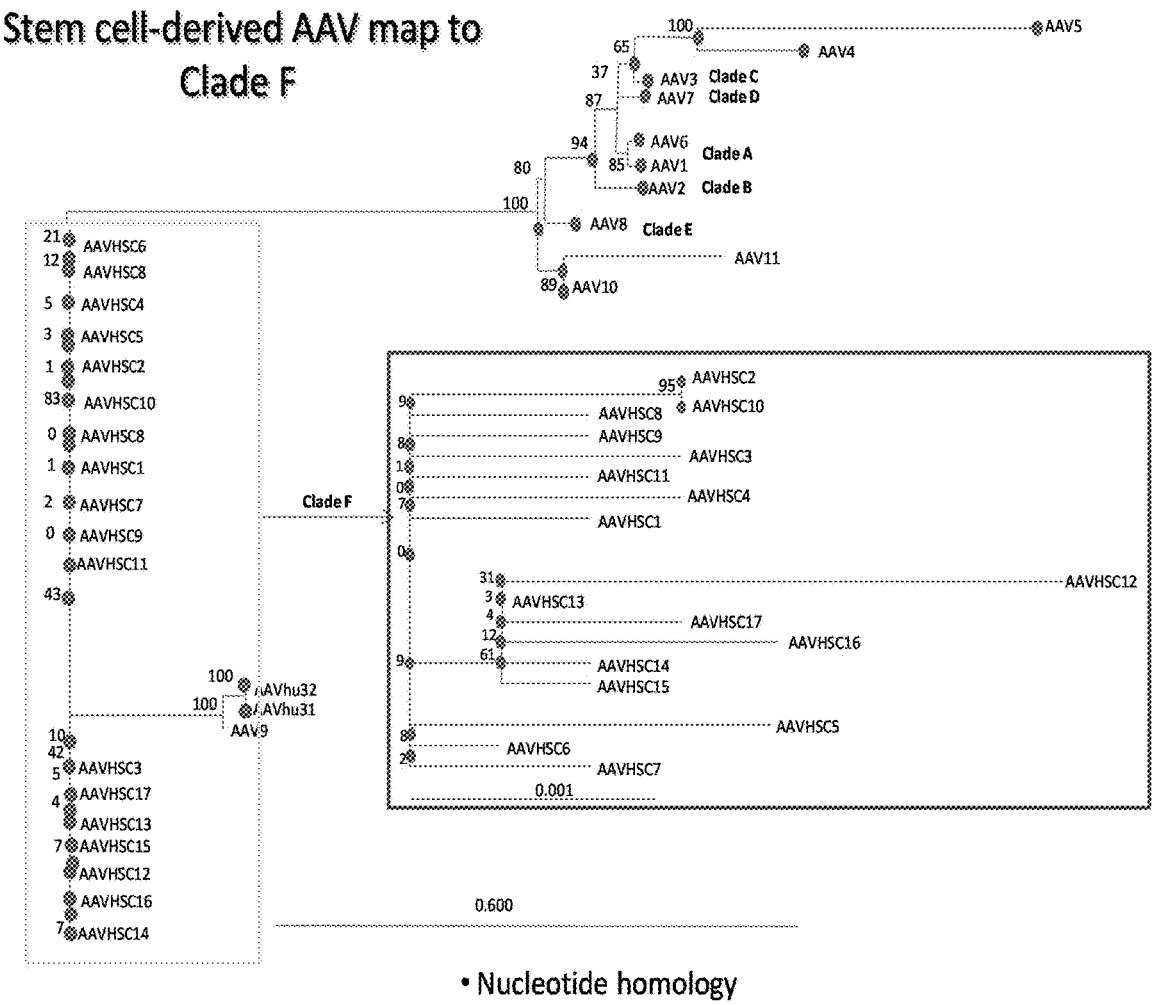
FIG. 23 shows a phylogram of the relationship of AAV Clade F viruses relative to each other and other AAV strains. The phylogram is based on nucleotide sequence homology of the capsid genes of AAVF viruses (Smith et al, Mol Ther. 2014 September; 22(9):1625-34).

Results. Stem cell-derived AAV were shown to map to AAV Clade F based on nucleotide sequence homology of the capsid genes (FIG. 23, Smith et al, Mol Ther. 2014 September; 22(9):1625-34). These stem cell-derived AAV were named AAVHSC1-17. These AAV are also referred to herein as AAVF1-17, respectively.

Figure 24:
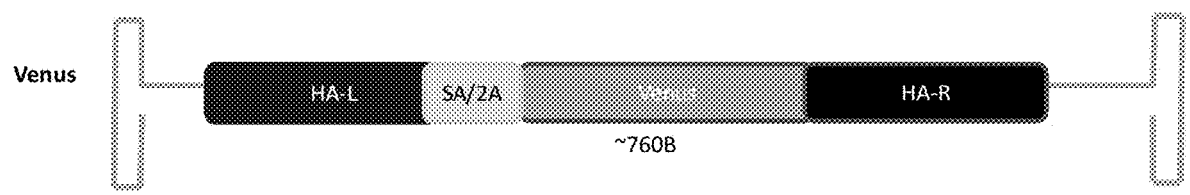
FIG. 24 shows a map of a single stranded AAV vector genome for the insertion of a large DNA insert. The single stranded AAV2 genome contained AAV2 ITRs, homology arms, regulatory sequences and the promoterless Venus open reading frame (ORF). Venus is a fluorescent reporter protein. The promoterless Venus containing the Venus ORF is downstream from a splice acceptor and 2A sequence. The Venus ORF is followed by a polyadenylation signal. Each homology arms is 800 bp long and targets Intron 1 of PPP1R12C gene on Chromosome 19
Figure 25:
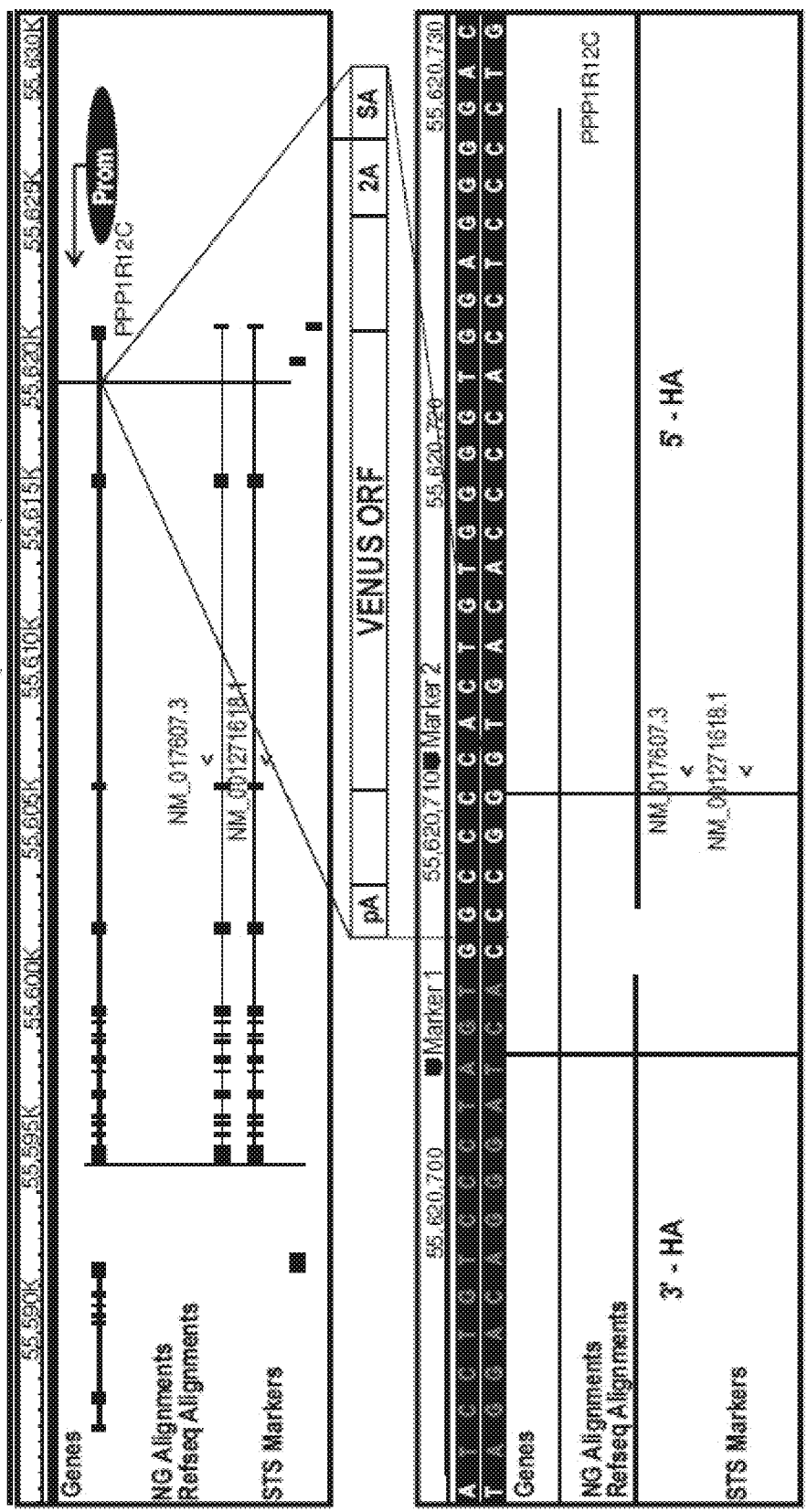
FIG. 25 shows a schematic of an insertion site of an editing moiety in AAVS1. The transgene cassette consisting of the Venus open reading frame and a splice acceptor site followed by 2A sequence is flanked on either side by homology arms. Homology arms are complementary to Intron 1 of the human PPP1R12C gene within the AAVS1 locus on chromosome 19 and mediate insertion of Venus into the site between the two homology arms.
Figure 35:
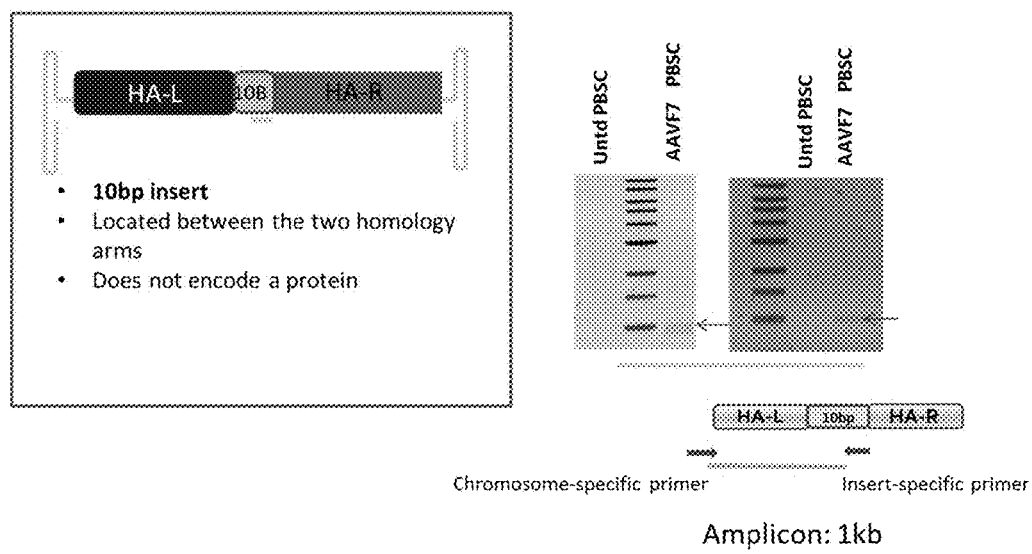
FIG. 35 shows that AAVF targets integration of small inserts into AAVS1-CD34+ cells.

A singled stranded AAV vector genome was used to design a correction genome containing homology arms and a large insert (FIG. 24). The insert contained a promoterless Venus open reading frame (ORF) downstream from a splice acceptor (SA) and a 2A sequence (2A) to allow for independent protein expression. Venus is a variant of yellow fluorescent protein (see, e.g., Nagai et al. Nat Biotechnol, 2002, 20(1): 87-90). The left and right homology arms (HA) were each 800 bp long and were complementary to sequences in Intron 1 of the human PPP1R12C located in the AAVS1 locus on chromosome 19 (FIG. 25). A similar single stranded AAV vector genome was designed with a 10 bp insert between the two homology arms (FIG. 35). The AAV locus is considered a safe harbor site for the insertion of heterologous transgenes.

The homology arms, the open reading frame and regulatory sequences were cloned between AAV2 inverted terminal repeats (ITRs). This correction genome was then packaged (pseudotyped) in different AAV capsids, including AAVHSC, AAV8, 9, 6 and 2. Recombinant viruses were then used to deliver the editing genome to the nuclei of target cells. Target cells tested included CD34+ erythroleukemia cell lines, liver cell lines and primary human CD34+ hematopoietic stem/progenitor cells and as well as their hematopoietic progeny.

Figure 26A:
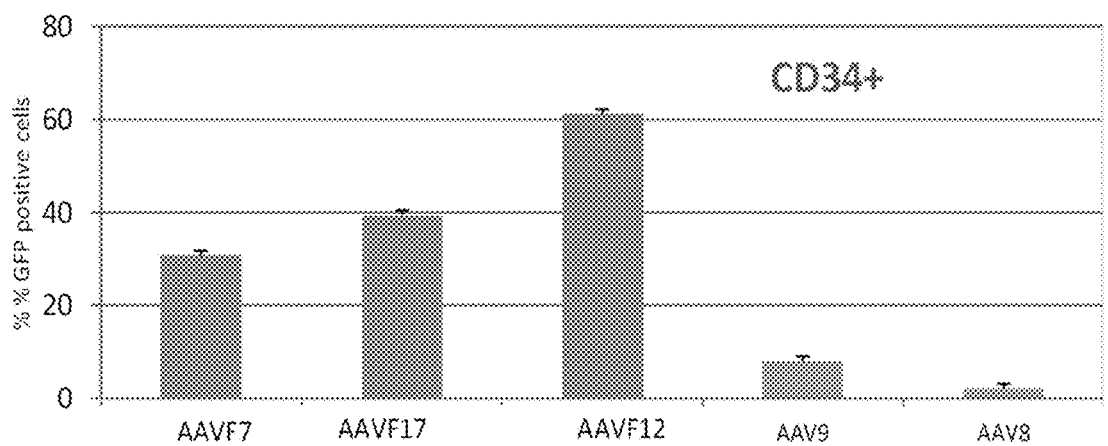
FIGS. 26A-F show targeted genomic insertion of a large protein coding sequence by recombinant AAVF vectors in human cell lines and primary cells demonstrating that AAVF-mediated genome editing is robust and that there is efficient editing in Human CD34+ cells and cell lines.
Figure 26B:
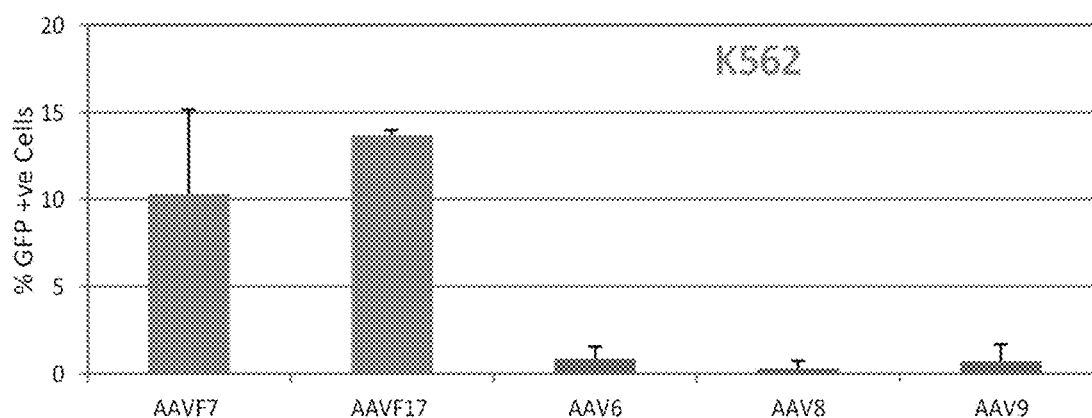
Figure 26C:
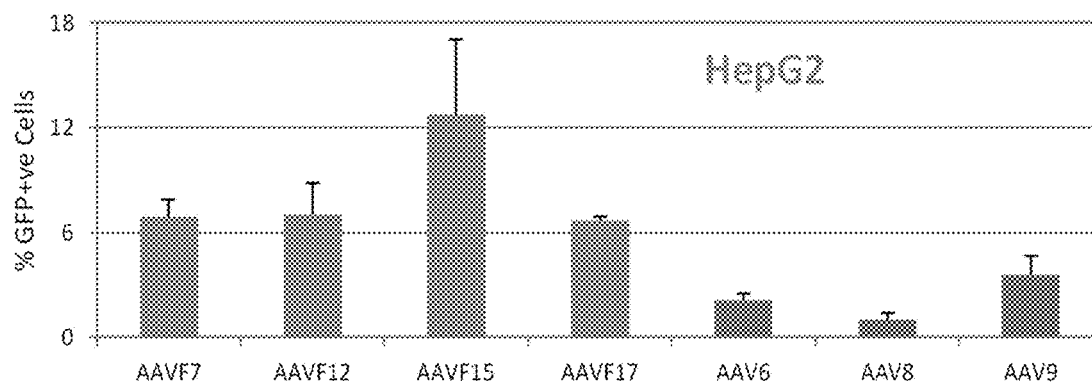
Figure 26D:
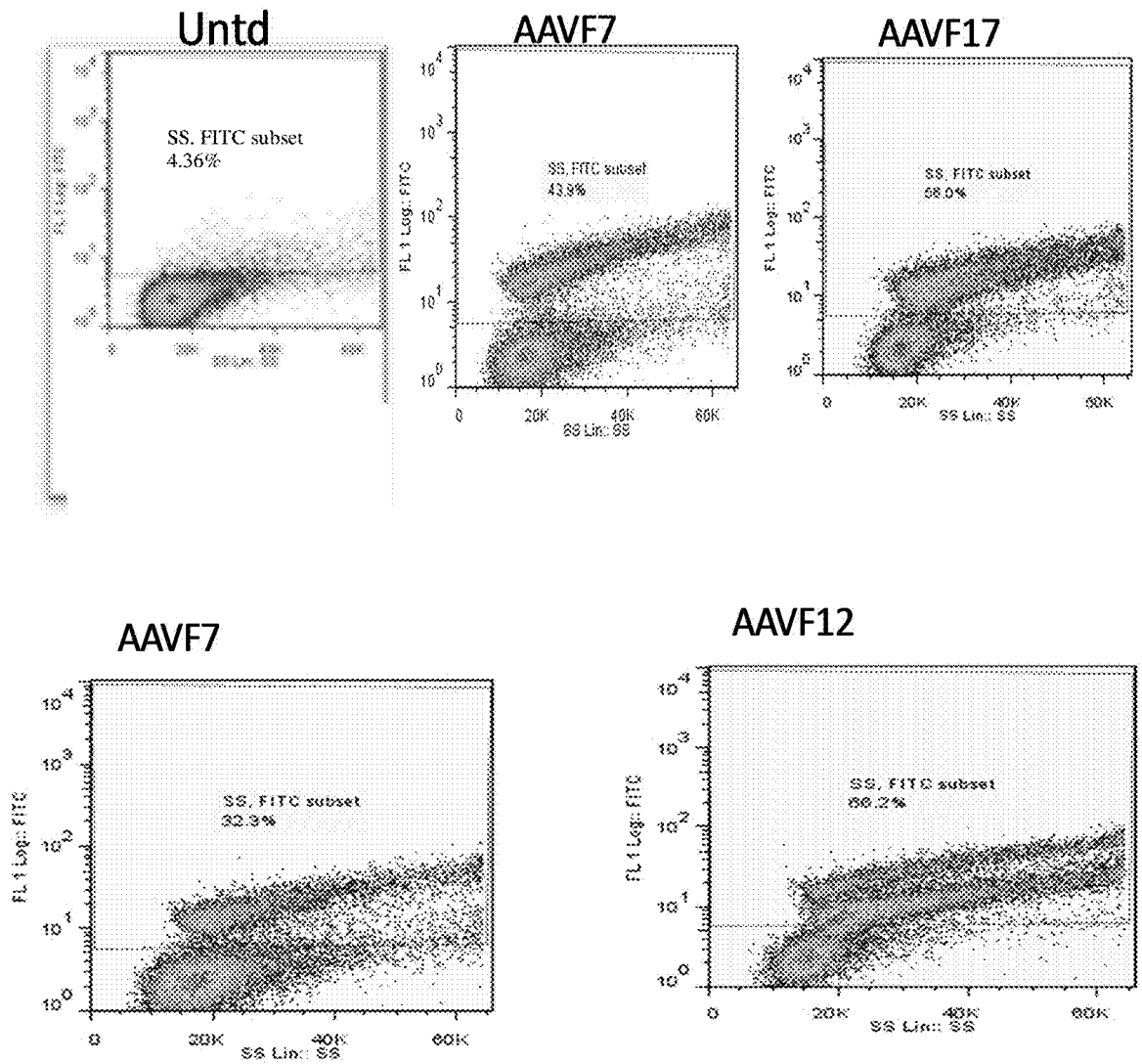
Figure 26E:
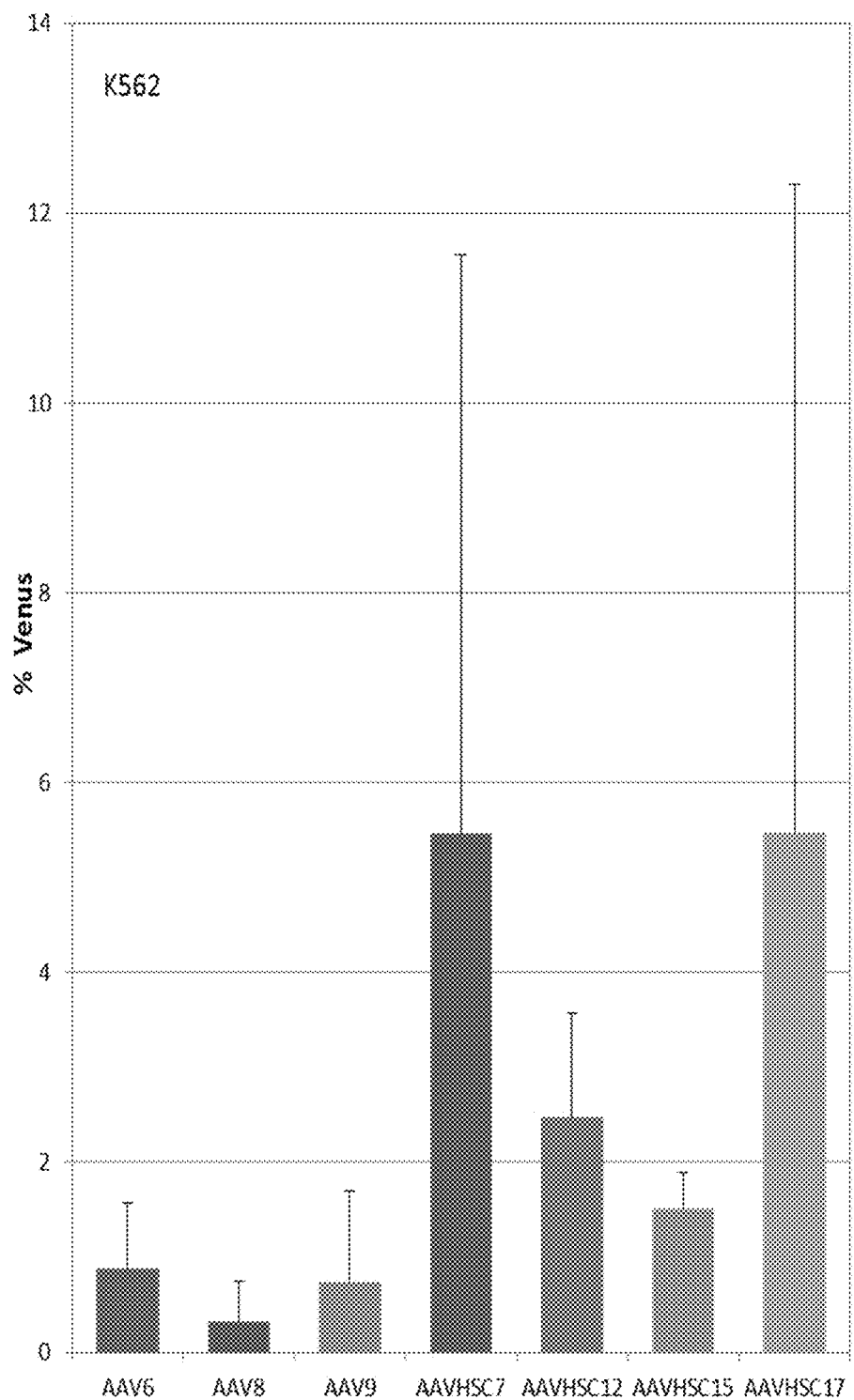
Figure 26F:
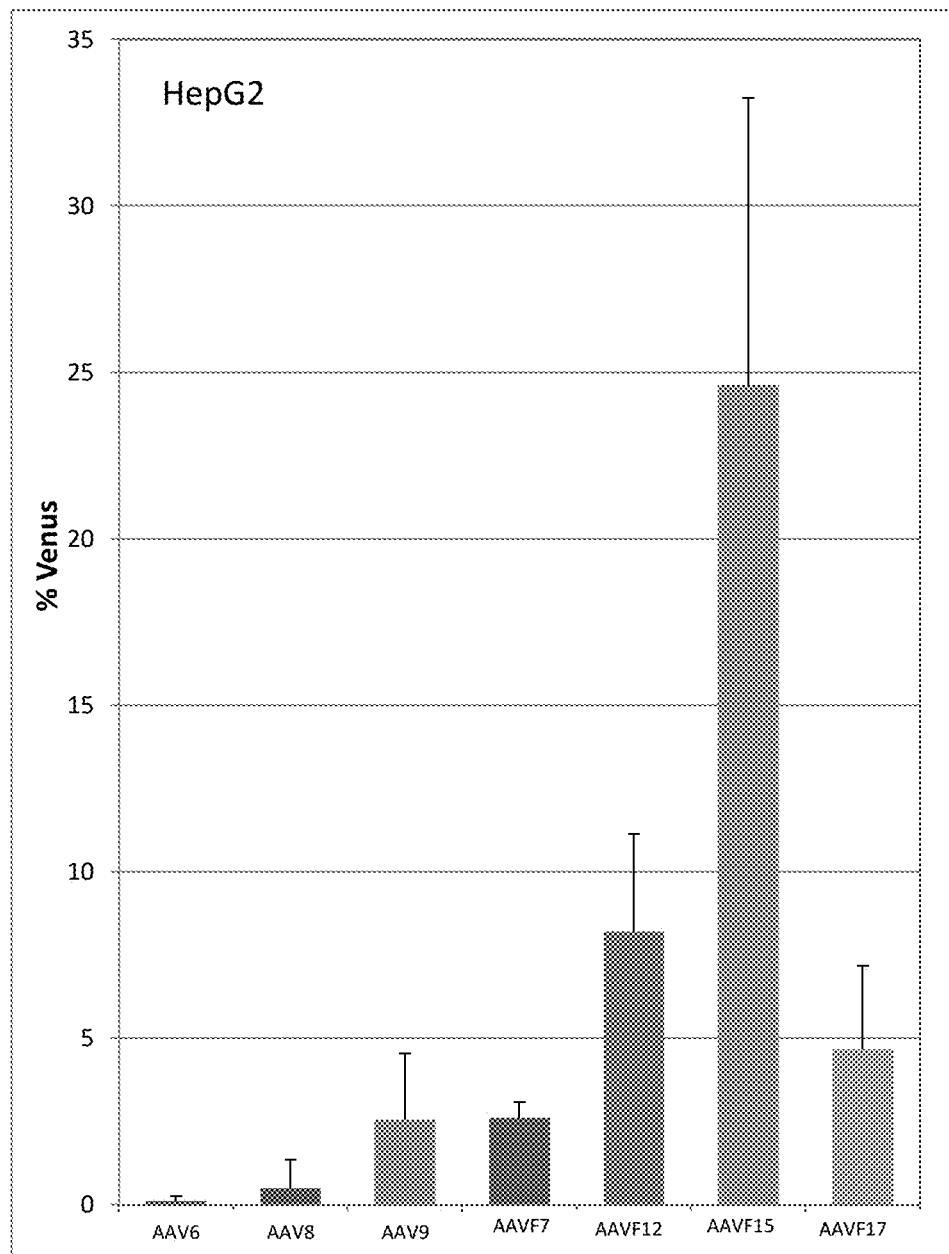

AAVF vectors containing the Venus ORF, preceded by and flanked by homology arms complementary to Intron 1 of the human PPP1R12C genes were used to deliver the editing genome to primary human CD34+ cytokine-primed peripheral blood stem cells (FIG. 26A), K562, a human CD34+ erythroleukemia cell line (FIG. 26B), and HepG2, a human liver cell line (FIG. 26C). Primary CD34+ cells supported the highest level of editing, up to 60% (FIGS. 26A-F). Immortalized cell lines, including K562 and HepG2, also showed significant levels of editing. In all cases, the level of editing achieved was consistently significantly higher than that achieved with non-Clade F viruses, including AAV6 and AAV8 (FIGS. 26A-F and FIG. 36).

Figure 27:
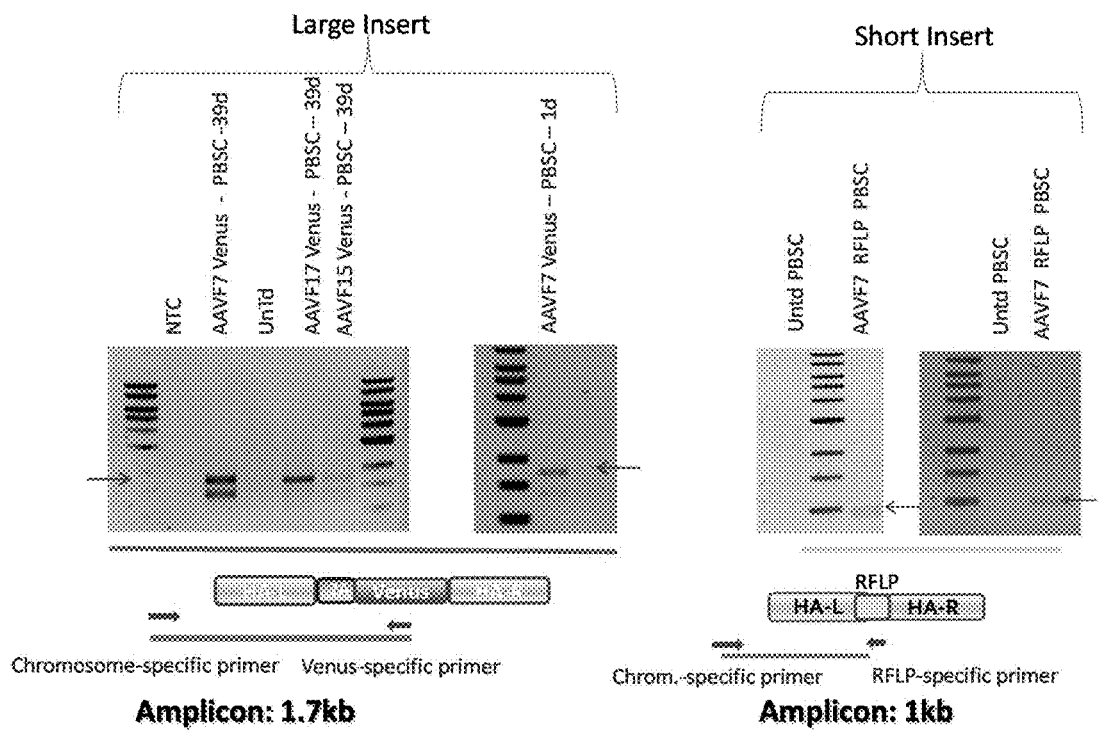
FIG. 27 shows a targeted integration assay for the detection of large and small inserts into the AAVS1 locus on the human chromosome 19. The schematic maps show the location of primers. The 5' primer is complementary to chromosomal sequences. The 3' primer is specific for the insert. The specific amplicon is predicted to be 1.7 kb for the large insert and 1 kb for the small insert. The split primer pair (chromosomal and insert specific) lends specificity to the targeted integration assay.
Figure 36:
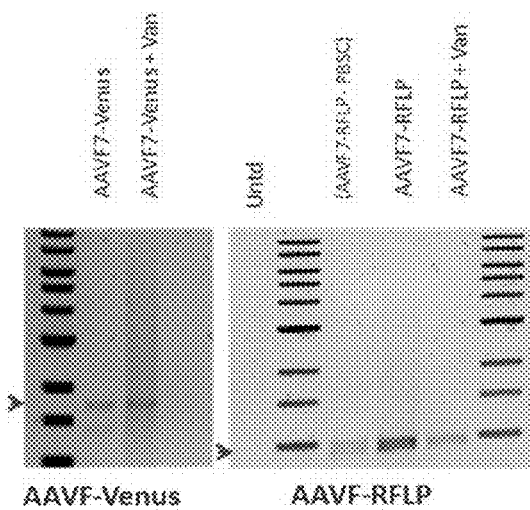
FIG. 36 shows AAV targeting of promoterless Venus & RFLP in a HepG2 (Hepatoma) cell line.

In another experiment, DNA extracted from cytokine primed CD34+ peripheral blood stem cells (PBSC) transduced with AAVF7, AAVF15 or AAVF17 vectors was amplified with a chromosome-specific primer and an insert-specific primer. The vectors included either a large insert (Venus) or a short insert (10 bp, RFLP). Gels showed that correctly sized amplicons were amplified from the edited CD34 cells (FIG. 27, FIG. 35, and FIG. 36). The presence of the 1.7 kb and 1 kb bands reflected correctly targeted integration of large and small inserts, respectively. Targeted integration was shown at both short and long-term time points after editing with AAVF vectors (FIG. 27).

Figure 28A:
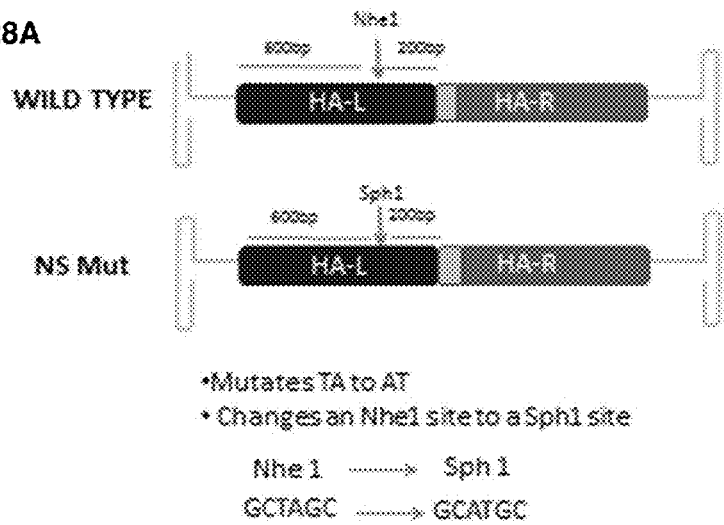
FIGS. 28A-E show that AAVF vectors mediate nucleotide substitution at specified genomic sites.
Figure 28B:
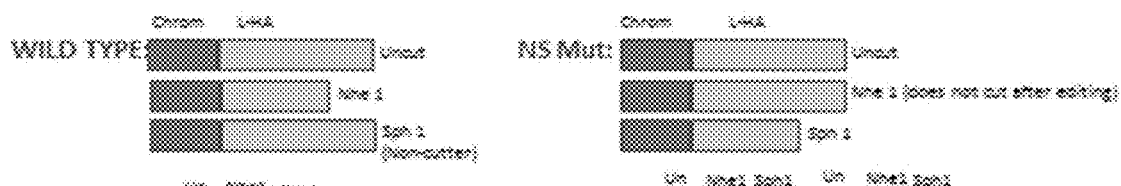
Figure 28C:
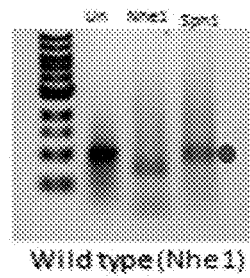
Figure 28D:
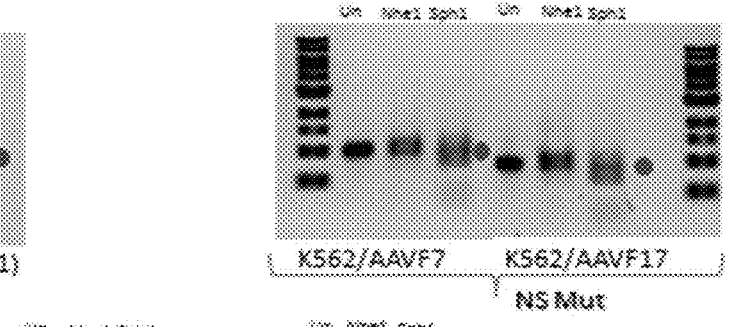
Figure 28E:
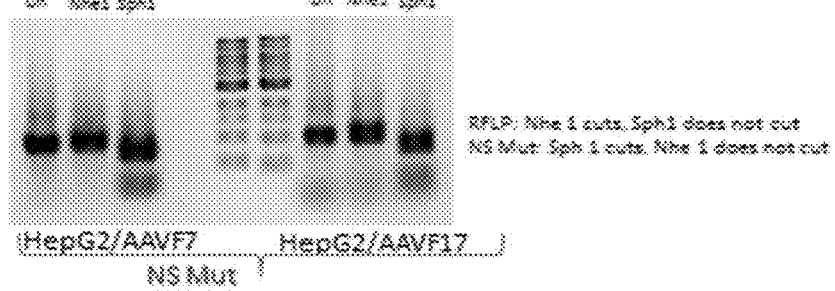
Figure 29:
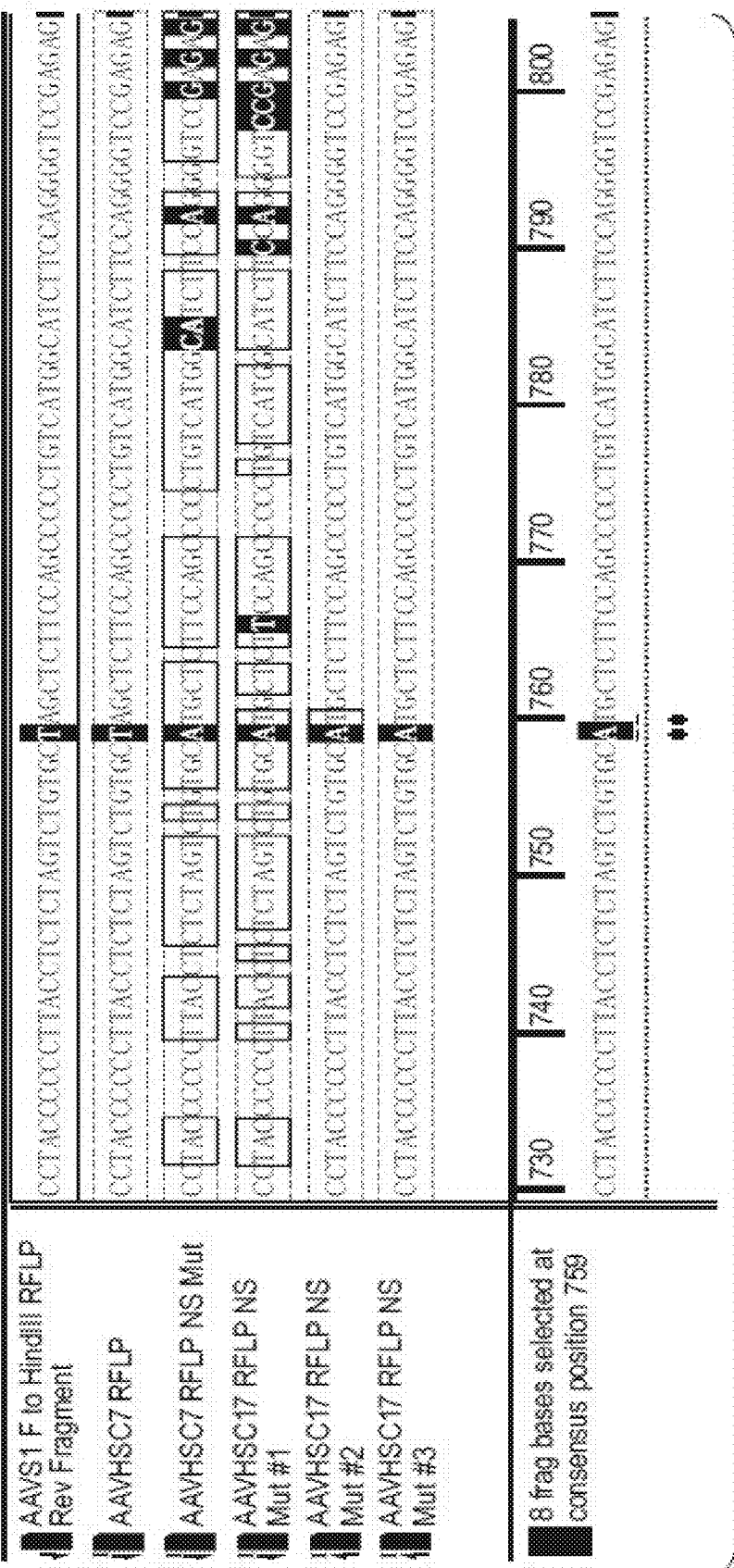
FIG. 29 shows a sequence analysis of DNA from cells edited with AAVF7 and AAVF17 Wild type or NS Mut vectors.
Figure 29:
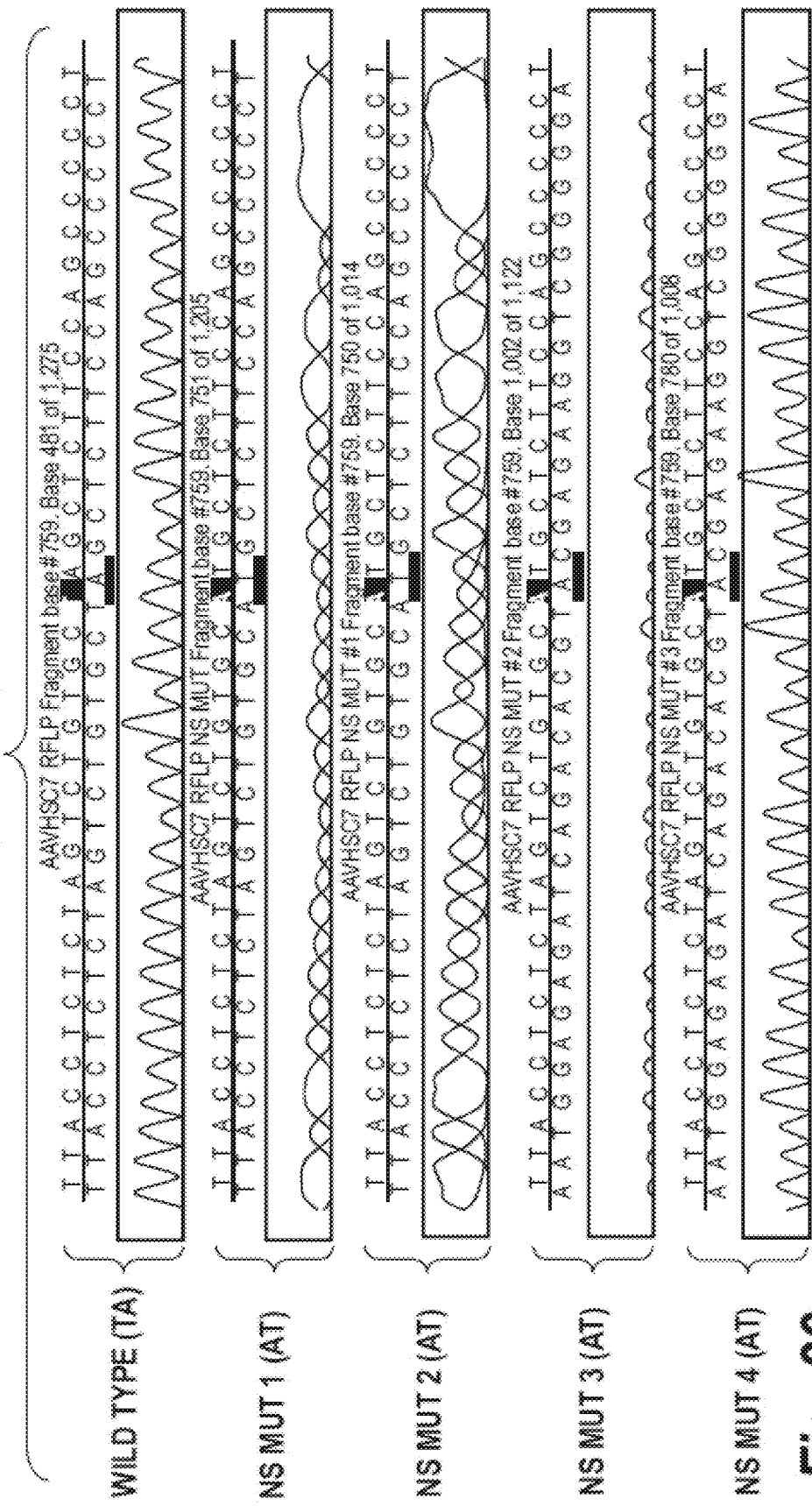

In another experiment, single stranded AAV vector genomes were designed for the insertion of a 10 bp insert in intron 1 of the human PPP1R12C gene (FIG. 28A). These vectors included a wild type left homology arm (HA-L) which contained a Nhe1 restriction enzyme recognition site (GCTAGC). The NS mut vector, was designed to change the TA sequence in the left homology arm on chromosome 19 to AT. This change results in the conversion of an Nhe1 site to an Sph1 site, changing the sequence from GCTAGC to GCATGC. FIG. 28B shows the relative sizes of the expected fragments created by cutting with Nhe1 or Sph1 when genomic DNA from K562 cells was edited using either the wild type or the NS Mut AAVF vectors. Actual amplicons derived from genomic DNA of K562 cells edited with a wild type AAVF vector were digested with Nhe 1, but not with Sph1, as predicted (FIG. 28C). Results with amplified K562 DNA after editing with AAVF7 or an AAVF17 vectors encoding either wild type or NS Mut genomes showed that digestion with Nhe1 no longer resulted in cleavage of the amplicon, comparable to the amplicon from unedited cells. Digestion with Sph1 resulted in cleavage, demonstrating that the Nhe1 site in the left homology arm of the chromosome was replaced by an Sph1 site (FIG. 28D). Electrophoresis of amplified DNA form a hepatocellular carcinoma cell line, HepG2, after editing with AAVF7 or an AAVF17 vectors encoding either wild type or NS Mut genomes showed that digestion with Nhe1 no longer resulted in cleavage of the amplicon, comparable to the amplicon from unedited cells (FIG. 28E). Digestion with Sph1 resulted in cleavage, demonstrating that the Nhe1 site in the left homology arm of the chromosome was replaced by an Sph1 site. Sequence analysis confirmed editing with AAVF7 and AAVF17 Wild type or NS Mut vectors (FIG. 29). These results demonstrate that both AAVF7 as well as AAVF17 successfully mediated the 2 nucleotide substitution in the chromosomal sequences in two different cell lines. These results also demonstrate the ability of AAVF vectors to mediate a 2 base pair substitution in genomic DNA of human cells, suggesting their use for correction of disease-causing mutations or induction of new mutations in the genome.

In another experiment, the potential requirement for cell division on the editing capacity of AAVF vectors was tested on healthy human CD34+ PBSC. BrdU was incorporated into transduced human CD34+ PBSC through pulsing with 10 µM of BrdU for 2 hours. AAVF transduced CD34+ cells were harvested, permeabilized and fixed prior to DNase treatment. After DNase treatment, treated cells were stained with anti-BrdU APC antibody for 20 minutes. BrdU labeling of in vitro edited cells was performed prior to harvesting using the APC BrdU Flow Kit (BD Biosciences) as per instructions. Cells were then analyzed by flow cytometry for Venus expression as well as BrdU labeling. Results revealed the similar frequencies of Venus expression in both the BrdU positive and negative populations, suggesting that cell division was not required for AAVF-mediated editing (FIG. 30).

Figure 31A:
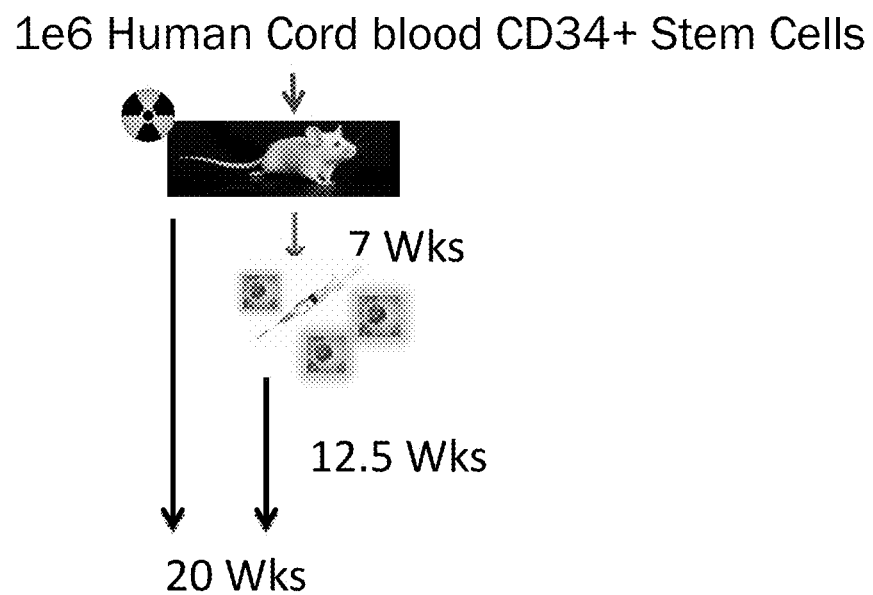
FIGS. 31A-C show efficient editing of engrafted human hematopoietic stem cells in vivo by systemically delivered AAVF vectors.
Figure 31B:
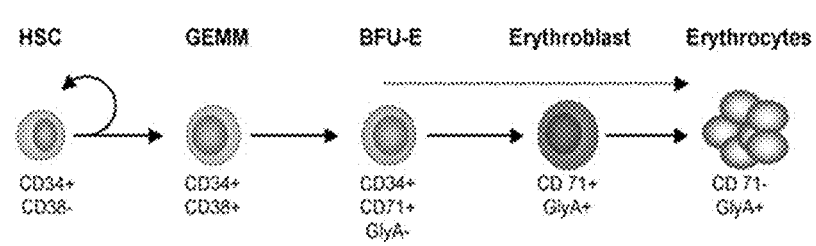
Figure 31C:
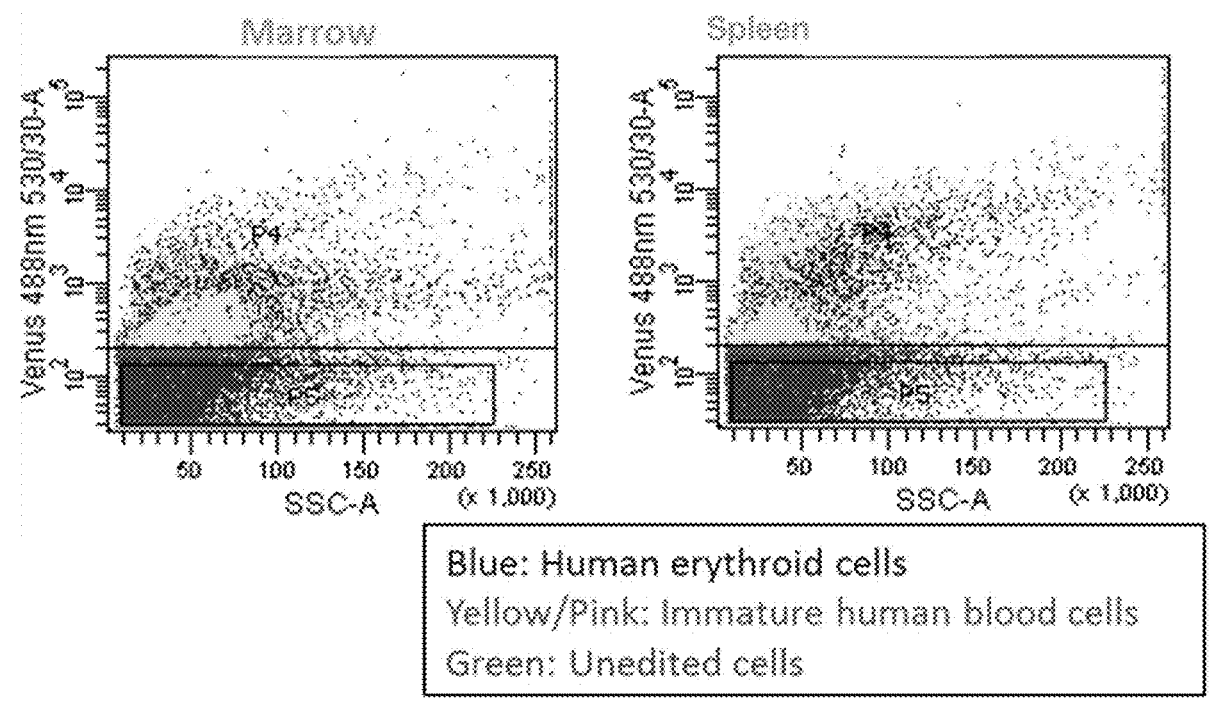
Figure 37:
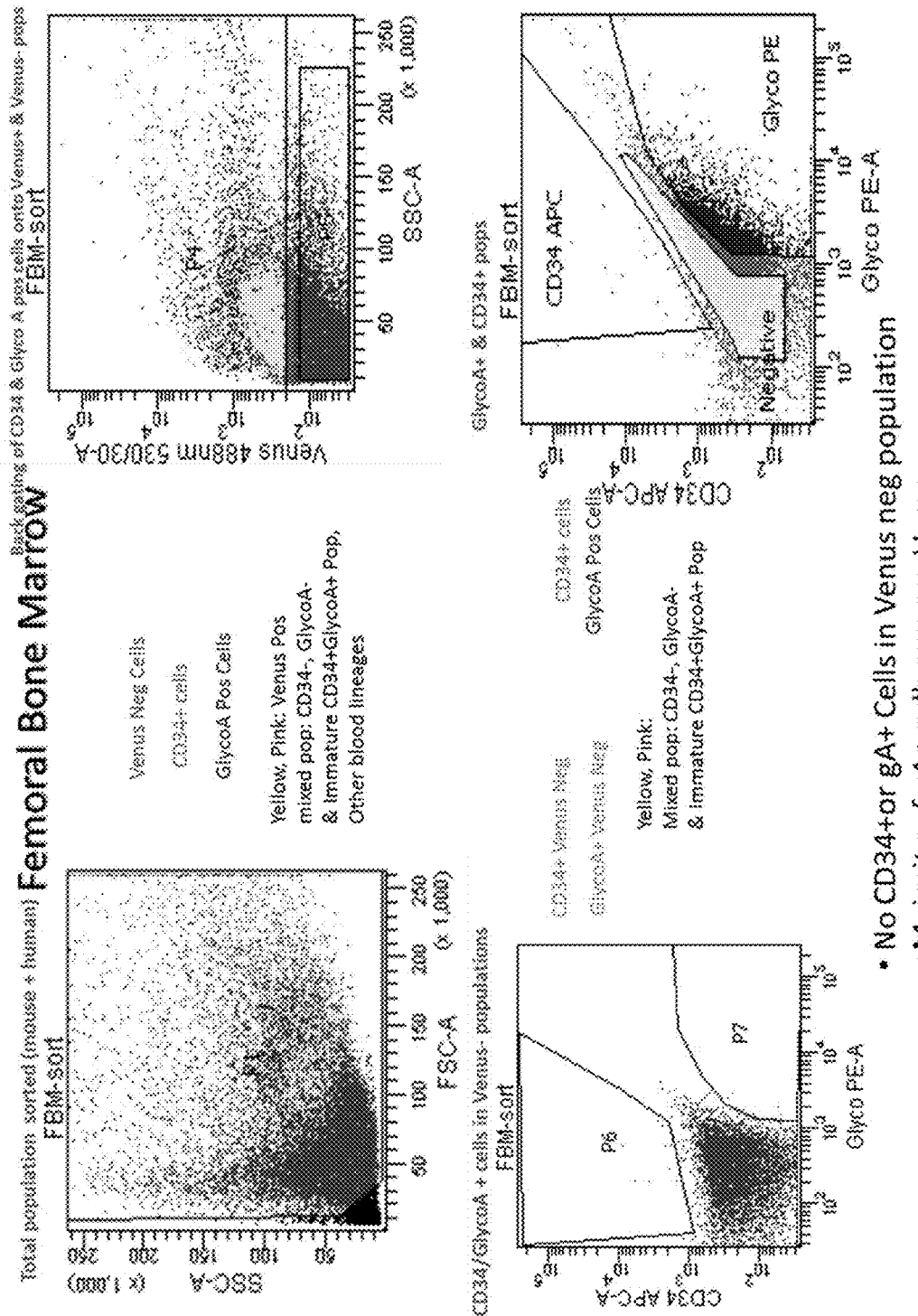
FIG. 37 shows representative femoral bone marrow flow cytometry graphs showing total population sorted, backgating of CD34 and glycoA positive cells onto Venus positive and Venus negative populations, CD34/GlycoA positive cells in Venus negative populations, and glycoA positive and CD34 positive populations.
Figure 38:
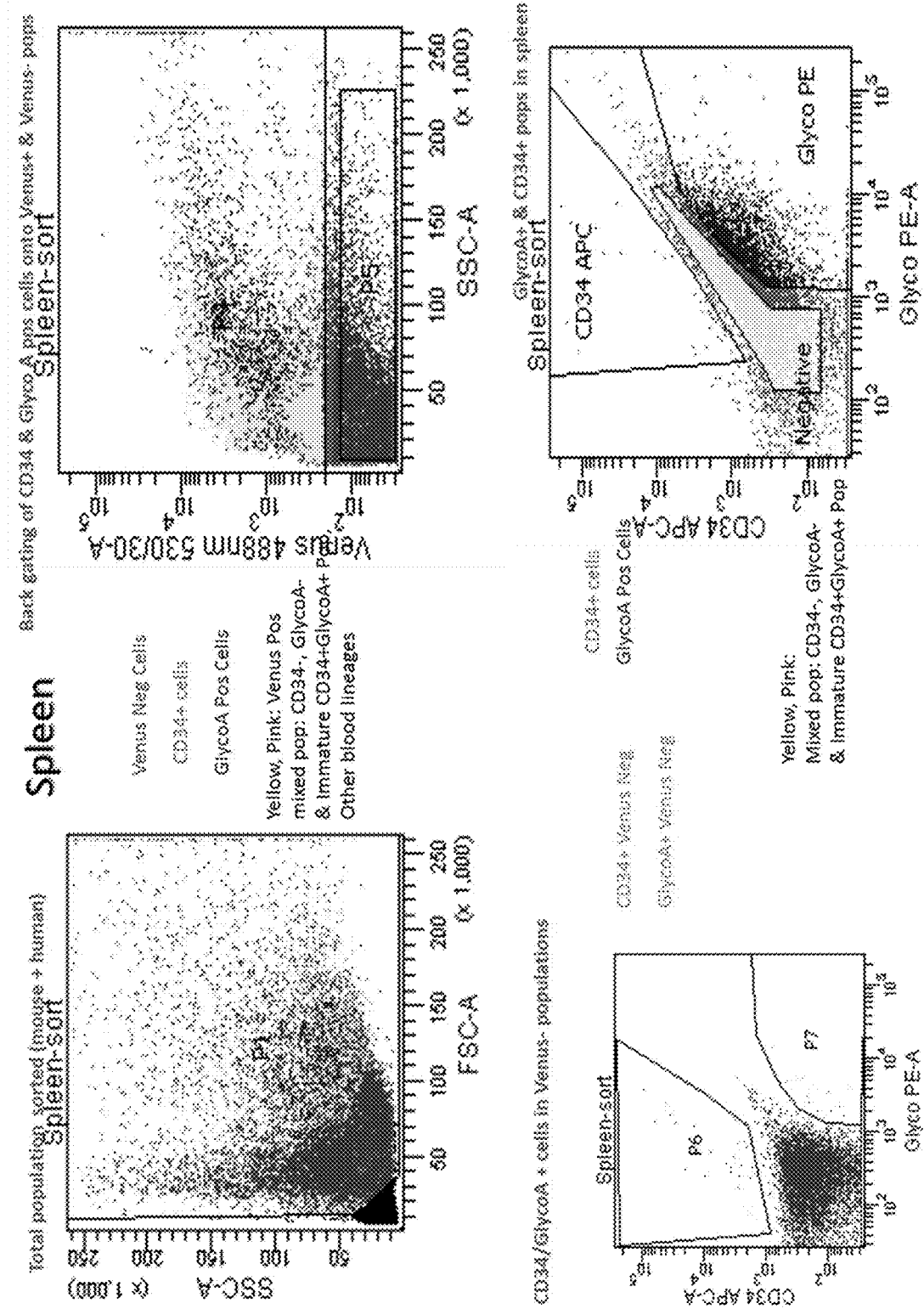
FIG. 38 shows representative spleen flow cytometry graphs showing total population sorted, backgating of CD34 and glycoA positive cells onto Venus positive and Venus negative populations, CD34/GlycoA positive cells in Venus negative populations, and glycoA positive and CD34 positive populations.

In another experiment, editing of engrafted human hematopoietic stem cells in vivo was tested by systemically delivered AAVF vectors immune deficient NOD/SCID mice engrafted with human cord blood CD34+ hematopoietic stem cells (FIGS. 31A and B). In both the marrow as well the spleen, the majority of human cells were found to express Venus, while no Venus expression was observed in mouse cells (FIG. 31C, FIG. 37 and FIG. 38). Since the mouse genome does not contain an AAVS1 locus complementary to the homology arms, these findings demonstrate the specificity of gene targeting. Of the human cells analyzed, Venus expression was observed in primitive CD34+ progenitor cells, as well as mature glycophorin A+ erythroid cells in both the marrow as well the spleen.

In another experiment, mice were engrafted with human cord blood CD34+ cells and AAVF-Venus was injected by an intravenous route either 1 or 7 weeks later. Vertebral or femoral marrow or spleen was harvested either 5, 6 or 13 weeks after intravenous injection of Venus. These represented cumulative times post-transplant of 6, 7 or 20 weeks. Results reveal that intravenous injection of AAVF-Venus results in editing of both the primitive (CD34+) as wells as the more mature, differentiated (CD45+) in vivo engrafted human hematopoietic cells. Cells of the human erythroid lineage demonstrated very efficient editing long-term after transplantation and injection (FIG. 32). AAVF-mediated editing was found to be stable long term, and was stably inherited by the differentiated progeny of in vivo engrafted human CD34+ cells (FIG. 32). The differentiated progeny of edited CD34+ cells expressed Venus long term (FIG. 32).

Figure 33:
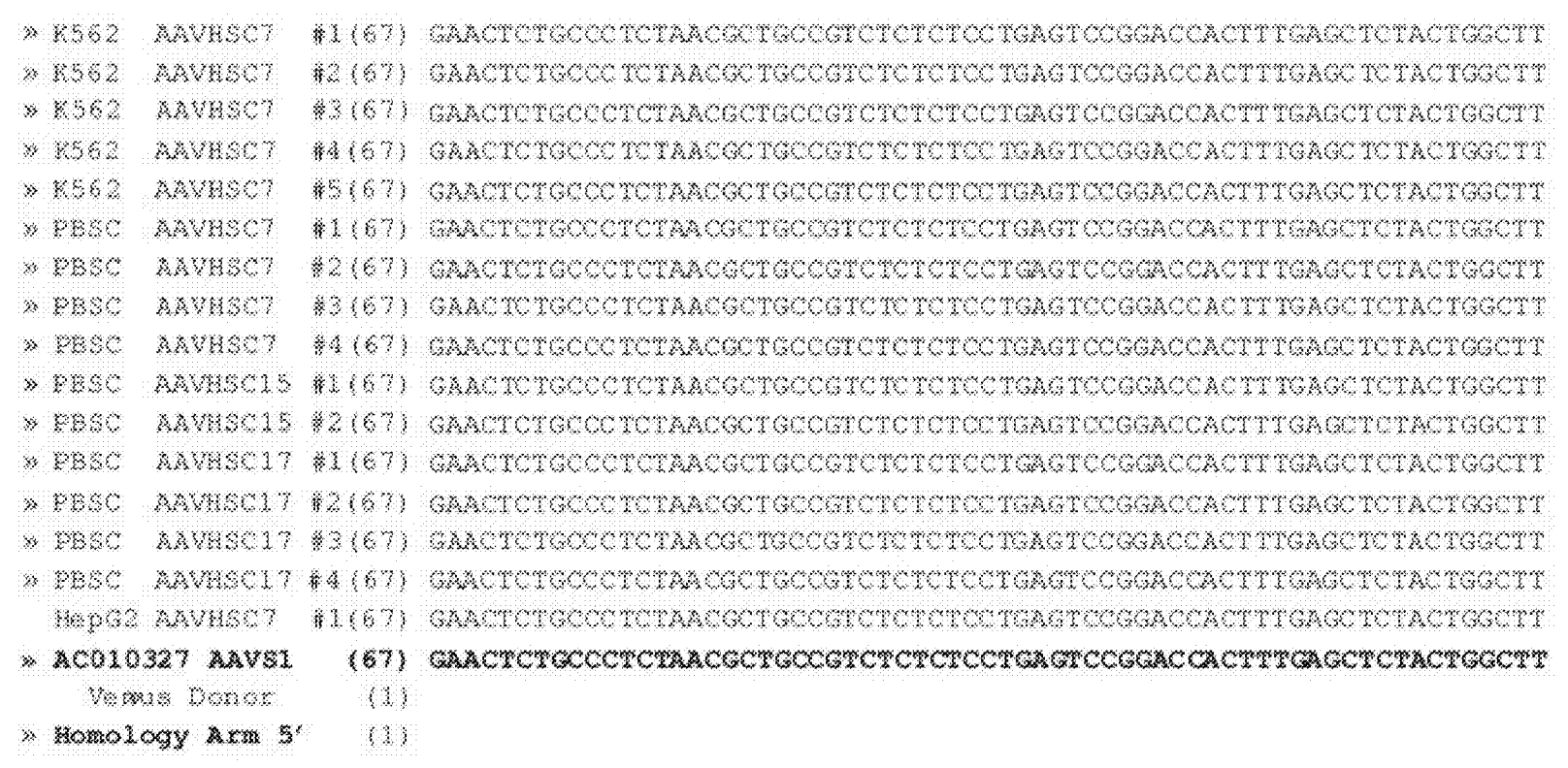
Figure 33:
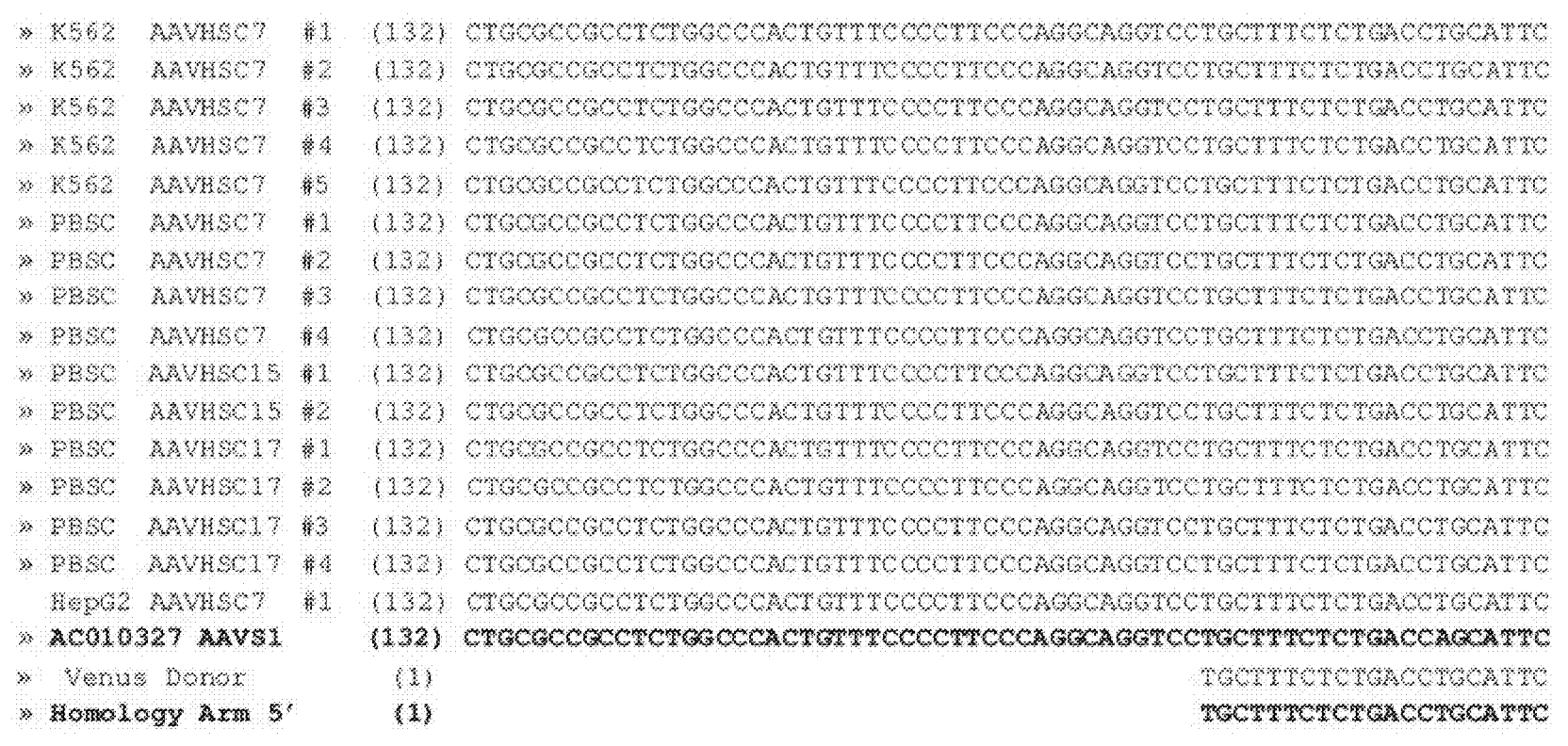
Figure 33:
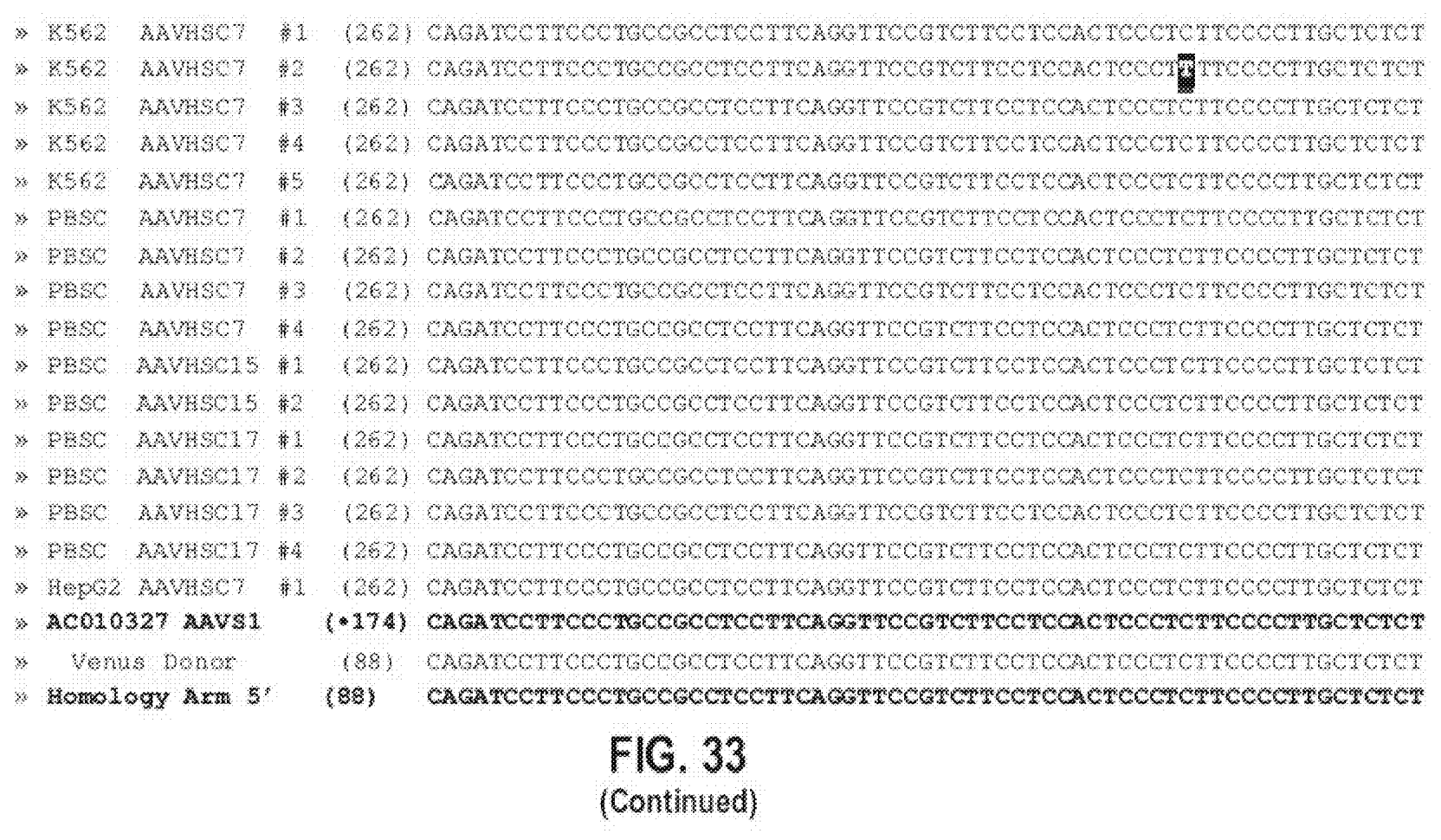
Figure 33:
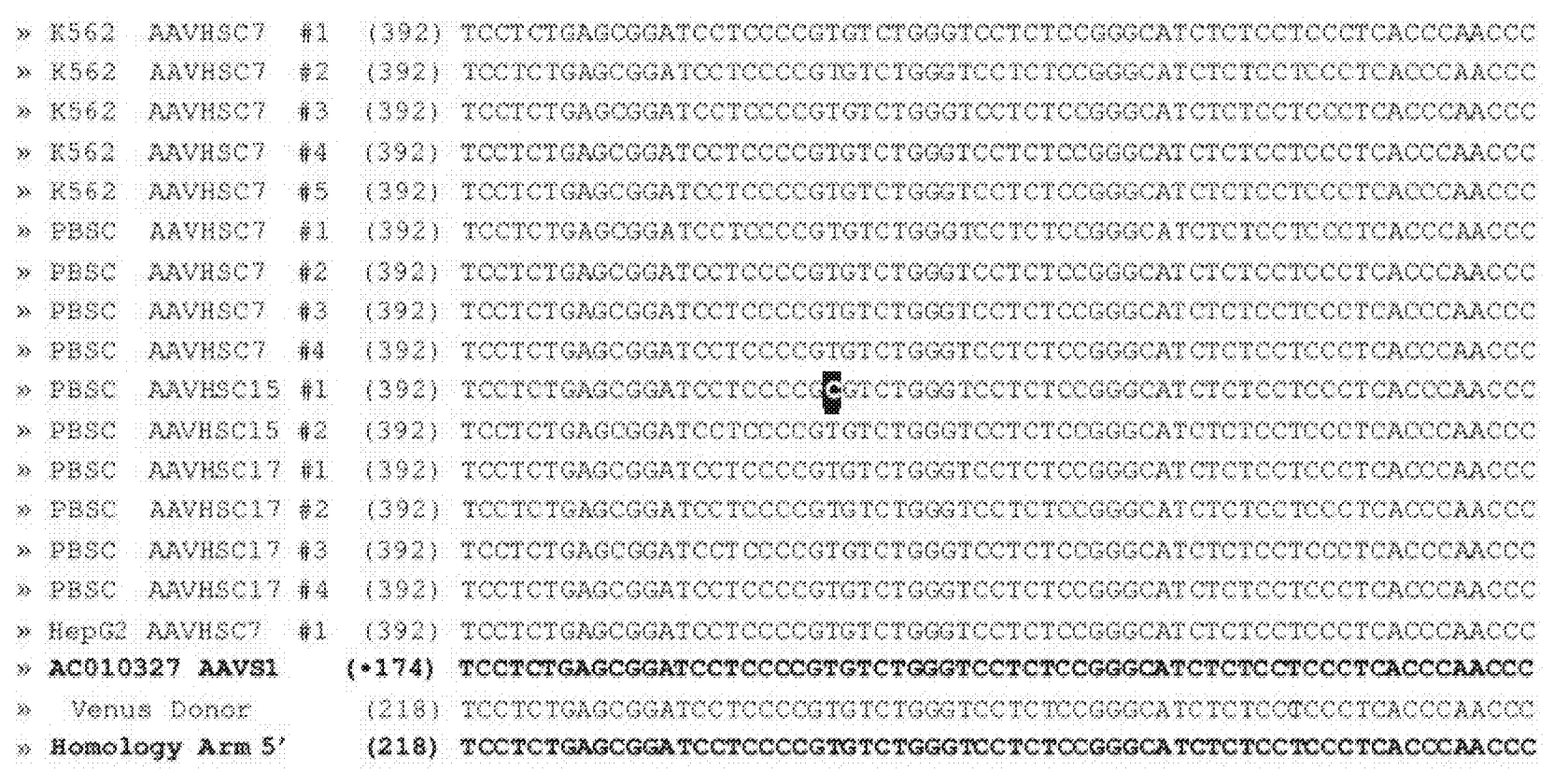
Figure 33:
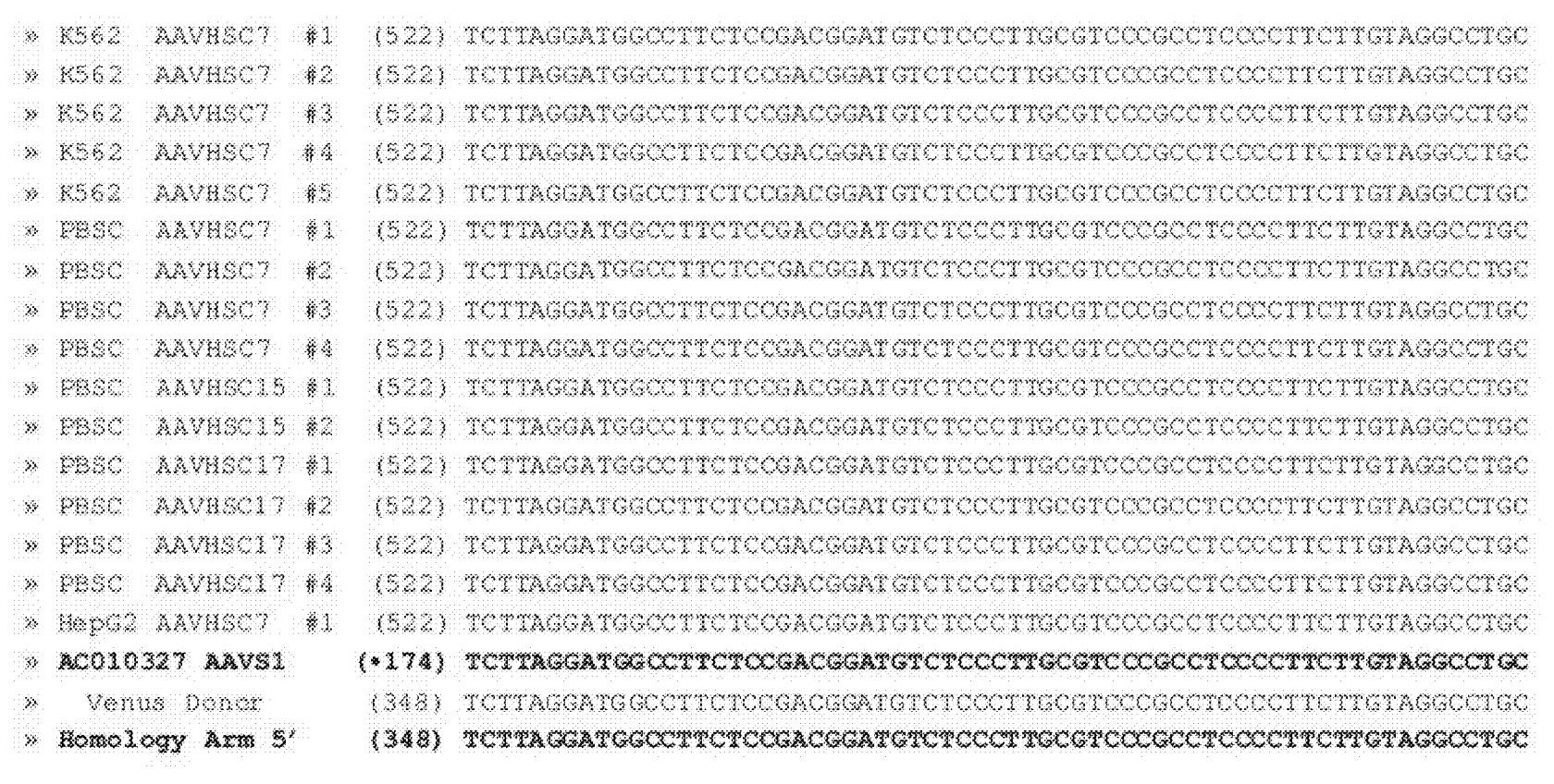
Figure 33:
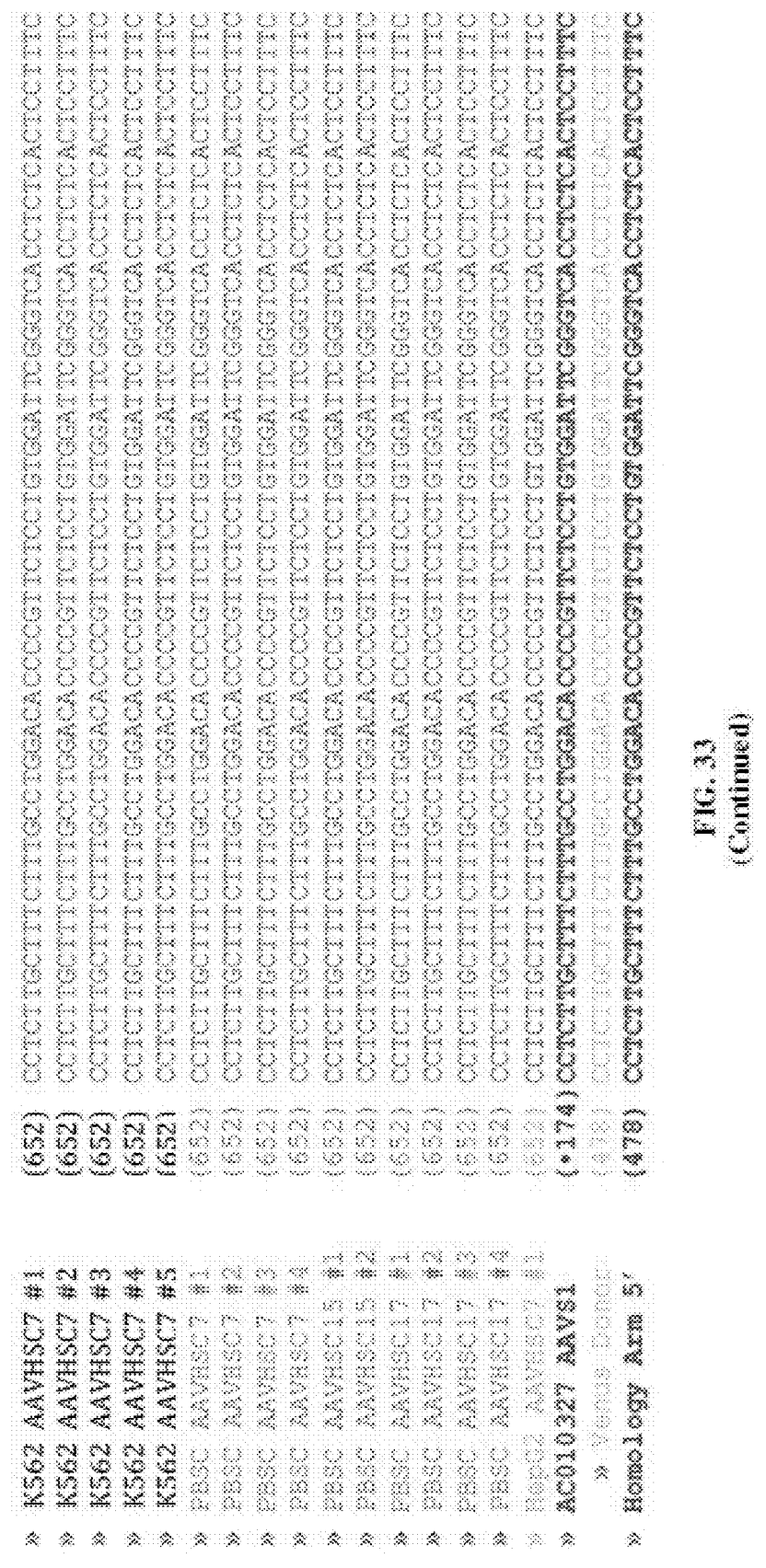
Figure 33:
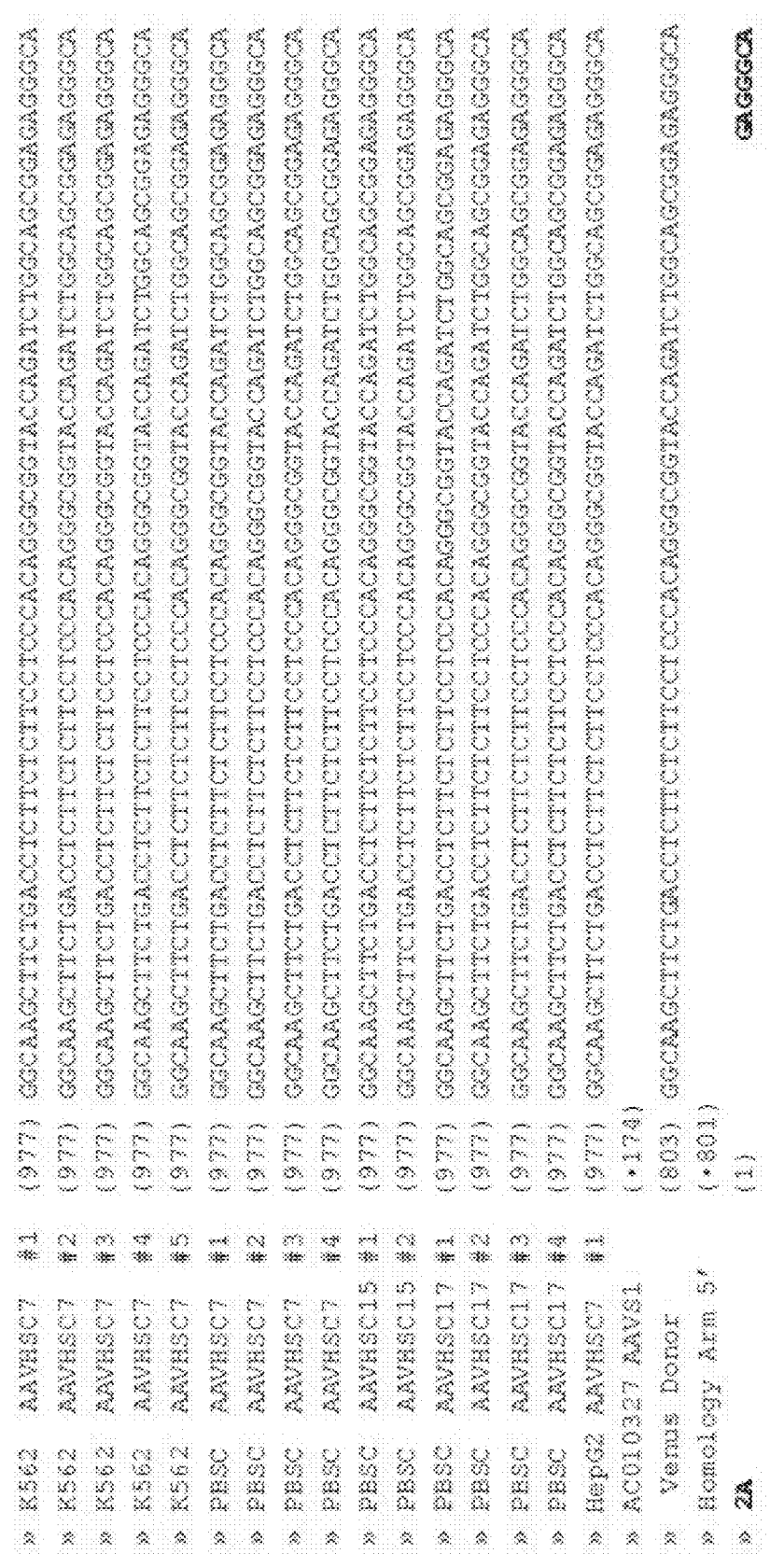
Figure 33:
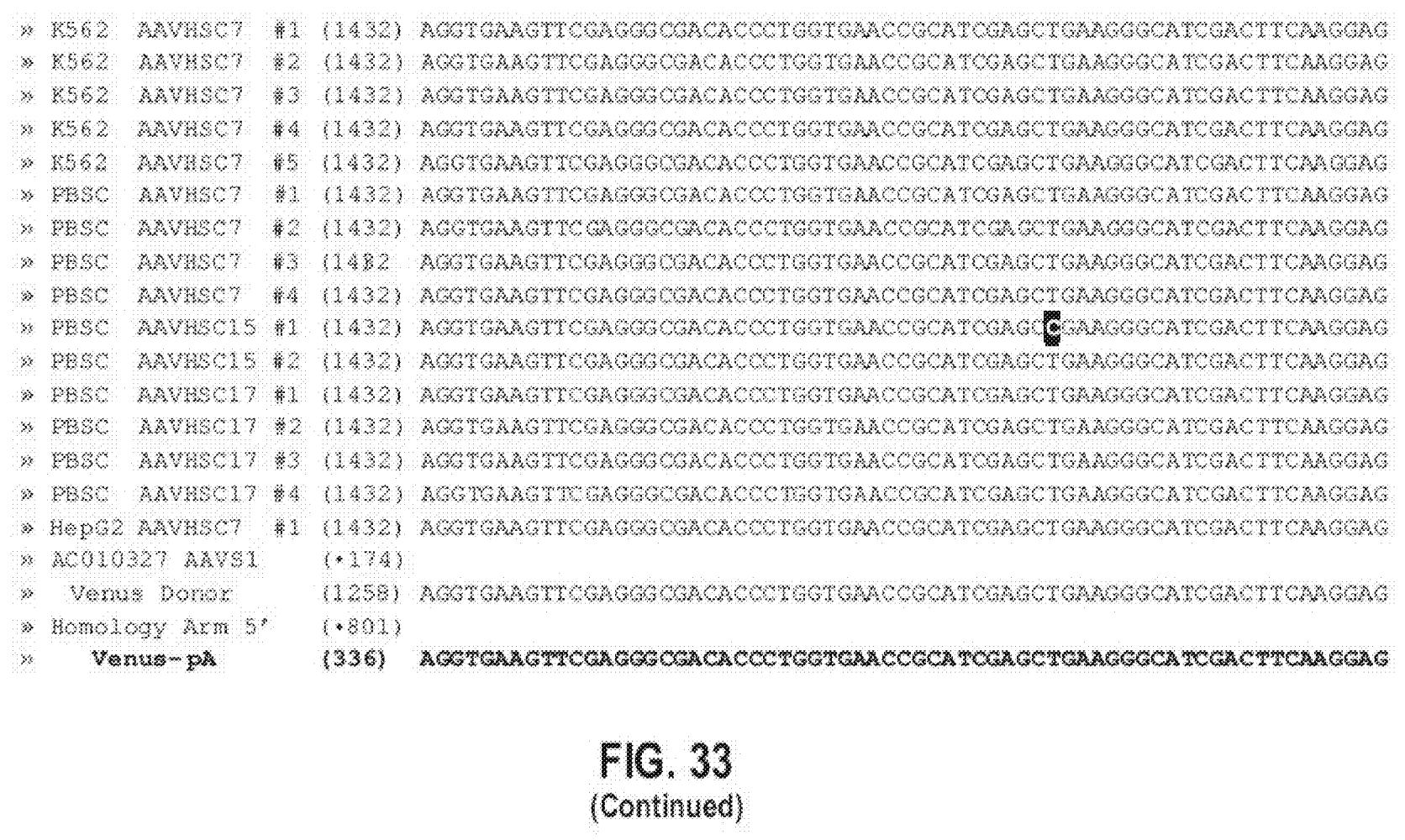
Figure 33:
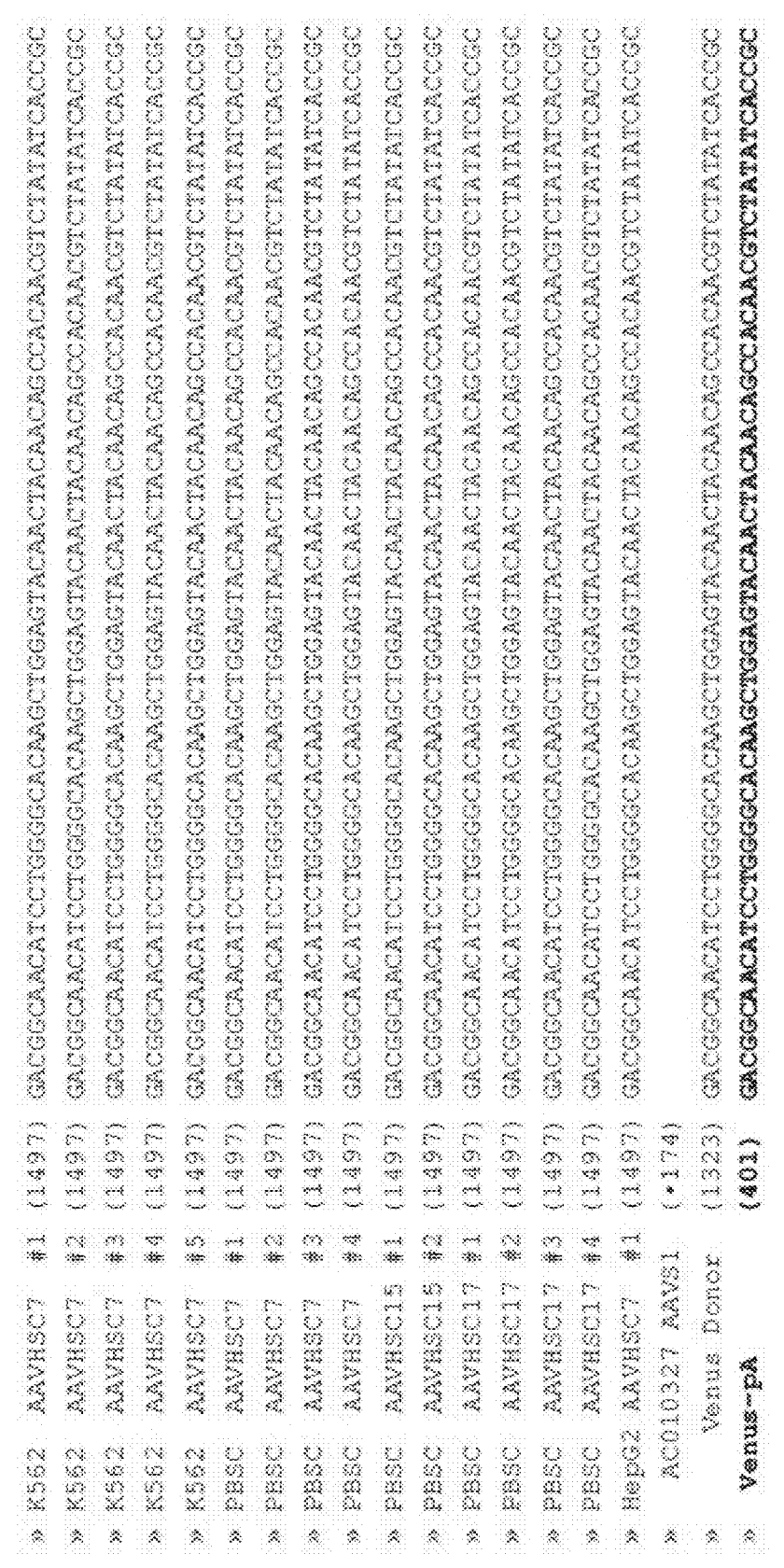
Figure 33:
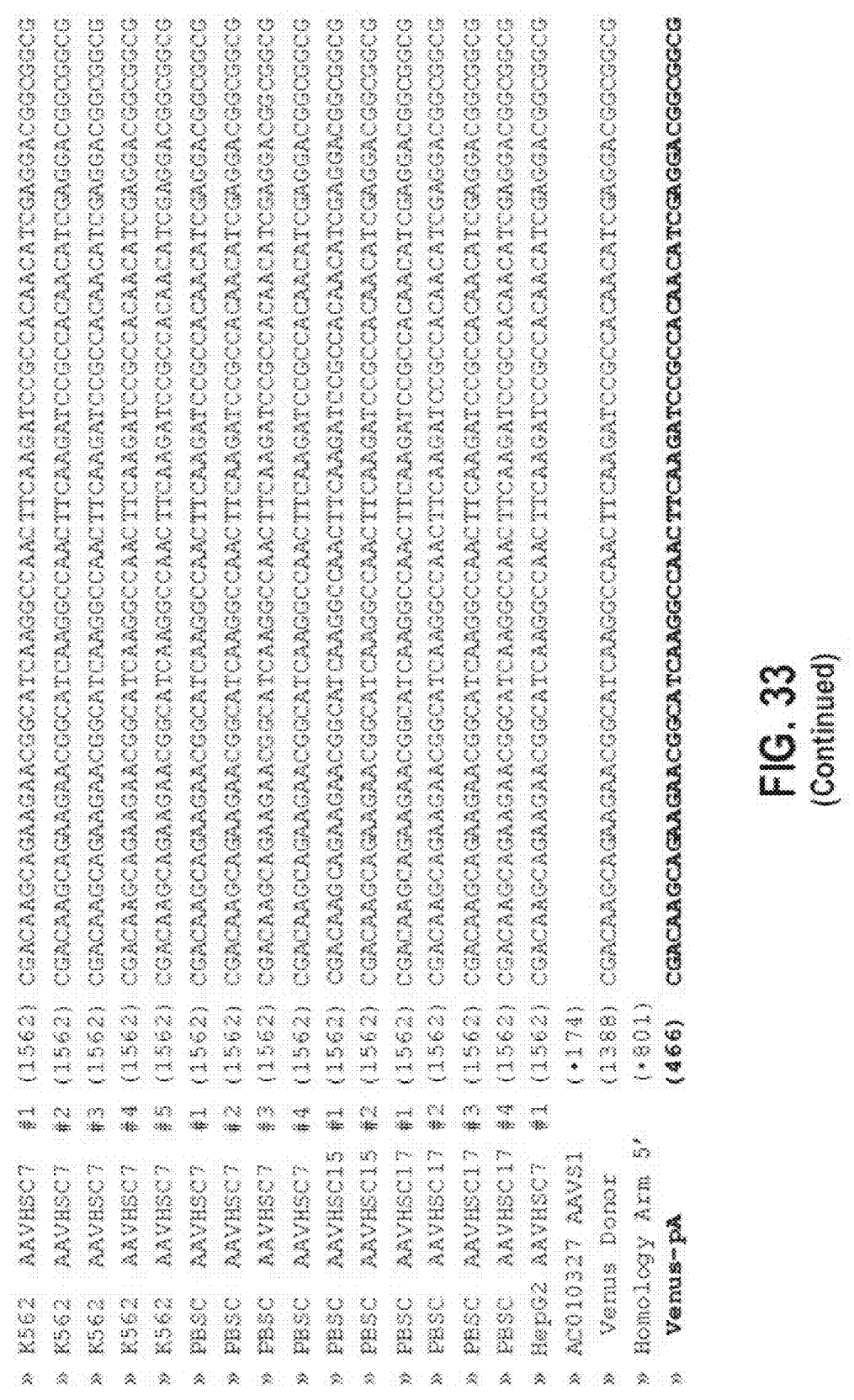

In another experiment, sequence analysis was performed for targeted chromosomal insertion of a promoterless SA/2A venus ORF in a K562 erythroleukemia cell line, primary human cytokine-primed peripheral blood CD34+ cells and a HepG2 human liver cell line (FIG. 33). Site-specifically integrated sequences were amplified using a chromosome-specific primer and an insert-specific primer. Results revealed precise insertion of the SA/2A Venus at the junction between the left and right homology arms in every case (FIG. 33).

Figure 34:
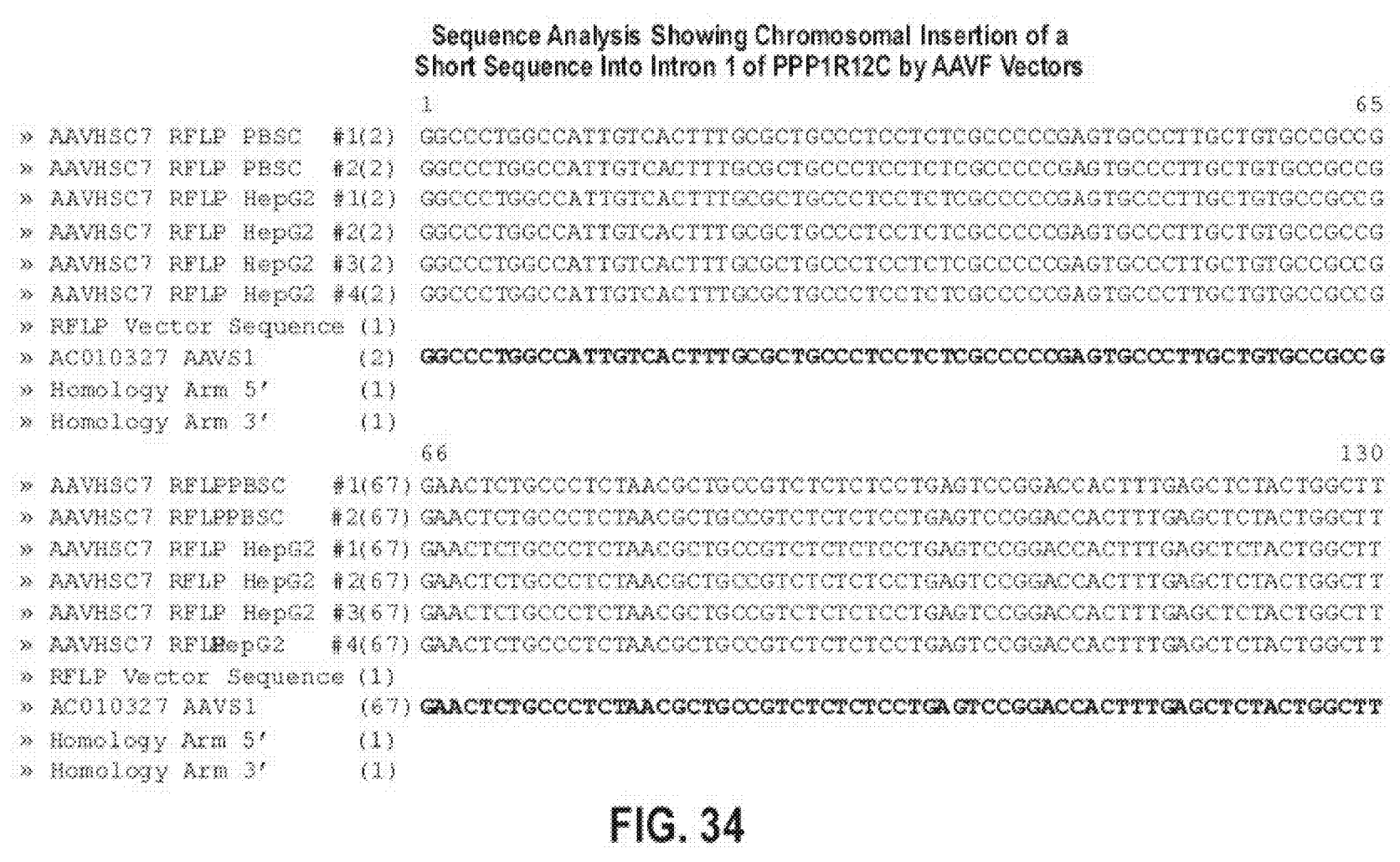
Figure 34:
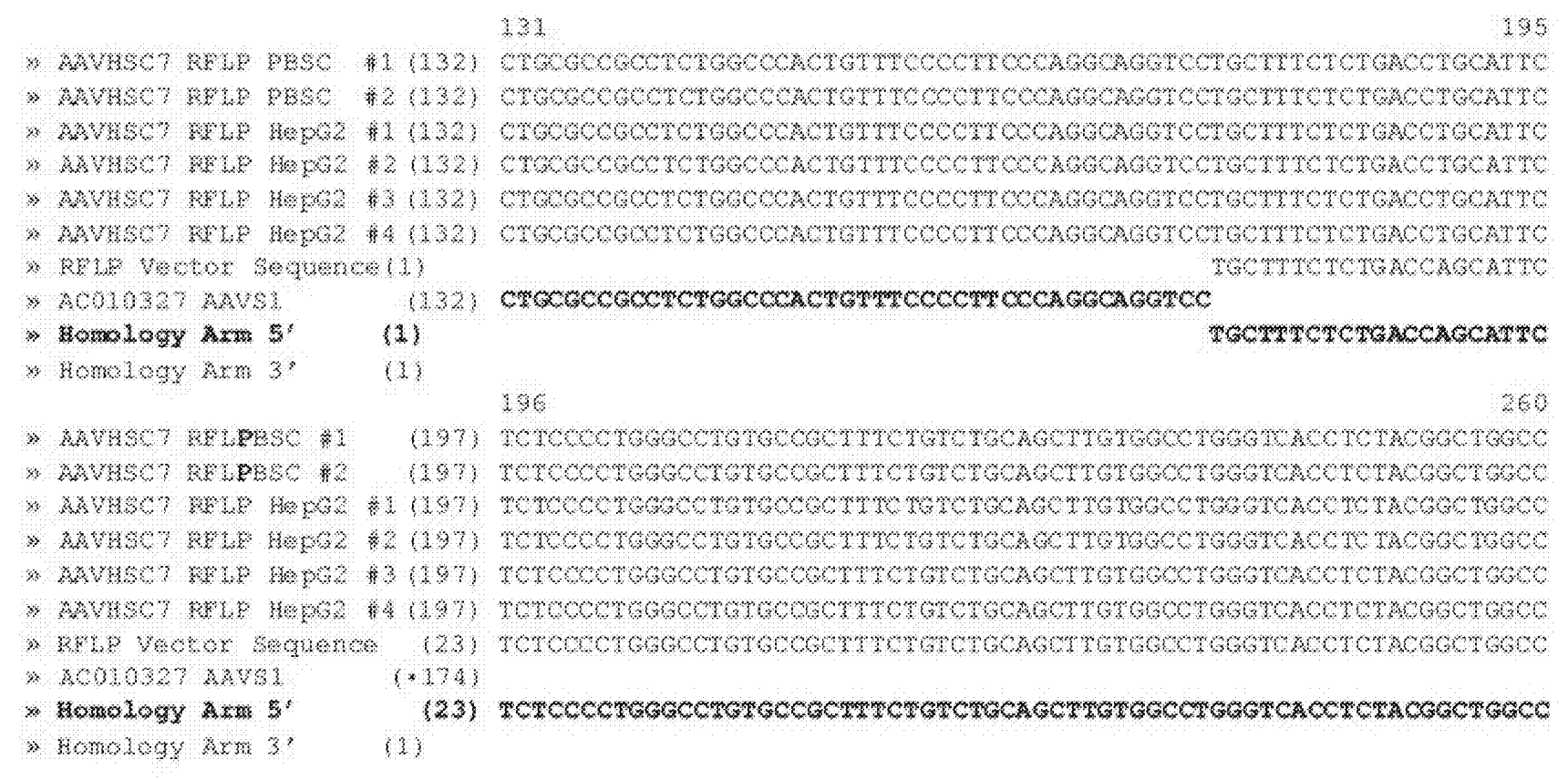
Figure 34:
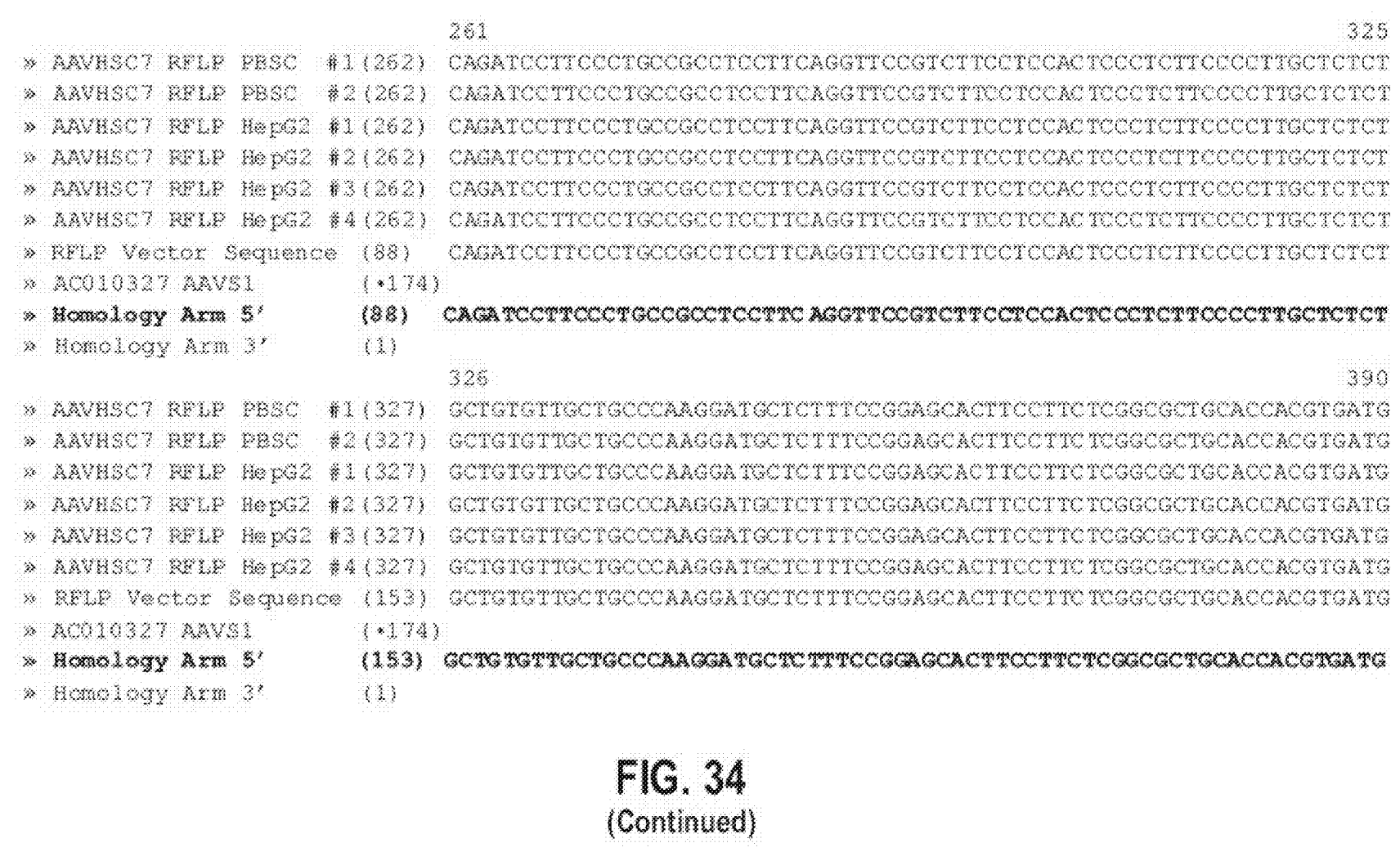
Figure 34:
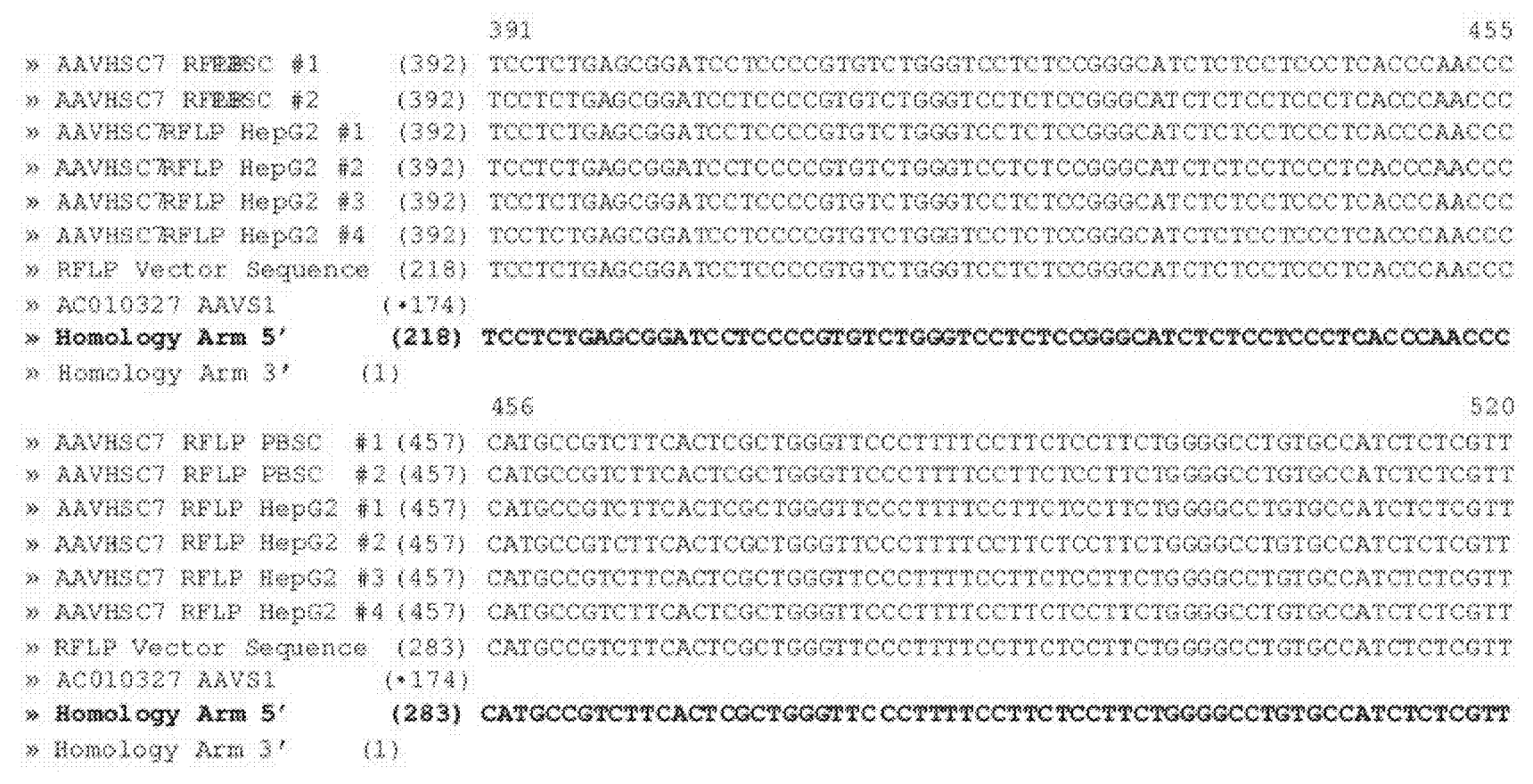
Figure 34:
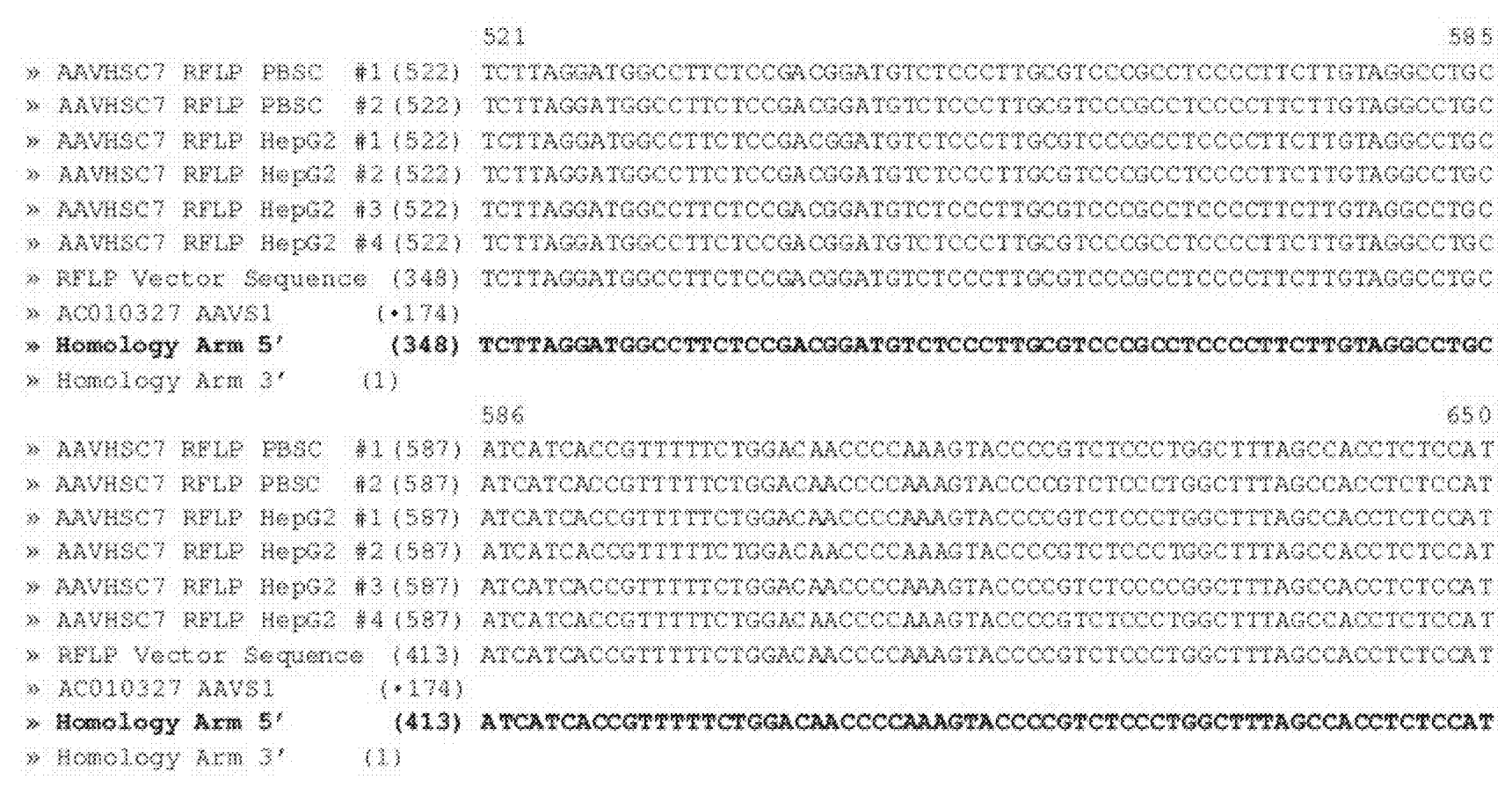
Figure 34:
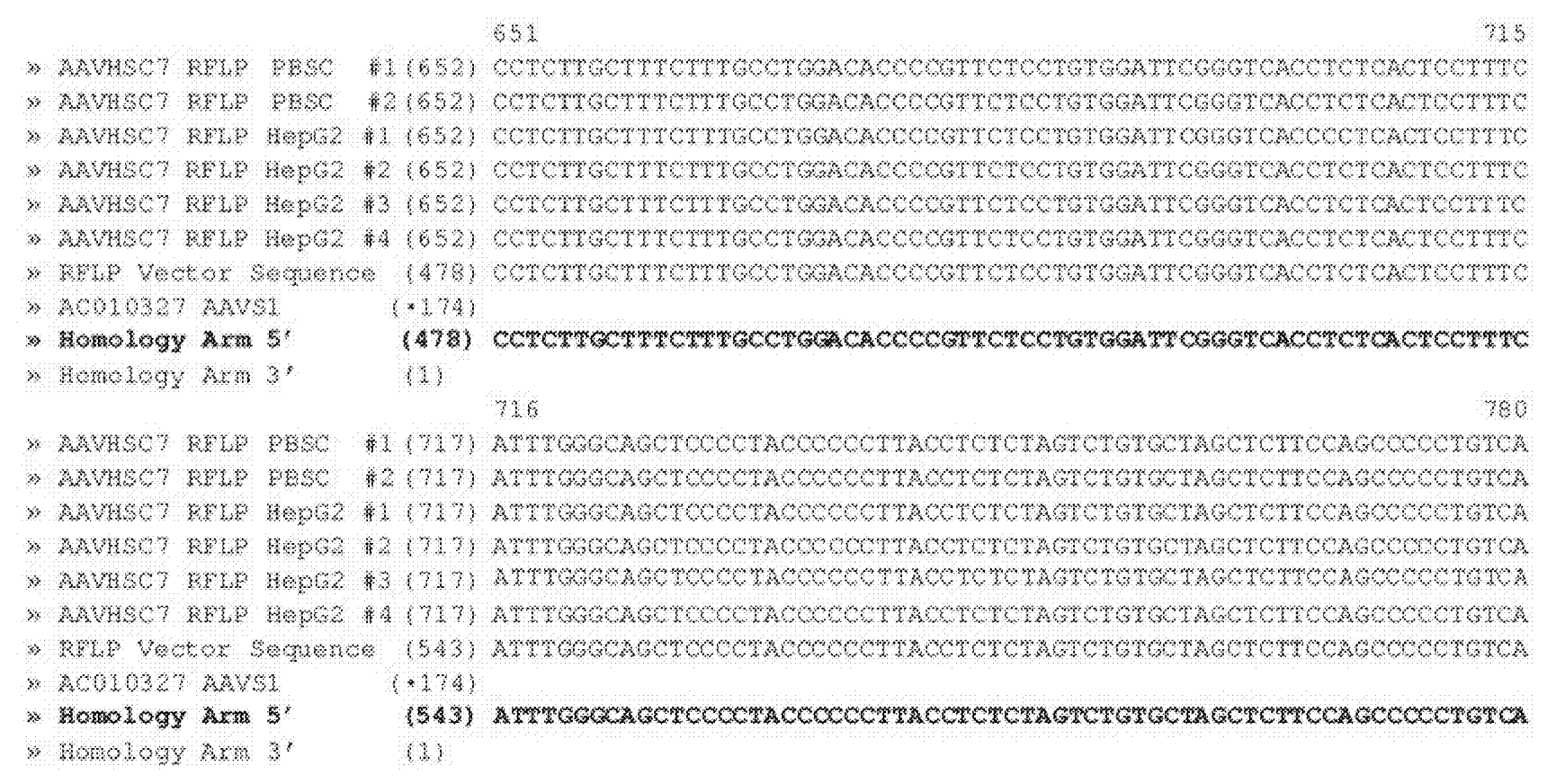
Figure 34:
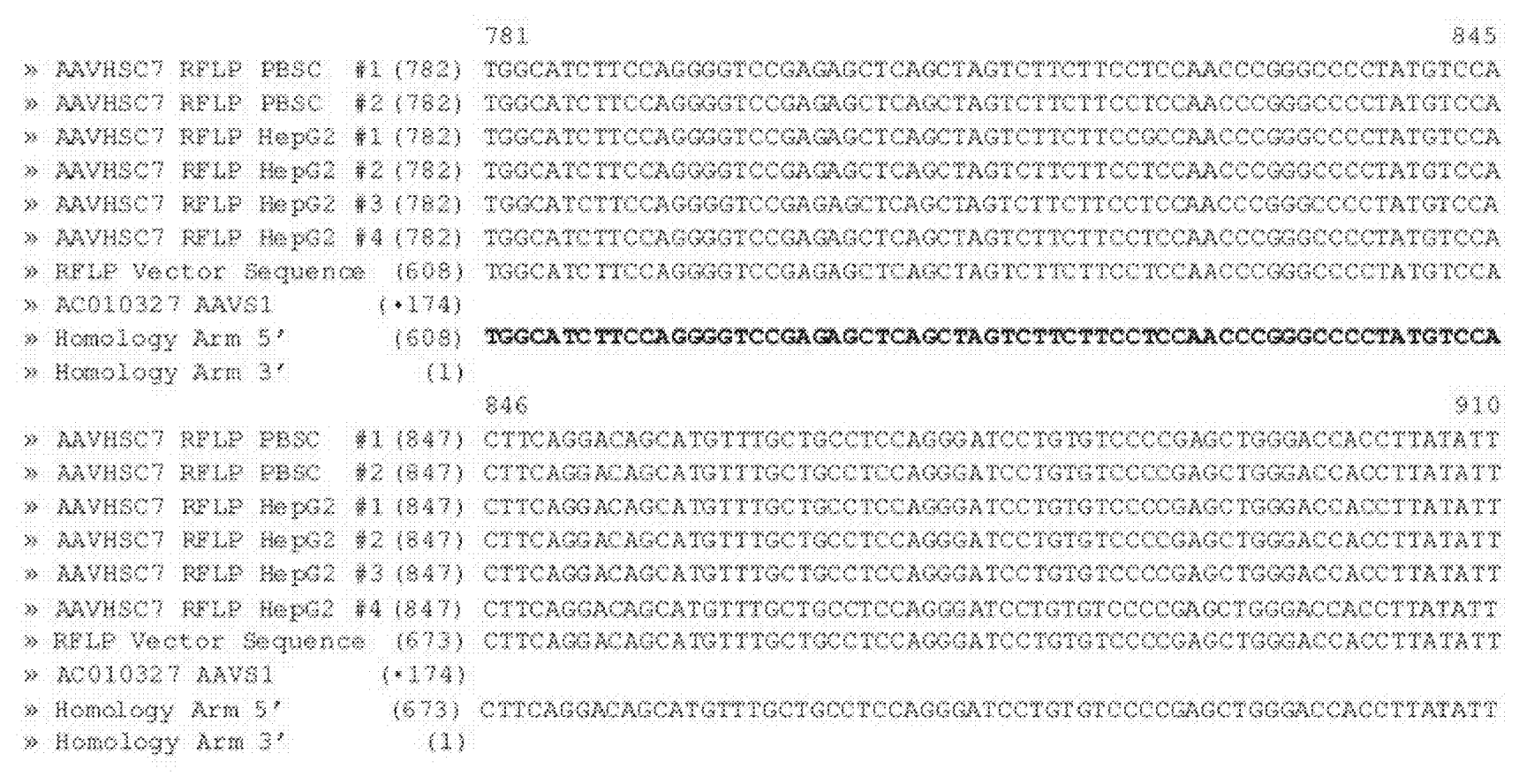
Figure 34:
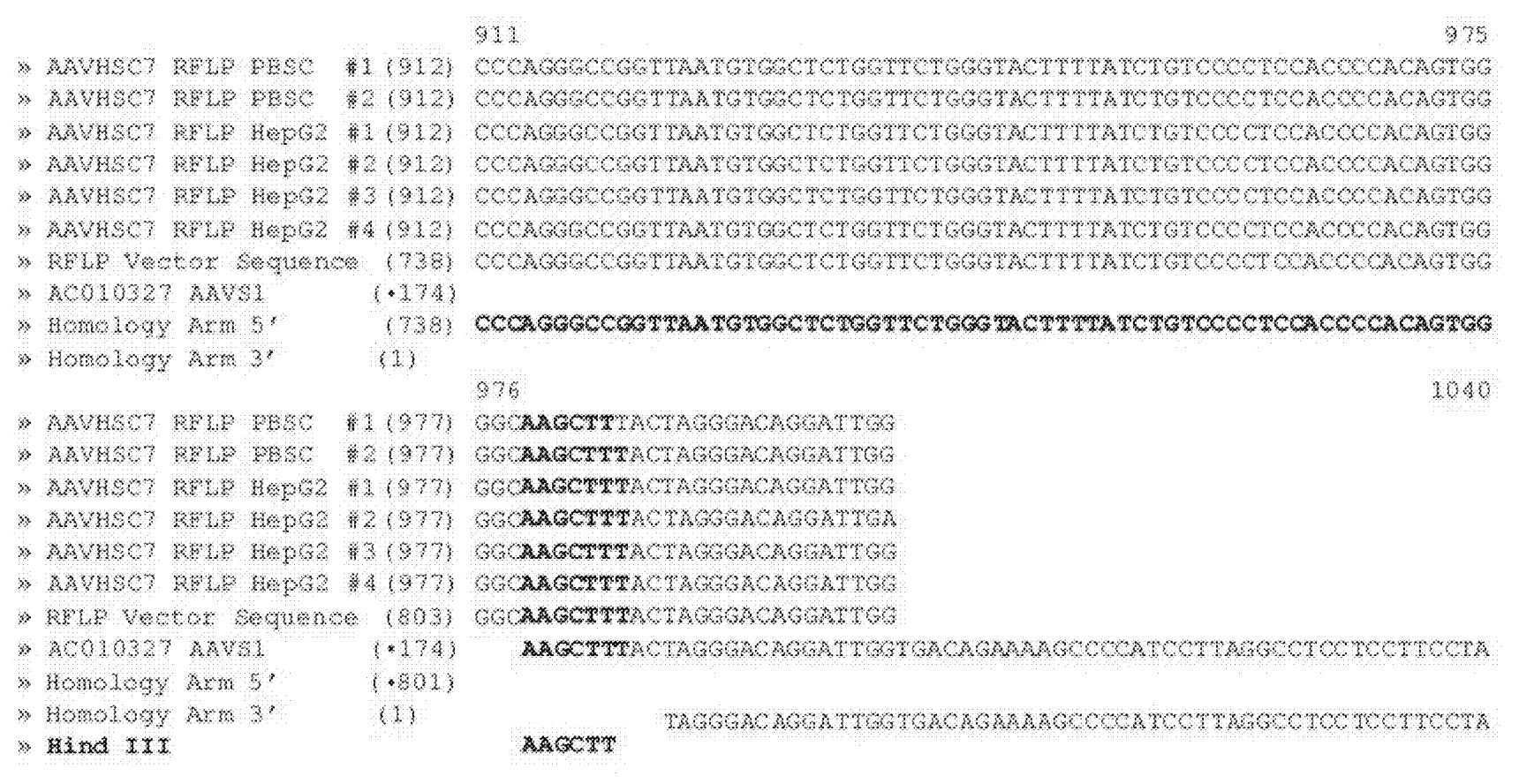

In another experiment, sequence analysis was performed for targeted chromosomal insertion of a 10 bp insert in primary human cytokine-primed peripheral blood CD34+ cells and a HepG2 human liver cell line (FIG. 34). Site-specifically integrated sequences were amplified using a chromosome-specific primer and an insert-specific primer. Results revealed precise insertion of the 10 bp insert at the junction between the left and right homology arms in every case (FIG. 34).

These data show that both large and short inserts can be successfully edited into a genome using AAV Clade F vectors and that the integration into the genome is precise. These data also show that AAV Clade F vectors could be used for high efficiency genome editing in the absence of an exogenous nuclease.

Example 5: Editing of the PPP1R12c Locus in Human Cell Lines

Methods

To assess the editing of human cell types by AAVF vectors, the following human cell lines were used:

| Cell Line | Tissue type |
|---|---|
| WI-38 | normal human diploid fibroblasts |
| MCF7 | human breast cancer cell line |
| Hep-G2 | human hepatocellular carcinoma cell line |
| K562 | CD34+ erythroleukemic cell line |
| Y79 | human retinoblastoma cell line |
| SCID-X1 LBL | human EBV-immortalized B cell line from a SCID-X1 patient |

The AAVF vectors used each contained a vector genome containing an editing element encoding a promoterless Venus reporter. The promoterless Venus contained the open reading frame (ORF) of Venus downstream from a splice acceptor (SA) and a 2A sequence (2A) to allow for independent protein expression. The left and right homology arms (HA) were each 800 bp long and were complementary to sequences in Intron 1 of human PPP1R12C located in the AAVS1 locus on chromosome 19. The AAVS1 locus is considered a safe harbor site for the insertion of heterologous transgenes. The editing element containing the homology arms, the Venus ORF, and regulatory sequences were cloned between AAV2 inverted terminal repeats (ITRs).

Cell Culture. All cell lines were grown in a humidified atmosphere of 5% CO2 at 37° C. and cultured as follows: SCID-X1 lymphoblasts (Coriell) were cultured in RPMI1640 (Gibco, cat #21875) supplemented with 15% fetal bovine serum (FBS) (Gibco, cat #26140); K562 cells (ATCC) were cultured in DMEM (Corning, cat #15-017-CVR) supplemented with 10% FBS (Gibco, cat #26140) and 1% L-glutamine (Gibco, cat #25030); HepG2 cells (ATCC) were cultured in EMEM (ATCC, cat #30-2003) supplemented with 10% FBS (Gibco, cat #26140); MCF-7 cells (ATCC) were cultured in MEM (Gibco, cat #11095) supplemented with 10% FBS (Gibco, cat #26140), 1% MEM non-essential amino acids (Gibco, cat #11140), 1% Sodium pyruvate (Gibco, cat #11360) and 10 µg/ml human recombinant insulin (Gibco, cat #12585-014); WI-38 fibroblasts (ATCC) and HEK293 cells (ATCC) were cultured in MEM (Gibco, cat #11095) supplemented with 10% FBS (Gibco, cat #26140), 1% MEM non-essential amino acids (Gibco, cat #11140) and 1% Sodium pyruvate (Gibco, cat #11360); and Y79 cells (ATCC) were cultured in RPMI1640 (Gibco, cat #A10491) supplemented with 20% FBS (Gibco, cat #26140).

AAVF-mediated editing of human cell lines. Adherent cells were seeded on day 0 at 20,000 cells/0.1 mL for a 96-well format or 20,000 cells/0.5 mL for a 24-well format. Cell counts were measured 24-h later (on day 1) prior to addition of the AAVF vectors. Suspension cells were seeded on day 1 on 20,000 cells/0.1 mL in a 96-well format or 20,000 cells/0.5 mL in 24-well plate format. On day 1, the AAVFs were added to the cells using a multiplicity of infection (MOI) of 150,000 vector genomes (VG)/cell. Before AAVF addition, the pipet tips used for transfer were coated with protamine sulfate (10 mg/ml). The AAVFs were thoroughly suspended on a vortex mixer at full speed for 30 seconds immediately before transduction. The volume of AAVF added to the cells did not exceed 5% of the total volume in the well. On day 3, cells were harvested (adherent cells were mildly trypsinized to remove them from the tissue culture plates), washed, and analyzed for Venus expression by flow cytometry using an Intellicyt flow cytometer fitted with a Hypercyt Autosampler. Editing was expressed as the percent of the total cell population that was Venus positive minus the background fluorescence observed in untransduced cells (typically less than 1% Venus positive cells). The AAVF editing experiments were carried out without the use of an exogenous nuclease.

Results

Editing of the human PPP1R12c locus was observed for all the AAVF tested and showed cell type selectivity (Table 3). In general, AAVF5 produced the highest levels of editing in each of the cell lines, from 12-45% of the total cell population, after 48 hours of infection. AAVF9 also produced high levels of gene editing in the B lymphoblast cell lines (SCID-X1 LBL and K562). AAVF17 produced the highest level of gene editing in normal human diploid fibroblasts (WI-38 cells) under these conditions. The AAVF1, AAVF4, AAVF7 vectors produced levels of editing that were consistently greater than that seen in untransduced cells but that were generally lower than the maximal levels observed with AAVF5, AAVF9, and AAVF17. These data demonstrate that the AAVFs have a broad tropism for human tissues and may be useful for gene editing in the liver, CNS (e.g., retina), tissue fibroblasts, breast, and lymphocytes among others.

TABLE 3

Editing of Human Cell Lines by AAVF

| Vector | Human Cell Lines | | | | | |
|---|---|---|---|---|---|---|
| | K562 | Hep-G2 | WI-38 | Y79 | MCF7 | SCID-X1 LBL |
| | Percent Venus Positive Cells | | | | | |
| AAVF1 | 2.06 | 1.92 | 1.39 | 0.7 | 2.71 | 0.57 |
| AAVF4 | 1.36 | 2.95 | 6.29 | 0.35 | 3.42 | 0.12 |
| AAVF5 | 45.32 | — | 11.85 | 12.5 | 20.47 | 45.02 |
| AAVF7 | 5.78 | 3.83 | 4.87 | 1.42 | 3.6 | 0.94 |
| AAVF9 | 18.06 | — | — | 2.46 | 6.14 | 6.79 |
| AAVF17 | 3.18 | 3.71 | 17.6 | 1.29 | 5.66 | 0.44 |

Example 6: AAVF Editing in Primary Human Cells

To assess the editing of primary human cells by AAVF vectors, primary cultures of human hepatocytes, hepatic sinusoidal endothelial cells, and skeletal muscle myoblasts were used.

The AAVF and AAV vectors used each packaged a vector genome encoding a promoter-less Venus reporter. The insert comprised a Venus open reading frame (ORF) downstream from a splice acceptor (SA) and a 2A sequence (2A) to allow for independent protein expression. The left and right homology arms (HA) were each 800 bp long and were complementary to sequences in Intron 1 of human PPP1R12C located in the AAVS1 locus on chromosome 19. The AAVS1 locus is considered a safe harbor site for the insertion of heterologous transgenes. The correction genome consisting of the homology arms, the open reading frame and regulatory sequences were cloned between AAV2 inverted terminal repeats (ITRs).

Methods

Cell culture. All primary human cells were cultured at 37° C., under 5% humidified CO2 in a tissue culture incubator. All materials and media components were obtained from Life Technologies unless specified otherwise.

Primary cultures of human hepatocytes were obtained from Invitrogen and were cultured on type I collagen coated plates as suggested by the manufacturer. Cells were recovered from storage in liquid nitrogen in Thawing/Plating Medium [32.5 mL William's E Medium (#A12176) 1.6 mL fetal bovine serum, 3.2 uL of 10 mM Dexamethazone and 0.9 mL of Plating Cocktail A per 35.0 mL final volume]. Plating cocktail A consisted of 0.5 mL Penicillin (10,000 U/mL)/Streptomycin (10,000 ug/mL) solution (Cat #15140), 0.05 mL of 4.0 mg human recombinant insulin/mL (Catalog #12585-014), 0.5 mL of 200 mM GlutaMAX™ solution (Catalog #35050) and 0.75 mL of 1.0M Hepes, pH7.4 (Catalog # 15630) per 1.8 mL final volume. Human hepatocytes were maintained in Maintenance media which contained 100 mL of Williams E Medium, 0.001 mL of dexamethasone, and 3.6 mL of Maintenance Cocktail B (Catalog #A13448) per 103.6 mL final volume.

Primary cultures of human skeletal muscle myoblasts were obtained from Lonza and were cultured in SkGM™ medium as described by the manufacturer.

SkGM™-2 Bullit™ Kit (Lonza, Catalog No. CC-3245) contained 0.5 mL human Epidermal Growth Factor [hEGF] (#0000482653), 0.5 mL Dexamethasone (#0000474738), 10 mL L-glutamine (#0000474740), 50 mL Fetal Bovine Serum (#0000474741), 0.5 mL Gentamicin/Amphotericin-B [GA] (#0000474736), in 500 mL SkGM-2 medium (#0000482653).

Primary cultures of human hepatic sinusoidal endothelial cells were purchased from Creative Bioarray and were cultured in SuperCult® Endothelial Cell Medium and grown on a gelatin-based coating as described by the manufacturer. SuperCult® Endothelial Cell Medium Supplement Kit (Catalog #ECM-500 Kit) contained 0.5 mL VEGF (#15206), 0.5 mL Heparin (#15250), 0.5 mL EGF (#15217), 0.5 mL FGF (#15204), 0.5 mL Hydrocortisone (#15318), 5.0 mL Antibiotic-Antimycotic Solution (#15179), 5.0 mL L-glutamine (#15409), 10.0 mL Endothelial Cell Supplement (#15604), 50.0 mL FBS (#15310), and 500.0 mL of SuperCult® Endothelial Cell Medium (#15517).

AAVF-mediated editing of primary human cells. Human primary hepatocytes were seeded on day 0 on $2\times10^4$ cells/0.1 mL for the 96-well format or $2\times10^4$ cells/0.5 mL for the 24-well format. Viral vectors were added 48 h later on day 2 as described below. Human skeletal muscle myoblasts, and human hepatic sinusoidal endothelial cells were seeded on day 1 at $2\times10^4$ cells/0.1 mL in a 96-well format or $2\times10^4$ cells/0.5 mL in a 24-well format. On day 2, the viral vectors were added to these cells at a multiplicity of infection (MOI) of 150,000 VG(Vector genomes)/cell (For AAVF5 an MOI of $5\times10^4$ VG/cell was used and for AAVF17 an MOI of $2.5\times10^4$ VG/cell was used). Prior to the addition of vector to the cells, all pipet tips used for vector transfer were coated with protamine sulfate (10 mg/mL) and the vectors were thoroughly mixed by vortexing for 30 seconds immediately before transduction. The volume of vector added to the cells did not exceed 5% of the total volume in the well.

The culture media for the human primary hepatocytes was refreshed on day 3. On day 4, cells were harvested (adherent cells were trypsinized) and analyzed for Venus expression by flow cytometry using an Intellicyt flow cytometer fitted with a Hypercyt Autosampler. Editing was expressed as the percent of the total cell population that was Venus positive minus the background fluorescence observed in un-transduced cells (typically less than 1% Venus positive cells).

Results

Editing of the human PPP1R12c locus was observed for all the AAVF tested and showed cell type selectivity (Table 4). In general, AAVF5 gave the highest levels of editing in each of the primary cell populations, from a low of 2% in human hepatocytes to 24% to 35% in primary skeletal myoblasts and hepatic sinusoidal endothelial cells, respectively, after 48-h of infection. AAVF7 and AAVF17 also produced high levels of gene editing in the primary hepatic sinusoidal endothelial cells and skeletal myoblasts. Levels of editing with the AAVF vectors in these cells were 10- to 50-fold higher than that observed with AAV2 or AAV6. The AAVF vectors produced levels of editing that were consistently greater than that seen in untransduced cells or cells transduced with a AAV2 or AAV6 packaging the promoterless Venus vector genome. Little or no editing was observed for either AAV2 or AAV6 in these cells. These data in primary human cells demonstrate that AAVF5, AAVF7, and AAVF17 have a broad tropism for human tissues and may be useful for gene therapy applications directed towards the liver, skeletal muscle, and endothelial cell populations, among others.

For comparison, each of the primary human cells populations were also transduced with AAVF gene transfer vectors packaging mCherry under control of the chicken beta actin (CBA) promoter. The ratios of protein expression of Venus/mCherry were then used to estimate an editing ratio—reflecting the ratio of number of cells having detectable protein expression in the various cell types using gene editing vectors of the experiment (Venus) to number of cells having detectable protein expression using the aforementioned gene transfer vectors (mCherry)—for AAV6, AAVF5, and AAVF7. As shown in Table 5, AAVF-mediated gene editing is generally more effective for protein expression than the corresponding AAVF-mediated gene transfer approach in the studied primary human cells, whereas AAV6-mediated gene editing was substantially the same as or slightly less effective than AAV6-mediated gene transfer in such cells. Notably, as also shown in Table 5, AAVF-mediated gene editing was higher than that observed with AAV6-mediated gene editing for the studied primary human cells. These data demonstrate that AAVF-mediated gene editing is more efficient than AAV6 in a variety of primary human cells, and that AAVF-mediated gene editing compares favorably over corresponding gene-transfer approaches in such cells.

The AAVF vectors packaging the mCherry reporter also effectively transduced primary human cells and showed cell type specificity (Table 6). For human umbilical vein endothelial cells (HUVEC) and hepatic sinusoidal endothelial cells (HSEC), transduction with AAVF9 produced 38-50% mCherry positive cells after 48-h of infection. AAVF9 also efficiently transduced human skeletal muscle myoblasts and to a lesser extent, all of the AAVF tested effectively transduced the HSEC under these conditions (Table 6). Without being bound by theory, it is likely that most, if not all, of the mCherry expression in these studies represents episomal expression of the reporter as no homology arms were present in the mCherry vector genomes with expression was driven by the CBA promoter.

TABLE 4

AAVF-Mediated Editing of Primary Human Cells

| Vector | HSEC | Hepatocytes | SMM |
|---|---|---|---|
| | | Percent Venus Positive Cells | |
| AAV2 | 0.34 | 0.06 | 0.52 |
| AAV6 | 0.00 | 0.00 | 0.00 |

TABLE 4-continued

AAVF-Mediated Editing of Primary Human Cells

| Vector | HSEC | Hepatocytes | SMM |
|---|---|---|---|
| | Percent Venus Positive Cells | | |
| AAVF5 | 34.70 | 2.00 | 24.20 |
| AAVF7 | 18.40 | 0.62 | 18.65 |
| AAVF17 | 21.40 | 1.37 | 19.60 |

TABLE 5

Editing ratios of AAVF in primary human cells

| | Hepatocytes | | SMM | |
|---|---|---|---|---|
| Vector | Venus/mCherry | AAVF/AAV6 | Venus/mCherry | AAVF/AAV6 |
| AAV6 | 0.84 | | 0.80 | |
| AAVF5 | 9.42 | 11.21 | 14.32 | 17.90 |
| AAVF7 | 0.95 | 1.10 | 13.05 | 16.30 |

| | MSEC | |
|---|---|---|
| Vector | Venus/mCherry | AAVF/AAV6 |
| AAV6 | 0.60 | |
| AAVF5 | 5.30 | 8.80 |
| AAVF7 | 2.70 | 4.50 |

HSEC = hepatic sinusoidal endothelial cells
SMM = skeletal muscle myoblasts

TABLE 6

Tranduction of Primary Human Cells with AAVF Vectors Packaging mCherry

| Vector | HSEC | Hepatocytes | SMM | HUVEC |
|---|---|---|---|---|
| | Percent mCherry positive cells | | | |
| AAVF1 | 7.04 | 0.13 | 1.65 | 1.47 |
| AAVF4 | 9.10 | 0.05 | 1.72 | 0.61 |
| AAVF5 | 4.00 | 0.01 | 1.03 | 0.71 |
| AAVF7 | 4.43 | 0.70 | 0.77 | 2.15 |
| AAVF9 | 38.24 | 1.05 | 29.27 | 50.13 |

Figure 39:
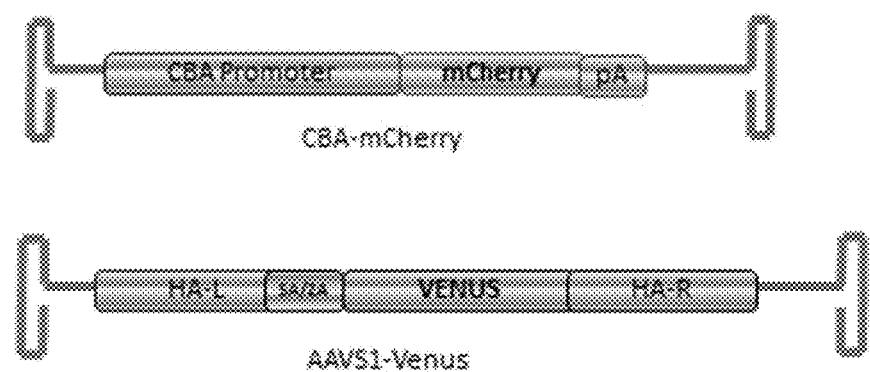
FIG. 39 shows maps of CBA-mCherry and AAS1-Venus vector genomes used to determine the relative transduction versus editing efficiencies of AAV vectors.

HSEC = hepatic sinusoidal endothelial cells
SMM = skeletal muscle myoblasts
HUVEC = human umbilical vein endothelial cells Example 7: Study of AAVF Relative Gene-Editing (HDR) Versus Gene-Transfer (Transduction) Efficiencies Two types of AAV-based vectors (CBA-mCherry gene transfer vectors, and AAVS1-Venus gene editing vectors, FIG. 39) were used to assess the relative gene-editing efficiency versus the gene-transfer transduction efficiency of AAVF vectors, as well as AAV2 and AAV6, as measured by relative protein expression. For the gene-transfer vectors, CBA-mCherry construct included the mCherry gene under the control of the chicken beta actin (CBA) promoter, and utilized a polyadenylation signal, but did not contain any homology arms. For the gene-editing vectors, AAVS1-Venus construct included the promoterless Venus open reading frame (ORF), with (HA-L) and right (HA-R) homology arms targeting the Venus ORF to Intron 1 of the PPP1R12C gene within the AAVS1 region of chromosome 19. There was also a splice acceptor (SA) and a 2A sequence upstream of the Venus ORF, which allowed the Venus transcript to be spliced out and expressed independent of the PPP1R12C gene.

Figure 40A:
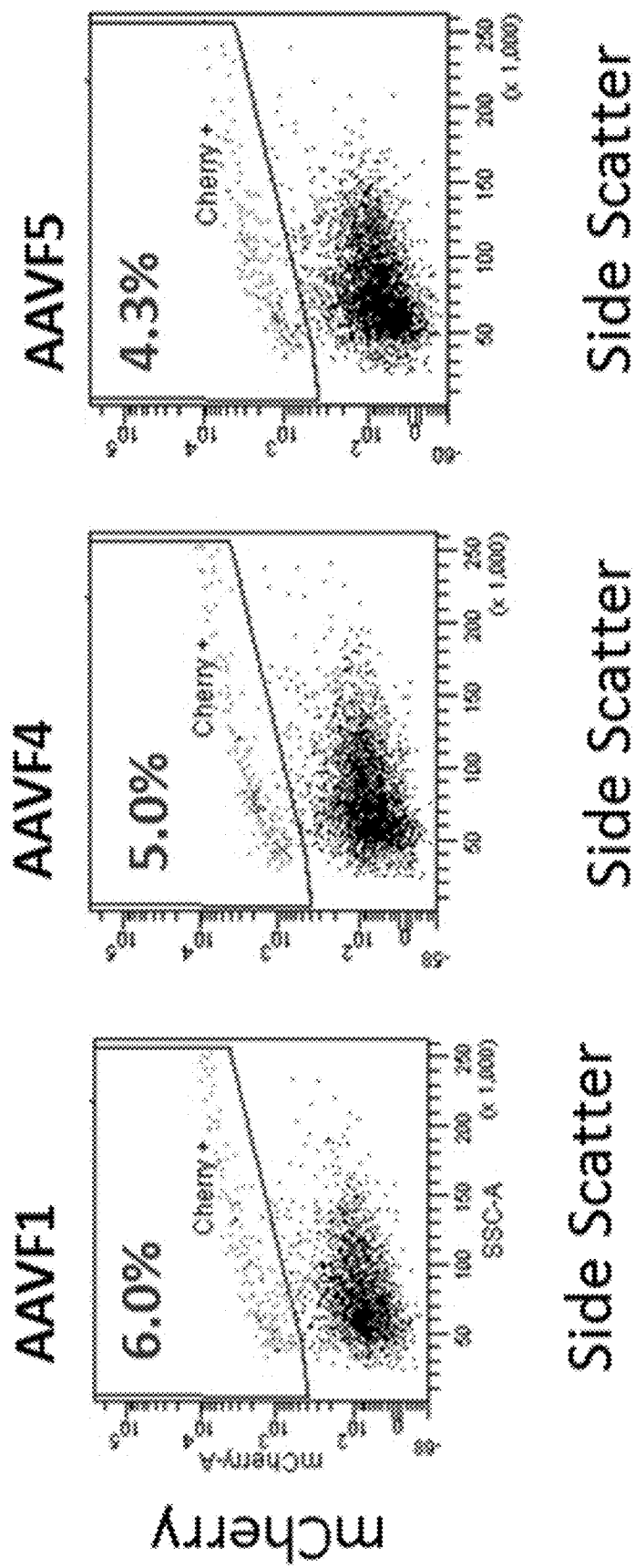
FIGS. 40A and 40B show flow cytometric profiles of mCherry (FIG. 40A) and Venus (FIG. 40B) expression in human CD34+ cord blood cells.
Figure 40A:
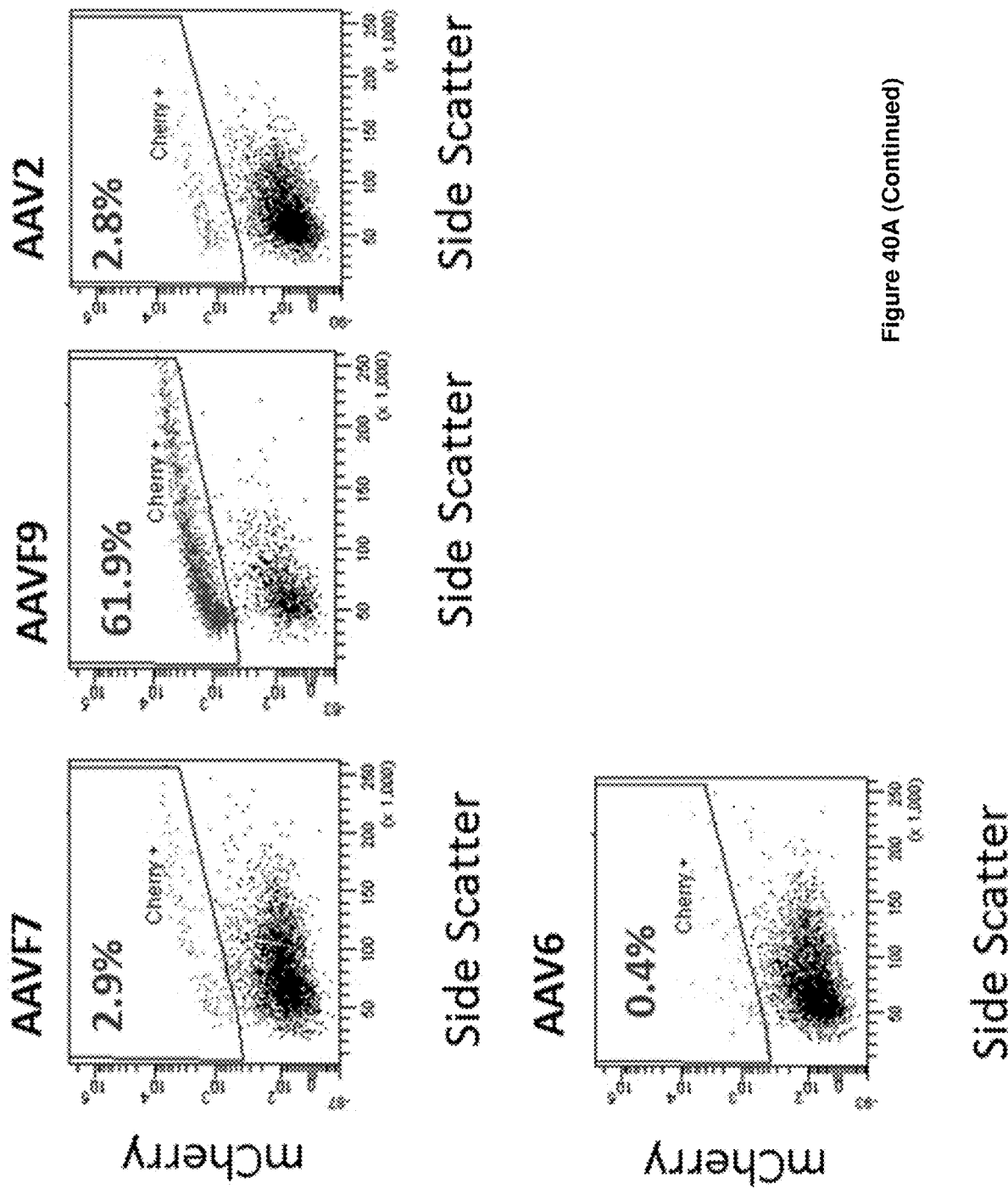
Figure 40B:
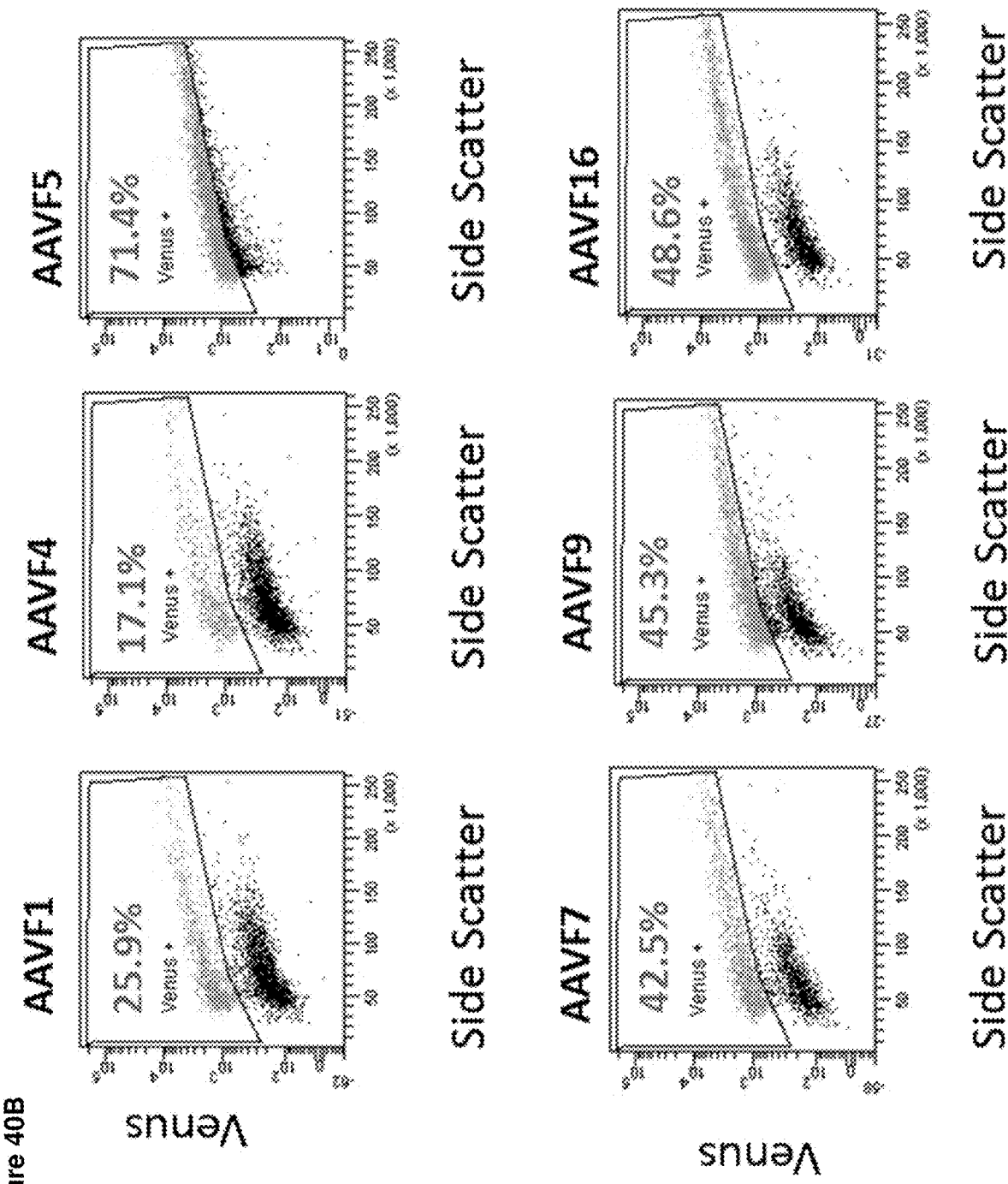
Figure 40B:
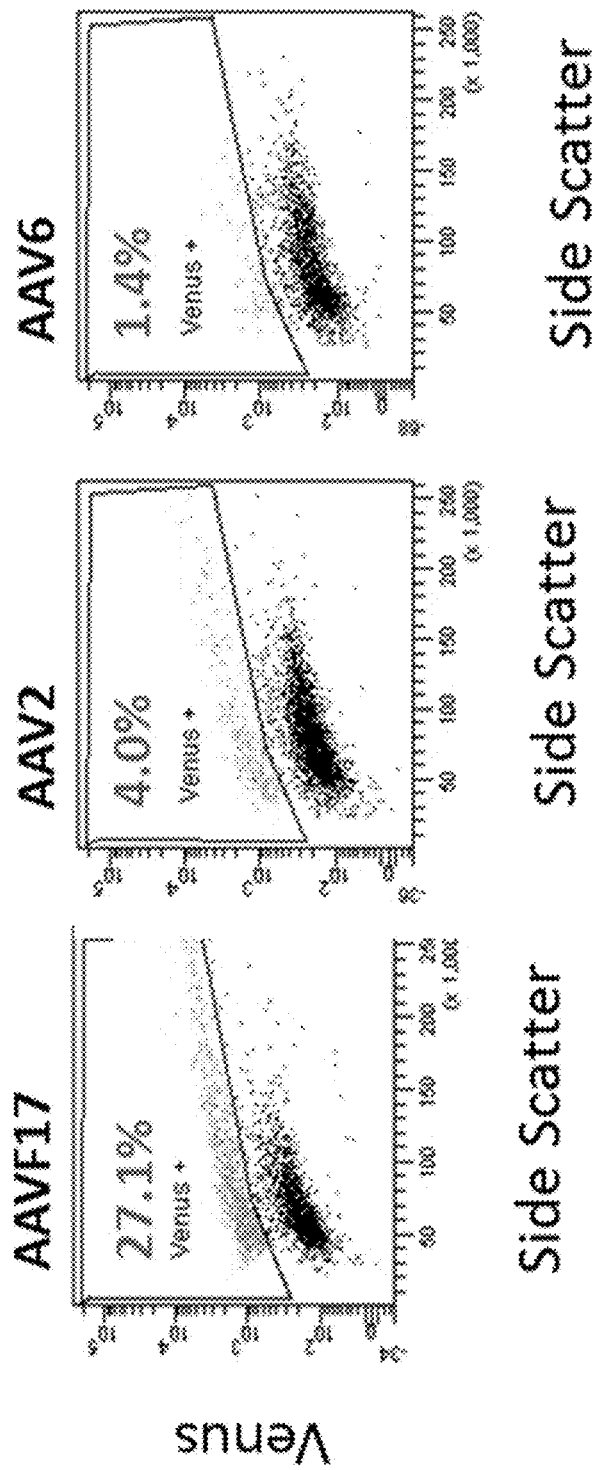

The ability of AAVF, AAV2 and AAV6 vectors to mediate gene editing versus gene transfer was compared in primary human cord blood CD34+ hematopoietic stem/progenitor cells. The cells used were pooled from multiple donors. Purified CD34+ cells were transduced with either gene transfer vectors (AAV*-CBA-mCherry) or gene editing vectors (AAV*-Venus) at a multiplicity of 150,000 vector genomes (VG) per cell. Forty eight hours later, cells were harvested and analyzed by flow cytometry (FIGS. 40A and 40B). The data shown includes subtraction of background untransduced cells.

It was hypothesized that mCherry expression would represent transduction efficiency, whereas Venus expression would represent gene editing efficiency. Without being bound by theory, the following is a summary of the potential mechanism of AAV transduction versus editing. Upon infection, AAV binds to cell surface receptors and is internalized prior to nuclear translocation and entry. In the nucleus, the AAV undergoes uncoating and vector genomes are released. These processes likely occur at the same rate for each given capsid in the same cell population, regardless of the vector genome. Following uncoating, the single stranded CBA-mCherry genome undergoes second strand synthesis prior to mCherry expression. On the other hand, the promoterless Venus editing vector is directed to the genomic region of complementarity on Chromosome 19. The SA/2A-Venus cassette which is bounded by the homology arms may then recombine into the chromosome at the internal junction of the homology arms via homology dependent repair (HDR) mechanisms. Following this recombination event, Venus is expressed in the successfully edited cells.

Figure 40C:
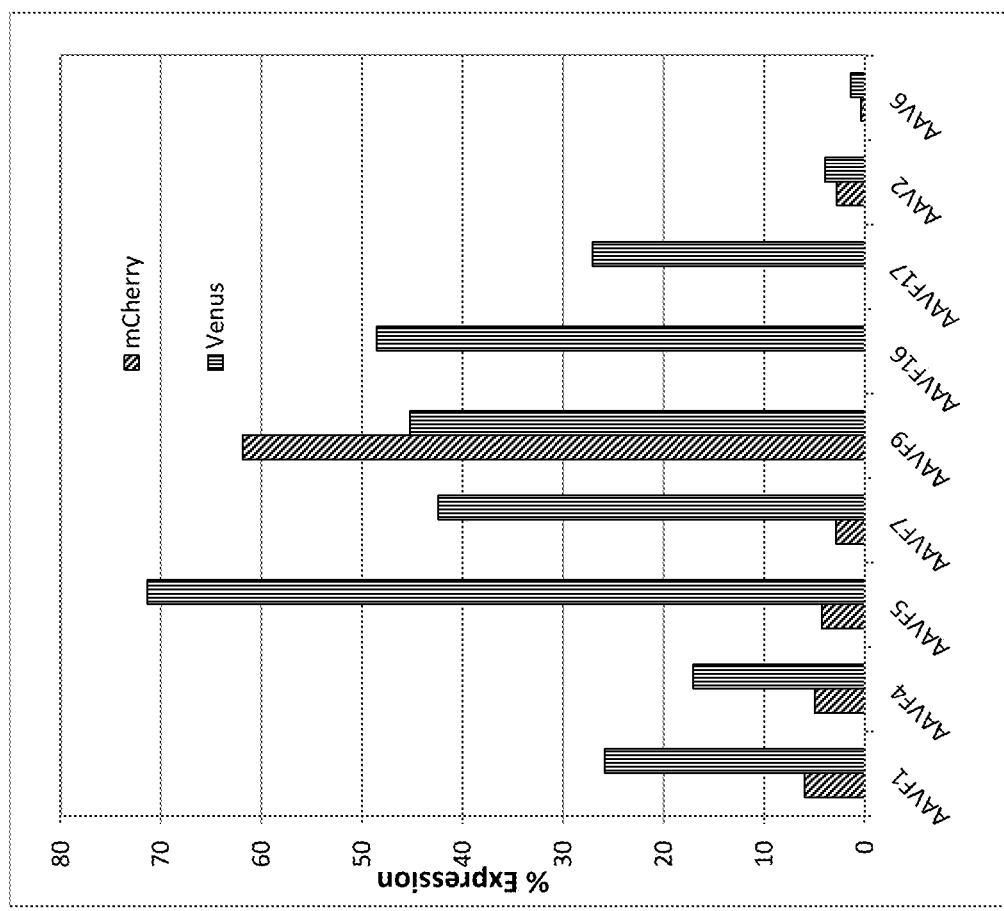
FIG. 40C shows quantitation of mCherry and Venus expression in CD34+ cells 48 hours after transduction.

Venus was expressed in a much higher proportion of cells than mCherry for all vectors except AAVF9 (FIGS. 40A and 40C). Venus expression was especially high following transduction with AAVF1, AAVF5, AAVF7, AAVF16 and AAVF17. The same capsids led to much lower levels of mCherry expression (FIGS. 40A and 40C). The least amount of both mCherry and Venus expression was observed following transduction with AAV2 and AAV6. A comparison of the relative expression of Venus to mCherry was also performed. Specifically, an editing ratio—reflecting the ratio of number of cells having detectable protein expression in the various cell types using gene editing vectors of the experiment (Venus) to the number of cells having detectable protein expression using the aforementioned gene transfer vectors (mCherry)—was determined. The editing ratio provides an estimate of the relative efficiency of editing mediated by each AAV capsid after normalization for the processes of virus entry through uncoating within the nucleus. All AAV vectors tested exhibited more efficient gene editing (Venus) as compared with gene transfer/transgene expression (mCherry), except for AAVF9 (FIG. 40D and Table 7). AAVF5 and AAVF7 displayed the highest editing ratio (FIG. 40D and Table 7). AAVF-mediated gene editing (Venus) was also compared relative to AAV 2- and AAV6-mediated gene editing (Venus) (Table 7, which shows the Venus:mCherry ratio of AAVF divided by the same ratio for either AAV2 or AAV6). The gene-editing effectiveness of AAVF gene-editing constructs compared favorably relative to AAV2- and AAV6-gene editing constructs. The editing ratios of AAVF5 and AAVF7 were the highest of the vectors compared, indicating that these vectors in particular mediate highly efficient editing.

TABLE 7

Editing-to-Transduction ratio in CD34+ CB Cells

| Vector | Ratio editing:transduction (Venus:mCherry) | Ratio AAVF editing:AAV6 editing | Ratio AAVF editing:AAV2 editing |
|---|---|---|---|
| AAVF1 | 4.32 | 1.23 | 3.02 |
| AAVF4 | 3.42 | 0.98 | 0.98 |
| AAVF5 | 16.60 | 4.74 | 11.62 |
| AAVF7 | 14.66 | 4.19 | 10.26 |
| AAVF9 | 0.73 | 0.21 | 0.51 |
| AAV2 | 1.43 | 0.41 | 1.00 |
| AAV6 | 3.50 | 1.00 | 2.45 |

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

REFERENCES

1. BAINBRIDGE, J. W., SMITH, A. J., BARKER, S. S., ROBBIE, S., HENDERSON, R., BALAGGAN, K., VISWANATHAN, A., HOLDER, G. E., STOCKMAN, A., TYLER, N., PETERSEN-JONES, S., BHATTACHARYA, S. S., THRASHER, A. J., FITZKE, F. W., CARTER, B. J., RUBIN, G. S., MOORE, A. T., and ALI, R. R. (2008). Effect of gene therapy on visual function in Leber's congenital amaurosis. N Engl J Med 358, 2231-2239.
2. BATCHU, R. B., SHAMMAS, M. A., WANG, J. Y., FREEMAN, J., ROSEN, N., and MUNSHI, N. C. (2002). Adeno-associated virus protects the retinoblastoma family of proteins from adenoviral-induced functional inactivation. Cancer Res 62, 2982-2985.
3. BELL, P., WANG, L., LEBHERZ, C., FLIEDER, D. B., BOVE, M. S., WU, D., GAO, G. P., WILSON, J. M., and WIVEL, N. A. (2005). No evidence for tumorigenesis of AAV vectors in a large-scale study in mice. Mol Ther 12, 299-306.
4. BERNS, K. I., and GIRAUD, C. (1996). Biology of adeno-associated virus. Curr Top Microbiol Immunol 218, 1-23.
5. BIFFI, A., and CESANI, M. (2008). Human hematopoietic stem cells in gene therapy: preclinical and clinical issues. Curr Gene Ther 8, 135-146.
6. BRANTLY, M. L., CHULAY, J. D., WANG, L., MUELLER, C., HUMPHRIES, M., SPENCER, L. T., ROUHANI, F., CONLON, T. J., CALCEDO, R., BETTS, M. R., SPENCER, C., BYRNE, B. J., WILSON, J. M., and FLOTTE, T. R. (2009). Sustained transgene expression despite T lymphocyte responses in a clinical trial of rAAV1-AAT gene therapy. Proc Natl Acad Sci USA.
7. CHATTERJEE, S., JOHNSON, P. R., and WONG, K. K., JR. (1992). Dual-target inhibition of HIV-1 in vitro by means of an adeno-associated virus antisense vector. Science 258, 1485-1488.
8. CHATTERJEE, S., LI, W., WONG, C. A., FISHER-ADAMS, G., LU, D., GUHA, M., MACER, J. A., FORMAN, S. J., and WONG, K. K., JR. (1999). Transduction of primitive human marrow and cord blood-derived hematopoietic progenitor cells with adeno-associated virus vectors. Blood 93, 1882-1894.
9. CHATTERJEE, S., WONG, KK. (1993). Adeno-Associated Viral Vectors for the Delivery of Antisense RNA. METHODS—LONDON—A COMPANION TO METHODS IN ENZYMOLOGY-5, 1.
10. CIDECIYAN, A. V., HAUSWIRTH, W. W., ALEMAN, T. S., KAUSHAL, S., SCHWARTZ, S. B., BOYE, S. L., WINDSOR, E. A., CONLON, T. J., SUMAROKA, A., PANG, J. J., ROMAN, A. J., BYRNE, B. J., and JACOBSON, S. G. (2009). Human RPE65 gene therapy for Leber congenital amaurosis: persistence of early visual improvements and safety at 1 year. Hum Gene Ther 20, 999-1004.
11. EINERHAND, M. P., ANTONIOU, M., ZOLOTUKHIN, S., MUZYCZKA, N., BERNS, K. I., GROSVELD, F., and VALERIO, D. (1995). Regulated high-level human beta-globin gene expression in erythroid cells following recombinant adeno-associated virus-mediated gene transfer. Gene Ther 2, 336-343.
12. FISHER-ADAMS, G., WONG, K. K., JR., PODSAKOFF, G., FORMAN, S. J., and CHATTERJEE, S. (1996). Integration of adeno-associated virus vectors in CD34+ human hematopoietic progenitor cells after transduction. Blood 88, 492-504.
13. FLOTTE, T. R., BRANTLY, M. L., SPENCER, L. T., BYRNE, B. J., SPENCER, C. T., BAKER, D. J., and HUMPHRIES, M. (2004). Phase I trial of intramuscular injection of a recombinant adeno-associated virus alpha 1-antitrypsin (rAAV2-CB-hAAT) gene vector to AAT-deficient adults. Hum Gene Ther 15, 93-128.
14. GAO, G., VANDENBERGHE, L. H., ALVIRA, M. R., LU, Y., CALCEDO, R., ZHOU, X., and WILSON, J. M. (2004). Clades of Adeno-associated viruses are widely disseminated in human tissues. J Virol 78, 6381-6388.
15. HACEIN-BEY-ABINA, S., VON KALLE, C., SCHMIDT, M., LE DEIST, F., WULFFRAAT, N., MCINTYRE, E., RADFORD, I., VILLEVAL, J. L., FRASER, C. C., CAVAZZANA-CALVO, M., and FISCHER, A. (2003). A serious adverse event after successful gene therapy for X-linked severe combined immunodeficiency. N Engl J Med 348, 255-256.
16. HAN, Z., ZHONG, L., MAINA, N., HU, Z., LI, X., CHOUTHAI, N. S., BISCHOF, D., WEIGEL-VAN AKEN, K. A., SLAYTON, W. B., YODER, M. C., and SRIVASTAVA, A. (2008). Stable integration of recombinant adeno-associated virus vector genomes after transduction of murine hematopoietic stem cells. Hum Gene Ther 19, 267-278.
17. JAYANDHARAN, G. R., ZHONG, L., LI, B., KACHNIARZ, B., and SRIVASTAVA, A. (2008). Strategies for improving the transduction efficiency of single-stranded adeno-associated virus vectors in vitro and in vivo. Gene Ther 15, 1287-1293.
18. KAPLITT, M. G., FEIGIN, A., TANG, C., FITZSIMONS, H. L., MATTIS, P., LAWLOR, P. A., BLAND, R. J., YOUNG, D., STRYBING, K., EIDELBERG, D., and DURING, M. J. (2007). Safety and tolerability of gene therapy with an adeno-associated virus (AAV) borne GAD gene for Parkinson's disease: an open label, phase I trial. Lancet 369, 2097-2105.
19. KELLS, A. P., HADACZEK, P., YIN, D., BRINGAS, J., VARENIKA, V., FORSAYETH, J., and BANKIEWICZ, K. S. (2009). Efficient gene therapy-based method for the delivery of therapeutics to primate cortex. Proc Natl Acad Sci USA 106, 2407-2411.

20. KESSLER, P. D., PODSAKOFF, G. M., CHEN, X., MCQUISTON, S. A., COLOSI, P. C., MATELIS, L. A., KURTZMAN, G. J., and BYRNE, B. J. (1996). Gene delivery to skeletal muscle results in sustained expression and systemic delivery of a therapeutic protein. Proc Natl Acad Sci USA 93, 14082-14087.

21. MANNO, C. S., CHEW, A. J., HUTCHISON, S., LARSON, P. J., HERZOG, R. W., ARRUDA, V. R., TAI, S. J., RAGNI, M. V., THOMPSON, A., OZELO, M., COUTO, L. B., LEONARD, D. G., JOHNSON, F. A., MCCLELLAND, A., SCALLAN, C., SKARSGARD, E., FLAKE, A. W., KAY, M. A., HIGH, K. A., and GLADER, B. (2003).
AAV-mediated factor IX gene transfer to skeletal muscle in patients with severe hemophilia B. Blood 101, 2963-2972.

22. MCCORMACK, M. P., and RABBITTS, T. H. (2004). Activation of the T-cell oncogene LMO2 after gene therapy for X-linked severe combined immunodeficiency. N Engl J Med 350, 913-922.

23. MILLER, D. G., ADAM, M. A., and MILLER, A. D. (1990). Gene transfer by retrovirus vectors occurs only in cells that are actively replicating at the time of infection. Mol Cell Biol 10, 4239-4242.

24. PAZ, H., WONG, C. A., LI, W., SANTAT, L., WONG, K. K., and CHATTERJEE, S. (2007). Quiescent subpopulations of human CD34-positive hematopoietic stem cells are preferred targets for stable recombinant adeno-associated virus type 2 transduction. Hum Gene Ther 18, 614-626.

25. PETRS-SILVA, H., DINCULESCU, A., LI, Q., MIN, S. H., CHIODO, V., PANG, J. J., ZHONG, L., ZOLOTUKHIN, S., SRIVASTAVA, A., LEWIN, A. S., and HAUSWIRTH, W. W. (2009). High-efficiency transduction of the mouse retina by tyrosine-mutant AAV serotype vectors. Mol Ther 17, 463-471.

26. PODSAKOFF, G., WONG, K. K., JR., and CHATTERJEE, S. (1994). Efficient gene transfer into nondividing cells by adeno-associated virus-based vectors. J Virol 68, 5656-5666.

27. PONNAZHAGAN, S., YODER, M. C., and SRIVASTAVA, A. (1997). Adeno-associated virus type 2-mediated transduction of murine hematopoietic cells with long-term repopulating ability and sustained expression of a human globin gene in vivo. J Virol 71, 3098-3104.

28. RAJ, K., OGSTON, P., and BEARD, P. (2001). Virus-mediated killing of cells that lack p53 activity. Nature 412, 914-917.

29. SANTAT, L., PAZ, H., WONG, C., LI, L., MACER, J., FORMAN, S., WONG, K. K., and CHATTERJEE, S. (2005). Recombinant AAV2 transduction of primitive human hematopoietic stem cells capable of serial engraftment in immune-deficient mice. Proc Natl Acad Sci USA 102, 11053-11058.

30. SRIVASTAVA, A. (2004). Gene delivery to human and murine primitive hematopoietic stem and progenitor cells by AAV2 vectors. Methods Mol Biol 246, 245-254.

31. TOWNE, C., SCHNEIDER, B. L., KIERAN, D., REDMOND, D. E., JR., and AEBISCHER, P. (2009). Efficient transduction of non-human primate motor neurons after intramuscular delivery of recombinant AAV serotype 6. Gene Ther.

32. ZHONG, L., CHEN, L., LI, Y., QING, K., WEIGEL-KELLEY, K. A., CHAN, R. J., YODER, M. C., and SRIVASTAVA, A. (2004a). Self-complementary adeno-associated virus 2 (AAV)-T cell protein tyrosine phosphatase vectors as helper viruses to improve transduction efficiency of conventional single-stranded AAV vectors in vitro and in vivo. Mol Ther 10, 950-957.

33. ZHONG, L., LI, B., JAYANDHARAN, G., MAH, C. S., GOVINDASAMY, L., AGBANDJEMCKENNA, M., HERZOG, R. W., WEIGEL-VAN AKEN, K. A., HOBBS, J. A., ZOLOTUKHIN, S., MUZYCZKA, N., and SRIVASTAVA, A. (2008a). Tyrosine phosphorylation of AAV2 vectors and its consequences on viral intracellular trafficking and transgene expression. Virology 381, 194-202.

34. ZHONG, L., LI, B., MAH, C. S., GOVINDASAMY, L., AGBANDJE-MCKENNA, M., COOPER, M., HERZOG, R. W., ZOLOTUKHIN, I., WARRINGTON, K. H., JR., WEIGEL-VAN AKEN, K. A., HOBBS, J. A., ZOLOTUKHIN, S., MUZYCZKA, N., and SRIVASTAVA, A. (2008b). Next generation of adeno-associated virus 2 vectors: point mutations in tyrosines lead to high-efficiency transduction at lower doses. Proc Natl Acad Sci USA 105, 7827-7832.

35. ZHONG, L., LI, W., YANG, Z., QING, K., TAN, M., HANSEN, J., LI, Y., CHEN, L., CHAN, R. J., BISCHOF, D., MAINA, N., WEIGEL-KELLEY, K. A., ZHAO, W., LARSEN, S. H., YODER, M. C., SHOU, W., and SRIVASTAVA, A. (2004b). Impaired nuclear transport and uncoating limit recombinant adeno-associated virus 2 vector-mediated transduction of primary murine hematopoietic cells. Hum Gene Ther 15, 1207-1218.

36. ZHONG, L., ZHAO, W., WU, J., LI, B., ZOLOTUKHIN, S., GOVINDASAMY, L., AGBANDJEMCKENNA, M., and SRIVASTAVA, A. (2007). A dual role of EGFR protein tyrosine kinase signaling in ubiquitination of AAV2 capsids and viral second-strand DNA synthesis. Mol Ther 15, 1323-1330.

37. ZHOU, S. Z., BROXMEYER, H. E., COOPER, S., HARRINGTON, M. A., and SRIVASTAVA, A. (1993). Adeno-associated virus 2-mediated gene transfer in murine hematopoietic progenitor cells. Exp Hematol 21, 928-933.

38. KHAN, I.G., HIRATA, R. K., RUSSELL, D. W. (2011) AAV-mediated gene targeting methods for human cells. Nat Protoc. 4, 482-501.

39. KHOTIN, R. M., LINDEN, R. M., and BERNS, K. I. (1992). Characterization of a preferred site on human chromosome 19q for integration of adeno-associated virus DNA by non-homologous recombination. EMBO 13, 5071-8.

40. GIRAUD, C., WINOCOUR, E., and BERNS, K. I. (1994). Site-specific integration by adeno-associated virus is directed by a cellular DNA sequence. Proc. Natl Acad Sci USA 21, 10039-43.

41. LINDEN, R. M., WARD, P., GIRAUD, C., WINOCOUR, E., and BERNS, K. I. (1996A). Site-specific integration by adeno-associated virus. Proc. Natl Acad Sci USA 21, 11288-94.

42. LINDEN, R. M., WINOCOUR, E., and BERNS, K. I. (1996B). The recombination signals for adeno-associated virus site-specific integration. Proc. Natl Acad Sci USA 15, 7966-72.

43. XU, L., O'MALLEY, T., SANDS, M. S., WANG, B., MEYERROSE, T., HASKINS, M. E., and PONDER, K. P (2004). In Vivo Transduction of Hematopoietic Stem Cells After Neonatal Intravenous Injection of an Amphotrophic Retroviral Vector in Mice. Mol. Ther. July; 10(1):37-44.

44. WANG, C. X., SATHER, B. D., WANG, X., ADAIR, J., KHAN, I., SINGH, S., LANG, S., ADAMS, A., CURINGA, G., KIEM, H-P., MIAO, C. H., RAWLINGS, D. J., and TORBETT, B. E. (2014). Rapamycin relieves lentiviral vector transduction resistance in human and mouse hematopoietic stem cells. Blood. August; 124(6):913-23.

45. CARBONARO, D. A., JIN, X., PETERSEN, D., WANG, X., DOREY, F., ML, K. S., ALDRICH, M., BLACKBURN, M. R., KELLEMS, R. E., and KOHN, D. B. (2006) In Vivo Transduction by Intravenous Injection of a Lentiviral Vector Expressing Human ADA into Neonatal ADA Gene Knockout Mice: A Novel Form of Enzyme Replacement Therapy for ADA Deficiency. Mol. Ther. Jim; 13(6):1110-20.

46. SMITH, L. J., UL-HASAN, T., CARVAINES, S. K., VAN VLIET, K., YANG, E., WONG, JR, K. K., AGBANDJE-MCKENNA, M., and CHATTERJEE, S. (2014) Gene Transfer Properties and Structural Modeling of Human Stem Cell-derived AAV. Mol. Ther. September; 22(9):1625-1634.

What is claimed is:

1. A replication-defective adeno-associated virus (AAV) comprising:
   (a) a correction genome comprising (i) an editing element for integration into a target locus of a chromosome in a cell, the editing element comprising a coding sequence of a gene operably linked to an exogenous promoter, (ii) a 5' homologous arm nucleotide sequence 5' of the editing element, having homology to a 5' region of the chromosome relative to the target locus, and (iii) a 3' homologous arm nucleotide sequence 3' of the editing element, having homology to a 3' region of the chromosome relative to the target locus; and
   (b) an AAV capsid comprising an AAV capsid protein comprising the amino acid sequence of amino acids 203-736 of SEQ ID NO: 16.

2. The AAV of claim 1, wherein the editing element comprises a polyadenylation sequence operably linked to the coding sequence.

3. The AAV of claim 1, wherein each of the 5' and 3' homologous arm nucleotide sequences independently has a nucleotide length of about 50 to 2000 nucleotides.

4. The AAV of claim 1, wherein the target locus is an intron.

5. The AAV of claim 1, wherein the correction genome comprises a 5' inverted terminal repeat (5' ITR) nucleotide sequence 5' of the 5' homologous arm nucleotide sequence, and a 3' inverted terminal repeat (3' ITR) nucleotide sequence 3' of the 3' homologous arm nucleotide sequence.

6. The AAV of claim 5, wherein the 5' ITR nucleotide sequence has at least 95% sequence identity to SEQ ID NO:36, and the 3' ITR nucleotide sequence has at least 95% sequence identity to SEQ ID NO:37.

7. The AAV of claim 1, wherein the correction genome is a single stranded genome.

8. A replication-defective adeno-associated virus (AAV) comprising:
   (a) a correction genome comprising (i) an editing element for integration into a target locus of a chromosome in a cell, the editing element comprising a coding sequence of a gene operably linked to an exogenous promoter, (ii) a 5' homologous arm nucleotide sequence 5' of the editing element, having homology to a 5' region of the chromosome relative to the target locus, and (iii) a 3' homologous arm nucleotide sequence 3' of the editing element, having homology to a 3' region of the chromosome relative to the target locus; and
   (b) an AAV capsid comprising an AAV capsid protein comprising the amino acid sequence of amino acids 138-736 of SEQ ID NO: 16.

9. The AAV of claim 8, wherein the editing element comprises a polyadenylation sequence operably linked to the coding sequence.

10. The AAV of claim 8, wherein each of the 5' and 3' homologous arm nucleotide sequences independently has a nucleotide length of about 50 to 2000 nucleotides.

11. The AAV of claim 8, wherein the target locus is an intron.

12. The AAV of claim 8, wherein the correction genome comprises a 5' inverted terminal repeat (5' ITR) nucleotide sequence 5' of the 5' homologous arm nucleotide sequence, and a 3' inverted terminal repeat (3' ITR) nucleotide sequence 3' of the 3' homologous arm nucleotide sequence.

13. The AAV of claim 12, wherein the 5' ITR nucleotide sequence has at least 95% sequence identity to SEQ ID NO:36, and the 3' ITR nucleotide sequence has at least 95% sequence identity to SEQ ID NO:37.

14. The AAV of claim 8, wherein the correction genome is a single stranded genome.

15. A replication-defective adeno-associated virus (AAV) comprising:
   (a) a correction genome comprising (i) an editing element for integration into a target locus of a chromosome in a cell, the editing element comprising a coding sequence of a gene operably linked to an exogenous promoter, (ii) a 5' homologous arm nucleotide sequence 5' of the editing element, having homology to a 5' region of the chromosome relative to the target locus, and (iii) a 3' homologous arm nucleotide sequence 3' of the editing element, having homology to a 3' region of the chromosome relative to the target locus; and
   (b) an AAV capsid comprising an AAV capsid protein comprising the amino acid sequence of SEQ ID NO: 16.

16. The AAV of claim 15, wherein the editing element comprises a polyadenylation sequence operably linked to the coding sequence.

17. The AAV of claim 15, wherein each of the 5' and 3' homologous arm nucleotide sequences independently has a nucleotide length of about 50 to 2000 nucleotides.

18. The AAV of claim 15, wherein the target locus is an intron.

19. The AAV of claim 15, wherein the correction genome comprises a 5' inverted terminal repeat (5' ITR) nucleotide sequence 5' of the 5' homologous arm nucleotide sequence, and a 3' inverted terminal repeat (3' ITR) nucleotide sequence 3' of the 3' homologous arm nucleotide sequence.

20. The AAV of claim 19, wherein the 5' ITR nucleotide sequence has at least 95% sequence identity to SEQ ID NO:36, and the 3' ITR nucleotide sequence has at least 95% sequence identity to SEQ ID NO:37.

21. The AAV of claim 15, wherein the correction genome is a single stranded genome.

22. A packaging system for recombinant preparation of an AAV, wherein the packaging system comprises
   (a) a Rep nucleotide sequence encoding one or more AAV Rep proteins;
   (b) a Cap nucleotide sequence encoding an AAV capsid protein as set forth in claim 1; and
   (c) a correction genome as set forth in claim 1,
wherein the packaging system is operative in a cell for enclosing the correction genome in the capsid to form the AAV.

23. A method for recombinant preparation of an AAV, the method comprising introducing the packaging system of claim 22 into a cell under conditions operative for enclosing the correction genome in the capsid to form the AAV.

24. A method for editing a target locus of a genome in a cell, the method comprising transducing the cell with the replication-defective adeno-associated virus (AAV) of claim 1.

* * * * *

SEQUENCE LISTING

```
<160> NUMBER OF SEQ ID NOS: 40

<210> SEQ ID NO 1
<211> LENGTH: 736
<212> TYPE: PRT
<213> ORGANISM: Artificial Sequence
<220> FEATURE:
<223> OTHER INFORMATION: adeno-associated AAV9

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
```

```
                290                 295                 300
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720
```

Tyr Ser Glu Pro Arg Pro Ile Gly Thr Arg Tyr Leu Thr Arg Asn Leu
                725                 730                 735

<210> SEQ ID NO 2
<211> LENGTH: 736
<212> TYPE: PRT
<213> ORGANISM: Artificial Sequence
<220> FEATURE:
<223> OTHER INFORMATION: novel AAV isolate

<400> SEQUENCE: 2

Met Thr Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Gln Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

```
Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 3
<211> LENGTH: 736
<212> TYPE: PRT
<213> ORGANISM: Artificial Sequence
<220> FEATURE:
```

<223> OTHER INFORMATION: novel AAV isolate

<400> SEQUENCE: 3

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
        180                 185                 190

Ala Ala Pro Ser Gly Val Gly Ser Leu Thr Met Ala Ser Gly Gly Gly
    195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
        260                 265                 270

Ala Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400
```

```
Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Gly Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Gly Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: novel AAV isolate

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30
```

-continued

```
Lys Ala Asn Gln Gln His Gln Asp Asn Ala Arg Gly Leu Val Leu Pro
         35                  40                  45

Gly Tyr Lys Tyr Leu Gly Pro Gly Asn Gly Leu Asp Lys Gly Glu Pro
 50                  55                  60

Ile Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
             115                 120                 125

Leu Gly Leu Val Glu Glu Ala Ala Lys Thr Ala Pro Gly Lys Lys Arg
 130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                 165                 170                 175

Gly Asp Thr Glu Ser Val Pro Asp Pro Gln Pro Ile Gly Glu Pro Pro
             180                 185                 190

Ala Ala Pro Ser Gly Val Gly Ser Leu Thr Met Ala Ser Gly Gly Gly
         195                 200                 205

Ala Pro Val Ala Asp Asn Asn Glu Gly Ala Asp Gly Val Gly Ser Ser
 210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                 245                 250                 255

Tyr Lys Gln Ile Ser Asn Ser Thr Ser Gly Gly Ser Ser Asn Asp Asn
             260                 265                 270

Ala Tyr Phe Gly Tyr Ser Thr Pro Trp Gly Tyr Phe Asp Phe Asn Arg
         275                 280                 285

Phe His Cys His Phe Ser Pro Arg Asp Trp Gln Arg Leu Ile Asn Asn
 290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                 325                 330                 335

Asn Leu Thr Ser Thr Val Gln Val Phe Thr Asp Ser Asp Tyr Gln Leu
             340                 345                 350

Pro Tyr Val Leu Gly Ser Ala His Glu Gly Cys Leu Pro Pro Phe Pro
         355                 360                 365

Ala Asp Val Phe Met Ile Pro Gln Tyr Gly Tyr Leu Thr Leu Asn Asp
 370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                 405                 410                 415

Phe Glu Asn Val Pro Phe His Ser Ser Tyr Ala His Ser Gln Ser Leu
             420                 425                 430

Asp Arg Leu Met Asn Pro Leu Ile Asp Gln Tyr Leu Tyr Tyr Leu Ser
         435                 440                 445

Lys Thr Ile Asn Gly Ser Gly Gln Asn Gln Gln Thr Leu Lys Phe Ser
```

```
            450                 455                 460
Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
                610                 615                 620

Thr Tyr Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 5
<211> LENGTH: 736
<212> TYPE: PRT
<213> ORGANISM: Artificial Sequence
<220> FEATURE:
<223> OTHER INFORMATION: novel AAV isolate

<400> SEQUENCE: 5

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
                35                  40                  45

Gly Tyr Lys Tyr Leu Gly Pro Gly Asn Gly Leu Asp Lys Gly Glu Pro
                50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
```

```
                    85                  90                  95
Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Asp
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510
```

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 6
<211> LENGTH: 736
<212> TYPE: PRT
<213> ORGANISM: Artificial Sequence
<220> FEATURE:
<223> OTHER INFORMATION: novel AAV isolate

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Leu Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Ser Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560
```

Thr Asn Glu Glu Ile Lys Thr Thr Asn Pro Val Ala Thr Glu Ser
        565                 570                 575

Tyr Gly Gln Val Ala Thr Asn His Gln Ser Ala Gln Ala Gln Ala Gln
    580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 7
<211> LENGTH: 736
<212> TYPE: PRT
<213> ORGANISM: Artificial Sequence
<220> FEATURE:
<223> OTHER INFORMATION: novel AAV isolate

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

```
Ala Ala Pro Ser Gly Val Gly Ser Leu Thr Met Ala Ser Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Arg Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
```

```
                    610                 615                 620
Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735
```

<210> SEQ ID NO 8
<211> LENGTH: 736
<212> TYPE: PRT
<213> ORGANISM: Artificial Sequence
<220> FEATURE:
<223> OTHER INFORMATION: novel AAV isolate

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
                35                  40                  45

Gly Tyr Lys Tyr Leu Gly Pro Gly Asn Gly Leu Asp Lys Gly Glu Pro
        50                  55                  60

Val Asn Ala Val Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
```

-continued

```
                245                 250                 255
Tyr Lys Gln Ile Ser Asn Ser Thr Ser Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
                290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
                370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Ile Asn Gly Ser Gly Gln Asn Gln Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
```

```
Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 9
<211> LENGTH: 736
<212> TYPE: PRT
<213> ORGANISM: Artificial Sequence
<220> FEATURE:
<223> OTHER INFORMATION: novel AAV isolate

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Arg Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720
```

Tyr Ser Glu Pro Arg Pro Ile Gly Thr Arg Tyr Leu Thr Arg Asn Leu
                725                 730                 735

<210> SEQ ID NO 10
<211> LENGTH: 736
<212> TYPE: PRT
<213> ORGANISM: Artificial Sequence
<220> FEATURE:
<223> OTHER INFORMATION: novel AAV isolate

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Cys Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

-continued

Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 736
<212> TYPE: PRT
<213> ORGANISM: Artificial Sequence
<220> FEATURE:
<223> OTHER INFORMATION: novel AAV isolate

<400> SEQUENCE: 11

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Arg Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
```

```
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                    485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                    565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
                610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Lys Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 12
<211> LENGTH: 736
<212> TYPE: PRT
<213> ORGANISM: Artificial Sequence
<220> FEATURE:
<223> OTHER INFORMATION: novel AAV isolate

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
```

-continued

```
                35                  40                  45
Gly Tyr Lys Tyr Leu Gly Pro Gly Asn Gly Leu Asp Lys Gly Glu Pro
 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Lys Tyr Asn His Ala
                 85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro His Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Asn
    450                 455                 460
```

```
Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Arg Ala Ser Ser Trp Ala Leu Asn
        500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Met Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 13
<211> LENGTH: 736
<212> TYPE: PRT
<213> ORGANISM: Artificial Sequence
<220> FEATURE:
<223> OTHER INFORMATION: novel AAV isolate

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95
```

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 14
<211> LENGTH: 736
<212> TYPE: PRT
<213> ORGANISM: Artificial Sequence
<220> FEATURE:
<223> OTHER INFORMATION: novel AAV isolate

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
```

```
                  565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 15
<211> LENGTH: 736
<212> TYPE: PRT
<213> ORGANISM: Artificial Sequence
<220> FEATURE:
<223> OTHER INFORMATION: novel AAV isolate

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
```

```
              195                 200                 205
Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620
```

```
Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Arg Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 16
<211> LENGTH: 736
<212> TYPE: PRT
<213> ORGANISM: Artificial Sequence
<220> FEATURE:
<223> OTHER INFORMATION: novel AAV isolate

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

-continued

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Ala Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Arg Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

```
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 17
<211> LENGTH: 736
<212> TYPE: PRT
<213> ORGANISM: Artificial Sequence
<220> FEATURE:
<223> OTHER INFORMATION: novel AAV isolate

<400> SEQUENCE: 17

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
                20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
        50                  55                  60
Val Asn Ala Ala Asp Ala Ala Leu Glu His Asp Lys Ala Tyr Asp Gln
65                  70                  75                  80
Gln Leu Lys Ala Gly Asp Asn Pro Tyr Leu Lys Tyr Asn His Ala Asp
                85                  90                  95
Ala Glu Phe Gln Glu Arg Leu Lys Glu Asp Thr Ser Phe Gly Gly Asn
            100                 105                 110
Leu Gly Arg Ala Val Phe Gln Ala Lys Lys Arg Leu Leu Glu Pro Leu
        115                 120                 125
Gly Leu Val Glu Glu Ala Ala Lys Thr Ala Pro Gly Lys Lys Arg Pro
130                 135                 140
Val Glu Gln Ser Pro Gln Glu Pro Asp Ser Ser Ala Gly Ile Gly Lys
145                 150                 155                 160
Ser Gly Ala Gln Pro Ala Lys Lys Arg Leu Asn Phe Gly Gln Thr Gly
                165                 170                 175
Asp Thr Glu Ser Val Pro Asp Pro Gln Pro Ile Gly Glu Pro Pro Ala
            180                 185                 190
Ala Pro Ser Gly Val Gly Ser Leu Thr Met Ala Ser Gly Gly Gly Ala
        195                 200                 205
Pro Val Ala Asp Asn Asn Glu Gly Ala Asp Gly Val Gly Ser Ser Ser
210                 215                 220
Gly Asn Trp His Cys Asp Ser Gln Trp Leu Gly Asp Arg Val Ile Thr
225                 230                 235                 240
Thr Ser Thr Arg Thr Trp Ala Leu Pro Thr Tyr Asn Asn His Leu Tyr
                245                 250                 255
Lys Gln Ile Ser Asn Ser Thr Ser Gly Gly Ser Ser Asn Asp Asn Ala
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn
290                 295                 300
```

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
        340                 345                 350

Pro Tyr Val Leu Gly Ser Ala His Glu Gly Cys Leu Pro Pro Phe Pro
    355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Ile Ala Trp Pro Arg Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Cys Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
```

<210> SEQ ID NO 18
<211> LENGTH: 2211
<212> TYPE: DNA
<213> ORGANISM: Artificial Sequence
<220> FEATURE:
<223> OTHER INFORMATION: novel AAV isolate

<400> SEQUENCE: 18

```
atggctgccg atggttatct tccagattgg ctcgaggaca accttagtga aggaattcgc      60
gagtggtggg cttgaaacc tggagcccct caacccaagg caaatcaaca acatcaagac     120
aacgctcgag gtcttgtgct tccgggttac aaataccttg acccggcaa cggactcgac     180
aaggggagc cggtcaacgc agcagacgcg gcggccctcg agcacgacaa ggcctacgac     240
cagcagctca aggccggaga caacccgtac ctcaagtaca ccacgccga cgccgagttc    300
caggagcggc tcaaagaaga tacgtctttt gggggcaacc tcgggcgagc agtcttccag    360
gccaaaaaga ggcttcttga acctcttggt ctggttgagg aagcggctaa gacggctcct    420
ggaaagaaga ggcctgtaga gcagtctcct caggaaccgg actcctccgc gggtattggc    480
aaatcgggtg cacagcccgc taaaaagaga ctcaatttcg gtcagactgg cgacacagag    540
tcagtcccag accctcaacc aatcggagaa cctcccgcag cccctcagg tgtgggatct    600
cttacaatgg cttcaggtgg tggcgcacca gtggcagaca taacgaagg tgccgatgga    660
gtgggtagtt cctcgggaaa ttggcattgc gattcccaat ggctgggga cagagtcatc    720
accaccagca cccgaacctg gccctgccc acctacaaca tcacctcta caagcaaatc    780
tccaacagca catctggagg atcttcaaat gacaacgcct acttcggcta cagcaccccc    840
tgggggtatt ttgacttcaa cagattccac tgccacttct caccacgtga ctggcagcga    900
ctcatcaaca caactggg attccggcct aagcgactca acttcaagct cttcaacatt    960
caggtcaaag aggttacgga caacaatgga gtcaagacca cgccaataa ccttaccagc   1020
acggtccagg tcttcacgga ctcagactat cagctcccgt acgtgctcgg gtcggctcac   1080
gagggctgcc tcccgccgtt cccagcgac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
ccttttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaaggga gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc caagcacag gcgcagaccg gctgggttca aaaccaagga   1800
atacttccgg gtatggtttg caggacaga gatgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
```

```
gtggagatcg agtgggagct gcagaaggaa aacagcaagc gctggaaccc ggagatccag    2100
tacacttcca actattacaa gtctaataat gttgaatttg ctgttaatac tgaaggtgta    2160
tatagtgaac cccgccccat tggcaccaga tacctgactc gtaatctgta a             2211

<210> SEQ ID NO 19
<211> LENGTH: 4679
<212> TYPE: DNA
<213> ORGANISM: Artificial Sequence
<220> FEATURE:
<223> OTHER INFORMATION: novel AAV isolate

<400> SEQUENCE: 19
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt gaagcggga      300 ggtttgaacg cgcagccgcc atgccggggt tttacgagat tgtgattaag gtccccagcg     360
accttgacga gcatctgccc ggcatttctg acagctttgt gaactgggtg gccgagaagg     420
aatgggagtt gccgccagat tctgacatgg atctgaatct gattgagcag gcaccctga     480 ccgtggccga gaagctgcag cgcgactttc tgacggaatg gcgccgtgtg agtaaggccc     540 cggaggcccct tttctttgtg caatttgaga agggagagag ctacttccac atgcacgtgc    600
tcgtggaaac caccggggtg aaatccatgg ttttgggacg tttcctgagt cagattcgcg    660
aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020
aggggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagcccgtg gaggacattt   1200
ccagcaatcg gatttataaa attttggaac taaacgggta cgatcccaa tatgcggctt   1260 ccgtctttct gggatgggcc acgaaaaagt tcggcaagag gaacaccatc tggctgtttg   1320
ggcctgcaac taccgggaag accaacatcg cggaggccat agcccacact gtgcccttct   1380
acgggtgcgt aaactggacc aatgagaact ttccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga atgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agacttttc cggtgggcaa   1740 aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
```

-continued

```
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaacccgtt tctgtcgtca aaaaggcgta tcagaaactg tgctacattc   2100
atcatatcat gggaaaggtg ccagacgctt gcactgcctg cgatctggtc aatgtggatt   2160
tggatgactg catcttttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgac aaagcctacg accggcagct cgacagcgga   2460
gacaacccgt acctcaagta caaccacgcc gacgcggagt tcaggagcg ccttaaagaa   2520
gatacgtctt ttgggggcaa cctcggacga gcagtcttcc aggcgaaaaa gagggttctt   2580
gaacctctgg gcctggttga ggaacctgtt aagacggctc cggaaaaaa gaggccggta   2640
gagcactctc ctgtggagcc agactcctcc tcgggaaccg gaaaggcggg ccagcagcct   2700
gcaagaaaaa gattgaattt tggtcagact ggagacgcag actcagtacc tgaccccag   2760
cctctcggac agccaccagc agccccctct ggtctgggaa ctaatacgat ggctacaggc   2820
agtggcgcac caatgcaga caataacgag ggcgccgacg gagtgggtaa ttcctcggga   2880
aattggcatt gcgattccac atggatgggc gacagagtca tcaccaccag cacccgaacc   2940
tgggccctgc ccacctacaa caaccacctc tacaaacaaa tttccagcca atcaggagcc   3000
tcgaacgaca atcactactt tggctacagc accccttggg ggtattttga cttcaacaga   3060
ttccactgcc acttttcacc acgtgactgg caaagactca tcaacaacaa ctggggattc   3120
cgacccaaga gactcaactt caagctcttt aacattcaag tcaaagaggt cacgcagaat   3180
gacggtacga cgacgattgc caataacctt accagcacgg ttcaggtgtt tactgactcg   3240
gagtaccagc tcccgtacgt cctcggctcg gcgcatcaag gatgcctccc gccgttccca   3300
gcagacgtct tcatggtgcc acagtatgga tacctcaccc tgaacaacgg gagtcaggca   3360
gtaggacgct cttcattta ctgcctggag tactttcctt ctcagatgct gcgtaccgga   3420
aacaactta ccttcagcta cacttttgag gacgttcctt tccacagcag ctacgctcac   3480
agccagagtc tggaccgtct catgaatcct ctcatcgacc agtacctgta ttacttgagc   3540
agaacaaaca ctccaagtgg aaccaccacg cagtcaaggc ttcagttttc tcaggccgga   3600
gcgagtgaca ttcgggacca gtctaggaac tggcttcctg gaccctgtta ccgccagcag   3660
cgagtatcaa agacatctgc ggataacaac aacagtgaat actcgtggac tggagctacc   3720
aagtaccacc tcaatggcag agactctctg gtgaatccgg gcccggccat ggcaagccac   3780
aaggacgatg aagaaaagtt ttttcctcag agcggggttc tcatctttgg gaagcaaggc   3840
tcagagaaaa caaatgtgga cattgaaaag gtcatgatta cagacgaaga ggaaatcagg   3900
acaaccaatc ccgtggctac ggagcagtat ggttctgtat ctaccaacct ccagagaggc   3960
aacagacaag cagctaccgc agatgtcaac acacaaggcg ttcttccagg catggtctgg   4020
caggacagag atgtgtacct tcaggggccc atctgggcaa agattccaca cacggacgga   4080
cattttcacc cctctcccct catgggtgga ttcggactta acacccctcc tccacagatt   4140
ctcatcaaga cacccccggt acctgcgaat ccttcgacca ccttcagtgc ggcaaagttt   4200
gcttccttca tcacacagta ctccacggga caggtcagcg tggagatcga gtgggagctg   4260
```

```
cagaaggaaa acagcaaacg ctggaatccc gaaattcagt acacttccaa ctacaacaag    4320
tctgttaatg tggactttac tgtggacact aatggcgtgt attcagagcc tcgcccatt    4380 ggcaccagat acctgactcg taatctgtaa ttgcttgtta atcaataaac cgtttaattc    4440
gtttcagttg aactttggtc tctgcgtatt tctttcttat ctagtttcca tggctacgta    4500
gataagtagc atggcgggtt aatcattaac tacaaggaac ccctagtgat ggagttggcc    4560
actccctctc tgcgcgctcg ctcgctcact gaggccgggc gaccaaaggt cgcccgacgc    4620
ccgggctttg cccgggcggc ctcagtgagc gagcgagcgc gcagagaggg agtggccaa     4679
```

<210> SEQ ID NO 20
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 20

```
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttcccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atgactgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
tccgggttac aaataccttg acccggcaa cggactcgac aaggggagc cggtcaacgc       540 agcagacgcg gcggccctcg agcacgacaa ggcctacgac cagcagctca aggccggaga     600
caacccgtac ctcaagtaca accacgccga cgccgagttc caggagcggc tcaaagaaga     660
tacgtctttt gggggcaacc tcgggcgagc agtcttccag gccaaaaaga ggcttcttga     720
acctcttggt ctggttgagg aagcggctaa gacggctcct ggaaagaaga ggcctgtaga     780
gcagtctcct caggaaccgg actcctccgc gggtattggc aaatcgggtg cacagcccgc     840
taaaaagaga ctcaatttcg gtcagactgg cgacacagag tcagtcccag accctcaacc     900
aatcggagaa cctcccgcag ccccctcagg tgtgggatct cttacaatgg cttcaggtgg     960
tggcgcacca gtggcagaca taacgaagg tgccgatgga gtgggtagtt cctcgggaaa     1020
ttggcattgc gattcccaat ggctggggga cagagtcatc accaccagca cccgaacctg     1080
ggccctgccc acctacaaca atcacctcta caagcaaatc tccaacagca catctggagg     1140
atcttcaaat gacaacgcct acttcggcta cagcaccccc tgggggtatt ttgacttcaa     1200
cagattccac tgccacttct caccacgtga ctggcagcga ctcatcaaca caaactgggg     1260
attccggcct aagcaactca acttcaagct cttcaacatt caggtcaaag aggttacgga     1320
caacaatgga gtcaagacca tcgccaataa ccttaccagc acggtccagg tcttcacgga     1380
ctcagactat cagctcccgt acgtgctcgg tcggctcac gagggctgcc tcccgccgtt     1440
cccagcggac gttttcatga ttcctcagta cgggtatctg acgcttaatg atggaagcca     1500
ggccgtgggt cgttcgtcct tttactgcct ggaatatttc ccgtcgcaaa tgctaagaac     1560
gggtaacaac ttccagttca gctacgagtt tgagaacgta cctttccata gcagctacgc     1620
```

| | |
|---|---|
| tcacagccaa agcctggacc gactaatgaa tccactcatc gaccaatact tgtactatct | 1680 |
| ctcaaagact attaacggtt ctggacagaa tcaacaaacg ctaaaattca gtgtggccgg | 1740 |
| acccagcaac atggctgtcc agggaagaaa ctacatacct ggacccagct accgacaaca | 1800 |
| acgtgtctca accactgtga ctcaaaacaa caacagcgaa tttgcttggc ctggagcttc | 1860 |
| ttcttgggct ctcaatggac gtaatagctt gatgaatcct ggacctgcta tggccagcca | 1920 |
| caaagaagga gaggaccgtt tctttccttt gtctggatct ttaattttg gcaaacaagg | 1980 |
| aactggaaga gacaacgtgg atgcggacaa agtcatgata accaacgaag aagaaattaa | 2040 |
| aactactaac ccggtagcaa cggagtccta tggacaagtg gccacaaacc accagagtgc | 2100 |
| ccaagcacag gcgcagaccg gctgggttca aaaccaagga atacttccgg gtatggtttg | 2160 |
| gcaggacaga gatgtgtacc tgcaaggacc catttgggcc aaaattcctc acacggacgg | 2220 |
| caactttcac ccttctccgc tgatgggagg gtttggaatg aagcacccgc ctcctcagat | 2280 |
| cctcatcaaa aacacacctg tacctgcgga tcctccaacg gccttcaaca aggacaagct | 2340 |
| gaactctttc atcacccagt attctactgg ccaagtcagc gtggagatcg agtgggagct | 2400 |
| gcagaaggaa aacagcaagc gctggaaccc ggagatccag tacacttcca actattacaa | 2460 |
| gtctaataat gttgaatttg ctgttaatac tgaaggtgta tatagtgaac cccgccccat | 2520 |
| tggcaccaga tacctgactc gtaatctgta attgcttgtt aatcaataaa ccgtttaatt | 2580 |
| cgtttcagtt gaactgcggc c | 2601 |

<210> SEQ ID NO 21
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 21

| | |
|---|---|
| ccatcgacgt cagacgcgga agcttcgatc aactacgcgg acaggtacca aaacaaatgt | 60 |
| tctcgtcacg tgggcatgaa tctgatgctg tttccctgca gacaatgcga gagactgaat | 120 |
| cagaattcaa atatctgctt cactcacggt gtcaaagact gtttagagtg ctttcccgtg | 180 |
| tcagaatctc aacccgtttc tgtcgtcaaa aaggcgtatc agaaactgtg ctacattcat | 240 |
| cacatcatgg gaaaggtgcc agacgcttgc actgcttgcg acctggtcaa tgtggacttg | 300 |
| gatgactgtg tttctgaaca ataaatgact taaaccaggt atggctgccg atggttatct | 360 |
| tccagattgg ctcgaggaca accttagtga aggaattcgc gagtggtggg ctttgaaacc | 420 |
| tggagcccct caacccaagg caaatcaaca acatcaagac aacgctcgag gtcttgtgct | 480 |
| tccgggttac aaataccttg acccggcaa cggactcgac aagggggagc cggtcaacgc | 540 |
| agcagacgcg gcggccctcg agcacgacaa ggcctacgac cagcagctca aggccggaga | 600 |
| caacccgtac ctcaagtaca accacgccga cgccgagttc caggagcggc tcaaagaaga | 660 |
| tacgtctttt gggggcaacc tcgggcgagc agtcttccag gccaaaaaga ggcttcttga | 720 |
| acctcttggt ctggttgagg aagcggctaa gacggctcct ggaaagaaga ggcctgtaga | 780 |
| gcagtctcct caggaaccgg actcctccgc gggtattggc aaatcgggtg cacagcccgc | 840 |
| taaaaagaga ctcaatttcg gtcagactgg cgacacagag tcagtcccag accctcaacc | 900 |
| aatcggagaa cctccgcag cccctcagg tgtgggatct cttacaatgg cttcaggtgg | 960 |
| tggcgcacca gtggcagaca ataacgaagg tgccgatgga gtgggtagtt cctcgggaaa | 1020 |
| ttggcattgc gattcccaat ggctggggga cagagtcatc accaccagca cccgaacctg | 1080 |

```
ggccctgccc acctacaaca atcacctcta caagcaaatc tccaacagca catctggagg    1140
atcttcaaat gacaacgcct acttcggcta cagcaccccc tgggggtatt ttgacttcaa    1200
cagattccac tgccacttct caccacgtga ctggcagcga ctcatcaaca caactgggg     1260 attccggcct aagcgactca acttcaagct cttcaacatt caggtcaaag aggttacgga    1320
caacaatgga gtcaagacca tcgccaataa ccttaccagc acggtccagg tcttcacgga    1380
ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acccagcaac atggctgtcc agggaagaaa ctacatacct ggacccagct accgacaaca    1800
acgtgtctca accactgtga ctcaaaacaa caacagcgaa tttgcttggc ctggggcttc    1860
ttcttgggct ctcaatggac gtaatagctt gatgaatcct ggacctgcta tggccagcca    1920
caaagaagga gaggaccgtt tctttccttt gtctggatct ttaattttg gcaaacaagg    1980 aactggaaga gacaacgtgg atgcggacaa agtcatgata accaacgaag aagaaattaa    2040
aactactaac ccggtagcaa cggagtccta tggacaagtg gccacaaacc accagagtgc    2100
ccaagcacag gcgcagaccg gctgggttca aaaccaagga atacttccgg gtatggtttg    2160
gcaggacaga gatgtgtacc tgcaaggacc catttgggcc aaaattcctc acacgggcgg    2220
caactttcac cctcctccgc tgatgggagg gtttggaatg aagcacccgc ctcctcagat    2280
cctcatcaaa aacacacctg tacctgcgga tcctccaacg ccttcaaca aggacaagct    2340 gaactctttc atcacccagt attctactgg ccaagtcagc gtggagatcg agtgggagct    2400
gcagaaggaa aacagcaagc gctggaaccc ggagatccag tacacttcca actattacaa    2460
gtctaataat gttgaatttg ctgttaatac tggaggtgta tatagtgaac cccgccccat    2520
tggcaccaga tacctgactc gtaatctgta attgcttgtt aatcaataaa ccgtttaatt    2580
cgtttcagtt gaactgcggc c                                              2601
```

<210> SEQ ID NO 22
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 22

```
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttcccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggactcg     300
gatgactgtg tttctgaaca ataaatgact taaaccaggt atggctgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
```

```
tccgggttac aaatacccttg acccggcaa cggactcgac aagggggagc cggtcaacgc    540
agcagacgcg gcggccctcg agcacgacaa ggcctacgac cagcagctca aggccggaga    600
caacccgtac ctcaagtaca accacgccga cgccgagttc caggagcggc tcaaagaaga    660
tacgtctttt gggggcaacc tcgggcgagc agtcttccag gccaaaaaga ggcttcttga    720
acctcttggt ctggttgagg aagcggctaa gacggctcct ggaagaaga ggcctgtaga    780
gcagtctcct caggaaccgg actcctccgc gggtattgac aaatcgggtg cacagcccgc    840
taaaaagaga ctcaatttcg gtcagactgg cgacacagag tcagtcccag accctcaacc    900
aatcggagaa cctcccgcag cccctcagg tgtgggatct cttacaatgg cttcaggtgg    960
tggcgcacca gtggcagaca ataacgaagg tgccgatgga gtgggtagtt cctcgggaaa   1020
ttggcattgc gattcccaat ggctggggga cagagtcatc accaccagca cccgaacctg   1080
ggccctgccc acctacaaca atcacctcta caagcaaatc tccaacagca catctggagg   1140
atcttcaaat gacaacgcct acttcggcta cagcaccccc tgggggtatt ttgacttcaa   1200
cagattccac tgccacttct caccacgtga ctggcagcga ctcatcaaca caactgggg   1260
attccggcct aagcgactca acttcaagct cttcaacatt caggtcaaag aggttacgga   1320
caacaatgga gtcaagacca tcgccaataa ccttaccagc acggtccagg tcttcacgga   1380
ctcggactat cagctcccgt acgtgctcgg gtcggctcac gagggctgcc tcccgccgtt   1440
cccagcggac gttttcatga ttcctcagta cgggtatctg acgcttaatg atggaagcca   1500
ggccgtgggt cgttcgtcct tttactgcct ggaatatttc ccgtcgcaaa tgctaagaac   1560
gggtaacaac ttccagttca gctacagagt tgagaacgta cctttccata gcagctacgc   1620
tcacagccaa agcctggacc gactaatgaa tccactcatc gaccaatact tgtactatct   1680
ctcaaagact attaacggtt ctggacagaa tcaacaaacg ctaaaattca gtgtggccgg   1740
acccagcaac atggctgtcc agggaagaaa ctacatacct ggacccagct accgacaaca   1800
acgtgtctca accactgtga ctcaaaacaa caacagcgaa tttgcttggc ctggagcttc   1860
ttcttgggct ctcaatggac gtaatagctt gatgaatcct ggacctgcta tggccagcca   1920
caaagaagga gaggaccgtt tctttccttt gtctggatct ttaattttg gcaaacaagg   1980
aactggaaga gacaacgtgg atgcggacaa agtcatgata accaacgaag aagaaattaa   2040
aactactaac ccggtagcaa cggagtccta tggacaagtg gccacaaacc accagagtgc   2100
ccaagcacag gcgcagaccg gctgggttca aaaccaagga atacttccgg gtatggtttg   2160
gcaggacaga gatgtgtacc tgcaaggacc catttgggcc aaaattcctc acacggacgg   2220
caactttcac ccttctccgc tgatgggagg gtttggaatg aagcacccgc ctcctcagat   2280
cctcatcaaa aacacacctg tacctgcgga tcctccaacg gccttcaaca aggacaagct   2340
gaactctttc atcacccagt attctactgg ccaagtcagc gtggagatcg agtgggagct   2400
gcagaaggaa aacagcaagc gctggaaccc ggagatccag tacacttcca actattacaa   2460
gtctaataat gttgaatttg ctgttaatac tgaaggtgta tatagtgaac cccgccccat   2520
tggcaccaga tacctgactc gtaatctgta attgcttgtt aatcaataaa ccgtttaatt   2580
cgtttcagtt gaactgcggc c                                             2601
```

<210> SEQ ID NO 23
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 23

```
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttcccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atggctgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
tccgggttac aaataccttg gacccggcaa cggactcgac aagggggagc cggtcaacgc     540
agcagacgcg gcggccctcg agcacgacaa ggcctacgac cagcagctca aggccggaga     600
caacccgtac ctcaagtaca accacgccga cgccgagttc caggagcggc tcaaagaaga     660
tacgtctttt gggggcaacc tcgggcgagc agtcctccag gccaaaaaga ggcttcttga     720
acctcttggt ctggttgagg aagcggctaa gacggctcct ggaaagaaga ggcctgtaga     780
gcagtctcct caggaaccgg actcctccgc gggtattggc aaatcgggtg cacagcccgc     840
taaaaagaga ctcaatttcg gtcagactgg cgacacagag tcagtcccag accctcaacc     900
aatcggagaa cctcccgcag ccccctcagg tgtgggatct cttacaatgg cttcaggtgg     960
tggcgcacca gtggcagaca ataacgaagg tgccgatgga gtgggtagtt cctcgggaaa    1020
ttggcattgc gattcccaat ggctggggga cagagtcatc accaccagca cccgaacctg    1080
ggccctgccc acctacaaca atcacctcta caagcaaatc tccaacagca catctggagg    1140
atcttcaaat gacaacgcct acttcggcta cagcaccccc tggggtatt ttgacttcaa    1200
cagattccac tgccacttct caccacgtga ctggcagcga ctcatcaaca caactgggg    1260
attccggcct aagcgactca acttcaagct cttcaacatt caggtcaaag aggttacgga    1320
caacaatgga gtcaagacca tcgccaataa ccttaccagc acgtccagg tcttcacgga    1380
ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
atccagcaac atggctgtcc agggaagaaa ctacatacct ggacccagct accgacaaca    1800
acgtgtctca accactgtga ctcaaaacaa caacagcgaa tttgcttggc ctggagcttc    1860
ttcttgggct ctcaatggac gtaatagctt gatgaatcct ggacctgcta tggccagcca    1920
caaagaagga gaggaccgtt tctttcctt gtctggatct ttaattttg gcaaacaagg    1980
aactggaaga gacaacgtgg atgcggacaa agtcatgata accaacgaag aagaaattaa    2040
aactactaac ccggtagcaa cggagtccta tggacaagtg gccacaaacc accagagtgc    2100
ccaagcacag gcgcagaccg gctgggttca aaaccaagga atacttccag gtatggtttg    2160
gcaggacaga gatgtgtacc tgcaaggacc catttgggcc aaaattcctc acacggacgg    2220
caactttcac ccttctccgc tgatgggagg gtttggaatg aagcacccgc ctcctcagat    2280
```

| | |
|---|---|
| cctcatcaaa aacacacctg tacctgcgga tcctccaacg gccttcaaca aggacaagct | 2340 |
| gaactctttc atcacccagt attctactgg ccaagtcagc gtggagatcg agtgggagct | 2400 |
| gcagaaggaa aacagcaagc gctggaaccc ggagatccag tacacttcca actattacaa | 2460 |
| gtctaataat gttgaatttg ctgttaatac tgaaggtgta tatagtgaac ccgcccat | 2520 |
| tggcaccaga tacctgactc gtaatctgta attgcttgtt aatcaataaa ccgtttaatt | 2580 |
| cgtttcagtt gaactgcggc c | 2601 |

<210> SEQ ID NO 24
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 24

| | |
|---|---|
| ccatcgacgt cagacgcgga agcttcgatc aactacgcgg acaggtacca aaacaaatgt | 60 |
| tctcgtcacg tgggcatgaa tctgatgctg tttccctgca gacaatgcga gagactgaat | 120 |
| cagaattcaa atatctgctt cactcacggt gtcaaagact gtttagagtg ctttcccgtg | 180 |
| tcagaatctc aacccgtttc tgtcgtcaaa aaggcgtatc agaaactgtg ctacattcat | 240 |
| cacatcatgg gaaaggtgcc agacgcttgc actgcttgcg acctggtcaa tgtggacttg | 300 |
| gatgactgtg tttctgaaca ataaatgact taaaccaggt atggctgccg atggttatct | 360 |
| tccagattgg ctcgaggaca accttagtga aggaattcgc gagtggtggg ctttgaaacc | 420 |
| tggagcccct caacccaagg caaatcaaca acatcaagac aacgctcgag gtcttgtgct | 480 |
| tccgggttac aaataccttg acccggcaa cggactcgac aaggggagc cggtcaacgc | 540 |
| agcagacgcg gcgcccctcg agcacgacaa ggcctacgac cagcagctca aggccggaga | 600 |
| caacccgtac ctcaagtaca accacgccga cgccgagttc caggagcggc tcaaagaaga | 660 |
| tacgtctttt gggggcaacc tcgggcgagc agtcttccag gccaaaaaga ggcttcttga | 720 |
| acctcttggt ctggttgagg aagcggctaa gacggctcct ggaaagaaga ggcctgtaga | 780 |
| gcagtctcct caggaaccgg actcctccgc gggtattggc aaatcgggtg cacagcccgc | 840 |
| taaaaagaga ctcaatttcg gtcagactgg cgacacagag tcagtcccag accctcaacc | 900 |
| aatcggagaa cctcccgcag cccctcagg tgtgggatct cttacaatgg cttcaggtgg | 960 |
| tggcgcacca gtggcagaca taacgaagg tgccgatgga gtgggtagtt cctcgggaaa | 1020 |
| ttggcattgc gattcccaat ggctggggga cagagtcatc accaccagca cccgaacctg | 1080 |
| ggccctgccc acctacaaca atcacctcta caagcaaatc tccaacagca catctggagg | 1140 |
| atcttcaaat gacaacgcct acttcggcta cagcaccccc tgggggtatt ttgacttcaa | 1200 |
| cagattccac tgccacttct caccacgtga ctggcagcga ctcatcaaca caactggg | 1260 |
| attccggcct aagcgactca acttcaagct cttcaacatt caggtcaaag aggttacgga | 1320 |
| caacaatgga gtcaagacca tcgccaataa ccttaccagc acggtccagg tcttcacgga | 1380 |
| ctcagactat cagctcccgt acgtgctcgg tcggctcac gagggctgcc tcccgccgtt | 1440 |
| cccagcggac gttttcatga ttcctcagta cgggtatctg acgcttaatg atggaagcca | 1500 |
| ggccgtgggt cgttcgtcct tttactgcct ggaatatttc ccgtcgcaaa tgctaagaac | 1560 |
| gggtaacaac ttccagttca gctacgagtt tgagaacgta ccttttccata gcagctacgc | 1620 |
| tcacagccaa agcctggacc gactaatgaa tccactcatc gaccaatact tgtactatct | 1680 |
| ctcaaagact attaacggtt ctggacagaa tcaacaaacg ctaaaattca gtgtggccgg | 1740 |

```
acccagcaac atggctgtcc agggaagaaa ctacatacct ggacccagct accgacaaca    1800
acgtgtctca accactgtga ctcaaaacaa caacagcgaa tttgcttggc ctggagcttc    1860
ttcttgggct ctcaatggac gtaatagctt gatgaatcct ggacctgcta tggccagcca    1920
caaagaagga gaggaccgtt tctttccttt gtctggatct ttaattttg gcaaacaagg     1980 aactggaaga acaacgtgg atgcggacaa agtcatgata accaacgaag aagaaattaa     2040
aactactaac ccggtagcaa cggagtccta tggacaagtg ccacaaacc accagagtgc     2100 ccaagcacgg gcgcagaccg gctgggttca aaaccaagga atacttccgg gtatggtttg    2160
gcaggacaga gatgtgtacc tgcaaggacc catttgggcc aaaattcctc acacggacgg    2220
caactttcac ccttctccgc tgatgggagg gtttggaatg aagcacccgc ctcctcagat    2280
cctcatcaaa aacacacctg tacctgcgga tcctccaacg gccttcaaca aggacaagct    2340
gaactctttc atcacccagt attctactgg ccaagtcagc gtggagatcg agtgggagct    2400
gcagaaggaa aacagcaagc gctggaaccc ggagatccag tacacttcca actattacaa    2460
gtctaataat gttgaatttg ctgttaatac tgaaggtgta tatagtgaac ccgccccat    2520 tggcaccaga tacctgactc gtaatctgta attgcttgtt aatcaataaa ccgtttaatt    2580
cgtttcagtt gaactgcggc c                                             2601

<210> SEQ ID NO 25
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 25
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttccgtg     180 tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atggctgccg atggttatct     360
tccagattgg ctcgaggaca accttagtga aggaattcgc gagtggtggg ctttgaaaacc    420 tggagcccct caacccaagg caaatcaaca acatcaagac aacgctcgag gtcttgtgct    480
tccgggttac aaataccttg gacccggcaa cggactcgac aaggggggagc cggtcaacgc    540 agcagacgcg gcggccctcg agcacgacag ggcctacgac cagcagctca aggccggaga    600
caacccgtac ctcaagtaca accacgccga cgccgagttc caggagcggc tcaaagaaga    660
tacgtctttt gggggcaacc tcgggcgagc agtcttccag gccaaaaaga ggcttcttga    720
acctcttggt ctggttgagg aagcggctaa gacggctcct ggaaagaaga ggcctgtaga    780
gcagtctcct caggaaccgg actcctccgc gggtattggc aaatcgggtg cacagcccgc    840
taaaaagaga ctcaatttcg gtcagactgg cgacacagag tcagtcccag accctcaacc    900
aatcggagaa cctcccgcag ccccctcagg tgtgggatct cttacaatgg cttcaggtgg    960
tggcgcacca gtggcagaca ataacgaagg tgccgatgga gtgggtagtt cctcgggaaa    1020
ttggcattgc gattcccaat ggctggggga cagagtcatc accaccagca cccgaacctg    1080
ggccctgccc acctacaaca atcacctcta caagcaaatc tccaacagca catctggagg    1140
```

```
atcttcaaat gacaacgcct acttcggcta cagcaccccc tgggggtatt ttgacttcaa    1200
cagattccac tgccacttct caccacgtga ctggcagcga ctcatcaaca caactgggg     1260 attccggcct aagcgactca acttcaagct cttcaacatt caggtcaaag aggttacgga    1320
caacaatgga gtcaagacca tcgccaataa ccttaccagc acggtccagg tcttcacgga    1380
ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acctagcaac atggctgtcc agggaagaaa ctacatacct ggacccagct accgacaaca    1800
acgtgtctca accactgtga ctcaaaacaa caacagcgaa tttgcttggc ctggagcttc    1860
ttcttgggct ctcaatggac gtaatagctt gatgaatcct ggacctgcta tggccagcca    1920
caaagaagga gaggaccgtt tctttccttt gtctggatct ttaattttg gcaaacaagg     1980 aactggaaga gacaacgtgg atgcggacaa agtcatgata accaacgaag aagaaattaa    2040
aactactaac ccggtagcaa cggagtccta tggacaagtg gccacaaacc accagagtgc    2100
ccaagcacag gcgcagaccg gctgggttca aaaccaagga atacttccgg gtatggttg     2160 gcaggacaga gatgtgtacc tgcaaggacc catttgggcc aaaattcctc acacggacgg    2220
caactttcac ccttctccgc tgatgggagg gtttggaatg aagcacccgc ctcctcagat    2280
cctcatcaaa aacacacctg tacctgcgga tcctccaacg gccttcaaca aggacaagct    2340
gaactctttc atcacccagt attctactgg ccaagtcagc gtggagatcg agtgggagct    2400
gcagaagaaa acagcaagc gctggaaccc ggagatccag tacacttcca actattacaa     2460
gtctaataat gttgaatttg ctgttaacac tgaaggtgta tatagtgaac ccgcccccat     2520
tggcaccaga tacctgactc gtaatctgta attgcttgtt aatcaataaa ccgtttaatt    2580
cgtttcagtt gaactgcggc c                                              2601
```

<210> SEQ ID NO 26
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 26

```
ccatcgacgt cagacgcgga agcttcgatc aactacgcgg acaggtacca aaacaaatgt     60
tctcgtcacg tgggcatgaa tctgatgctg tttccctgca gacaatgcga gagactgaat    120
cagaattcaa atatctgctt cactcacggt gtcaaagact gtttagagtg ctttcccgtg    180
tcagaatctc aacccgtttc tgtcgtcaaa aaggcgtatc agaaactgtg ctacattcat    240
cacatcatgg gaaaggtgcc agacgcttgc actgcttgcg acctggtcaa tgtggacttg    300
gatgactgtg tttctgaaca ataaatgact taaaccaggt atggctgccg atggttatct    360
tccagattgg ctcgaggaca accttagtga aggaattcgc gagtggtggg ctttgaaacc    420
tggagcccct caacccaagg caaatcaaca acatcaagac aacgctcgag tcttgtgct     480 tccgggttac aaatacctttg acccggcaa cggactcgac aagggggagc cgatcaacgc    540
agcagacgcg gcggccctcg agcacgacaa ggcctacgac cagcagctca aggccggaga    600
```

```
caacccgtac ctcaagtaca accacgccga cgccgagttc caggagcggc tcaaagaaga      660
tacgtctttt gggggcaacc tcgggcgagc agtcttccag gccaaaaaga ggcttcttga      720
acctcttggt ctggttgagg aagcggctaa gacggctcct ggaagaagaa ggcctgtaga      780
gcagtctcct caggaaccgg actcctccgc gggtattggc aaatcgggtg cacagcccgc      840
taaaaagaga ctcaatttcg gtcagactgg cgacacagag tcagtcccag accctcaacc      900
aatcggagaa cctcccgcag cccctcagg tgtgggatct cttacaatgg cttcaggtgg       960
tggcgcacca gtggcagaca ataacgaagg tgccgatgga gtgggtagtt cctcgggaaa     1020
ttggcattgc gattcccaat ggctggggga cagagtcatc accaccagca cccgaacctg     1080
ggccctgccc acctacaaca atcacctcta caagcaaatc tccaacagca catctggagg     1140
atcttcaaat gacaacgcct acttcggcta cagcaccccc tggggtatt ttgacttcaa      1200 cagattccac tgccacttct caccacgtga ctggcagcga ctcatcaaca caactgggg    1260 attccggcct aagcgactca acttcaagct cttcaacatt caggtcaaag aggttacgga    1320
caacaatgga gtcaagacca tcgccaataa ccttaccagc acggtccagg tcttcacgga    1380
ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggg cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acccagcaac atggctgtcc agggaagaaa ctacatacct ggacccagct accgacaaca    1800
acgtgtctca accactgtga ctcaaaacaa caacagcgaa tttgcttggc ctggagcttc    1860
ttcttgggct ctcaatggac gtaatagctt gatgaatcct ggacctgcta tggccagcca    1920
caaagaagga gaggaccgtt tctttcctt gtctggatct ttaattttg gcaaacaagg      1980 aactggaaga gacaacgtgg atgcggacaa agtcatgata accacgaag aagaaattaa    2040 aactactaac ccggtagcaa cggagtccta tggacaagtg gccacaaacc accagagtgc    2100
ccaagcacag gcgcagaccg gctgggttca aaaccaagga atacttccgg gtatggtttg    2160
gcaggacaga gatgtgtacc tgcaaggacc catttgggcc aaaattcctc acacgtacgg    2220
caactttcac ccttctccgc tgatgggagg gttggaatg aagcacccgc ctcctcagat      2280
cctcatcaaa aacacacctg tacctgcgga tcctccaacg gccttcaaca aggacaagct    2340
gaactctttc atcacccagt attctactgg ccaagtcagc gtggagatcg agtgggagct    2400
gcagaaggaa aacagcaagc gctggaaccc ggagatccag tacacttcca actattacaa    2460
gtctaataat gttgaatttg ctgttaatac tgaaggtgta tatagtgaac ccgcccat     2520 tggcaccaga tacctgactc gtaatctgta attgcttgtt aatcaataaa ccgtttaatt    2580
cgtttcagtt gaactgcggc c                                               2601
```

<210> SEQ ID NO 27
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 27

```
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttcccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atggctgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
tccgggttac aaatacctttg acccggcaa cggactcgac aaggggggagc cggtcaacgc     540 agtagacgcg gcggccctcg agcacgacaa ggcctacgac cagcagctca aggccggaga     600
caacccgtac ctcaagtaca accacgccga cgccgagttc caggagcggc tcaaagaaga     660
tacgtctttt gggggcaacc tcgggcgagc agtcttccag gccaaaaaga ggcttcttga     720
acctcttggt ctggttgagg aagcggctaa gacggctcct ggaaagaaga ggcctgtaga     780
gcagtctcct caggaaccgg actcctccgc gggtattggc aaatcgggtg cacagcccgc     840
taaaaagaga ctcaatttcg gtcagactgg cgacacagag tcagtcccag accctcaacc     900
aatcggagaa cctcccgcag ccccctcagg tgtgggatct cttacaatgg cttcaggtgg     960
tggcgcacca gtggcagaca ataacgaagg tgccgatgga gtgggtagtt cctcgggaaa    1020
ttggcattgc gattcccaat ggctggggga cagagtcatc accaccagca cccgaacctg    1080
ggccctgccc acctacaaca atcacctcta caagcaaatc tccaacagca catctggagg    1140
atcttcaaat gacaacgcct acttcggcta cagcaccccc tgggggtatt ttgacttcaa    1200
cagattccac tgccacttct caccacgtga ctggcagcga ctcatcaaca caactgggg    1260 atttcggcct aagcgactca acttcaagct cttcaacatt caggtcaaag aggttacgga    1320
caacaatgga gtcaagacca tcgccaataa ccttaccagc acgtccagg tcttcacgga    1380 ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acccagcaac atggctgtcc agggaagaaa ctacatacct ggacccagct accgacaaca    1800
acgtgtctca accactgtga ctcaaaacaa caacagcgaa tttgcttggc ctggagcttc    1860
ttcttgggct ctcaatggac gtaatagctt gatgaatcct ggacctgcta tggccagcca    1920
caaagaagga gaggaccgtt tctttccttt gtctggatct ttaattttg gcaaacaagg    1980 aactggaaga gacaacgtgg atgcggacaa agtcatgata accaacgaag aagaaattaa    2040
aactactaac ccggtagcaa cggagtccta tggacaagtg ccacaaaacc accagagtgc    2100
ccaagcacag gcgcagaccg gctgggttca aaaccaagga atacttccgg gtatggtttg    2160
gcaggacaga gatgtgtacc tgcaaggacc catttgggcc aaaattcctc acacggacgg    2220
caactttcac ccttctccgc tgatgggagg gtttggaatg aagcacccgc ctcctcagat    2280
cctcatcaaa aacacacctg tacctgcgga tcctccaacg gccttcaaca aggacaagct    2340
gaactctttc atcacccagt attctactgg ccaagtcagc gtggagatcg agtgggagct    2400
```

```
gcagaaggaa acacagcaagc gctggaaccc ggagatccag tacacttcca actattacaa    2460
gtctaataat gttgaatttg ctgttaatac tgaaggtgta tatagtgaac cccgccccat    2520
tggcaccaga tacctgactc gtaatctgta attgcttgtt aatcaataaa ccgtttaatt    2580
cgtttcagtt gaactgcggc c                                              2601

<210> SEQ ID NO 28
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 28
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttcccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atggctgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
tccgggttac aaataccttg gacccggcaa cggactcgac aagggggagc cggtcaacgc     540
agcagacgcg gcggccctcg agcacgacaa ggcctacgac cagcagctca aggccggaga     600
caacccgtac ctcaagtaca accacgccga cgccgagttc caggagcggc tcaaagaaga     660
tacgtctttt gggggcaacc tcgggcgagc agtcttccag gccaaaaaga ggcttcttga     720
acctcttggt ctggttgagg aagcggctaa gacggctcct ggaaagaaga ggcctgtaga     780
gcagtctcct cgggaaccgg actcctccgc gggtattggc aaatcgggtg cacagcccgc     840
taaaaagaga ctcaatttcg gtcagactgg cgacacagag tcagtcccag accctcaacc     900
aatcggagaa cctcccgcag cccccctcagg tgtgggatct cttacaatgg cttcaggtgg     960
tggcgcacca gtggcagaca taacgaaggt gccgatgga gtgggtagtt cctcgggaaa    1020
ttggcattgc gattcccaat ggctggggga cagagtcatc accaccagca cccgaacctg    1080
ggccctgccc acctacaaca atcacctcta caagcaaatc tccaacagca catctggagg    1140
atcttcaaat gacaacgcct acttcggcta cagcaccccc tgggggtatt ttgacttcaa    1200
cagattccac tgccacttct caccacgtga ctggcagcga ctcatcaaca caactgggg    1260 attccggcct aagcgactca acttcaagct cttcaacatt caggtcaaag aggttacgga    1320
caacaatgga gtcaagacca tcgccaataa ccttaccagc acgtccagg tcttcacgga    1380 ctcagactat cagctcccgt acgtgctcgg tcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acccagcaac atggctgtcc agggaagaaa ctacatacct ggacccagct accgacaaca    1800
```

```
acgtgtctca accactgtga ctcaaaacaa caacagcgaa tttgcttggc ctggagcttc    1860
ttcttgggct ctcaatggac gtaatagctt gatgaatcct ggacctgcta tggccagcca    1920
caaagaagga gaggaccgtt tctttccttt gtctggatct ttaattttg gcaaacaagg    1980 aactggaaga gacaacgtgg atgcggacaa agtcatgata accaacgaag aagaaattaa    2040
aactactaac ccggtagcaa cggagtccta tggacaagtg ccacaaaacc accagagtgc    2100
ccaagcacag cgcagaccg gctgggttca aaaccaagga atacttccgg gtatggtttg    2160
gcaggacaga gatgtgtacc tgcaaggacc catttgggcc aaaattcctc acacggacgg    2220
caactttcac ccttctccgc tgatggggag gtttggaatg aagcacccgc ctcctcagat    2280
cctcatcaaa aacacacctg tacctgcgga tcctccaacg gccttcaaca aggacaagct    2340
gaactctttc atcacccagt attctactgg ccaagtcagc gtggagatcg agtgggaact    2400
gcagaaggaa aacagcaagc gctggaaccc ggagatccag tacacttcca actattacaa    2460
gtctaataat gttgaatttg ctgttaatac tgaaggtgta tatagtgaac ccgcccat    2520 tggcaccaga tacctgactc gtaatctgta attgcttgtt aatcaataaa ccgtttaatt    2580
cgtttcagtt gaactgcggc c                                             2601

<210> SEQ ID NO 29
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 29
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg cttccccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atggctgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
tccgggttac aaataccttg acccggcaa cggactcgac aaggggggagc cggtcaacgc     540 agcagacgcg gcggcccctcg agcacgacaa ggcctacgac cagcagctca aggccggaga     600
caacccgtac ctcaagtaca ccacgccga cgccgagttc caggagcggc tcaaagaaga     660 tacgtcttt ttgggggcaacc tcgggcgagc agtctttcag gccaaaaaga ggcttcttga     720
acctcttggt ctggttgagg aagcggctaa gacggctcct ggaaagaaga ggcctgtaga     780
gcagtctcct caggaaccgg actcctccgc gggtattggc aaatcgggtg cacagcccgc     840
taaaaagaga ctcaatttcg gtcagactgg cgacacagag tcagtcccag accctcaacc     900
aatcggagaa cctcccgcag ccccctcagg tgtgggatct cttacaatgg cttcatgtgg     960
tggcgcacca gtggcagaca taacgaaggt gccgatggga gtgggtagtt cctcgggaaa    1020
ttggcattgc gattcccaat ggctggggga cagagtcatc accaccagca cccgaacctg    1080
ggccctgccc acctacaaca atcacctcta caagcaaatc tccaacagca catctggagg    1140
atcttcaaat gacaacgcct acttcggcta cagcaccccc tggggggtatt ttgacttcaa    1200 cagattccac tgccacttct caccacgtga ctggcagcga ctcatcaaca caactgggg    1260
```

```
attccggcct aagcgactca acttcaagct cttcaacatt caggtcaaag aggttacgga   1320
caacaatgga gtcaagacca tcgccaataa ccttaccagc acggtccagg tcttcacgga   1380
ctcagactat cagctcccgt acgtgctcgg gtcggctcac gagggctgcc tcccgccgtt   1440
cccagcggac gttttcatga ttcctcagta cgggtatctg acgcttaatg atggaagcca   1500
ggccgtgggt cgttcgtcct tttactgcct ggaatatttc ccgtcgcaaa tgctaagaac   1560
gggtaacaac ttccagttca gctacgagtt tgagaacgta cctttccata gcagctacgc   1620
tcacagccaa agcctggacc gactaatgaa tccactcatc gaccaatact tgtactatct   1680
ctcaaagact attaacggtt ctggacagaa tcaacaaacg ctaaaattca gtgtggccgg   1740
acccagcaac atggctgtcc agggaagaaa ctacatacct ggacccagct accgacaaca   1800
acgtgtctca accactgtga ctcaaaacaa caacagcgaa tttgcttggc ctggagcttc   1860
ttcttgggct ctcaatggac gtaatagctt gatgaatcct ggacctgcta tggccagcca   1920
caaagaagga gaggaccgtt tctttccttt gtctggatct ttaattttg gcaaacaagg   1980 aactggaaga gacaacgtgg atgcggacaa agtcatgata accaacgaag aagaaattaa   2040
aactactaac ccggtagcaa cggagtccta tggacaagtg gccacaaacc accagagtgc   2100
ccaagcacag gcgcagaccg gctgggttca aaaccaagga atacttccgg gtatggtttg   2160
gcaggacaga gatgtgtacc tgcaaggacc catttgggcc aaaattcctc acacggacgg   2220
caactttcac ccttctccgc tgatgggagg gtttggaatg aagcaccgc  tcctcagat   2280 cctcatcaaa aacacacctg tacctgcgga tcctccaacg gccttcaaca aggacaagct   2340
gaactctttc atcacccagt attctactgg ccaagtcagc gtggagatcg agtgggagct   2400
gcagaaggaa aacagcaagc gctggaaccc ggagatccag tacacttcca actattacaa   2460
gtctaataat gttgaatttg ctgttaatac tgaaggtgta tatagtgaac cccgccccat   2520
tggcaccaga tacctgactc gtaatctgta attgcttgtt aatcaataaa ccgtttaatt   2580
cgtttcagtt gaactgcggc c                                             2601
```

<210> SEQ ID NO 30
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 30

```
ccatcgacgt cagacgcgga agcttcgatc aactacgcgg acaggtacca aaacaaatgt    60
tctcgccacg tgggcatgaa tctgatgctg tttccctgca gacaatgcga gagactgaat   120
cagaattcaa atatctgctt cactcacggt gtcaaagact gtttagagtg ctttcccgtg   180
tcagaatctc aacccgtttc tgtcgtcaaa aaggcgtatc agaaactgtg ctacattcat   240
cacatcatgg gaaaggtgcc agacgcttgc actgcttgcg acctggtcaa tgtggacttg   300
gatgactgtg tttctgaaca ataaatgact taaaccaggt atggctgccg atggttatct   360
tccagattgg ctcgaggaca accttagtga aggaattcgc gagtggtggg ctttgaaacc   420
tggagcccct caacccaagg caaatcaaca acatcaagac aacgctcgag gtcttgtgct   480
tccgggttac aaataccttg acccggcaa cggactcgac aagggggagc cggtcaacgc   540
agcagacgcg gcgccctcg agcacgacaa ggcctacgac cagcagctca aggcggaga    600 caacccgtac ctcaagtaca ccacgccga cgccgagttc caggagcggc tcaaagaaga   660
```

```
tacgtctttt gggggcaacc tcgggcgagc agtcttccag gccaaaaaga ggcttcttga      720
acctcttggt ctggttgagg aagcggctaa gacggctcct ggaaagaaga ggcctgtaga      780
gcagtctcct caggaaccgg actcctccgc gggtattggc aaatcgggtg cacagcccgc      840
taaaaagaga ctcaatttcg gtcagactgg cgacacagag tcagtcccag accctcaacc      900
aatcggagaa cctcccgctg cccctcagg tgtgggatct cttacaatgg cttcaggtgg       960
tggcgcacca gtggcagaca ataacgaagg tgccgatgga gtgggtagtt cctcgggaaa      1020
ttggcattgc gattcccaat ggctggggga cagagtcatc accaccagca cccgaacctg      1080
ggccctgccc acctacaaca atcacctcta aagcaaatc tccaacagca catctggagg       1140
atcttcaaat gacaacgcct acttcggcta cagcacccc tggggtatt ttgacttcaa        1200 cagattccac tgccacttct caccacatga ctggcagcga ctcatcaaca caactgggg      1260 attccggcct aagcgactca acttcaagct cttcaacatt caggtcaaag aggttacgga      1320
caacaatgga gtcaagacca tcgccaataa ccttaccagc acgtccagg tcttcacgga       1380 ctcagactat cagctcccgt acgtgctcgg gtcggctcac gagggctgcc tcccgccgtt      1440
cccagcggac gttttcatga ttcctcagta cgggtatctg acgcttaatg atggaagcca      1500
ggccgtgggt cgttcgtcct tttactgcct ggaatatttc ccgtcgcaaa tgctaagaac      1560
gggtaacaac ttccagttca gctacgagtt tgagaacgta cctttccata gcagctacgc      1620
tcacagccaa agcctggacc gactaatgaa tccactcatc gaccaatact tgtactatct      1680
ctcaaagact attaacggtt ctggacagaa tcaacaaacg ctaaaattca atgtggccgg      1740
acccagcaac atggctgtcc agggaagaaa ctacatacct ggacccagct accgacaaca      1800
acgtgtctca accactgtga ctcaaaacaa caacagcgaa tttgcctggc ctagagcttc      1860
ttcttgggct ctcaatggac gtaatagctt gatgaatcct ggacctgcta tggccagcca      1920
caaagaagga gaggaccgtt tcttccttt gtctggatct ttaattttg gcaaacaagg       1980 aactggaaga gacaacgtgg atgcggacaa agtcatgata accaacgaag aagaaattaa      2040
aactactaac ccggtagcaa cggagtccta tggacaagtg gccacaaacc accagagtgc     2100
ccaagcacag gcgcagaccg gctgggttca aaaccaagga atacttccgg gtatggtttg      2160
gcaggacaga gatgtgtacc tgcaaggacc catttgggcc aaaattcctc acacggacgg      2220
caactttcac ccttctccgc tgatgggagg gtttggaatg aagcacccgc ctcctcagat      2280
cctcatcaaa aacacacctg tacctgcgga tcctccaacg gccttcaaca aggacaagct      2340
gaactctttc atcacccagt attctactgg ccaagtcagc atggagatcg agtgggagct      2400
gcagaaggaa aacagcaagc gctggaaccc ggagatccag tacacttcca actattacaa      2460
gtctaataat gttgaatttg ctgttaatac tgaaggtgta tatagtgaac cccgcccat       2520 tggcaccaga tacctgactc gtaatctgta attgcttgtt aatcaataaa ccgtttaatt      2580
cgtttcagtt gaactgcggc c                                                2601

<210> SEQ ID NO 31
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 31
ccatcgacgt cagacgcgga agcttcgatc aactacgcgg acaggtacca aaacaaatgt       60
tctcgtcacg tgggcatgaa tctgatgctg tttccctgca gacaatgcga gagactgaat     120
```

```
cagaattcaa atatctgctt cactcacggt gtcaaagact gtttagagtg ctttcccgtg    180
tcagaatctc aacccgtttc tgtcgtcaaa aaggcgtatc agaaactgtg ctacattcat    240
cacatcatgg gaaaggtgcc agacgcttgc actgcttgcg acctggtcaa tgtggacttg    300
gatgactgtg tttctgaaca ataaatgact taaaccaggt atggctgccg atggttatct    360
tccagattgg ctcgaggaca accttagtga aggaattcgc gagtggtggg ctttgaaacc    420
tggagcccct caacccaagg caaatcaaca acatcaagac aacgctcgag gtcttgtgct    480
tccgggttac aaataccttg acccggcaa cggactcgac aagggggagc cggtcaacgc     540
agcagacgcg gcggccctcg agcacgacaa ggcctacgac cagcagctca aggccggaga    600
caacccgtac ctcaagtaca accacgccga cgccgagttc caggagcggc tcaaagaaga    660
tacgtctttt gggggcaacc tcgggcgagc agtcttccag gccaaaaaga ggcttcttga    720
acctcttggt ctggttgagg aagcggctaa gacggctcct ggaagaagaa ggcctgtaga    780
gcagtctcct caggaaccgg actcctccgc gggtattggc aaatcgggtg cacagcccgc    840
taaaaagaga ctcaatttcg gtcagactgg cgacacagag tcagtcccag accctcaacc    900
aatcggagaa cctcccgcag ccccctcagg tgtgggatct cttacaatgg cttcaggtgg    960
tggcgcacca gtggcagaca ataacgaagg tgccgatgga gtgggtagtt cctcgggaaa   1020
ttggcattgc gattcccaat ggctgggggga cagagtcatc accaccagca cccgaacctg   1080
ggccctgccc acctacaaca atcacctcta caagcaaatc tccaacagca catctggagg   1140
atcttcaaat gacaacgcct acttcggcta cagcaccccc tgggggtatt ttgacttcaa   1200
cagattccac tgccacttct caccacgtga ctggcagcga ctcatcaaca caactgggg    1260 attccggcct aagcgactca acttcaagct cttcaacatt caggtcaaag aggttacgga   1320
caacaatgga gtcaagacca tcgccaataa ccttaccagc acggtccagg tcttcacgga   1380
ctcagactat cagctcccgt acgtgctcgg gtcggctcac gagggctgcc tcccgccgtt   1440
cccagcggac gttttcatga ttcctcagta cgggtatctg acgcttaatg atggaagcca   1500
ggccgtgggt cgttcgtcct tttactgcct ggaatatttc ccgtcgcaaa tgctaagaac   1560
gggtaacaac ttcagttca gctacgagtt tgagaacgta cctttccata gcagctacgc    1620
tcacagccaa agcctggacc gactaatgaa tccactcatc gaccaatact tgtactatct   1680
ctcaaagact attaacggtt ctggacagaa tcaacaaacg ctaaaattca gtgtggccgg   1740
acccagcaac atggctgtcc agggaagaaa ctacatacct ggacccagct accgacaaca   1800
acgtgtctca accactgtga ctcaaaacaa caacagcgaa tttgcttggc ctagagcttc   1860 ttctttgggct ctcaatggac gtaatagctt gatgaatcct ggacctgcta tggccagcca   1920
caaagaagga gaggaccgtt tctttcctttt gtctggatct ttaatttttg gcaaacaagg   1980
aactggaaga gacaacgtgg atgcggacaa agtcatgata accaacgaag aagaaattaa   2040
aactactaac ccggtagcaa cggagtccta tggacaagtg gccacaaacc accagagtgc   2100
ccaagcacag gcgcagaccg gctgggttca aaaccaagga atacttccgg gtatggtttg   2160
gcaggacaga gatgtgtacc tgcaaggacc catttgggcc aaaattcctc acacggacgg   2220
caactttcac ccttctccgc tgatgggagg gtttggaatg aagcacccgc ctcctcagat   2280
cctcatcaaa aacacacctg tacctgcgga tcctccaacg gccttcaaca aggacaagct   2340
gaactctttc atcaccccagt attctactgg ccaagtcagc gtggagatcg agtgggagct   2400
gcagaaggaa aacagcaagc gctggaaccc ggagatccag tacacttcca actattacaa   2460
```

-continued

```
gtctaataat gttgaatttg ctgttaatac tgaaggtgta tatagtgaac cccgccccat    2520
tggcaccaga tacctgactc gtaatctgta attgcttgtt aatcaataaa ccgtttaatt    2580
cgtttcagtt gaactgcggc c                                              2601

<210> SEQ ID NO 32
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 32
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttcccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atggctgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
tccgggttac aaataccttg gacccggcaa cggactcgac aaggggggagc cggtcaacgc     540 agcagacgcg gcggcccctcg agcacgacaa ggcctacgac cagcagctca aggccggaga     600
caacccgtac ctcaagtaca accacgccga cgccgagttc caggagcggc tcaaagaaga     660
tacgtctttt gggggcaacc tcgggcgagc agtcttccag gccaaaaaga ggcttcttga     720
acctcttggt ctggttgagg aagcggctaa gacggctcct ggaaagaaga ggcctgtaga     780
gcagtctcct caggaaccgg actcctccgc gggtattggc aaatcgggtg cacagcccgc     840
taaaaagaga ctcaatttcg gtcagactgg cgacacagag tcagtcccag accctcaacc     900
aatcggagaa cctcccgcag ccccctcagg tgtgggatct cttacaatgg cttcaggtgg     960
tggcgcacca gtggcagaca taacgaagg tgccgatgga gtgggtagtt cctcgggaaa    1020
ttggcattgc gattcccaat ggctggggga cagagtcatc accaccagca cccgaacctg    1080
ggccctgccc acctacaaca atcacctcta caagcaaatc tccaacagca catctggagg    1140
atcttcaaat gacaacgcct acttcggcta cagcaccccc tgggggtatt ttgacttcaa    1200
cagattccac tgccacttct caccacgtga ctggcagcga ctcatcaaca caactggggg    1260
attccggcct aagcgactca acttcaagct cttcaacatt caggtcaaag aggttacgga    1320
caacaatgga gtcaagacca tcgccaataa ccttaccagc acggtccagg tcttcacgga    1380
ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta ccttccccata gcagctacgc    1620 tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acccagcaac atggctgtcc agggaagaaa ctacatacct ggacccagct accgacaaca    1800
acgtgtctca accactgtga ctcaaaacaa caacagcgaa tttgcttggc ctagagcttc    1860
ttcttgggct ctcaatggac gtaatagctt gatgaatcct ggacctgcta tggccagcca    1920
```

```
caaagaagga gaggaccgtt tctttccttt gtctggatct ttaattttg gcaaacaagg      1980 aactggaaga gacaacgtgg atgcggacaa agtcatgata accaacgaag aagaaattaa     2040
aactactaac ccggtagcaa cggagtccta tggacaagtg ccacaaacc accagagtgc      2100 ccaagcacag gcgcagaccg gctgggttca aaaccaagga atacttccgg gtatggtttg     2160
gcaggacaga gatgtgtacc tgcaaggacc catttgggcc aaaattcctc acacggacgg     2220
caactttcac ccttctccgc tgatgggagg gtttggaatg aagcacccgc ctcctcagat     2280
cctcatcaaa aacacacctg tacctgcgga tcctccaacg gccttcaaca aggacaagct     2340
gaactctttc atcacccagt attctactgg ccaagtcagc gtggagatcg agtgggagcg     2400
gcagaaggaa aacagcaagc gctggaaccc ggagatccag tacacttcca actattacaa     2460
gtctaataat gttgaatttg ctgttaatac tgaaggtgta tatagtgaac ccgcccccat     2520
tggcaccaga tacctgactc gtaatctgta attgcttgtt aatcaataaa ccgtttaatt     2580
cgtttcagtt gaactgcggc c                                               2601
```

<210> SEQ ID NO 33
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 33

```
ccatcgacgt cagacgcgga agcttcgatc aactacgcgg acaggtacca aaacaaatgt      60
tctcgtcacg tgggcatgaa tctgatgctg tttccctgca gacaatgcga gagactgaat      120
cagaattcaa atatctgctt cactcacggt gtcaaagact gtttagagtg ctttcccgtg      180
tcagaatctc aacccgtttc tgtcgtcaaa aaggcgtatc agaaactgtg ctacattcat      240
cacatcatgg gaaaggtgcc agacgcttgc actgcttgcg acctggtcaa tgtggacttg      300
gatgactgtg tttctgaaca ataaatgact taaaccaggt atggctgccg atggttatct      360
tccagattgg ctcgaggaca accttagtga aggaattcgc gagtggtggg ctttgaaacc      420
tggagcccct caacccaagg caaatcaaca acatcaagac aacgctcgag gtcttgtgct      480
tccgggttac aaataccttg acccggcaa cggactcgac aagggggagc cggtcaacgc      540
agcagacgcg gcggccctcg agcacgacaa ggcctacgac cagcagctca aggccggaga     600
caacccgtac ctcaagtaca accacgccga cgccgagttc caggagcggc tcaaagaaga     660
tacgtctttt gggggcaacc tcgggcgagc agtcttccag gccaaaaaga ggcttcttga     720
acctcttggt ctggttgagg aagcggctaa gacggctcct ggaaagaaga ggcctgtaga     780
gcagtctcct caggaaccgg actcctccgc gggtattggc aaatcgggtg cacagcccgc     840
taaaaagaga ctcaatttcg gtcagactgg cgacacagag tcagtcccag accctcaacc     900
aatcggagaa cctcccgcag ccccctcagg tgtgggatct cttacaatgg cttcaggtgg     960
tggcgcacca gtggcagaca taacgaagg tgccgatgga gtgggtagtt cctcgggaaa     1020
ttggcattgc gattcccaat ggctggggga cagagtcatc accaccagca cccgaacctg     1080
ggccctgccc acctacaaca tcacctcta caagcaaatc tccaacagca catctggagg     1140
atcttcaaat gacaacgcct acttcggcta cagcaccccc tgggggtatt ttgacttcaa     1200
cagattccac tgccacttct cacccacgtga ctggcagcga ctcatcaaca caactgggg     1260 attccggcct aagcgactca acttcaagct cttcaacatt caggtcaaag aggttacgga     1320
```

```
caacaatgga gtcaagacca tcgccaataa ccttaccagc acggtccagg tcttcgcgga    1380
ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acccagcaac atggctgtcc agggaagaaa ctacatacct ggacccagct accgacaaca    1800
acgtgtctca accactgtga ctcaaaacaa caacagcgaa tttgcttggc ctagagcttc    1860 ttctttgggct ctcaatggac gtaatagctt gatgaatcct ggacctgcta tggccagcca    1920
caaagaagga gaggaccgtt tctttccttt gtctggatct ttaatttttg gcaaacaagg    1980
aactggaaga caacgtgg atgcggacaa agtcatgata accacgaag aagaaattaa    2040 aactactaac ccggtagcaa cggagtccta tggacaagtg gccacaaacc accagagtgc    2100
ccaagcacag gcgcagaccg gctgggttca aaaccaagga atacttccgg gtatggttg    2160 gcaggacaga gatgtgtacc tgcaaggacc catttgggcc aaaattcctc acacggacgg    2220
caactttcac ccttctccgc tgatgggagg gtttggaatg aagcacccgc ctcctcagat    2280
cctcatcaaa aacacacctg tacctgcgga tcctccaacg gccttcaaca aggacaagct    2340
gaactctttc atcacccagt attctactgg ccaagtcagc gtggagatcg agtgggagct    2400
gcagaaggaa aacagcaagc gctggaaccc ggagatccag tacacttcca actattacaa    2460
gtctaataat gttgaatttg ctgttaatac tgaaggtgta tatagtgaac cccgccccat    2520
tggcaccaga tacctgactc gtaatctgta attgcttgtt aatcaataaa ccgtttaatt    2580
cgtttcagtt gaactgcggc c                                               2601

<210> SEQ ID NO 34
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 34
ccatcgacgt cagacgcgga agcttcgatc aactacgcgg acaggtacca aaacaaatgt      60
tctcgtcacg tgggcatgaa tctgatgctg tttccctgca gacaatgcga gagactgaat     120
cagaattcaa atatctgctt cactcacggt gtcaaagact gtttagagtg ctttcccgtg     180
tcagaatctc aacccgtttc tgtcgtcaaa aaggcgtatc agaaactgtg ctacattcat     240
cacatcatgg gaaaggtgcc agacgcttgc actgcttgcg acctggtcaa tgtggacttg     300
gatgactgtg tttctgaaca ataaatgact taaaccaggt atggctgccg atggttatct     360
tccagattgg ctcgaggaca accttagtga aggaattcgc gagtggtggg ctttgaaacc     420
tggagcccct caacccaagg caaatcaaca acatcaagac aacgctcgag gtcttgtgct     480
tccgggttac aaataccttg acccggcaa cggactcgac aaggggagc cggtcaacgc     540 agcagacgcg gcggccctcg agcacgacaa ggcctacgac cagcagctca aggccggaga     600
caacccgtac ctcaagtaca accacgccga cgccgagttc caggagcggc tcaaagaaga     660
tacgtctttt gggggcaacc tcgggcgagc agtcttccag gccaaaaaga ggcttcttga     720
acctcttggt ctggttgagg aagcggctaa gacggctcct ggaaagaaga ggcctgtaga     780
```

```
gcagtctcct caggaaccgg actcctccgc gggtattggc aaatcgggtg cacagcccgc    840
taaaaagaga ctcaatttcg gtcagactgg cgacacagag tcagtcccag accctcaacc    900
aatcggagaa cctcccgcag cccctcagg tgtgggatct cttacaatgg cttcaggtgg     960
tggcgcacca gtggcagaca ataacgaagg tgccgatgga gtgggtagtt cctcgggaaa   1020
ttggcattgc gattcccaat ggctggggga cagagtcatc accaccagca cccgaacctg   1080
ggccctgccc acctacaaca atcacctcta aagcaaatc tccaacagca catctggagg    1140
atcttcaaat gacaacgcct acttcggcta cagcaccccc tgggggtatt ttgacttcaa   1200
cagattccac tgccacttct caccacgtga ctggcagcga ctcatcaaca caactgggg    1260 attccggcct aagcgactca acttcaagct cttcaacatt caggtcaaag aggttacgga   1320
caacaatgga gtcaagacca tcgccaataa ccttaccagc acggtccagg tcttcacgga   1380
ctcagactat cagctcccgt acgtgctcgg gtcggctcac gagggctgcc tcccgccgtt   1440
cccagcggac gttttcatga ttcctcagta cgggtatctg acgcttaatg atggaagcca   1500
ggccgtgggt cgttcgtcct tttactgcct ggaatatttc ccgtcgcaaa tgctaagaac   1560
gggtaacaac ttccagttca gctacgagtt tgagaacgta cctttccata gcagctacgc   1620
tcacagccaa agcctggacc gactaatgaa tccactcatc gaccaatact tgtactatct   1680
ctcaaagact attaacggtt ctggacagaa tcaacaaacg ctaaaattca gtgtggccgg   1740
acccagcaac atggctgtcc agggaagaaa ctacatacct ggacccagct accgacaaca   1800
acgtgtctca accactgtga ctcaaaacaa caacagcgaa attgcttggc ctagagcttc   1860
ttcttgggct ctcaatggac gtaatagctt gatgaatcct ggacctgcta tggccagcca   1920
caaagaagga gaggaccgtt tctttccttt gtctggatct ttaattttg gcaaacaagg   1980 aactggaaga gacaacgtgg atgcggacaa agtcatgata accaacgaag aagaaattaa   2040
aactactaac ccagtagcaa cggagtccta tggacaagtg gccacaaacc accagagtgc   2100
ccaagcacag gcgcagaccg gctgggttca aaaccaagga atacttccgg gtatggtttg   2160
gcaggacaga gatgtgtacc tgcaaggacc catttgggcc aaaattcctc acacggacgg   2220
caactttcac ccttctccgc tgatgggagg gtttggaatg aagcacccgc ctcctcagat   2280
cctcatcaaa aacacacctg tacctgcgga tcctccaacg gccttcaaca aggacaagct   2340
gaactctttc atcaccagt attctactgg ccaagtcagc gtggagatcg agtgggagct   2400
gcagaaggaa aacagcaagc gctggaaccc ggagatccag tacacttcca actattgcaa   2460
gtctaataat gttgaatttg ctgttaatac tgaaggtgta tatagtgaac ccgcccca    2520 tggcaccaga tacctgactc gtaatctgta attgcttgtt aatcaataaa ccgtttaatt   2580
cgtttcagtt gaactgcggc c                                            2601
```

<210> SEQ ID NO 35
<211> LENGTH: 2601
<212> TYPE: DNA
<213> ORGANISM: Artificial Sequence
<220> FEATURE:
<223> OTHER INFORMATION: novel AAV isolate

<400> SEQUENCE: 35

```
ccatcgacgt cagacgcgga agcttcgatc aactacgcgg acaggtacca aaacaaatgt     60
tctcgtcacg tggcatgaa tctgatgctg tttccctgca gacaatgcga gagactgaat    120
cagaattcaa atatctgctt cactcacggt gtcaaagact gtttagagtg ctttcccgtg    180
```

```
tcagaatctc aacccgtttc tgtcgtcaaa aaggcgtatc agaaactgtg ctacattcat    240
cacatcatgg gaaaggtgcc agacgcttgc actgcttgcg acctggtcaa tgtggacttg    300
gatgtctgtg tttctgaaca ataaatgact taaaccaggt atggctgccg atggttatct    360
tccagattgg ctcgaggaca accttagtga aggaattcgc gagtggtggg ctttgaaacc    420
tggagcccct caacccaagg caaatcaaca acatcaagac aacgctcgag gtcttgtgct    480
tccgggttac aaataccttg gacccggcaa cggactcgat aaggggggagc cggtcaacgc    540
agcagacgcg gcggccctcg agcacgacaa ggcctacgac cagcagctca aggccggaga    600
caacccgtac ctcaagtaca accacgccga cgccgagttc caggagcggc tcaaagaaga    660
tacgtctttt gggggcaacc tcgggcgagc agtcttccag gccaaaaaga ggcttcttga    720
acctcttggt ctggttgagg aagcggctaa cacggctcct ggaaagaaga ggcctgtaga    780
gcagtctcct caggaaccgg actcctccgc gggtattggc aaatcgggtg cacagcccgc    840
taaaaagaga ctcaatttcg gtcagactgg cgacacagag tcagtcccag accctcaacc    900
aatcggagaa cctcccgcag cccccctcagg tgtgggatct cttacaatgg cttcaggtgg    960
tggcgcacca gtggcagaca ataacgaagg tgccgatgga gtgggtagtt cctcgggaaa    1020
ttggcattgc gattcccaat ggctggggga cagagtcatc accaccagca cccgaacctg    1080
ggccctgccc acctacaaca atcacctcta caagcaaatc tccaacagca catctggagg    1140
atcttcaaat gacaacgcct acttcggcta cagcaccccc tggggtatt tttgacttcaa    1200
cagattccac tgccacttct caccacgtga ctggcagcga ctcatcaaca caactgggg    1260
attccggcct aagcgactca acttcaagct cttcaacatt caggtcaaag aggttacgga    1320
caacaatgga gtcaagacca tcgccaataa ccttaccagc acgtccagg tcttcacgga    1380
ctcagactat cagctcccgt acgtgctcgg gtcggctcac gagggctgcc tcccgccgtt    1440
cccagcggac gttttcatga ttcctcagta cgggtatctg acgcttaatg atggaagcca    1500
ggccgtgggt cgttcgtcct tttactgcct ggaatatttc ccgtcgcaaa tgctaagaac    1560
gggtaacaac ttccagttca gctacgagtt tgagaacgta cctttccata gcagctacgc    1620
tcacagccaa agcctggacc gactaatgaa tccactcatc gaccaatact tgtactatct    1680
ctcaaagact attaacggtt ctggacagaa tcaacaaacg ctaaaattca gtgtggccgg    1740
acccagcaac atggctgtcc agggaagaaa ctacatacct ggacccagct accgacaaca    1800
acgtgtctca accactgtga ctcaaaacaa caacagcgaa tttgcttggc ctagagcttc    1860
ttcttgggct ctcaatggac gtaatagctt gatgaatcct ggacctgcta tggccagcca    1920
caaagaagga gaggaccgtt tctttcctt gtctggatct ttaattttttg gcaaacaagg    1980
aactggaaga gacaacgtgg atgcggacaa agtcatgata accaacgaag aagaaattaa    2040
aactactaac ccggtagcaa cggagtccta tggacaagtg gccacaaacc accagagtgc    2100
ccaagcacag gcgcagaccg gctgggttca aaaccaagga atacttccgg gtatggttttg    2160
gcaggacaga gatgtgtacc tgcaaggacc catttgggcc aaaattcctc acacggacgg    2220
caactttcac ccttctccgc tgatgggagg gtttggaatg aagcacccgc ctcctcagat    2280
cctcatcaaa aacacacctg tacctgcgga tcctccaacg gccttcaaca aggacaagct    2340
gaactctttc atcacccagt attctactgg ccaagtcagc gtggagatcg agtgggagct    2400
gcagaaggaa aacagcaagc gctggaaccc ggagatccag tacacttcca actattacaa    2460
gtctaataat gttgaatttg ctgttaatac tgaaggtgta tatagtgaac ccgcccccat    2520
tggcaccaga tacctgactc gtaatctgta attgcttgtt aatcaataaa ccgtttaatt    2580
```
cgtttcagtt gaactgcggc c                                              2601

<210> SEQ ID NO 36
<211> LENGTH: 145
<212> TYPE: DNA
<213> ORGANISM: Artificial Sequence
<220> FEATURE:
<223> OTHER INFORMATION: AAV2 5' ITR

<400> SEQUENCE: 36
ttggccactc cctctctgcg cgctcgctcg ctcactgagg ccgggcgacc aaaggtcgcc    60
cgacgcccgg gctttgcccg gcggcctca gtgagcgagc gagcgcgcag agagggagtg    120
gccaactcca tcactagggg ttcct                                          145

<210> SEQ ID NO 37
<211> LENGTH: 145
<212> TYPE: DNA
<213> ORGANISM: Artificial Sequence
<220> FEATURE:
<223> OTHER INFORMATION: AAV2 3' ITR

<400> SEQUENCE: 37
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120 gagcgcgcag agagggagtg gccaa                                          145

<210> SEQ ID NO 38
<211> LENGTH: 167
<212> TYPE: DNA
<213> ORGANISM: Artificial Sequence
<220> FEATURE:
<223> OTHER INFORMATION: AAV5 5' ITR

<400> SEQUENCE: 38
ctctcccccc tgtcgcgttc gctcgctcgc tggctcgttt gggggggtgg cagctcaaag    60
agctgccaga cgacggccct ctggccgtcg ccccccaaa cgagccagcg agcgagcgaa    120
cgcgacaggg gggagagtgc cacactctca agcaagggg ttttgta                  167

<210> SEQ ID NO 39
<211> LENGTH: 167
<212> TYPE: DNA
<213> ORGANISM: Artificial Sequence
<220> FEATURE:
<223> OTHER INFORMATION: AAV5 3' ITR

<400> SEQUENCE: 39
tacaaaacct ccttgcttga gagtgtggca ctctcccccc tgtcgcgttc gctcgctcgc    60
tggctcgttt gggggggtgg cagctcaaag agctgccaga cgacggccct ctggccgtcg   120 ccccccaaa cgagccagcg agcgagcgaa cgcgacaggg gggagag                  167

<210> SEQ ID NO 40
<211> LENGTH: 621
<212> TYPE: PRT
<213> ORGANISM: Artificial Sequence
<220> FEATURE:
<223> OTHER INFORMATION: AAV2 Rep

<400> SEQUENCE: 40

Met Pro Gly Phe Tyr Glu Ile Val Ile Lys Val Pro Ser Asp Leu Asp
1               5                   10                  15

```
Glu His Leu Pro Gly Ile Ser Asp Ser Phe Val Asn Trp Val Ala Glu
             20                  25                  30

Lys Glu Trp Glu Leu Pro Pro Asp Ser Asp Met Asp Leu Asn Leu Ile
         35                  40                  45

Glu Gln Ala Pro Leu Thr Val Ala Glu Lys Leu Gln Arg Asp Phe Leu
     50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
             100                 105                 110

Arg Glu Lys Leu Ile Gln Arg Ile Tyr Arg Gly Ile Glu Pro Thr Leu
         115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430
```

-continued

```
Thr Thr Phe Glu His Gln Gln Pro Leu Gln Asp Arg Met Phe Lys Phe
        435                 440                 445
Glu Leu Thr Arg Arg Leu Asp His Asp Phe Gly Lys Val Thr Lys Gln
    450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
                500                 505                 510
Ala Gln Pro Ser Thr Ser Asp Ala Glu Ala Ser Ile Asn Tyr Ala Asp
        515                 520                 525
Arg Tyr Gln Asn Lys Cys Ser Arg His Val Gly Met Asn Leu Met Leu
        530                 535                 540
Phe Pro Cys Arg Gln Cys Glu Arg Met Asn Gln Asn Ser Asn Ile Cys
545                 550                 555                 560
Phe Thr His Gly Gln Lys Asp Cys Leu Glu Cys Phe Pro Val Ser Glu
                565                 570                 575
Ser Gln Pro Val Ser Val Val Lys Lys Ala Tyr Gln Lys Leu Cys Tyr
                580                 585                 590
Ile His His Ile Met Gly Lys Val Pro Asp Ala Cys Thr Ala Cys Asp
        595                 600                 605
Leu Val Asn Val Asp Leu Asp Cys Ile Phe Glu Gln
        610                 615                 620
```